US008715943B2

(12) United States Patent
Princen et al.

(10) Patent No.: US 8,715,943 B2
(45) Date of Patent: May 6, 2014

(54) METHODS FOR IMPROVING INFLAMMATORY BOWEL DISEASE DIAGNOSIS

(71) Applicant: Nestec S.A., Vevey (CH)

(72) Inventors: Fred Princen, La Jolla, CA (US); Steven Lockton, San Diego, CA (US); Lisa J. Croner, San Diego, CA (US); Frederick A. Fletcher, San Diego, CA (US); Thomas Stockfisch, Escondido, CA (US); Sharat Singh, Rancho Santa Fe, CA (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/840,779

(22) Filed: Mar. 15, 2013

(65) Prior Publication Data

US 2013/0225439 A1     Aug. 29, 2013

Related U.S. Application Data

(63) Continuation of application No. PCT/US2012/061202, filed on Oct. 19, 2012.

(60) Provisional application No. 61/550,293, filed on Oct. 21, 2011, provisional application No. 61/553,853, filed on Oct. 31, 2011, provisional application No. 61/567,096, filed on Dec. 5, 2011, provisional application No. 61/570,271, filed on Dec. 13, 2011.

(51) Int. Cl.
*G01N 33/53* (2006.01)
*G01N 33/566* (2006.01)
*C12Q 1/68* (2006.01)

(52) U.S. Cl.
USPC ............ 435/7.1; 435/6.11; 436/501; 702/19; 702/20

(58) Field of Classification Search
None
See application file for complete search history.

(56) References Cited

U.S. PATENT DOCUMENTS 5,750,355 A    5/1998  Targan et al.
5,916,748 A    6/1999  Targan et al.
(Continued)

FOREIGN PATENT DOCUMENTS

WO    WO 98/37415     8/1998
WO    WO 01/89361 A2  11/2001
(Continued)

OTHER PUBLICATIONS

Schoepfer et al., "Phenotypic Associations of Crohn's Disease with Antibodies to Flagellins A4-Fla2 and Fla-X, ASCA, p-ANCA, PAB, and NOD2 Mutations in a Swiss Cohort," Inflamm. Bowel Dis. 2009, 15:1358-1367.*

(Continued)

*Primary Examiner* — Samuel Woolwine
*Assistant Examiner* — Kaijiang Zhang
(74) *Attorney, Agent, or Firm* — Kilpatrick Townsend & Stockton LLP

(57) ABSTRACT

The present invention provides methods and systems to predict and diagnose inflammatory bowel disease (IBD) and subtypes such as ulcerative colitis (UC) and Crohn's disease (CD) by detecting the presence, absence, level, and/or genotype of one or more sero-genetic-inflammation markers. Advantageously, with the present invention, it is possible to provide a diagnosis of IBD versus non-IBD, to rule out IBD that is inconclusive for CD and UC, and to differentiate between CD and UC with increased accuracy.

30 Claims, 20 Drawing Sheets

(56) References Cited

U.S. PATENT DOCUMENTS

| | | | |
|---|---|---|---|
| 5,932,429 | A | 8/1999 | Targan et al. |
| 6,033,864 | A | 3/2000 | Braun et al. |
| 6,074,835 | A | 6/2000 | Braun et al. |
| 6,218,129 | B1 | 4/2001 | Walsh et al. |
| 6,309,643 | B1 | 10/2001 | Braun et al. |
| 6,835,815 | B2 | 12/2004 | Nunez |
| 6,858,391 | B2 | 2/2005 | Nunez |
| 7,060,442 | B2 | 6/2006 | Nunez |
| 7,060,493 | B2 | 6/2006 | Nunez |
| 7,375,086 | B2 | 5/2008 | Nunez |
| 7,592,437 | B2 | 9/2009 | Hugot et al. |
| 7,873,479 | B2 | 1/2011 | Lois et al. |
| 8,137,915 | B2 | 3/2012 | Hugot et al. |
| 8,315,818 | B2 | 11/2012 | Lois et al. |
| 2002/0068313 | A1 | 6/2002 | Braun |
| 2003/0204507 | A1 | 10/2003 | Li et al. |
| 2004/0043931 | A1 | 3/2004 | Hersberg et al. |
| 2004/0137536 | A1 | 7/2004 | Boone et al. |
| 2004/0242972 | A1 | 12/2004 | Adak et al. |
| 2005/0054021 | A1 | 3/2005 | Targan et al. |
| 2005/0060295 | A1 | 3/2005 | Gould et al. |
| 2005/0164929 | A1 | 7/2005 | Alvarez et al. |
| 2006/0003392 | A1 | 1/2006 | Oh et al. |
| 2006/0154276 | A1 | 7/2006 | Lois et al. |
| 2008/0131439 | A1 | 6/2008 | Lois et al. |
| 2011/0045476 | A1 | 2/2011 | Barken et al. |
| 2011/0159521 | A1 | 6/2011 | Gong et al. |

FOREIGN PATENT DOCUMENTS

| | | |
|---|---|---|
| WO | WO 03/053220 A2 | 7/2003 |
| WO | WO 2004/037073 | 5/2004 |
| WO | WO 2004/048600 A2 | 6/2004 |
| WO | WO 2004/095021 A1 | 11/2004 |
| WO | WO 2005/078452 A1 | 8/2005 |
| WO | 2006/063093 A2 | 6/2006 |
| WO | 2007/064964 A1 | 6/2007 |
| WO | 2008/109782 A2 | 9/2008 |
| WO | 2008/141148 A2 | 11/2008 |
| WO | 2010/056682 A2 | 5/2010 |
| WO | 2010/120814 A1 | 10/2010 |

OTHER PUBLICATIONS

Abreu, M. et al., "Use of serologic tests in Crohn's disease," Clin. Perspect. Gastroenterol., 2001, 155-164.

Arnott, I. et al., "Sero-reactivity to microbial components in Crohn's disease is associated with disease severity and progression, but not NOD2/CARD15 genotype," American Journal of Gastroenterology, 2004, 99:2376-2384.

Lois, A. et al., "Development of a hybrid algorithm based on learning classifiers that improves diagnosis of inflammatory bowel disease and differentiation between Crohn's and ulcerative colitis in a six-marker system," Gastroenterology, 2006, 130(4, Suppl. 2):A323. XP009115454.

Dubinsky, M., "Clinical utility of serodiagnostic testing in suspect pediatric inflammatory bowel disease," The American Journal of Gastroenterology, 2001, 96(3):758-765.

Fleshner, P. et al., "High level perinuclear antineutrophil cytoplasmic antibody (pANCA) in ulcerative colitis patients before colectomy predicts the development of chronic pouchitis after ileal pouch-anal anastomosis," Gut, 2001, 49(5):671-677.

Nakamura, R. et al., "Advances in clinical laboratory tests for inflammatory bowel disease," Clinica Chimica Acta, 2003, 335:9-20.

Restriction Requirement mailed on Jun. 22, 2010 for U.S. Appl. No. 11/841,699, filed Aug. 20, 2007; 6 pages.

Reumaux, D., "Serological markers in inflammatory bowel disease," Best Practice and Research Clinical Gastroenterology, 2003, 17(1):19-35.

Ruemele, F. et al., "Diagnostic accuracy of serological assays in pediatric inflammatory bowel disease," Gastroenterology, 1998, 115(4):822-829.

Targan, S., "The utility of ANCA and ASCA in Inflammatory bowel disease," Inflamm. Bowel Dis., 1999, 5(1):61-3.

Targan, S. et al., "Antibodies to CBir1 flagellin define a unique response that is associated independently with complicated Crohn's disease," Gastroenterology, 2005, 128:2020-2028.

Vasiliauskas, E. et al., "Marker antibody expression stratifies Crohn's disease into immunologically homogenous subgroups with distinct clinical characteristics Vasiliauskas," Gut, 2000, 47(4):487-496.

Vernier, G. et al., "Relevance of serologic studies in inflammatory bowel disease," Current Gastroenterology Reports, 2004, 6(6): 482-487. XP2009115628.

Zhao, H. et al. "Entity identification for heterogeneous database integration—a multiple classifier system approach and empirical evaluation," Information Systems, 2005, 30(2):119-132. XP025366573.

Bousvaros, A et al., "Elevated serum vascular endothelial growth factor in children and young adult with Crohn's disease," Dig. Dis. Sci., 44:424-430, 1999.

Henriksen, M et al., "C-reactive protein: a predictive factor of inflammation in inflammatory bowel disease. Results from a prospective population-based study," Gut, 57:1518-1523, 2008.

Jones, SC et al., "Adhesion molecules in inflammatory bowel disease," Gut, 36:724-730, 1995.

Khor, B et al., "Genetics and pathogenesis of inflammatory bowel disease," Nature, 474:307-317, 2011.

Lees, CW et al., "Genetics of inflammatory bowel disease: implications for disease pathogenesis and natural history," Expert Rev. Gastroenterol. Hepatol., 3:513-534, 2009.

Abreu, M.T. et al., "Mutations in NOD2 are associated with fibrostenosing disease in patients with Crohn's disease," Gastroenterology, 2002,123:679-688.

Annese V. et al., "Variants of CARD15 are associated with an aggressive clinical course of Crohn's disease—an IG-IBD study," Am. J. Gastroenterol., 2005, 100:84-92.

Baert F. et al., "Medical therapy for Crohn's disease: top-down or step-up?" Dig. Dis. 2007, 25:260-266.

Baert F. et al., "Mucosal healing predicts sustained clinical remission in patients with early-stage Crohn's Disease," Gastroenterology, 2010, 138:463-468.

Cosnes J. et al., "Impact of the increasing use of immunosuppressants in Crohn's disease on the need for intestinal surgery," Gut, 2005, 54:237-241.

Cruyssen B.V. et al., "CARD15 polymorphisms are associated with anti-*Saccharomyces cerevisiae* antibodies in caucasian Crohn's disease patients," Clin. Exp. Immunol., 2005, 140:354-359.

Dalwadi H. et al., "The Crohn's disease-associated bacterial protein I2 is a novel enteric t cell superantigen," Immunity, 2001, 15:149-158.

Desir B. et al., "Utility of serum antibodies in determining clinical course in pediatric Crohn's Disease, " Clin. Gastroenterol. and Hepatol., 2004, 2:139-146.

Devlin S. et al., "NOD2 Variants and Antibody Response to Microbial Antigens in Crohn's Disease Patients and Their Unaffected Relatives," Gastroenterology, 2006, 132(2):576-586.

D'Haens G. et al., "Early combined immunosuppression or conventional management in patients with newly diagnosed Crohn's disease: an open randomised trial," Lancet, 2008, 371:660-667.

Dubinsky M. et al., "Increased immune reactivity predicts aggressive complicating crohn's disease in children," Clin. Gastroent. Hepatol., 2008, 6(10):1105-1111.

Dubinsky M. et al., "Serum immune responses predict rapid disease progression among children with Crohn's disease: immune responses predict disease progression," Am. J. Gastroenterology, 2006, 101(2):360-367.

Faubion W. et al., "The natural history of corticosteroid therapy for inflammatory bowel disease: a population-based study," Gastroenterology, 2001, 121:255-260.

Ferrante M. et al., "New serological markers in inflammatory bowel disease are associated with complicated disease behavior," Gut, 2007; 56:1394-1403.

Ferrante M. et al., "Predictors of early response to infliximab in patients with ulcerative colitis," Inflamm. Bowel Dis., 2007, 13:123-128.

(56) References Cited

OTHER PUBLICATIONS

Hanauer S.B., "Positioning biologic agents in the treatment of Crohn's disease," Inflamm. Bowel Dis., 2009, 15:1570-1582.

Landers C.J. et al., "Selected loss of tolerance evidenced by Crohn's disease-associated immune responses to auto and microbial antigens," Gastroenterology, 2002, 123:689-699.

Lichtenstein G.R., "Emerging prognostic markers to determine Crohn's disease natural history and improve management strategies: a review of recent literature," Gastroenterol. & Hepatol., 2010, 6:99-107.

Loftus E.V. et al., "The epidemiology and natural history of Crohn's disease in population-based patient cohorts from North America: a systematic review," Aliment. Pharmacol. Ther., 2002, 16:51-60.

Louis E. et al., "Behaviour of Crohn's disease according to the Vienna classification: changing pattern over the course of the disease," Gut, 2001, 49:777-782.

Mow W. et al., "Association of antibody responses to microbial antigens and complications of small bowel Crohn's disease," Gastroenterology, 2003, 126(2):414-424.

Munkholm P. et al., "Frequency of glucocorticoid resistance and dependency in Crohn's disease," Gut, 1994, 35:360-362.

Papadakis K. et al, "Anti-flagellin (CBir1) phenotypic and genetic Crohn's disease associations," Inflammatory Bowel Diseases, 2007, 13(5):524-530.

Rieder F. et al., "Serum anti-glycan antibodies predict complicated Crohn's disease behavior: A cohort study," Inflamm. Bowel Dis. 2010, 16:1367-1375.

Sendid B. et al., "Specific antibody response to oligomannosidic epitopes in Crohn's disease," Clin. Diagn. Lab. Immunol., 1996, 3:219-226.

Sutton C.L. et al., "Identification of a novel bacterial sequence associated with Crohn's disease," Gastroenterology, 2000, 119:23-31.

Voices of Progress Annual Report 2008 [CCFA web site], Aug. 31, 2008, Available at: http://www.ccfa.org/images/ar09/fullannualrep09.pdf.

Wei B. et al., "*Pseudomonas fluorescens* encodes the Crohn's disease-associated I2 sequence and T-cell superantigen," Infect. Immun., 2002, 70:6567-6575.

\* cited by examiner

IBD sgi Performs Better than IBD Serology 7 in Differentiating CD vs. UC

In a head-to-head comparison, IBD sgi demonstrated improved overall performance over IBD Serology 7 in differentiating CD vs. UC

Overall Diagnostic Performance
*IBD sgi vs. IBD Serology 7*

In a head-to-head comparison of diagnostic performance, IBD sgi demonstrated absolute and relative improvements over IBD Serology 7 n=373

|  | IBD sgi | IBD Serology 7 | Absolute Improvement | Relative Improvement |
|---|---|---|---|---|
| IBD vs. Non-IBD (AUC) | 0.87 | 0.80 | 7% | 9% |
| CD / UC (AUC) | 0.93 | 0.78 | 15% | 19% |

IBD vs nonIBD

|  | AUC | 95%CI |  |
|---|---|---|---|
| sgi | 0.87 | 0.8442 – 0.9070 |  |
| Ser7 | 0.80 | 0.7682 – 0.8507 | p=0.0001 |

CD vs UC

|  | AUC | 95%CI |  |
|---|---|---|---|
| sgi | 0.93 | 0.8585 – 0.9354 |  |
| Ser7 | 0.78 | 0.7144 – 0.8403 | p<0.0001 |

*FIG. 20*

METHODS FOR IMPROVING INFLAMMATORY BOWEL DISEASE DIAGNOSIS

CROSS-REFERENCES TO RELATED APPLICATIONS

The present application is a continuation of PCT/US2012/061202, filed Oct. 19, 2012, which application claims priority to U.S. Provisional Application No. 61/550,293, filed Oct. 21, 2011, U.S. Provisional Application No. 61/553,853, filed Oct. 31, 2011, U.S. Provisional Application No. 61/567,096, filed Dec. 5, 2011, and U.S. Provisional Application No. 61/570,271, filed Dec. 13, 2011, the disclosures of which are hereby incorporated by reference in their entirety for all purposes.

BACKGROUND OF THE INVENTION

Inflammatory bowel disease (IBD), which occurs worldwide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases and how these diseases will progress. The cost of IBD and IBS is compounded by lost productivity, with people suffering from these disorders missing at least 8 more days of work annually than the national average.

Inflammatory bowel disease has many symptoms in common with irritable bowel syndrome, including abdominal pain, chronic diarrhea, weight loss, and cramping, making definitive diagnosis extremely difficult. Of the 5 million people suspected of suffering from IBD in the United States, only 1 million are diagnosed as having IBD. The difficulty in differentially diagnosing IBD and determining its outcome hampers early and effective treatment of these diseases. Thus, there is a need for rapid and sensitive testing methods for determining IBD and its subtypes.

Over the years, little progress has been made in precisely diagnosing clinical subtypes of IBD. Thus, there is an urgent need for improved methods for diagnosing an individual with IBD, and determining the subtype, such as Crohn's Disease (CD) or ulcerative colitis. Since 70% of CD patients will ultimately need a GI surgical operation, the ability to diagnose those patients early in their disease state to mitigate unnecessary surgery in the future is important. The present invention satisfies these needs and provides related advantages as well.

BRIEF SUMMARY OF THE INVENTION

The present invention provides methods and systems for the diagnosis of inflammatory bowel disease (IBD) and/or the determination of subtypes including ulcerative colitis (UC) and Crohn's Disease (CD) or categorizing the sample as inconclusive (e.g., IBD sample that is inconclusive for CD and UC). Advantageously, with the present invention, it is possible to diagnose patients with IBD, and if the patient has IBD, diagnose either UC or CD.

In certain aspects, the present invention provides a diagnostic model that comprises two separate random forests, one for IBD vs. non-IBD and the other for UC vs. CD. In another embodiment, the present invention provides a model comprising four class outcomes (non-IBD, CD, UC, Inconclusive). In still yet another embodiment, the present invention provides a single model comprising a 3 class outcome (non-IBD, CD, UC).

In particular embodiments, the present invention provides methods and systems to diagnose IBD or nonIBD and/or to differentiate between clinical subtypes of IBD such as UC and CD or categorizing the sample as inconclusive by analyzing a sample to determine the presence or absence of one, two, three, four, or more variant alleles (e.g., single nucleotide polymorphisms or SNPs) in the ATG16L1 (e.g., rs2241880, rs3828309), ECM1 (e.g., rs7511649, rs3737240 and rs13294), NKX2-3 (e.g., rs1190140, rs10883365 and rs6584283) and/or STAT3 (e.g., rs744166) genes. In certain aspects of these embodiments, the present invention may further include analyzing a sample to determine the presence (or absence) or concentration level of one or more serological and inflammation markers such as, e.g., ASCA-A, ASCA-G, anti-OmpC, anti-CBir1, anti-Fla2, anti-FlaX, VEGF, CRP, SAA, ICAM, VCAM, ANCA (e.g., by ELISA) and/or pANCA (e.g., by one or more indirect fluorescent antibody (IFA) assays to detect an IBD-specific pANCA perinuclear pattern and/or pANCA DNase sensitivity), pANCA2 to diagnose IBD or non-IBD, and/or to differentiate between clinical subtypes of IBD such as IC, UC and CD or categorizing the sample as inconclusive.

In one embodiment, the present invention provides a method for diagnosing inflammatory bowel disease (IBD) and/or a clinical subtype thereof in an individual, wherein the clinical subtype is ulcerative colitis (UC) or Crohn's disease (CD) or inconclusive, the method comprising:
  (a) analyzing a sample obtained from the individual to determine the presence, level or genotype of one or more markers selected from the group consisting of a serological marker, a genetic marker, an inflammation marker, and a combination thereof in the sample to obtain a marker profile;
  (b) applying a first random forest statistical analysis to the marker profile to obtain a decision whether the marker profile is an IBD sample or a nonIBD sample;
  (c) optionally applying a decision tree or set of rules to the sample designated as an IBD sample to determine if the IBD sample is an inconclusive sample; and
  (d) optionally applying a second random forest statistical analysis to the IBD sample to determine a clinical subtype.

In certain embodiments, the IBD diagnostic assay comprises an initial node for determining whether a sample is pANCA2 negative as a first step to direct individual specimens to either a Decision Tree Method or the Random Forest Algorithm depending on their pANCA2 value. In certain instances, pANCA2 samples with either a negative (0 or "not detected") or a weak (+1) pANCA determination are removed and subjected to a decision matrix or set of rules for making a clinical prediction of IBD.

In another embodiment, the present invention provides for diagnosing inflammatory bowel disease (IBD) and/or a clinical subtype thereof in an individual, wherein the clinical subtype is ulcerative colitis (UC) or Crohn's disease (CD) or inconclusive, the method comprising:
  (a) analyzing a sample obtained from the individual to determine the presence, level or genotype of one or more markers selected from the group consisting of a serological marker, a genetic marker, an inflammation marker, and a combination thereof in the sample to obtain a marker profile;

(b) applying a first random forest statistical analysis to the marker profile to obtain a decision whether the marker profile is an IBD sample or a nonIBD sample;

(c) applying a decision tree or set of rules to the sample designated as an IBD sample to determine if the IBD sample is an inconclusive sample; and (d) if the sample is not inconclusive, but is an IBD sample, applying a second random forest statistical analysis to the IBD sample to determine a clinical subtype.

These and other aspects, objects and embodiments will become more apparent when read with the following detailed description and figures.

BRIEF DESCRIPTION OF THE DRAWINGS

FIG. 20 illustrates a comparison of the overall diagnostic performance between IBD sgi and IBD Serology 7 for IBD vs. non-IBD and CD vs. UC.

DETAILED DESCRIPTION OF THE INVENTION

I. Introduction

The present invention is based, in part, upon the surprising discovery that the accuracy of diagnosing inflammatory bowel disease (IBD) and subtypes thereof can be substantially improved by detecting the presence, level, or genotype of certain markers in a biological sample from an individual. As such, in one embodiment, the present invention provides diagnostic platforms based on a serological and/or genetic panel of markers.

The present invention provides methods and systems to improve the diagnosis of IBD and subgroups thereof such as, e.g., indeterminate colitis (IC), ulcerative colitis (UC), Crohn's disease (CD), and inconclusive for CD and UC ("Inconclusive"). In some instances, the methods described herein accurately predict IBD, a disease which is known to be very difficult to diagnose and predict outcome. In other instances, the methods described herein utilize multiple serological, protein, and/or genetic markers, alone or in combination with one or more algorithms or other types of statistical analysis, to provide physicians valuable diagnostic or prognostic insight. In some instances, the methods and systems of the present invention provide an indication of a patient's projected response to biological therapy. In other instances, the methods and systems of the present invention utilize multiple markers (e.g., serological, protein, and/or genetic) in conjunction with statistical analysis (e.g., quartile analysis) to provide prognostic value by identifying patients with complicated disease or a risk of developing disease complications (e.g., internal stricturing or internal penetrating disease) and/or a need for surgical intervention, while also assisting in assessing the rate of disease progression. In certain instances, the methods enable classification of disease severity along a continuum of IBD subgroups including IC, UC and CD. Moreover, the methods guide therapeutic decisions of patients with advanced disease. In other instances, the use of multiple markers (e.g., serological, protein, and/or genetic) provides the ability to distinguish responders from non-responders and guides initial therapeutic options (e.g., whether or not to prescribe aggressive treatment), with the potential to change disease behavior.

Figure 1:
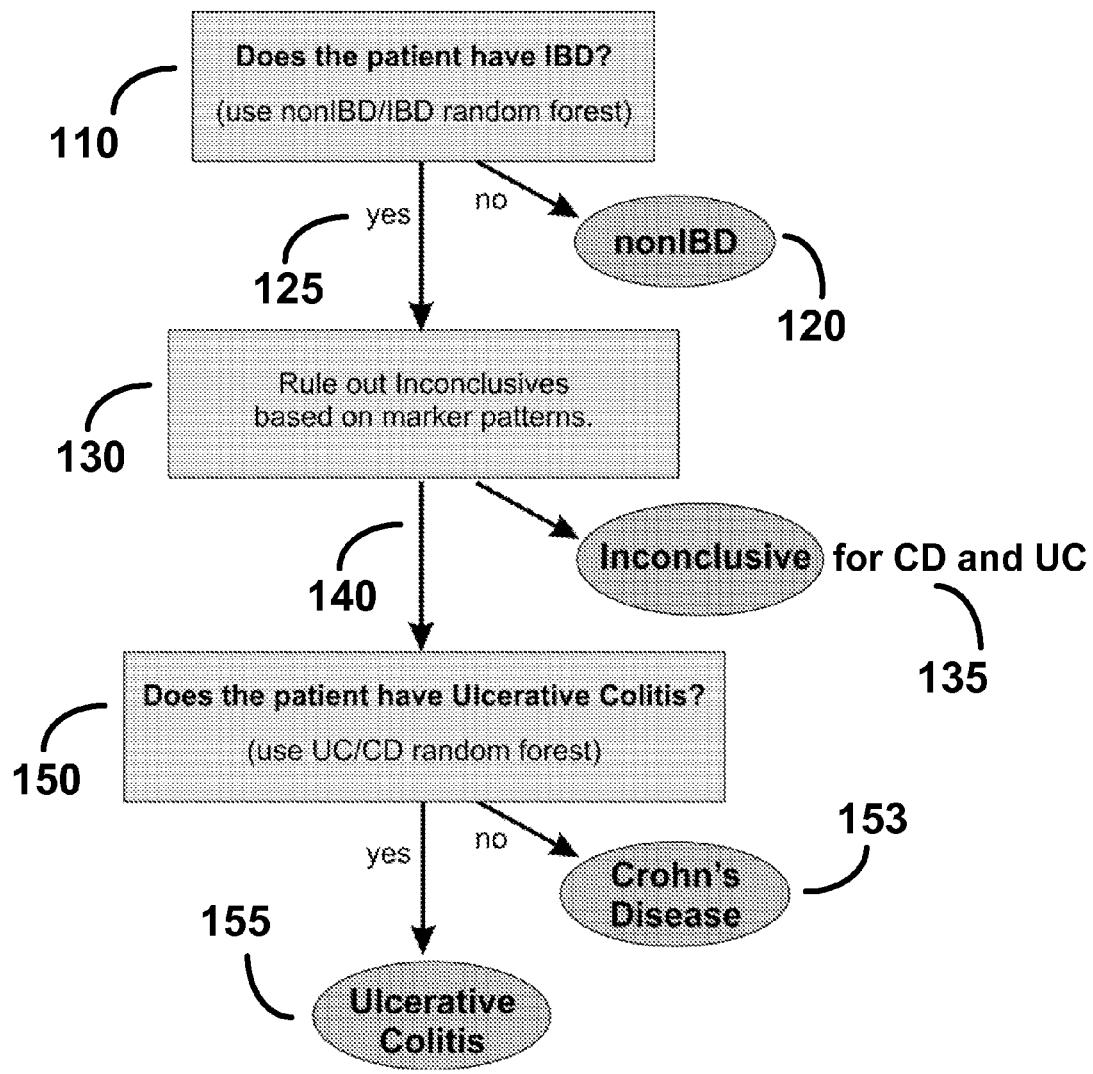
FIG. 1 illustrates a flowchart for an exemplary embodiment of an IBD diagnostic assay of the invention comprising a two-step random forest algorithm.

FIG. 1 illustrates a flowchart for an exemplary embodiment of an IBD diagnostic assay of the present invention comprising a two-step random forest algorithm. In certain embodiments, the IBD diagnostic assay applies the measurements from 17 sero-genetic-inflammation (sgi) biological markers (e.g., ANCA, ASCA-A, ASCA-G, anti-FlaX, anti-A4-Fla2, pANCA, anti-OmpC, anti-CBir1, ATG16L1, CRP, SAA, ICAM, VCAM, ECM1, STAT3, VEGF, NKX2-3, and combinations thereof) and computes a score based on a first random forest model for predicting IBD vs. non-IBD (110). The first random forest model determines if a patient has IBD. If the score is less than the IBD vs. non-IBD cut-off (e.g., <0.64), the sample is predicted to be from a patient having IBD (125). Otherwise, the sample is predicted to be from a patient having non-IBD (120). Samples predicted to have IBD proceed to the next step of the algorithm, which is a decision tree or set of rules designed to rule out categorizing the sample as inconclusive (130). If a sample matches the pattern for either of the "indeterminate" rules, the algorithm predicts the sample as having IBD, but is inconclusive for UC and CD (135). Otherwise, the sample proceeds to the next step of the algorithm (140), which is a second random forest model for predicting UC vs. CD (150). The IBD diagnostic assay applies the measurements from 11 sgi biological markers (e.g., ANCA, ASCA-A, ASCA-G, anti-FlaX, anti-A4-Fla2, pANCA, anti-OmpC, anti-CBir1, ECM1, STAT3, VEGF, and combinations thereof) to compute a model score based on the second random forest model for predicting UC vs. CD. If the score is less than the UC vs. CD cut-off (e.g., 0.35), the algorithm predicts the sample as having CD (153). Or else, the algorithm predicts the sample as having UC (155).

Figure 2:
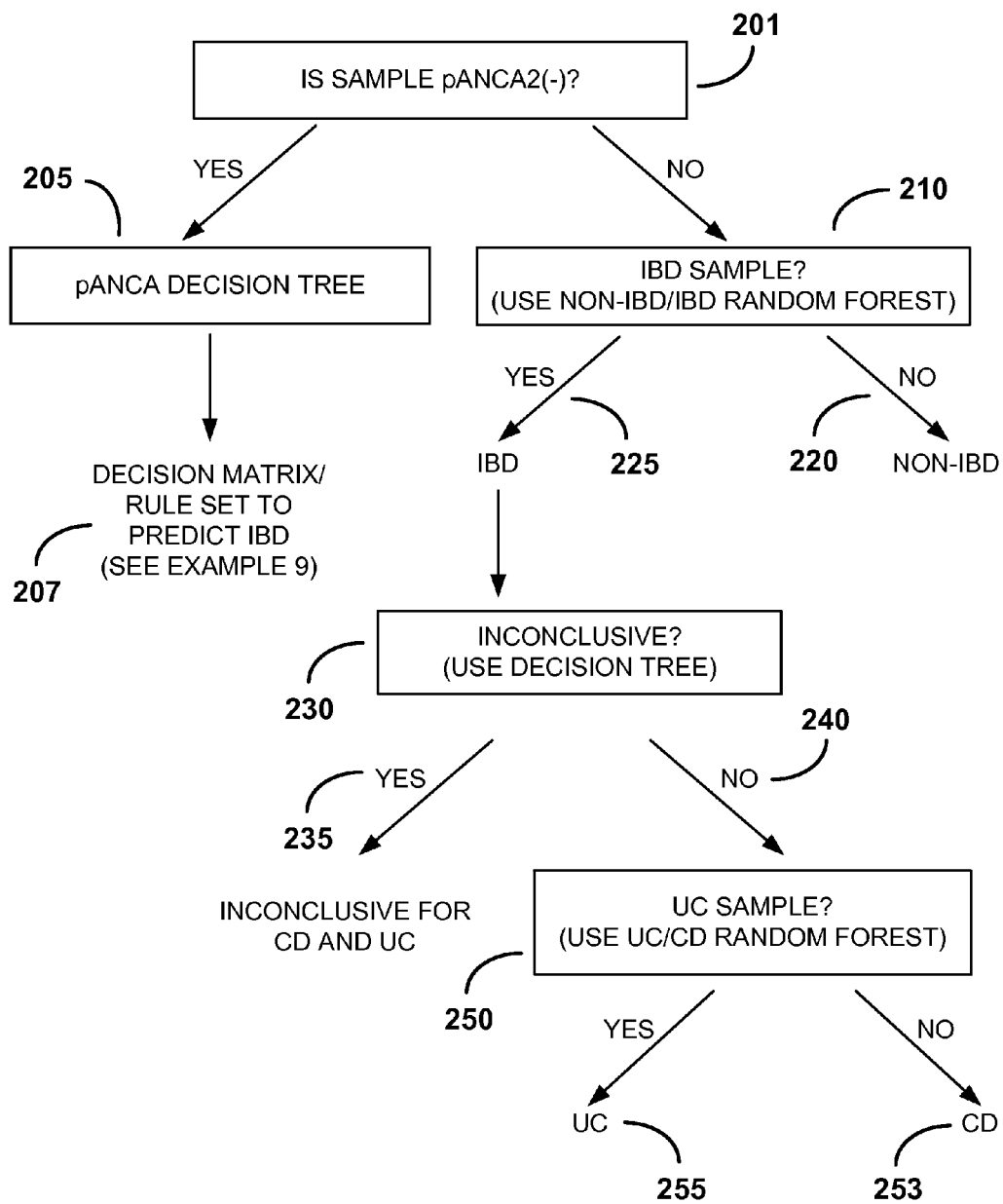
FIG. 2 illustrates a flowchart for another exemplary embodiment of an IBD diagnostic assay of the invention comprising a two-step random forest algorithm (right pathway) and a separate pANCA decision tree (left pathway).

FIG. 2 illustrates a flowchart for another exemplary embodiment of an IBD diagnostic assay of the invention comprising a two-step random forest algorithm (right pathway) and a separate pANCA decision tree (left pathway). In certain embodiments, the IBD diagnostic assay comprises an initial node (201) for determining whether a sample is pANCA2 negative as a first step to direct individual specimens to either the Decision Tree Method (205) or the Random Forest Algorithm (210), depending on their pANCA2 value. In certain instances, pANCA2 samples with either a negative (0 or "not detected") or a weak (+1) pANCA determination are removed from the sgi algorithm queue (right pathway) and subjected to a decision matrix or set of rules for making a clinical prediction of IBD (207). An exemplary decision matrix for predicting IBD following pANCA decision tree analysis is described in Example 9. As such, in certain aspects, the pANCA decision tree (205) can be implemented as an alternate path for making predictive IBD diagnoses in clinical specimens with pANCA2 (−) assay results.

FIG. 2 also illustrates an exemplary path for analyzing pANCA2 positive samples (right pathway). In certain embodiments, pANCA2 samples with a positive (+2, +3, or +4) pANCA determination are processed using an IBD diagnostic assay and subjected to a two-step random forest algorithm analogous to the two-step random forest algorithm described in FIG. 1. In certain instances, the IBD diagnostic assay applies the measurements from 17 sero-genetic-inflammation (sgi) biological markers (e.g., ANCA, ASCA-A, ASCA-G, anti-FlaX, anti-A4-Fla2, pANCA, anti-OmpC, anti-CBir1, ATG16L1, CRP, SAA, ICAM, VCAM, ECM1, STAT3, VEGF, NKX2-3, and combinations thereof) and computes a score based on a first random forest model for predicting IBD vs. non-IBD (210). The first random forest model determines if a patient has IBD. If the score is less than the IBD vs. non-IBD cut-off (e.g., <0.64), the sample is predicted to be from a patient having IBD (225). Otherwise, the sample is predicted to be from a patient having non-IBD (220). Samples predicted to have IBD proceed to the next step of the algorithm, which is a decision tree or set of rules designed to rule out categorizing the sample as inconclusive (230). If a sample matches the pattern for either of the "indeterminate" rules, the algorithm predicts the sample as having IBD, but is inconclusive for UC and CD (235). Otherwise, the sample proceeds to the next step of the algorithm (240), which is a second random forest model for predicting UC vs. CD (250). The IBD diagnostic assay applies the measurements from 11 sgi biological markers (e.g., ANCA, ASCA-A, ASCA-G, anti-FlaX, anti-A4-Fla2, pANCA, anti-OmpC, anti-CBir1, ECM1, STAT3, VEGF, and combinations thereof) to compute a model score based on the second random forest model for predicting UC vs. CD. If the score is less than the UC vs. CD cut-off (e.g., 0.35), the algorithm predicts the sample as having CD (253). Or else, the algorithm predicts the sample as having UC (255).

In certain instances, the methods and systems of the present invention comprise a step having a "transformation" or "machine" associated therewith. For example, an ELISA technique may be performed to measure the presence or concentration level of many of the markers described herein. An ELISA includes transformation of the marker, e.g., an autoantibody, into a complex between the marker (e.g., autoantibody) and a binding agent (e.g., antigen), which then can be measured with a labeled secondary antibody. In many instances, the label is an enzyme which transforms a substrate into a detectable product. The detectable product measurement can be performed using a plate reader such as a spectrophotometer. In other instances, genetic markers are determined using various amplification techniques such as PCR. Method steps including amplification such as PCR result in the transformation of single or double strands of nucleic acid into multiple strands for detection. The detection can include the use of a fluorophore, which is performed using a machine such as a fluorometer.

In certain embodiments, the methods further comprise comparing the results from the statistical analysis (i.e., diagnostic profile) to a reference (i.e., diagnostic model) to aid in the diagnosis of IBD. In particular embodiments, the methods utilize multiple serological, protein, and/or genetic markers to provide physicians with valuable diagnostic insight.

Advantageously, by using a diagnostic profile composed of multiple markers (e.g., serological, genetic, inflammatory, etc.) alone or in conjunction with statistical analysis, the assay methods and systems of the present invention provide diagnostic value by identifying patients having IBD and IBD subgroups such as IC, UC, CD, and inconclusive. In certain instances, the present invention enables classification of disease severity along a continuum of IBD subgroups including, but not limited to, IC, UC, CD, and inconclusive.

II. Definitions

As used herein, the following terms have the meanings ascribed to them unless specified otherwise.

The term "classifying" includes "associating" or "categorizing" a sample or an individual with a disease state or prognosis. In certain instances, "classifying" is based on statistical evidence, empirical evidence, or both. In certain embodiments, the methods and systems of classifying use a so-called training set of samples from individuals with known disease states or prognoses. Once established, the training data set serves as a basis, model, or template against which the features of an unknown sample from an individual are compared, in order to classify the unknown disease state or provide a prognosis of the disease state in the individual. In some instances, "classifying" is akin to diagnosing the disease state and/or differentiating the disease state from another disease state. In other instances, "classifying" is akin to providing a prognosis of the disease state in an individual diagnosed with the disease state.

The term "inflammatory bowel disease" or "IBD" includes gastrointestinal disorders such as, e.g., Crohn's disease (CD), ulcerative colitis (UC), indeterminate colitis (IC), and IBD that is inconclusive for CD vs. UC ("Inconclusive"). Inflammatory bowel diseases (e.g., CD, UC, IC, and Inconclusive) are distinguished from all other disorders, syndromes, and abnormalities of the gastroenterological tract, including irritable bowel syndrome (IBS). U.S. Pat. No. 7,873,479, entitled "Methods of Diagnosing Inflammatory Bowel Disease" is incorporated herein by reference in its entirety for all purposes.

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.*, 11:267-86 (1997)). One skilled in the art will appreciate that samples such as serum samples can be diluted prior to the analysis of marker levels.

The term "marker" includes any biochemical marker, serological marker, genetic marker, or other clinical or echographic characteristic that can be used in the diagnosis of IBD, in the prediction of the probable course and outcome of IBD, and/or in the prediction of the likelihood of recovery from the disease. Non-limiting examples of such markers include serological markers such as an anti-neutrophil antibody (e.g., ANCA, pANCA, and the like), an anti-*Saccharomyces cerevisiae* antibody (e.g., ASCA-IgA, ASCA-IgG), an antimicrobial antibody (e.g., anti-OmpC antibody, anti-I2 antibody, anti-Fla2 antibody, anti-FlaX antibody, anti-CBir1 antibody), an acute phase protein (e.g., CRP), an apolipoprotein (e.g., SAA), a defensin (e.g., β defensin), a growth factor (e.g., EGF, VEGF), a cytokine (e.g., TWEAK, IL-1β, IL-6), a cadherin (e.g., E-cadherin), a cellular adhesion molecule (e.g., ICAM-1, VCAM-1); genetic markers (e.g., SNPs) such as ATG16L1, ECM1, NKX2-3, STAT3, and NOD2/CARD15; and combinations thereof. Non-limiting examples of genetic markers include variant alleles in the GLI1 (e.g., rs2228224 and/or rs2228226), MDR1 (e.g., rs2032582), ATG16L1 (e.g., rs2241880, rs3828309), ECM1 (e.g., rs7511649, rs373240, rs13294), NKX2-3 (e.g., rs1190140, rs10883365, rs6584283), STAT3 (e.g., rs744166), and NOD2/CARD15 (e.g., rs2066847, rs2066845, rs5743293) genes. In some embodiments, the markers are utilized in combination with one or more (e.g., a plurality of) statistical analyses to aid or provide a diagnosis or prognosis of IBD in an individual. In certain instances, the diagnosis can be IBD or a clinical subtype thereof such as Crohn's disease (CD), ulcerative colitis (UC), indeterminate colitis (IC), or inconclusive IBD. In certain other instances, the prognosis can be the need for surgery (e.g., the likelihood or risk of needing small bowel surgery), development of a clinical subtype of CD or UC (e.g., the likelihood or risk of being susceptible to a particular clinical subtype CD or UC such as the stricturing, penetrating, or inflammatory CD subtype), development of one or more clinical factors (e.g., the likelihood or risk of being susceptible to a particular clinical factor), development of intestinal cancer (e.g., the likelihood or risk of being susceptible to intestinal cancer), or recovery from the disease (e.g., the likelihood of remission).

The present invention relies, in part, on determining the presence (or absence) or level (e.g., concentration) of at least one marker in a sample obtained from an individual. As used herein, the term "detecting the presence of at least one marker" includes determining the presence of each marker of interest by using any quantitative or qualitative assay known to one of skill in the art. In certain instances, qualitative assays that determine the presence or absence of a particular trait, variable, genotype, and/or biochemical or serological substance (e.g., protein or antibody) are suitable for detecting each marker of interest. In certain other instances, quantitative assays that determine the presence or absence of DNA, RNA, protein, antibody, or activity are suitable for detecting each marker of interest. As used herein, the term "detecting the level of at least one marker" includes determining the level of each marker of interest by using any direct or indirect quantitative assay known to one of skill in the art. In certain instances, quantitative assays that determine, for example, the relative or absolute amount of DNA, RNA, protein, antibody, or activity are suitable for detecting the level of each marker of interest. One skilled in the art will appreciate that any assay useful for detecting the level of a marker is also useful for detecting the presence or absence of the marker.

The term "marker profile" includes 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, or more diagnostic and/or prognostic marker(s), wherein the markers can be a serological marker, a protein marker, a genetic marker, and the like. In some embodiments, the marker profile together with a statistical analysis can provide physicians and caregivers valuable diagnostic and prognostic insight. In other embodiments, the marker profile with optionally a statistical analysis provides a projected response to biological therapy. By using multiple markers (e.g., serological, protein, genetic, etc.) in conjunction with statistical analyses, the assays described herein provide diagnostic, prognostic and therapeutic value by identifying patients with IBD or a clinical subtype thereof, predicting risk of developing complicated disease, assisting in assessing the rate of disease progression (e.g., rate of progression to complicated disease or surgery), and assisting in the selection of therapy.

The term "diagnostic profile" includes 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, or more marker(s) of an individual, wherein the marker(s) can be a serological marker, a protein marker, a genetic marker, and the like. A statistical analysis transforms the marker profile into a diagnostic profile. A preferred statistical analysis is a quartile score and the quartile score for each of the markers can be summed to generate a quartile sum score.

The term "diagnostic model" includes serological models, genetic models, sero-genetic-inflammatory models, and a combination thereof. In a preferred aspect, a retrospective analysis is done on a cohort of known disease outcomes with known complications and surgical procedures performed. In one aspect, a regression analysis (e.g., logistic regression) can be performed on the presence or concentration level of one or more serological markers and/or the genotype of one or more genetic markers to develop a diagnostic model. The model can be illustrated or depicted in, e.g., a look-up table, graph or other display. A diagnostic profile of an individual can then be compared to a diagnostic model and the diagnosis determined (e.g., the risk or probability of having a disease).

The term "individual," "subject," or "patient" typically includes humans, but also includes other animals such as, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as an I2 protein can have one or more modifications such as amino acid additions, deletions, or substitutions relative to the amino acid sequence of the naturally-occurring I2 protein, provided that the modified polypeptide retains substantially at least one biological activity of I2 such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The term "clinical factor" includes a symptom in an individual that is associated with IBD. Examples of clinical factors include, without limitation, diarrhea, abdominal pain, cramping, fever, anemia, weight loss, anxiety, depression, and combinations thereof. In some embodiments, a diagnosis or prognosis of IBD is based upon a combination of analyzing a sample obtained from an individual to determine the presence, level, or genotype of one or more markers by applying one or more statistical analyses and determining whether the individual has one or more clinical factors.

The term "symptom" or "symptoms" and variants thereof includes any sensation, change or perceived change in bodily function that is experienced by an individual and is associated with a particular diseases or that accompanies a disease and is regarded as an indication of the disease. Disease for which symptoms in the context of the present invention can be associated with include inflammatory bowel disease (IBD), ulcerative colitis (UC) or Crohn's disease (CD).

In a preferred aspect, the methods of invention are used after an individual has been diagnosed with IBD. However, in other instances, the methods can be used to diagnose IBD or can be used as a "second opinion" if, for example, IBD is suspected or has been previously diagnosed using other methods. In preferred aspects, the methods can be used to diagnose UC or differentiate between UC and CD. The term "diagnosing IBD" and variants thereof includes the use of the methods and systems described herein to determine the presence or absence of IBD. The term "diagnosing UC" includes the use of the methods and systems described herein to determine the presence or absence of UC, as well as to differentiate between UC and CD. The terms can also include assessing the level of disease activity in an individual. In some embodiments, a statistical analysis is used to diagnose a mild, moderate, severe, or fulminant form of IBD or UC based upon the criteria developed by Truelove et al., *Br. Med. J.*, 12:1041-1048 (1955). In other embodiments, a statistical analysis is used to diagnose a mild to moderate, moderate to severe, or severe to fulminant form of IBD or UC based upon the criteria developed by Hanauer et al., *Am. J. Gastroenterol.*, 92:559-566 (1997). One skilled in the art will know of other methods for evaluating the severity of IBD or UC in an individual.

In certain instances, the methods of the invention are used in order to diagnose IBD, diagnose UC or differentiate IC from UC and/or CD and differentiate between UC and CD or categorizing the sample as inconclusive. The methods can be used to monitor the disease, both progression and regression. The term "monitoring the progression or regression of IBD or UC" includes the use of the methods and marker profiles to determine the disease state (e.g., presence or severity of IBD or the presence of UC) of an individual. In certain instances, the results of a statistical analysis are compared to those results obtained for the same individual at an earlier time. In some aspects, the methods of the present invention can also be used to predict the progression of IBD or UC, e.g., by determining a likelihood for IBD or UC to progress either rapidly or slowly in an individual based on the presence or level of at least one marker in a sample. In other aspects, the methods of the present invention can also be used to predict the regression of IBD or UC, e.g., by determining a likelihood for IBD or UC to regress either rapidly or slowly in an individual based on the presence or level of at least one marker in a sample.

The term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

The term "genotype" refers to the genetic composition of an organism, including, for example, whether a diploid organism is heterozygous or homozygous for one or more variant alleles of interest.

The term "polymorphism" refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (i.e., single nucleotide polymorphism or SNP). Polymorphic markers include restriction fragment length polymorphisms, variable number of tandem repeats (VNTR's), hyper-variable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The allele occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

The term "single nucleotide polymorphism (SNP)" and variants thereof refers to a change of a single nucleotide with a polynucleotide, including within an allele. This can include the replacement of one nucleotide by another, as well as deletion or insertion of a single nucleotide. Most typically, SNPs are biallelic markers although tri- and tetra-allelic markers can also exist. By way of non-limiting example, a nucleic acid molecule comprising SNP A\C may include a C or A at the polymorphic position. For combinations of SNPs, the term "haplotype" is used, e.g. the genotype of the SNPs in a single DNA strand that are linked to one another. In some embodiments, the term "haplotype" can be used to describe a combination of SNP alleles, e.g., the alleles of the SNPs found together on a single DNA molecule. In further embodiments, the SNPs in a haplotype can be in linkage disequilibrium with one another.

The term "specific" or "specificity" and variants thereof, when used in the context of polynucleotides capable of detecting variant alleles (e.g., polynucleotides that are capable of discriminating between different alleles), includes the ability to bind or hybridize or detect one variant allele without binding or hybridizing or detecting the other variant allele. In some embodiments, specificity can refer to the ability of a polynucleotide to detect the wild-type and not the mutant or variant allele. In other embodiments, specificity can refer to the ability of a polynucleotide to detect the mutant or variant allele and not the wild-type allele.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

In quartile analysis, there are three numbers (values) that divide a range of data into four equal parts. The first quartile (also called the 'lower quartile') is the number below which lies the 25 percent of the bottom data. The second quartile (the 'median') divides the range in the middle and has 50 percent of the data below it. The third quartile (also called the 'upper quartile') has 75 percent of the data below it and the top 25 percent of the data above it. As a non-limiting example, quartile analysis can be applied to the concentration level of a marker such as an antibody or other protein marker described herein, such that a marker level in the first quartile (<25%) is assigned a value of 1, a marker level in the second quartile (25-50%) is assigned a value of 2, a marker level in the third quartile (51%-<75%) is assigned a value of 3, and a marker level in the fourth quartile (75%-100%) is assigned a value of 4.

As used herein, "quartile sum score" or "QSS" includes the sum of quartile scores for all of the markers of interest. As a non-limiting example, a quartile sum score for a panel of 6 markers (e.g., serological, protein, and/or genetic) may range from 6-24, wherein each of the individual markers is assigned a quartile score (Q) of 1-4 based upon the presence or absence of the marker, the concentration level of the marker, or the genotype of the marker.

III. Description of the Embodiments

In one embodiment, the present invention provides a method for diagnosing inflammatory bowel disease (IBD) and/or a clinical subtype thereof in an individual, the method comprising:
  (a) analyzing a sample obtained from the individual to determine the presence, level or genotype of one or more markers selected from the group consisting of a serological marker, a genetic marker, an inflammation marker, and a combination thereof in the sample to obtain a marker profile;
  (b) applying a first algorithm (e.g., a random forest or logistic regression) to the marker profile to obtain a decision whether the marker profile is an IBD sample or a nonIBD sample;
  (c) optionally applying a decision tree or set of rules to the sample designated as an IBD sample to determine if the IBD sample an inconclusive sample; and
  (d) optionally applying a second algorithm (e.g., a random forest or logistic regression) to the IBD sample to determine a clinical subtype.

In a second embodiment, the present invention provides for diagnosing inflammatory bowel disease (IBD) and/or a clinical subtype thereof in an individual, the method comprising:
  (a) analyzing a sample obtained from the individual to determine the presence, level or genotype of one or more markers selected from the group consisting of a serological marker, a genetic marker, an inflammation marker, and a combination thereof in the sample to obtain a marker profile;
  (b) applying a first algorithm such as a random forest to the marker profile to obtain a decision whether the marker profile is an IBD sample or a nonIBD sample;
  (c) applying a decision tree or set of rules to the sample designated as an IBD sample to determine if the IBD sample is an inconclusive sample; and
  (d) if the sample is not inconclusive, but an IBD sample, applying a second algorithm such as a random forest to the IBD sample to determine a clinical subtype.

In certain embodiments, the methods further comprise comparing the results from the statistical analysis (i.e., diagnostic profile) to a reference (i.e., diagnostic model) to aid in the diagnosis of IBD. In particular embodiments, the methods utilize multiple serological, protein, and/or genetic markers to provide physicians with valuable diagnostic insight.

In certain embodiments, the methods and systems herein measure a first serological marker of pANCA to determine a value of pANCA2. In certain aspects, pANCA is assigned a value of 0 when it is not detected or when it is DNAse cytoplasmic sensitive. pANCA is assigned a value of 1 when it is DNAse Sensitive 1+P, DNAse Sensitive 2+P, DNAse Sensitive 3+P, or DNAse Sensitive 4+P, wherein 1+P through 4+P indicate increasing amounts and intensity of fluorescence label based on visual assessment. For example, if the pANCA values are +2, +3 or +4 in a sample, then the pANCA2 value is positive.

In certain other aspects, pANCA2 is assigned a value of 0 (negative) when pANCA is not detected, pANCA is DNAse cytoplasmic sensitive, or DNAse Sensitive 1+P. pANCA2 is given a value of 1 (positive), when pANCA is DNAse Sensitive 2+P, DNAse Sensitive 3+P or DNAse Sensitive 4+P.

As is explained in detail herein, when pANCA2 is negative, the methods and systems further comprise:
  a) determining whether the pANCA2 negative sample is directly predictive of Crohn's disease by measuring a serum marker panel, wherein the serum marker panel is a member of the group consisting of ASCA-IgA, ASCA-IgG, and OmpC-IgA and comparing each of the serum markers of the serum marker panel to a cutoff value to determine if the sample is consistent with Crohn's disease; or
  b) determining whether the pANCA2 negative sample is consistent with Crohn's disease by measuring a CD count panel, wherein the CD count panel is a member of the group consisting of ASCA-IgA, ASCA-IgG, OmpC-IgA, CBir1-IgG, A4-Fla2-IgG and FlaX-IgG to form a CD count value, wherein when the CD count value is greater than or equal to 2, the sample is consistent with Crohn's disease; or
  c) determining whether in the pANCA2 negative sample having a pANCA value of zero, is consistent or inconsistent with IBD by measuring ANCA ELISA and comparing the ANCA ELISA value to a reference value and designating the sample as being consistent or inconsistent with IBD based on the ANCA ELISA value; or
  d) determining whether in the pANCA2 negative sample having a pANCA value of zero, is consistent with IBD or is inconclusive of IBD by measuring ANCA ELISA and comparing the ANCA ELISA value and considering the CD count value to determine whether the sample is consistent or inconsistent with IBD or is consistent with IBD and inconclusive for Crohn's disease or ulcerative colitis; or
  e) determining whether in the pANCA2 negative sample having a pANCA value of one, is consistent or inconsistent with IBD by measuring ANCA ELISA and comparing the ANCA ELISA value to a cut-off value to determine whether the sample is consistent with IBD or is inconsistent with IBD.

In certain instances, if the value for ASCA-IgA in part a above is greater than or equal to 69 EU/mL, then the sample is consistent with Crohn's disease.

In other instances, if the value of ASCA-IgG in part a above is greater than or equal to 40 EU/mL, then the sample is consistent with Crohn's disease.

In still other instances, if the value for OmpC-IgA in part a above is greater than or equal to 60 EU/mL, then the sample is consistent with Crohn's disease.

Moreover, the systems and methods provide assigning a Crohn's disease (CD) count value. For example, in part b above, the CD count value is determined using the following rules.
  i. if ASCA-IgA is greater than or equal to 8.5 EU/mL (above the ASCA-IgA reference range), then adding +1 to the CD count value;
  ii. if ASCA-IgG is greater than or equal to 17.8 EU/mL (above the ASCA-IgG reference range), then adding +1 to the CD count value;
  iii. if OmpC-IgA is greater than or equal to 10.9 EU/mL (above the OmpC-IgA reference range), then adding +1 to the CD count value;
  iv. if 2 or more flagellin markers are above their respective reference ranges, then adding +1 to the CD count value;
  v. if any flagellin is greater than or equal to 100 EU/mL, then adding +1 to the CD count value; and if the total CD count value is greater than or equal to 2, then designating that the sample is consistent with Crohn's disease.

In certain instances, the reference value for CBir1-IgG is greater than or equal to 78.4 EU/mL.

In certain other instances, the reference value for A4-Fla2-IgG is greater than or equal to 44.8 EU/mL.

In yet other instances, the reference value for FlaX-IgG is greater than or equal to 33.4 EU/mL.

In certain other aspects, the methods and systems herein further comprise for part c above, if pANCA is zero (not detected), then:
  i. designating the sample as being inconsistent with IBD if ANCA ELISA is less than 20 EU/mL; or
  ii. designating the sample as being consistent with ulcerative colitis if ANCA ELISA is greater than 27.4 EU/mL; or
  iii. designating the sample as being inconsistent with IBD if ANCA ELISA is greater than or equal to 20 and less than or equal to 27.4 EU/mL and the CD count value is zero; or
  iv. designating the sample as being consistent with IBD but inconclusive for Crohn's disease or ulcerative colitis if ANCA ELISA is greater than or equal to 20 and less than or equal to 27.4 EU/mL and the CD count value is one.

In yet other aspects, the methods and systems herein further comprise that when pANCA is one:
  i. designating the sample as being inconsistent with IBD if ANCA ELISA is less than 13.7 EU/mL; or
  ii. designating that the sample as being consistent with ulcerative colitis if ANCA ELISA is greater than or equal to 13.7 EU/mL.

The present invention provides methods and systems for improved diagnosis of inflammatory bowel disease (IBD) and to differentiate ulcerative colitis (UC) and Crohn's disease (CD). In certain instances, the methods and systems enable classification of disease severity along a continuum of IBD subgroups rather than merely as CD or UC. In certain instances, the methods categorize the sample as being inconclusive. By identifying patients with complicated disease and assisting in assessing the specific disease type, the methods and systems described herein provide invaluable information to assess the severity of the disease and treatment options. In some embodiments, applying a statistical analysis to a profile of serological, protein, and/or genetic markers improves the accuracy of predicting IBD, UC and CD, and also enables the selection of appropriate treatment options, including therapy such as biological, conventional, surgery, or some combination thereof.

The present invention provides methods and systems improved for diagnosis of ulcerative colitis (UC) and to differentiate between UC and Crohn's disease (CD). In certain instances, the methods and systems enable classification of disease severity along a continuum of IBD subgroups rather than merely as CD or UC. By identifying patients with complicated disease and assisting in assessing the specific disease type, the methods and systems described herein provide invaluable information to assess the severity of the disease and treatment options. In some embodiments, applying a statistical analysis to a profile of serological, protein, and/or genetic markers improves the accuracy of predicting UC, and also enables the selection of appropriate treatment options, including therapy such as biological, conventional, surgery, or some combination thereof.

The present invention provides methods and systems for improved diagnosis of Crohn's disease (CD) and to differentiate between UC and CD. In certain instances, the methods and systems enable classification of disease severity along a continuum of IBD subgroups rather than merely as CD or UC. By identifying patients with complicated disease and assisting in assessing the specific disease type, the methods and systems described herein provide invaluable information to assess the severity of the disease and treatment options. In some embodiments, applying a statistical analysis to a profile of serological, protein, and/or genetic markers improves the accuracy of predicting CD, and also enables the selection of appropriate treatment options, including therapy such as biological, conventional, surgery, or some combination thereof.

The present invention provides methods and systems for improved diagnosis of inflammatory bowel disease (IBD) and to differentiate it from non-IBD. The present invention also provides methods and systems to diagnose non-inflammatory bowel disease (non-IBD) and to differentiate it from IBD. In certain instances, the methods and systems enable classification of disease severity along a continuum of IBD subgroups rather than merely as CD or UC. By identifying patients with complicated disease and assisting in assessing the specific disease type, the methods and systems described herein provide invaluable information to assess the severity of the disease and treatment options. In some embodiments, applying a statistical analysis to a profile of serological, protein, and/or genetic markers improves the accuracy of predicting IBD and non-IBD, and also enables the selection of appropriate treatment options, including therapy such as biological, conventional, surgery, or some combination thereof.

The present invention provides methods and systems for improved diagnosis of inconclusive as well as differentiate it from UC and CD. In certain instances, the methods and systems enable classification of disease severity along a continuum of IBD subgroups rather than merely as CD or UC. By identifying patients with complicated disease and assisting in assessing the specific disease type, the methods and systems described herein provide invaluable information to assess the severity of the disease and treatment options. In some embodiments, applying a statistical analysis to a profile of serological, protein, and/or genetic markers improves the accuracy of predicting subtypes, and also enables the selection of appropriate treatment options, including therapy such as biological, conventional, surgery, or some combination thereof.

In some embodiments, the method of the present invention is performed in an individual with symptoms of UC. In additional embodiments, the symptoms of UC include, but are not limited to, rectal inflammation, rectal bleeding, rectal pain, diarrhea, abdominal cramps, abdominal pain, fatigue, weight loss, fever, colon rupture, and combinations thereof.

In some embodiments, the method of the present invention entails analysis of a biological sample selected from the group consisting of whole blood, tissue, saliva, cheek cells, hair, fluid, plasma, serum, cerebrospinal fluid, buccal swabs, mucus, urine, stools, spermatozoids, vaginal secretions, lymph, amniotic fluid, pleural liquid, tears, and combinations thereof.

In some aspects, the present invention provides methods and systems to diagnose IBD and to differentiate between subtypes of IBD such as UC and CD. In particular embodiments, the methods and systems of the present invention utilize one or a plurality of (e.g., multiple) genetic markers, alone or in combination with one or a plurality of serological and/or protein markers, and alone or in combination with one or a plurality of algorithms (e.g., random forest model and decision tree or set of rules) or other types of statistical analysis (e.g., quartile analysis), to aid or assist in identifying patients with IBD, CD and/or UC and providing physicians with valuable diagnostic insight.

In some embodiments, the method of diagnosing IBD comprises detection of the NKX2-3 (rs1190140) variant allele. In other embodiments, the method of diagnosing IBD preferably employs detection of the NKX2-3 (rs10883365) variant allele. In yet other embodiments, the method of diagnosing IBD employs detection of the NKX2-3 (rs6584283) variant allele. In some preferred embodiments, the method of diagnosing IBD comprises detection of the ATG16L1 (rs2241880) variant allele. In further embodiments, the method of diagnosing IBD comprises detection of the ATG16L1 (rs3828309) variant allele. In some embodiments, the method of diagnosing IBD employs detection of the ECM1 (rs7511649) variant allele. In other preferred embodiments, the method of diagnosing IBD comprises detection of the ECM1 (rs373240) variant allele. In yet other embodiments, the method of diagnosing IBD comprises detection of the ECM1 (rs13294) variant allele. In some preferred embodiments, the method of diagnosing IBD comprises detection of the STAT3 (rs744166) variant allele.

In some embodiments, the method of diagnosing UC comprises detection of the NKX2-3 (rs1190140) variant allele. In other embodiments, the method of diagnosing UC comprises detection of the NKX2-3 (rs10883365) variant allele. In yet other embodiments, the method of diagnosing UC comprises detection of the NKX2-3 (rs6584283) variant allele. In some embodiments, the method of diagnosing UC comprises detection of the ATG16L1 (rs2241880) variant allele. In further embodiments, the method of diagnosing UC comprises detection of the ATG16L1 (rs3828309) variant allele. In some embodiments, the method of diagnosing UC comprises detection of the ECM1 (rs7511649) variant allele. In other embodiments, the method of diagnosing UC comprises detection of the ECM1 (rs373240) variant allele. In yet other embodiments, the method of diagnosing UC comprises detection of the ECM1 (rs13294) variant allele. In some embodiments, the method of diagnosing UC comprises detection of the STAT3 (rs744166) variant allele.

In some embodiments, the method of diagnosing CD comprises detection of the NKX2-3 (rs1190140) variant allele. In other embodiments, the method of diagnosing CD comprises detection of the NKX2-3 (rs10883365) variant allele. In yet other embodiments, the method of diagnosing CD comprises detection of the NKX2-3 (rs6584283) variant allele. In some embodiments, the method of diagnosing CD employs detection of the ATG16L1 (rs2241880) variant allele. In further embodiments, the method of diagnosing CD comprises detection of the ATG16L1 (rs3828309) variant allele. In some embodiments, the method of diagnosing CD comprises detection of the ECM1 (rs7511649) variant allele. In other embodiments, the method of diagnosing CD comprises detection of the ECM1 (rs373240) variant allele. In yet other embodiments, the method of diagnosing CD comprises detection of the ECM1 (rs13294) variant allele. In some embodiments, the method of diagnosing CD comprises detection of the STAT3 (rs744166) variant allele.

In other embodiments, the method of diagnosing IBD comprises detection of one or more variant alleles selected from the group consisting of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166).

In other embodiments, the method of diagnosing IC and/or categorizing a sample as being inconclusive comprises detection of one or more variant alleles selected from the group consisting of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166).

In other embodiments, the method of diagnosing UC comprises detection of one or more variant alleles selected from the group consisting of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166).

In other embodiments, the method of diagnosing CD comprises detection of one or more variant alleles selected from the group consisting of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166).

The presence or absence of a variant allele in a genetic marker can be determined using an assay described herein. Assays that can be used to determine variant allele status include, but are not limited to, electrophoretic analysis assays, restriction length polymorphism analysis assays, sequence analysis assays, hybridization analysis assays, PCR analysis assays, allele-specific hybridization, oligonucleotide ligation allele-specific elongation/ligation, allele-specific amplification, single-base extension, molecular inversion probe, invasive cleavage, selective termination, restriction length polymorphism, sequencing, single strand conformation polymorphism (SSCP), single strand chain polymorphism, mismatch-cleaving, denaturing gradient gel electrophoresis, and combinations thereof. These assays have been well-described and standard methods are known in the art. See, e.g., Ausubel et al., *Current Protocols in Molecular Biology*, John Wiley & Sons, Inc. New York (1984-2008), Chapter 7 and Supplement 47; Theophilus, et al., "PCR Mutation Detection Protocols," Humana Press, (2002); Innis et al., *PCR Protocols*, San Diego, Academic Press, Inc. (1990); Maniatis, et al., *Molecular Cloning: A Laboratory Manual*, Cold Spring Harbor Lab., New York, (1982); Ausubel et al., *Current Protocols in Genetics and Genomics*, John Wiley & Sons, Inc. New York (1984-2008); and Ausubel et al., *Current*

Protocols in Human Genetics, John Wiley & Sons, Inc. New York (1984-2008); all incorporated herein by reference in their entirety for all purposes.

In particular embodiments, the method described herein improves the diagnosis of UC compared to ANCA and/or pANCA-based methods of diagnosing UC.

In other embodiments, the method of diagnosing IBD and/or subgroups including UC and CD comprises an additional step of analyzing the biological sample for the presence or level of a serological marker, wherein detection of the presence or level of the serological marker in conjunction with the presence of one or more variant alleles further improves the diagnosis of IBD and/or subgroups including UC and CD.

In yet other embodiments, the method of diagnosing IBD and/or subgroups including UC and CD comprises detection of a serological marker selected from an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, or any combination of the markers described herein.

In further embodiments, the method of diagnosing IBD and/or subgroups including UC and CD utilizes an anti-neutrophil antibody that is selected from one of ANCA and pANCA, or a combination of ANCA and pANCA. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof.

In yet further additional embodiments, the method of diagnosing IBD and/or subgroups including UC and CD utilizes an anti-*Saccharomyces cerevisiae* antibody that is selected from the group consisting of anti-*Saccharomyces cerevisiae* immunoglobulin A (ASCA-IgA), anti-*Saccharomyces cerevisiae* immunoglobulin G (ASCA-IgG), and a combination thereof.

In yet other embodiments, the method of diagnosing IBD and/or subgroups including UC and CD utilizes an antimicrobial antibody that is selected from the group consisting of an anti-outer membrane protein C (anti-OmpC) antibody, an anti-I2 antibody, an anti-flagellin antibody (e.g., anti-CBir1 antibody, anti-Fla2 antibody (i.e., anti-A4-Fla2), and anti-FlaX antibody), and a combination thereof.

In yet other embodiments, the method of diagnosing IBD and/or subgroups including UC and CD utilizes an acute phase protein such as, but not limited to C-Reactive protein (CRP).

In yet other embodiments, the method of diagnosing IBD and/or subgroups including UC and CD utilizes an apolipoprotein such as, but not limited to serum amyloid A (SAA).

In yet other embodiments, the method of diagnosing IBD and/or subgroups including UC and CD utilizes a defensin that is selected from the group consisting of β defensin (BD1), β defensin-2 (BD2), or combination thereof.

In yet other embodiments, the method of diagnosing IBD and/or subgroups including UC and CD utilizes a growth factor that is selected from the group consisting of epidermal growth factor (EGF), vascular endothelial growth factor (VEGF), or combination thereof.

In yet other embodiments, the method of diagnosing IBD and/or subgroups including UC and CD utilizes a cytokine that is selected from the group consisting of TNF-related weak inducer of apoptosis (TWEAK), IL-1β, IL-6, or a combination thereof.

In yet other embodiments, the method of diagnosing IBD and/or subgroups including UC and CD utilizes a cadherin such as, but not limited to, E-cadherin.

In yet other embodiments, the method of diagnosing IBD and/or subgroups including UC and CD utilizes a cellular adhesion molecule selected from the group consisting of inter-cellular adhesion molecule 1 (ICAM-1 or ICAM), vascular cellular adhesion molecule 1 (VCAM-1 or VCAM), or combination thereof.

In other embodiments, the serological marker comprises or consists of ANCA, pANCA (e.g., pANCA IFA and/or DNAse-sensitive pANCA IFA), ASCA-IgA, ASCA-IgG, anti-OmpC antibody (OmpC), anti-CBir-1 antibody (CBir1), anti-Fla2 antibody (Fla2 or A4-Fla2), anti-FlaX antibody (FlaX), or a combination thereof.

In other embodiments, the inflammation marker comprises or consists of VEGF, CRP, SAA, ICAM, VCAM, or a combination thereof.

The presence or (concentration) level of the serological marker or the inflammation marker can be detected (e.g., determined, measured, analyzed, etc.) with a hybridization assay, amplification-based assay, immunoassay, immunohistochemical assay, or a combination thereof. Non-limiting examples of assays, techniques, and kits for detecting or determining the presence or level of one or more serological markers in a sample are described herein. Non-limiting examples of assays, techniques, and kits for detecting or determining the presence or level of one or more inflammation markers in a sample are described herein.

In particular embodiments, the methods and systems of the present invention utilize one or a plurality of (e.g., multiple) genetic markers, alone or in combination with one or a plurality of serological and/or inflammation markers.

In one aspect, the present invention provides a method for diagnosing ulcerative colitis (UC) in an individual diagnosed with inflammatory bowel disease (IBD) and/or suspected of having UC. In some embodiments, the method comprises: (i) analyzing a biological sample obtained from the individual to determine the presence, absence or level of a plurality of sero-genetic-inflammation markers in a biological sample, wherein the gene is one or more of ATG16L1, ECM1, STAT3, or NKX2-3, the serological marker is one or more of ANCA, pANCA (e.g., pANCA IFA and/or DNAse-sensitive pANCA IFA), ASCA-IgA, ASCA-IgG, anti-OmpC antibody, anti-CBir-1 antibody, anti-Fla2 antibody, anti-FlaX antibody, and the inflammation marker is one or more of VEGF, CRP, SAA, ICAM-1, or VCAM-1, in the sample to obtain a marker profile; and (ii) applying a statistical analysis to the marker profile to obtain a diagnostic profile for the individual to aid in the diagnosis of UC.

In another aspect, the present invention provides a method for diagnosing Crohn's disease (CD) in an individual diagnosed with inflammatory bowel disease (IBD) and/or suspected of having CD. In some embodiments, the method comprises: (i) analyzing a biological sample obtained from the individual to determine the presence, absence or level of a plurality of sero-genetic-inflammation markers in a biological sample, wherein the gene is one or more of ATG16L1, ECM1, STAT3, or NKX2-3, the serological marker is one or more of ANCA, pANCA (e.g., pANCA IFA and/or DNAse-sensitive pANCA IFA), ASCA-IgA, ASCA-IgG, anti-OmpC antibody, anti-CBir-1 antibody, anti-Fla2 antibody, anti-FlaX antibody, and the inflammation marker is one or more of VEGF, CRP, SAA, ICAM-1, or VCAM-1, in the sample to obtain a marker profile; and (ii) applying a statistical analysis to the marker profile to obtain a diagnostic profile for the individual to aid in the diagnosis of CD.

In another aspect, the present invention provides a method for diagnosing indeterminate colitis (IC) in an individual diagnosed with inflammatory bowel disease (IBD) and/or suspected of having IC. In some embodiments, the method comprises: (i) analyzing a biological sample obtained from the individual to determine the presence, absence or level of a plurality of sero-genetic-inflammation markers in a biological sample, wherein the gene is one or more of ATG16L1, ECM1, STAT3, or NKX2-3, the serological marker is one or more of ANCA, pANCA (e.g., pANCA IFA and/or DNAse-sensitive pANCA IFA), ASCA-IgA, ASCA-IgG, anti-OmpC antibody, anti-CBir-1 antibody, anti-Fla2 antibody, anti-FlaX antibody, and the inflammation marker is one or more of VEGF, CRP, SAA, ICAM-1, or VCAM-1, in the sample to obtain a marker profile; and (ii) applying a statistical analysis to the marker profile to obtain a diagnostic profile for the individual to aid in the diagnosis of IC.

In some embodiments, the method of the present invention includes an additional step comprising associated the diagnostic profile for the individual to a diagnostic model to aid in the diagnosis of UC, CD or IC.

In some embodiments, the method of differentiating between IBD and non-IBD involves detection of the presence, absence, or level of a plurality of sero-genetic-inflammation markers in a biological sample. In particular embodiments, the detection of the presence, absence or level of a plurality of sero-genetic-inflammation markers is indicative of IBD and not indicative of non-IBD.

In particular embodiments, the method of differentiating between UC and CD involves detection of the presence, absence, or level of a plurality of sero-genetic-inflammation markers in a biological sample from a patient determined to have IBD. In some embodiments, the detection of the presence, absence or level of a plurality of sero-genetic-inflammation markers is indicative of UC and not indicative of CD. In other embodiments, the detection of the presence, absence or level of a plurality of sero-genetic-inflammation markers is indicative of CD and not indicative of UC.

In other embodiments, the present invention provides methods for detecting the association of at least one sero-genetic-inflammation marker selected from the group consisting of a serological marker such as an anti-neutrophil antibody, an anti-*Saccharomyces cerevisiae* antibody, an antimicrobial antibody, an acute phase protein, an apolipoprotein, a defensin, a growth factor, a cytokine, a cadherin; a genetic marker such as gene variants of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166); and any combination of the markers with the presence of ulcerative colitis (UC) in a group of individuals. In some specific embodiments, the method comprises: (i) obtaining biological samples from a group of individuals diagnosed with IBD and/or suspected of having UC; (ii) screening the biological samples to determine the presence, absence or level of at least one sero-genetic-inflammation marker selected from the group consisting of a serological marker such as an anti-neutrophil antibody, an anti-*Saccharomyces cerevisiae* antibody, an antimicrobial antibody, an acute phase protein, an apolipoprotein, a defensin, a growth factor, a cytokine, a cadherin; a genetic marker such as gene variants of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166); and any combination thereof; and (iii) evaluating whether one or more of the serological markers show a statistically significant distribution that is skewed towards a group of individuals diagnosed with IBD and/or suspected of having UC, wherein the comparison is between a group of individuals diagnosed with IBD and/or suspected of having UC and a group of control individuals.

In yet another embodiments, the present invention provides methods for detecting the association of at least one sero-genetic-inflammation marker selected from the group consisting of a serological marker such as an anti-neutrophil antibody, an anti-*Saccharomyces cerevisiae* antibody, an antimicrobial antibody, an acute phase protein, an apolipoprotein, a defensin, a growth factor, a cytokine, a cadherin; a genetic marker such as gene variants of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166); and any combination of the markers with the presence of Crohn's disease (CD) in a group of individuals. In some specific embodiments, the method comprises: (i) obtaining biological samples from a group of individuals diagnosed with IBD and/or suspected of having CD; (ii) screening the biological samples to determine the presence, absence or level of at least one sero-genetic-inflammation marker selected from the group consisting of a serological marker such as an anti-neutrophil antibody, an anti-*Saccharomyces cerevisiae* antibody, an antimicrobial antibody, an acute phase protein, an apolipoprotein, a defensin, a growth factor, a cytokine, a cadherin; a genetic marker such as gene variants of ATG16L1 (e.g., rs2241880, rs3828309), ECM1 (e.g., rs7511649, rs373240, rs13294), NKX2-3 (e.g., rs1190140, rs10883365, rs6584283), and STAT3 (e.g., rs744166); and any combination thereof; and (iii) evaluating whether one or more of the serological markers show a statistically significant distribution that is skewed towards a group of individuals diagnosed with IBD and/or suspected of having CD, wherein the comparison is between a group of individuals diagnosed with IBD and/or suspected of having CD and a group of control individuals.

In other embodiments, the genetic marker is at least one of the genes set forth in Tables A-E (e.g., Table A, B, C, D, and/or E). In some embodiments, the genetic marker is NKX2-3. In other embodiments, the genetic marker is ATG16L1. In yet other embodiments, the genetic marker is ECM1. In certain embodiments, the genetic marker is STAT3. The genotype of the genetic marker can be detected (e.g., determined, analyzed, etc.) by genotyping an individual for the presence or absence of one or more variant alleles such as, for example, one or more single nucleotide polymorphisms (SNPs) in one or more genetic markers. In some embodiments, the SNP is at least one of the SNPs set forth in Tables B-E (e.g., Table B, C, D, and/or E). Non-limiting examples of techniques for detecting or determining the genotype of one or more genetic markers in a sample are described herein. In certain embodiments, the genetic marker is ATG16L1, ECM1, NKX2-3 and/or STAT3. In certain instances, the presence or absence of one or more ATG16L1, ECM1, NKX2-3 and/or STAT3 SNPs is determined in combination with the presence or level of one or more markers selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. Non-limiting examples include ASCA-IgA, ASCA-IgG, anti-OmpC antibody, anti-CBir-1 antibody, anti-flagellin antibody, pANCA (e.g., pANCA IFA and/or DNAse-sensitive pANCA IFA), CRP, SAA, ANCA, VEGF, ICAM, VCAM, or a combination thereof.

In further aspects, a panel for measuring one or more of the markers described herein may be constructed to provide relevant information related to the approach of the invention for diagnosing IBD and/or differentiating UC and CD. Such a panel may be constructed to detect or determine the presence (or absence) or level of at least 1, 2, 3, 4, 5, 6, 7, 8, 9, 10, 11, 12, 13, 14, 15, 16, 17, 18, 19, 20, 25, 30, 35, 40, or more individual markers such as the genetic, biochemical, serological, protein, inflammatory, or other markers described herein. A marker profile of the present invention comprises the measurement of one or more of the markers described herein. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

In some embodiments, the analysis of markers could be carried out in a variety of physical formats. For example, microtiter plates or automation could be used to facilitate the processing of large numbers of test samples. Alternatively, single sample formats could be developed to facilitate treatment, diagnosis, and prognosis in a timely fashion.

In certain embodiments, the methods further comprise comparing the results from the statistical analysis (i.e., diagnostic profile) to a reference (i.e., diagnostic model) to aid in the diagnosis of IBD. In particular embodiments, the methods utilize multiple serological, protein, and/or genetic markers to provide physicians with valuable diagnostic insight.

In the methods of the present invention, the marker profile can be determined by detecting the presence, level, or genotype of at least 2, 3, 4, 5, 6, 7, 8, 9, 10, 11, 12, 13, 14, 15, 16, 17, 18, 19, or 20 markers. In particular embodiments, the sample is serum, plasma, whole blood, and/or stool. In other embodiments, the individual is diagnosed with Crohn's disease (CD), ulcerative colitis (UC), or inconclusive.

The statistical analysis applied to the marker profile can comprise any of a variety of statistical methods, models, and algorithms described herein. In particular embodiments, the statistical analysis is a quartile analysis. In some instances, the quartile analysis converts the presence, level or genotype of each marker into a quartile score. As a non-limiting example, the diagnosis of IBD can be made based upon a quartile sum score (QSS) for the individual that is obtained by summing the quartile score for each of the markers. In other embodiments, the statistical analysis comprises one or more learning statistical classifier systems as described herein. In particular embodiments, the statistical analysis comprises a combination of at least two learning statistical classifier systems. A non-limiting example of such a combination includes a decision/classification tree (e.g., a classification and regression tree (C&RT), a random forest, etc.) and a neural network, e.g., applied in tandem. In certain instances, the methods comprise applying a first statistical analysis (e.g., a decision/classification tree or a random forest) to the presence, level, or genotype determined for each of the markers to generate a prediction or probability value, and then applying a second statistical analysis (e.g., e.g., a decision/classification tree or a random forest) to the prediction or probability value and the presence, level, or genotype determined for each of the markers to aid in the diagnosis of IBD (e.g., by classifying the sample as an IBD sample or non-IBD sample) and/or differentiating UC and CD. In certain embodiments, a first random forest is applied to a marker profile, followed by a decision tree or set of rules, followed by yet anther random forest.

In other embodiments, the diagnostic profile is a quartile sum score (QSS) for the individual and the QSS is compared to a diagnostic model (e.g., a serological model, a sero-genetic-inflammatory model, standardized risk scale, etc.). In certain embodiments, the individual is predicted to have a higher probability of disease when the QSS is greater than 5, 6, 7, 8, 9, 10, 11, 12, 13, 14, 15, 16, 17, 18, 19, 20, 21, 22, 23, 24, etc. (e.g., preferably greater than 10).

In certain embodiments, the diagnostic model is established using a retrospective cohort with known outcomes of a clinical subtype of IBD (e.g., CD, or UC). In preferred embodiments, the diagnostic model is selected from the group consisting of a serological model, a sero-genetic-inflammatory model, a genetic model, and a combination thereof. In one particular embodiment, the serological model is derived by applying logistic regression analysis to the presence or level of one or more serological markers determined in the retrospective cohort. In another particular embodiment, the sero-genetic-inflammatory model is derived by applying logistic regression analysis to the presence or level of one or more serological markers and the genotype of one or more genetic markers determined in the retrospective cohort. In other embodiments, the sero-genetic-inflammatory model is derived by applying a random forest model to the presence or level of one or more serological markers and the genotype of one or more genetic markers determined in the retrospective cohort.

In particular embodiments, the methods described herein provide a prediction of UC or CD diagnosis at a rate of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) based on an individual's diagnostic profile, e.g., the individual's QSS, optionally in combination with the presence or absence of one or more variant alleles in one or more genetic markers, e.g., ATG16L1, STAT3, ECM1, and/or NKX2-3, and the level of one or more serological markers, e.g., ASCA-IgA, ASCA-IgG, anti-OmpC antibody, anti-CBir-1 antibody, anti-flagellin antibody, pANCA (e.g., pANCA IFA and/or DNAse-sensitive pANCA IFA), CRP, SAA, ANCA, VEGF, ICAM, VCAM, or a combination thereof.

In certain embodiments, the reference (concentration) level corresponds to a (concentration) level of one of the markers in a sample from an individual not having CD (e.g., healthy individual, non-CD individual, non-IBD individual, UC individual, etc.). In certain other embodiments, the reference genotype corresponds to a wild-type genotype (e.g., non-variant allele or SNP) of one of the genetic markers.

In particular embodiments, the methods described herein provide a prediction of disease at a rate of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) based on an individual's diagnostic profile, such as, e.g., the individual's QSS, optionally in combination with the presence or absence of one or more variant alleles in one or more genetic markers, e.g., ATG16L1, ECM1, NKX2-3 and/or STAT3, and the level of one or more serological markers, e.g., ASCA-IgA, ASCA-IgG, anti-OmpC antibody, anti-CBir-1 antibody, anti-flagellin antibody, pANCA (e.g., pANCA IFA and/or DNAse-sensitive pANCA IFA), CRP, SAA, ANCA, VEGF, ICAM, VCAM, or a combination thereof.

In certain embodiments, the reference (concentration) level corresponds to a (concentration) level of one of the markers in a sample from an individual not having IBD (e.g., healthy individual, non-IBD individual, non-CD individual, non-UC individual, etc.). In certain other embodiments, the reference genotype corresponds to a wild-type genotype (e.g., non-variant allele or SNP) of one of the genetic markers.

In particular embodiments, the methods described herein provide a probability of IBD (or a clinical subtype thereof) of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) based on an individual's marker levels and/or genotypes.

In certain embodiments, the methods further comprise comparing the results from the statistical analysis (i.e., diagnostic profile) to a reference (i.e., diagnostic model) to aid in the diagnosis of IBD. In some instances, the diagnostic model comprises a display, print-out, and/or report such as a look-up table or graph. In other instances, the diagnostic profile is a quartile sum score (QSS) for the individual and the QSS is compared to a diagnostic model. In some embodiments, the individual is predicted to have a higher probability of having IBD when the QSS is greater than 5, 6, 7, 8, 9, 10, 11, 12, 13, 14, 15, 16, 17, 18, 19, 20, 21, 22, 23, 24, etc.

In certain preferred embodiments, the IBD diagnostic algorithm of the present invention uses measurements from 17 sero-genetic-inflammatory biological markers (e.g., ANCA, ASCA-A, ASCA-G, pANCA, FlaX, SAA, Fla2, ICAM, OmpC, CBir1, VCAM, CRP, NKX2-3, ATG16L1, STAT3, ECM1, and VEGF) to compute a model score based on the first random forest model for predicting IBD vs. non-IBD (110). The first random model determines if a patient's sample is an IBD or a nonIBD sample. If the score is less than the IBD vs. non-IBD cut-off (e.g., <0.64), the sample is predicted to be from a patient having IBD i.e., an IBD sample (125). Otherwise, the sample is predicted to be from a patient having non-IBD (120). Samples predicted to have IBD, proceed to the next step of the algorithm, which is a decision tree or set of rules designed to rule out Indeterminate Colitis (IC) or rule out categorizing the sample as inconclusive (130). If a sample matches the pattern for either of the IC rules, the algorithm predicts that the IBD sample is IC or it categorizes the sample as inconclusive (135). Otherwise, the sample proceeds to the next step of the algorithm (140), which is a second random forest model for predicting UC or CD (150). The diagnostic algorithm of the present invention uses measurements from 11 sero-genetic-inflammatory biological markers (e.g., ANCA, ASCA-A, ASCA-G, FlaX, Fla2, pANCA, OmpC, CBir1, ECM1, STAT3, VEGF and combinations thereof) to compute a model score based on the second random forest model for predicting UC or CD. If the score is less than the UC vs. CD cut-off (e.g., 0.35), the algorithm predicts the sample as having CD (153). If the score is greater than the cut-off, the algorithm predicts the sample as having UC (155).

In certain embodiments, an IC rule or inconclusive rule can be ANCA≥Q3, pANCA2 positive, and either anti-Cbir1 antibody or anti-Fla2 antibody or anti-FlaX antibody≥Q3. In other embodiments, an IC rule can be pANCA2 positive, and any two of the serological anti-flagellin antibody (e.g., anti-Cbir1 antibody or anti-Fla2 antibody or anti-FlaX antibody) markers≥Q3. In certain aspects, an IC rule is also an inconclusive rule.

One skilled in the art would know that the methods of the present invention comprise using 2, 3, 4, 5, 6, 7, 8, 9, 10, 11, 12, 13, 14, 15, 16, or 17 sero-genetic-inflammation markers for an IBD diagnostic test, wherein the diagnostic test comprises a diagnostic algorithm, wherein the algorithm is developed from a sample set (e.g. training set) comprising 2, 3, 4, 5, 6, 7, 8, 9, 10, 11, 12, 13, 14, 15, 16, or 17 sero-genetic-inflammatory markers. Non-limiting examples of serogenetic markers include e.g., ANCA, ASCA-A, ASCA-G, pANCA, FlaX, SAA, Fla2, ICAM, OmpC, CBir1, VCAM, CRP, NKX2-3, ATG16L1, STAT3, ECM1, VEGF and combinations thereof.

In some embodiments, the diagnostic model comprises a display, print-out, and/or report such as a look-up table or graph. In particular embodiments, the look-up table or graph provides a cumulative probability of the individual having or not having IBD. In certain other embodiments, the look-up table or graph provides a cumulative probability of the individual having or not having IBD. In certain other embodiments, the look-up table or graph provides a cumulative probability of the individual having or not having IC. In other embodiments, the look-up table or graph provides a cumulative probability of the individual having or not having CD. The look-up table or graph can also provide a cumulative probability of the individual having or not having UC.

IV. Clinical Subtypes of IBD

Inflammatory bowel disease (IBD) is a group of inflammatory conditions of the large intestine and small intestine. The main forms of IBD are Crohn's disease (CD) and ulcerative colitis (UC). Other less common forms of IBD include, e.g., indeterminate colitis (IC), collagenous colitis, lymphocytic colitis, ischemic colitis, diversion colitis, Behçet's syndrome, infective colitis, and the like. IBD that is inconclusive for CD and UC is also included herein as a form of IBD.

A. Crohn's Disease

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

Crohn's disease may be categorized by the behavior of disease as it progresses. This was formalized in the Vienna classification of Crohn's disease. See, Gasche et al., *Inflamm. Bowel Dis.,* 6:8-15 (2000). There are three categories of disease presentation in Crohn's disease: (1) stricturing, (2) penetrating, and (3) inflammatory. Stricturing disease causes narrowing of the bowel which may lead to bowel obstruction or changes in the caliber of the feces. Penetrating disease creates abnormal passageways (fistulae) between the bowel and other structures such as the skin. Inflammatory disease (also known as non-stricturing, non-penetrating disease) causes inflammation without causing strictures or fistulae.

As such, Crohn's disease represents a number of heterogeneous disease subtypes that affect the gastrointestinal tract and may produce similar symptoms. As used herein in reference to CD, the term "clinical subtype" includes a classification of CD defined by a set of clinical criteria that distinguish one classification of CD from another. As non-limiting examples, subjects with CD can be classified as having stricturing (e.g., internal stricturing), penetrating (e.g., internal penetrating), or inflammatory disease as described herein, or these subjects can additionally or alternatively be classified as having fibrostenotic disease, small bowel disease, internal perforating disease, perianal fistulizing disease, UC-like disease, the need for small bowel surgery, the absence of features of UC, or combinations thereof.

In certain instances, subjects with CD can be classified as having complicated CD, which is a clinical subtype characterized by stricturing or penetrating phenotypes. In certain other instances, subjects with CD can be classified as having a form of CD characterized by one or more of the following complications: fibrostenosis, internal perforating disease, and the need for small bowel surgery. In further instances, subjects with CD can be classified as having an aggressive form of fibrostenotic disease requiring small bowel surgery. Criteria relating to these subtypes have been described, for example, in Gasche et al., *Inflamm. Bowel Dis.,* 6:8-15 (2000); Abreu et al., *Gastroenterology,* 123:679-688 (2002); Vasiliauskas et al., *Gut,* 47:487-496 (2000); Vasiliauskas et al., *Gastroenterology,* 110:1810-1819 (1996); and Greenstein et al., *Gut,* 29:588-592 (1988).

The "fibrostenotic subtype" of CD is a classification of CD characterized by one or more accepted characteristics of fibrostenosing disease. Such characteristics of fibrostenosing disease include, but are not limited to, documented persistent intestinal obstruction or an intestinal resection for an intestinal obstruction. The fibrostenotic subtype of CD can be accompanied by other symptoms such as perforations, abscesses, or fistulae, and can further be characterized by persistent symptoms of intestinal blockage such as nausea, vomiting, abdominal distention, and inability to eat solid food. Intestinal X-rays of patients with the fibrostenotic subtype of CD can show, for example, distention of the bowel before the point of blockage.

The requirement for small bowel surgery in a subject with the fibrostenotic subtype of CD can indicate a more aggressive form of this subtype. Additional subtypes of CD are also known in the art and can be identified using defined clinical criteria. For example, internal perforating disease is a clinical subtype of CD defined by current or previous evidence of entero-enteric or entero-vesicular fistulae, intra-abdominal abscesses, or small bowel perforation. Perianal perforating disease is a clinical subtype of CD defined by current or previous evidence of either perianal fistulae or abscesses or rectovaginal fistula. The UC-like clinical subtype of CD can be defined by current or previous evidence of left-sided colonic involvement, symptoms of bleeding or urgency, and crypt abscesses on colonic biopsies. Disease location can be classified based on one or more endoscopic, radiologic, or pathologic studies.

One skilled in the art understands that overlap can exist between clinical subtypes of CD and that a subject having CD can have more than one clinical subtype of CD. For example, a subject having CD can have the fibrostenotic subtype of CD and can also meet clinical criteria for a clinical subtype characterized by the need for small bowel surgery or the internal perforating disease subtype. Similarly, the markers described herein can be associated with more than one clinical subtype of CD.

B. Ulcerative Colitis

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra).

In certain instances, with respect to UC, the variability of symptoms reflect differences in the extent of disease (i.e., the amount of the colon and rectum that are inflamed) and the intensity of inflammation. Disease starts at the rectum and moves "up" the colon to involve more of the organ. UC can be categorized by the amount of colon involved. Typically, patients with inflammation confined to the rectum and a short segment of the colon adjacent to the rectum have milder symptoms and a better prognosis than patients with more widespread inflammation of the colon.

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

The different types of ulcerative colitis are classified according to the location and the extent of inflammation. As used herein in reference to UC, the term "clinical subtype" includes a classification of UC defined by a set of clinical criteria that distinguish one classification of UC from another. As non-limiting examples, subjects with UC can be classified as having ulcerative proctitis, proctosigmoiditis, left-sided colitis, pancolitis, fulminant colitis, and combinations thereof. Criteria relating to these subtypes have been described, for example, in Kornbluth et al., *Am. J. Gastroenterol.*, 99: 1371-85 (2004).

Ulcerative proctitis is a clinical subtype of UC defined by inflammation that is limited to the rectum. Proctosigmoiditis is a clinical subtype of UC which affects the rectum and the sigmoid colon. Left-sided colitis is a clinical subtype of UC which affects the entire left side of the colon, from the rectum to the place where the colon bends near the spleen and begins to run across the upper abdomen (the splenic flexure). Pancolitis is a clinical subtype of UC which affects the entire colon. Fulminant colitis is a rare, but severe form of pancolitis. Patients with fulminant colitis are extremely ill with dehydration, severe abdominal pain, protracted diarrhea with bleeding, and even shock.

In some embodiments, classification of the clinical subtype of UC is important in planning an effective course of treatment. While ulcerative proctitis, proctosigmoiditis, and left-sided colitis can be treated with local agents introduced through the anus, including steroid-based or other enemas and foams, pancolitis must be treated with oral medication so that active ingredients can reach all of the affected portions of the colon.

One skilled in the art understands that overlap can exist between clinical subtypes of UC and that a subject having UC can have more than one clinical subtype of UC. Similarly, the prognostic markers described herein can be associated with more than one clinical subtype of UC.

C. Indeterminate Colitis

Indeterminate colitis (IC) is a clinical subtype of IBD that includes both features of CD and UC. Such an overlap in the symptoms of both diseases can occur temporarily (e.g., in the early stages of the disease) or persistently (e.g., throughout the progression of the disease) in patients with IC. Clinically, IC is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with IC. In certain aspects, the set of rules or decision tree or set of rules categorizes the sample as inconclusive or IC.

V. IBD Markers

A variety of IBD markers, including biochemical markers, serological markers, protein markers, genetic markers, and other clinical or echographic characteristics, are suitable for use in the methods of the present invention for diagnosing or predicting IBD, or for aiding or improving the diagnosis or prediction of IBD. See, e.g., U.S. Publication No. 20110045476 and PCT Application No. PCT/US2011/039174, the disclosures of which are hereby incorporated by reference in their entirety for all purposes. In certain aspects, the diagnostic methods described herein utilize the application of an algorithm (e.g., statistical analysis) to the presence, concentration level, or genotype determined for one or more of the IBD markers to aid or assist in diagnosis or prediction of IBD.

Non-limiting examples of IBD markers include: (i) biochemical, serological, and protein markers such as, e.g., cytokines, growth factors, anti-neutrophil antibodies, anti-*Saccharomyces cerevisiae* antibodies, antimicrobial antibodies, acute phase proteins, apolipoproteins, defensins, cadherins, cellular adhesion molecules, and combinations thereof; (ii) genetic markers such as, e.g., any one or a combination of the genes set forth in Tables A-E; and (iii) a combination of serological and genetic markers.

A. Cytokines

The determination of the presence or level of at least one cytokine in a sample can be useful in the present invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, for example, in the regulation of body weight, hematopoiesis, angiogenesis, wound healing, insulin resistance, the immune response, and the inflammatory response.

In certain aspects, the presence or level of at least one cytokine including, but not limited to, TNF-α, TNF-related weak inducer of apoptosis (TWEAK), osteoprotegerin (OPG), IFN-α, IFN-β, IFN-γ, IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27 is determined in a sample. In certain other aspects, the presence or level of at least one chemokine such as, for example, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and $CX_3CL1$ is determined in a sample. In certain further aspects, the presence or level of at least one adipocytokine including, but not limited to, leptin, adiponectin, resistin, active or total plasminogen activator inhibitor-1 (PAI-1), visfatin, and retinol binding protein 4 (RBP4) is determined in a sample.

In certain instances, the presence or level of a particular cytokine is detected at the level of mRNA expression with an assay such as, for example, a hybridization assay or an amplification-based assay. In certain other instances, the presence or level of a particular cytokine is detected at the level of protein expression using, for example, an immunoassay (e.g., ELISA) or an immunohistochemical assay. Suitable ELISA kits for determining the presence or level of a cytokine in a sample such as a serum, plasma, saliva, or urine sample are available from, e.g., R&D Systems, Inc. (Minneapolis, Minn.), Neogen Corp. (Lexington, Ky.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.).

B. Growth Factors

The determination of the presence or level of one or more growth factors in a sample can be useful in the present invention. As used herein, the term "growth factor" includes any of a variety of peptides, polypeptides, or proteins that are capable of stimulating cellular proliferation and/or cellular differentiation.

In certain aspects, the presence or level of at least one growth factor including, but not limited to, epidermal growth factor (EGF), heparin-binding epidermal growth factor (HB-EGF), vascular endothelial growth factor (VEGF), pigment epithelium-derived factor (PEDF; also known as SER-PINF1), amphiregulin (AREG; also known as schwannoma-derived growth factor (SDGF)), basic fibroblast growth factor (bFGF), hepatocyte growth factor (HGF), transforming growth factor-α (TGF-α), transforming growth factor-β (TGF-β), bone morphogenetic proteins (e.g., BMP1-BMP15), platelet-derived growth factor (PDGF), nerve growth factor (NGF), β-nerve growth factor (β-NGF), neurotrophic factors (e.g., brain-derived neurotrophic factor (BDNF), neurotrophin 3 (NT3), neurotrophin 4 (NT4), etc.), growth differentiation factor-9 (GDF-9), granulocyte-colony stimulating factor (G-CSF), granulocyte-macrophage colony stimulating factor (GM-CSF), myostatin (GDF-8), erythropoietin (EPO), and thrombopoietin (TPO) is determined in a sample. Preferably, the presence or level of VEGF is determined.

VEGF is encoded by the vascular endothelial growth factor gene (VEGF; Entrez GeneID:7422) and is produced after differential splicing of the transcript (see, e.g., Genbank Accession No. NM_001025366.2 (isoform a), NM_003376.5 (isoform b), NM_001025367.2 (isoform c), NM_001025368.2 (isoform d), NM_001025369.2 (isoform e), NM_001025370.2 (isoform f), NM_001033756.2 (isoform g), NM_001171622.1 (isoform h), NM_001171623.1 (isoform i), NM_001171624.1 (isoform j), NM_001171625.1 (isoform k), NM_001171626.1 (isoform l), NM_001171627.1 (isoform m), NM_001171628.1 (isoform n), NM_001171629.1 (isoform o), NM_001171630.1 (isoform p), NM_001204384.1 (isoform q), and NM_001204385.1 (isoform r)), and processing of the precursor polypeptide splice isoform (Genbank Accession No. NP_001020537.2 (isoform a), NP_003367.4 (isoform b), NP_001020538.2 (isoform c), NP_001020539.2 (isoform d), NP_001020540.2 (isoform e), NP_001020541.2 (isoform f), NP_001028928.1 (isoform g), 011165093.1 (isoform h), NP_001165094.1 (isoform i), NP_001165095.1 (isoform j), NP_001165096.1 (isoform k), NP_001165097.1 (isoform l), NP_001165098.1 (isoform m), NP_001165099.1 (isoform n), NP_001165100.1 (isoform o), NP_001165101.1 (isoform p), NP_001191313.1 (isoform q), and NP_00191314.1 (isoform r)).

In certain instances, the presence or level of a particular growth factor is detected at the level of mRNA expression with an assay such as, for example, a hybridization assay or an amplification-based assay. In certain other instances, the presence or level of a particular growth factor is detected at the level of protein expression using, for example, an immunoassay (e.g., ELISA) or an immunohistochemical assay. Suitable ELISA kits for determining the presence or level of a growth factor in a sample such as a serum, plasma, saliva, or urine sample are available from, e.g., Antigenix America Inc. (Huntington Station, N.Y.), Promega (Madison, Wis.), R&D Systems, Inc. (Minneapolis, Minn.), Invitrogen (Camarillo, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

C. Anti-Neutrophil Antibodies

The determination of ANCA levels and/or the presence or absence of pANCA in a sample can be useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G. Preferably, the presence or level of ANCA IgG is determined. In particular embodiments, both the presence or absence of a perinuclear pANCA staining pattern and the presence or absence of pANCA staining that is sensitive to DNase treatment are detected, e.g., using separate indirect fluorescent antibody (IFA) assays.

ANCA levels in a sample from an individual can be determined, for example, using an immunoassay such as an enzyme-linked immunosorbent assay (ELISA) with alcohol-fixed neutrophils. The presence or absence of a particular category of ANCA such as pANCA can be determined, for example, using an immunohistochemical assay such as an indirect fluorescent antibody (IFA) assay. In certain embodiments, the presence or absence of pANCA in a sample is determined using an immunofluorescence assay with DNase-treated, fixed neutrophils. In addition to fixed neutrophils, antibodies directed against human antibodies can be used for detection. Antigens specific for ANCA are also suitable for determining ANCA levels, including, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, Bacteroides antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

In certain embodiments, the pANCA biomarker is a binary rather than a numerical variable since its value is either positive or negative. In some embodiments, a pANCA-positive status is associated with a lower rate and/or risk of complications (e.g., internal stricturing disease, internal penetrating disease, and/or surgery). In some instances, the quartile scoring for pANCA is inverted, such that a positive status is scored as "1" and a negative status is scored as "4".

D. Anti-*Saccharomyces cerevisiae* Antibodies

The determination of the presence or level of ASCA (e.g., ASCA-IgA, ASCA-IgG, ASCA-IgM, etc.) in a sample can also be useful in the present invention. The term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA- IgG" includes antibodies of the immunoglobulin G isotype that react specifically with *S. cerevisiae*.

The determination of whether a sample is positive for ASCA-IgA or ASCA-IgG is made using an antibody specific for human antibody sequences or an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosaccharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man $\beta(1-2)$ D-Man $\beta(1-2)$ D-Man $\beta(1-2)$ D-Man-OR, D-Man $\alpha(1-2)$ D-Man $\alpha(1-2)$ D-Man $\alpha(1-2)$ D-Man-OR, and D-Man $\alpha(1-3)$ D-Man $\alpha(1-2)$ D-Man $\alpha(1-2)$ D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction technique known in the art, including, for example, by autoclaving, or can be obtained commercially (see, e.g., Lindberg et a, *Gut*, 33:909-913 (1992)). The acid-stable fraction of PPM is also useful in the statistical algorithms of the present invention (Sendid et al., *Clin. Diag. Lab. Immunol.*, 3:219-226 (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.*, 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. J. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man (1-3) Man (1-2) Man (1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

E. Anti-Microbial Antibodies

The determination of the presence or level of an anti-OmpC antibody in a sample can be useful in the present invention. As used herein, the term "anti-outer membrane protein C antibody" or "anti-OmpC antibody" includes antibodies directed to a bacterial outer membrane porin as described in, e.g., U.S. Pat. No. 7,138,237 and PCT Patent Publication No. WO 01/89361. The term "outer membrane protein C" or "OmpC" refers to a bacterial porin that is immunoreactive with an anti-OmpC antibody. The term anti-OmpC antibody encompasses all immunoglobulin isotypes including, without limitation, immunoglobulin A and G. Preferably, the presence or level of anti-OmpC IgA is determined.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display. Determination of anti-OmpC antibody levels in a sample can be done by using an ELISA assay or a histological assay.

The determination of the presence or level of anti-I2 antibody in a sample can also be useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The microbial I2 protein is a polypeptide of 100 amino acids sharing some similarity weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display. Determination of anti-I2 antibody levels in a sample can be done by a histological assay or an ELISA assay as described in in, e.g., U.S. Pat. No. 7,873,479.

The determination of the presence or level of anti-flagellin antibody in a sample can also be useful in the present invention. As used herein, the term "anti-flagellin antibody" includes antibodies directed to a protein component of bacterial flagella as described in, e.g., U.S. Pat. No. 7,361,733 and PCT Patent Publication No. WO 03/053220. The term "flagellin" refers to a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as CBir1 flagellin, A4-Fla2 flagellin (Fla2), flagellin X (FlaX), flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Butyrivibrio fibrisolvens*, and bacterium found in the cecum, by recombinant expression of a nucleic acid encoding a flagellin antigen, by synthetic means such as solution or solid phase peptide synthesis, or by using phage display. Determination of anti-flagellin (e.g., anti-CBir1, anti-Fla2, and/or anti-FlaX) antibody levels in a sample can be done by using an ELISA assay or a histological assay. Preferably, the presence or level of anti-CBir1 IgG, anti-Fla2 IgG, and/or anti-FlaX IgG is determined.

F. Acute Phase Proteins

The determination of the presence or level of one or more acute-phase proteins in a sample can be useful in the present invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein, AGP), ceruloplasmin, haptoglobin, and combinations thereof. Non-limiting examples of negative acute-phase proteins include albumin, transferrin, transthyretin, transcortin, retinol-binding protein, and combinations thereof. Preferably, the presence or level of CRP and/or SAA is determined.

In certain instances, the presence or level of a particular acute-phase protein is detected at the level of mRNA expression with an assay such as, for example, a hybridization assay or an amplification-based assay. In certain other instances, the presence or level of an acute-phase protein such as CRP or SAA is detected at the level of protein expression using, for example, an immunoassay (e.g., ELISA or an immuno electrochemiluminescence assay) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410. Additional methods for determining CRP levels include, e.g., immunoturbidimetry assays, rapid immunodiffusion assays, and visual agglutination assays.

C-reactive protein (CRP) is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558. The human CRP mRNA (coding) sequence is set forth in, e.g., Genbank Accession No. NM_000567. One skilled in the art will appreciate that CRP is also known as PTX1, MGC88244, and MGC149895.

G. Apolipoproteins

The determination of the presence or level of one or more apolipoproteins in a sample can be useful in the present invention. Apolipoproteins are proteins that bind to fats (lipids). They form lipoproteins, which transport dietary fats through the bloodstream. Dietary fats are digested in the intestine and carried to the liver. Fats are also synthesized in the liver itself. Fats are stored in fat cells (adipocytes). Fats are metabolized as needed for energy in the skeletal muscle, heart, and other organs and are secreted in breast milk. Apolipoproteins also serve as enzyme co-factors, receptor ligands, and lipid transfer carriers that regulate the metabolism of lipoproteins and their uptake in tissues. Examples of apolipoproteins include, but are not limited to, ApoA (e.g., ApoA-I, ApoA-II, ApoA-IV, ApoA-V), ApoB (e.g., ApoB48, ApoB100), ApoC (e.g., ApoC-I, ApoC-II, ApoC-III, ApoC-IV), ApoD, ApoE, ApoH, serum amyloid A (SAA), and combinations thereof. Preferably, the presence or level of SAA is determined.

In certain instances, the presence or level of a particular apolipoprotein is detected at the level of mRNA expression with an assay such as, for example, a hybridization assay or an amplification-based assay. In certain other instances, the presence or level of a particular apolipoprotein such as SAA is detected at the level of protein expression using, for example, an immunoassay (e.g., ELISA or an immuno electrochemiluminescence assay) or an immunohistochemical assay. Suitable ELISA kits for determining the presence or level of SAA in a sample such as serum, plasma, saliva, urine, or stool are available from, e.g., Antigenix America Inc. (Huntington Station, N.Y.), Abazyme (Needham, Mass.), USCN Life (Missouri City, Tex.), and/or U.S. Biological (Swampscott, Mass.).

Serum amyloid A (SAA) proteins are a family of apolipoproteins associated with high-density lipoprotein (HDL) in plasma. Different isoforms of SAA are expressed constitutively (constitutive SAAs) at different levels or in response to inflammatory stimuli (acute phase SAAs). These proteins are predominantly produced by the liver. The conservation of these proteins throughout invertebrates and vertebrates suggests SAAs play a highly essential role in all animals. Acute phase serum amyloid A proteins (A-SAAs) are secreted during the acute phase of inflammation. The human SAA polypeptide sequence is set forth in, e.g., Genbank Accession No. NP_000322. The human SAA mRNA (coding) sequence is set forth in, e.g., Genbank Accession No. NM_000331. One skilled in the art will appreciate that SAA is also known as PIG4, TP53I4, MGC 111216, and SAA1.

H. Defensins

The determination of the presence or level of one or more defensins in a sample can be useful in the present invention. Defensins are small cysteine-rich cationic proteins found in both vertebrates and invertebrates. They are active against bacteria, fungi, and many enveloped and nonenveloped viruses. They typically consist of 18-45 amino acids, including 6 (in vertebrates) to 8 conserved cysteine residues. Cells of the immune system contain these peptides to assist in killing phagocytized bacteria, for example, in neutrophil granulocytes and almost all epithelial cells. Most defensins function by binding to microbial cell membranes, and once embedded, forming pore-like membrane defects that allow efflux of essential ions and nutrients. Non-limiting examples of defensins include α-defensins (e.g., DEFA1, DEFA1A3, DEFA3, DEFA4), β-defensins (e.g., β defensin-1 (DEFB1), β defensin-2 (DEFB2), DEFB103A/DEFB103B to DEFB107A/DEFB107B, DEFB 110 to DEFB133), and combinations thereof.

In certain instances, the presence or level of a particular defensin is detected at the level of mRNA expression with an assay such as, for example, a hybridization assay or an amplification-based assay. In certain other instances, the presence or level of a particular defensin is detected at the level of protein expression using, for example, an immunoassay (e.g., ELISA or an immuno electrochemiluminescence assay) or an immunohistochemical assay. Suitable ELISA kits for determining the presence or level of defensins in a sample such as serum, plasma, saliva, urine, or stool are available from, e.g., Alpco Diagnostics (Salem, N.H.), Antigenix America Inc. (Huntington Station, N.Y.), PeproTech (Rocky Hill, N.J.), and/or Alpha Diagnostic Intl. Inc. (San Antonio, Tex.).

β-defensins are antimicrobial peptides implicated in the resistance of epithelial surfaces to microbial colonization. They are the most widely distributed of all defensins, being secreted by leukocytes and epithelial cells of many kinds. For example, they can be found on the tongue, skin, cornea, salivary glands, kidneys, esophagus, and respiratory tract. The human DEFB1 polypeptide sequence is set forth in, e.g., Genbank Accession No. NP_005209. The human DEFB1 mRNA (coding) sequence is set forth in, e.g., Genbank Accession No. NM_005218. One skilled in the art will appreciate that DEFB1 is also known as BD1, HBD1, DEFB-1, DEFB101, and MGC51822. The human DEFB2 polypeptide sequence is set forth in, e.g., Genbank Accession No. NP_004933. The human DEFB2 mRNA (coding) sequence is set forth in, e.g., Genbank Accession No. NM_004942. One skilled in the art will appreciate that DEFB2 is also known as SAP1, HBD-2, DEFB-2, DEFB102, and DEFB4.

I. Cadherins

The determination of the presence or level of one or more cadherins in a sample can be useful in the present invention. Cadherins are a class of type-1 transmembrane proteins which play important roles in cell adhesion, ensuring that cells within tissues are bound together. They are dependent on calcium ($Ca^{2+}$) ions to function. The cadherin superfamily includes cadherins, protocadherins, desmogleins, and desmocollins, and more. In structure, they share cadherin repeats, which are the extracellular $Ca^{2+}$-binding domains. Cadherins suitable for use in the present invention include, but are not limited to, CDH1—E-cadherin (epithelial), CDH2—N-cadherin (neural), CDH12—cadherin 12, type 2 (N-cadherin 2), CDH3—P-cadherin (placental), CDH4—R-cadherin (retinal), CDH5—VE-cadherin (vascular endothelial), CDH6—K-cadherin (kidney), CDH7—cadherin 7, type 2, CDH8—cadherin 8, type 2, CDH9—cadherin 9, type 2 (T1-cadherin), CDH10—cadherin 10, type 2 (T2-cadherin), CDH11—OB-cadherin (osteoblast), CDH13—T-cadherin—H-cadherin (heart), CDH15—M-cadherin (myotubule), CDH16—KSP-cadherin, CDH17—LI cadherin (liver-intestine), CDH18—cadherin 18, type 2, CDH19—cadherin 19, type 2, CDH20—cadherin 20, type 2, and CDH23—cadherin 23, (neurosensory epithelium).

In certain instances, the presence or level of a particular cadherin is detected at the level of mRNA expression with an assay such as, for example, a hybridization assay or an amplification-based assay. In certain other instances, the presence or level of a particular cadherin is detected at the level of protein expression using, for example, an immunoassay (e.g., ELISA or an immuno electrochemiluminescence assay) or an immunohistochemical assay. Suitable ELISA kits for determining the presence or level of cadherins in a sample such as serum, plasma, saliva, urine, or stool are available from, e.g., R&D Systems, Inc. (Minneapolis, Minn.) and/or GenWay Biotech, Inc. (San Diego, Calif.).

E-cadherin is a classical cadherin from the cadherin superfamily. It is a calcium dependent cell-cell adhesion glycoprotein comprised of five extracellular cadherin repeats, a transmembrane region, and a highly conserved cytoplasmic tail. The ectodomain of E-cadherin mediates bacterial adhesion to mammalian cells and the cytoplasmic domain is required for internalization. The human E-cadherin polypeptide sequence is set forth in, e.g., Genbank Accession No. NP_004351. The human E-cadherin mRNA (coding) sequence is set forth in, e.g., Genbank Accession No. NM_004360. One skilled in the art will appreciate that E-cadherin is also known as UVO, CDHE, ECAD, LCAM, Arc-1, CD324, and CDH1.

J. Cellular Adhesion Molecules (IgSF CAMs)

The determination of the presence or level of one or more immunoglobulin superfamily cellular adhesion molecules in a sample can be useful in the present invention. As used herein, the term "immunoglobulin superfamily cellular adhesion molecule" (IgSF CAM) includes any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include Neural Cell Adhesion Molecules (NCAMs; e.g., NCAM-120, NCAM-125, NCAM-140, NCAM-145, NCAM-180, NCAM-185, etc.), Intercellular Adhesion Molecules (ICAMs, e.g., ICAM-1, ICAM-2, ICAM-3, ICAM-4, and ICAM-5), Vascular Cell Adhesion Molecule-1 (VCAM-1), Platelet-Endothelial Cell Adhesion Molecule-1 (PECAM-1), L1 Cell Adhesion Molecule (L1CAM), cell adhesion molecule with homology to L1CAM (close homolog of L1) (CHL1), sialic acid binding Ig-like lectins (SIGLECs; e.g., SIGLEC-1, SIGLEC-2, SIGLEC-3, SIGLEC-4, etc.), Nectins (e.g., Nectin-1, Nectin-2, Nectin-3, etc.), and Nectin-like molecules (e.g., Necl-1, Necl-2, Necl-3, Necl-4, and Necl-5). Preferably, the presence or level of ICAM-1 and/or VCAM-1 is determined.

1. Intercellular Adhesion Molecule-1 (ICAM-1)

ICAM-1 is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1 and VCAM-1. The increased expression of adhesion molecules recruit more lymphocytes to the infected tissue, resulting in tissue inflammation (see, Goke et al., *J., Gastroenterol.*, 32:480 (1997); and Rijcken et al., *Gut*, 51:529 (2002)). ICAM-1 is encoded by the intercellular adhesion molecule 1 gene (ICAM1; Entrez GeneID:3383; Genbank Accession No. NM_000201) and is produced after processing of the intercellular adhesion molecule 1 precursor polypeptide (Genbank Accession No. NP_000192).

2. Vascular Cell Adhesion Molecule-1 (VCAM-1)

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

In certain instances, the presence or level of an IgSF CAM is detected at the level of mRNA expression with an assay such as, e.g., a hybridization assay or an amplification-based assay. In certain other instances, the presence or level of an IgSF CAM such as ICAM-1 or VCAM-1 is detected at the level of protein expression using, for example, an immunoassay (e.g., ELISA or an immuno electrochemiluminescence assay) or an immunohistochemical assay. Suitable antibodies and/or ELISA kits for determining the presence or level of ICAM-1 and/or VCAM-1 in a sample such as a tissue sample, biopsy, serum, plasma, saliva, urine, or stool are available from, e.g., Invitrogen (Camarillo, Calif.), Santa Cruz Biotechnology, Inc. (Santa Cruz, Calif.), and/or Abcam Inc. (Cambridge, Mass.).

K. Genetic Markers

The determination of the presence or absence of allelic variants in one or more genetic markers in a sample is also useful in the present invention. Non-limiting examples of genetic markers include, but are not limited to, any of the genes set forth in Tables A-E or a combination thereof. Preferably, the presence or absence of at least one single nucleotide polymorphism (SNP) in one or more of the ATG16L1, STAT3, NKX2-3 and ECM1 genes is detected.

Table A provides an exemplary list of IBD, UC, and CD genes wherein genotyping for the presence or absence of one or more allelic variants (e.g., SNPs) therein is useful in the diagnostic methods of the invention. Table B provides additional exemplary genetic markers and corresponding SNPs that can be genotyped in accordance with the diagnostic methods of the invention. Tables C-E provide additional exemplary IBD, UC and CD genetic markers and corresponding SNPs that can be genotyped in accordance with the diagnostic methods described herein.

TABLE A

IBC, CD & UC Genes.

| IBD Genes (CD & UC) | Colonic IBD Genes | UC Genes | CD Genes |
|---|---|---|---|
| IL23R | HLA regions | ECM1 | NOD2 |
| IL12B/p40 | | IL10 | ATG16L1 |
| JAK2 | | IFNg | IRGM |
| STAT3 | | IL22 | NLRP3 |
| NKX2.3 | | IL26 | 5p13/PTGER4 |
| 3p21/MST1 | | OTUD3 | PTPN2 |
| CCNY | | PLA2G2E | TNFSF15 (TL1A) |
| IL18RAP | | ARPC2 | IBD5/5q31 |
| LYRM4 | | | ZNF365 |
| CDKAL4 | | | PTPN22 |
| TNFRSF6B | | | CCR6 |
| PSMG1 | | | LRRK2 |
| | | | ICOSLG |
| | | | ITLN1 |
| | | | ORMDL3 |

TABLE B

IBD, CD & UC Genes & SNPs.

| Gene | SNP |
|---|---|
| NOD2/CARD15 | rs2066847 |
| IL23R | rs11465804 |
| ATG16L1 | rs3828309 |
| MST1 | rs3197999 |
| PTGER4 | rs4613763 |
| IRGM | rs11747270 |
| TNFSF15 | rs4263839 |
| ZNF365 | rs10995271 |
| NKX2-3 | rs11190140 |
| PTPN2 | rs2542151 |
| PTPN22 | rs2476601 |
| ITLN1 | rs2274910 |
| IL12B | rs10045431 |
| CDKAL1 | rs6908425 |
| CCR6 | rs2301436 |
| JAK2 | rs10758669 |
| C11orf30 | rs7927894 |
| LRRK2, MUC19 | rs11175593 |
| ORMDL3 | rs2872507 |
| STAT3 | rs744166 |
| ICOSLG | rs762421 |
| GCKR | rs780094 |
| BTNL2, SLC26A3, HLA-DRB1, HLA-DQA1 | rs3763313 |
| PUS10 | rs13003464 |
| CCL2, CCL7 | rs991804 |
| LYRM4 | rs12529198 |
| SLC22A23 | rs17309827 |
| IL18RAP | rs917997 |
| IL12RB2 | rs7546245 |
| IL12RB1 | rs374326 |
| CD3D | rs3212262 |
| CD3G | rs3212262 |
| CD247 | rs704853 |
| JUN | rs6661505 |
| CD3E | rs7937334 |
| IL18R1 | rs1035127 |
| CCR5 | |
| MAPK14 | rs2237093 |
| IL18 | rs11214108 |
| IFNG | rs10878698 |
| MAP2K6 | rs2905443 |
| STAT4 | rs1584945 |
| IL12A | rs6800657 |
| TYK2 | rs12720356 |
| ETV5 | rs9867846 |
| MAPK8 | rs17697885 |

TABLE B-continued

IBD, CD & UC Genes & SNPs.

| Gene | SNP |
|---|---|

TABLE C

CD Genes & SNPs.

| Gene | SNP |
|---|---|
| NOD2 (R702W) | rs2066844 |
| NOD2 (G908R) | rs2066845 |
| NOD2 (3020insC) | rs5743293 |
| ATG16L1 (T300A) | rs2241880 |
| ATG16L1 | rs3828309 |
| IRGM | rs13361189 |
| IRGM | rs4958847 |
| IRGM | rs1000113 |
| IRGM | rs11747270 |
| TL1A/TNFSF15 | rs6478109 |
| TL1A/TNFSF15 | rs6478108 |
| TL1A/TNFSF15 | rs4263839 |
| PTN22 | rs2476601 |
| CCR6 | rs1456893 |
| CCR6 | rs2301436 |
| 5p13/PTGER4 | rs1373692 |
| 5p13/PTGER4 | rs4495224 |
| 5p13/PTGER4 | rs7720838 |
| 5p13/PTGER4 | rs4613763 |
| ITLN1 | rs2274910 |
| ITLN1 | rs9286879 |
| ITLN1 | rs11584383 |
| IBD5/5q31 | rs2188962 |
| IBD5/5q31 | rs252057 |
| IBD5/5q31 | rs10067603 |
| GCKR | rs780094 |
| TNFRSF6B | rs1736135 |
| ZNF365 | rs224136 |
| ZNF365 | rs10995271 |
| C11orf30 | rs7927894 |
| LRRK2; MUC19 | rs1175593 |
| DLG5 | rs2165047 |
| IL-27 | rs8049439 |
| TLR2 | rs4696480 |
| TLR2 | rs3804099 |
| TLR2 | rs3804100 |
| TLR2 | rs5743704 |
| TLR2 | rs2405432 |
| TLR4 (D299G) | rs4986790 |
| TLR4 (T399I) | rs4986791 |
| TLR4 (S360N) | rs4987233 |
| TLR9 | rs187084 |
| TLR9 | rs352140 |
| NFC4 | rs4821544 |
| KIF21B | rs11584383 |
| IKZF1 | rs1456893 |
| C11orf30 | rs7927894 |
| CCL2, CCL7 | rs991804 |
| ICOSLG | rs762421 |
| TNFAIP3 | rs7753394 |
| FLJ45139 | rs2836754 |
| PTGER4 | rs4613763 |

TABLE D

UC Genes & SNPs.

| Gene | SNP |
|---|---|
| ECM1 | rs7511649 |
| ECM1 (T130M) | rs3737240 |
| ECM1 (G290S) | rs13294 |
| GLI1 (G933D) | rs2228224 |
| GLI1 (Q1100E) | rs2228226 |

TABLE D-continued

UC Genes & SNPs.

| Gene | SNP |
|---|---|
| MDR1 (3435C > T) | rs1045642 |
| MDR1 (A893S/T) | rs2032582 |
| MAGI2 | rs6962966 |
| MAGI2 | rs2160322 |
| IL26 | rs12815372 |
| IFNG, IL26 | rs1558744 |
| IFNG, IL26 | rs971545 |
| IL26 | rs2870946 |
| ARPC2 | rs12612347 |
| IL10, IL19 | rs3024493 |
| IL10, IL19 | rs3024505 |
| IL23R | rs1004819 |
| IL23R | rs2201841 |
| IL23R | rs11209026 |
| IL23R | rs11465804 |
| IL23R | rs10889677 |
| BTLN2 | rs9268480 |
| HLA-DRB1 | rs660895 |
| MEP1 | rs6920863 |
| MEP1 | rs2274658 |
| MEP1 | rs4714952 |
| MEP1 | rs1059276 |
| PUS10 | rs13003464 |
| PUS10 | rs6706689 |
| RNF186 | rs3806308 |
| RNF186 | rs1317209 |
| RNF186 | rs6426833 |
| FCGR2A, C | rs10800309 |
| CEP72 | rs4957048 |
| DLD, LAMB1 | rs4598195 |
| CAPN10, KIF1A | rs4676410 |

TABLE E

IBP Genes & SNPs.

| Gene | SNP |
|---|---|
| IL23R (R381Q) | rs11209026 |
| IL23R | rs11805303 |
| IL23R | rs7517847 |
| IL12B/p40 | rs1368438 |
| IL12B/p40 | rs10045431 |
| IL12B/p40 | rs6556416 |
| IL12B/p40 | rs6887695 |
| IL12B/p40 | rs3212227 |
| STAT3 | rs744166 |
| JAK2 | rs10974914 |
| JAK2 | rs10758669 |
| NKX2-3 | rs6584283 |
| NKX2-3 | rs10883365 |
| NKX2-3 | rs11190140 |
| IL18RAP | rs917997 |
| LYRM4 | rs12529198 |
| CDKAL1 | rs6908425 |
| MAGI2 | rs2160322 |
| TNFRSF6B | rs2160322 |
| TNFRSF6B | rs2315008 |
| TNFRSF6B | rs4809330 |
| PSMG1 | rs2094871 |
| PSMG1 | rs2836878 |
| PTPN2 | rs2542151 |
| MST1/3p21 | rs9858542 |
| MST1/3p21 | rs3197999 |
| SLC22A23 | rs17309827 |
| MHC | rs660895 |
| XBP1 | rs35873774 |
| ICOSLG1 | rs762421 |
| BTLN2 | rs3763313 |
| BTLN2 | rs2395185 |
| BTLN2 | rs9268480 |
| ATG5 | rs7746082 |
| CUL2, CREM | rs17582416 |

TABLE E-continued

IBP Genes & SNPs.

| Gene | SNP |
| --- | --- |
| CARD9 | rs4077515 |
| ORMDL3 | rs2872507 |
| ORMDL3 | rs2305480 |

Additional SNPs useful in the present invention include, e.g., rs2188962, rs9286879, rs11584383, rs7746082, rs1456893, rs1551398, rs17582416, rs3764147, rs1736135, rs4807569, rs7758080, and rs8098673. See, e.g., Barrett et al., *Nat. Genet.*, 40:955-62 (2008).

1. ATG16L1

ATG16L1, also known as autophagy related 16-like 1, is a protein involved the intracellular process of delivering cytoplasmic components to lysosomes, a process called autophagy. Autophagy is a process used by cells to recycle cellular components. Autophagy processes are also involved in the inflammatory response and facilitates immune system destruction of bacteria. The ATG16L1 protein is a WD repeated containing component of a large protein complex and associates with the autophagic isolation membrane throughout autophagosome formation (Mizushima et al., *Journal of Cell Science* 116(9):1679-1688 (2003) and Hampe et al., Nature Genetics 39:207-211 (2006)). ATG16L1 has been implicated in Crohn's Disease (Rioux et al., *Nature Genetics* 39(5):596-604 (2007)). See also, e.g., Márquez et al., *Inflamm. Bowel Disease* 15(11):1697-1704 (2009); Mizushima et al., *J. Cell Science* 116:1679-1688 (2003); and Zheng et al., *DNA Sequence: The J of DNA Sequencing and Mapping* 15(4): 303-5 (2004)).

The determination of the presence of absence of allelic variants such as SNPs in the ATG16L1 gene is particularly useful in the present invention. As used herein, the term "ATG16L1 variant" or variants thereof includes a nucleotide sequence of an ATG16L1 gene containing one or more changes as compared to the wild-type ATG16L1 gene or an amino acid sequence of an ATG16L1 polypeptide containing one or more changes as compared to the wild-type ATG16L1 polypeptide sequence. ATG16L1, also known as autophagy related 16-like 1, has been localized to human chromosome 2.

Gene location information for ATG16L1 is set forth in, e.g., GeneID:55054. The mRNA (coding) and polypeptide sequences of human ATG16L1 are set forth in, e.g., NM_017974.3 or NM_030803.6 and NP_060444.3 or NP_110430.5 respectively. In addition, the complete sequence of human chromosome 2 (2q37.1), GRCh37 primary reference assembly, which includes ATG16L1, is set forth in, e.g., GenBank Accession No. NT_005120.16. Furthermore, the sequence of ATG16L1 from other species can be found in the GenBank database.

The rs2241880 SNP that finds use in the methods of the present invention is located at nucleotide position 1098 of NM_017974.3, as an A to G transition, corresponding to a change from threonine to alanine at position 281 of NP_060444.3 or at position 1155 of NM_030803.6, as an A to G transition, corresponding to a change from threonine to alanine at position 300 of NP_110430.5. The presence of the ATG16L1 rs2241880 SNP and other variants can be detected, for example, by allelic discrimination assays or sequence analysis.

2. ECM1

ECM1, also known as extracellular matrix protein, is a glycoprotein expressed in the small and large intestines. It interacts with the basement membrane and inhibits matrix metalloproteinase 9. ECM1 also strongly activates NF-κB signaling, which is a key regulator of immune response.

The determination of the presence or absence of allelic variants such as SNPs in the ECM1 gene is particularly useful in the present invention. As used herein, the term "ECM1 variant" or variants thereof includes a nucleotide sequence of an ECM1 gene containing one or more changes as compared to the wild-type ECM1 gene or an amino acid sequence of an ECM1 polypeptide containing one or more changes as compared to the wild-type ECM1 polypeptide sequence. The ECM1 gene has been localized to on human chromosome 1q21 (Fisher et al., *Nature Genetics.*, 40:710-712 (2008)).

Gene location information for ECM1 is set forth in, e.g., GeneID:1893. The mRNA (coding) sequences of human ECM1 are set forth in, e.g., NM_001202858.1, NM_022664.2, and NM_004425.3. The respective polypeptide sequences are set forth NP_001189787.1, NP_004416.2 and NP_073155.2. In addition, the complete sequence of human chromosome 1 (1q21) GRCh37.p5 primary reference assembly, which includes ECM1, is set forth in, e.g., GenBank Accession No. NC_000001.10. Furthermore, the sequence of ECM1 from other species can be found in the GenBank database.

Various SNPs near and within the ECM1 gene have been previously described. For instance, ECM1 SNPs, identified in a nonsynonymous SNP scan for ulcerative colitis, have been associated with UC (Fisher et al., *Nature Genetics.*, 40:710-712 (2008)). Non-limiting examples of ECM1 SNPs include rs3737240, rs7511649, rs13294, rs12724450, rs11205386, rs11205387, rs9661040, rs875514, and rs11810419. The presence of the ECM1 rs3737240 SNP and other variants can be detected, for example, by allelic discrimination assays or sequence analysis.

3. NKX2-3

NKX2-3, a member of the NKX family of homeodomain-containing transcription factors, has been implicated in the development of the gut, spleen and gut-associated lymphoid tissue.

The determination of the presence or absence of allelic variants such as SNPs in the NKX2-3 gene is particularly useful in the present invention. As used herein, the term "NKX2-3 variant" or variants thereof includes a nucleotide sequence of a NKX2-3 gene containing one or more changes as compared to the wild-type NKX2-3 gene or an amino acid sequence of a NKX2-3 polypeptide containing one or more changes as compared to the wild-type NKX2-3 polypeptide sequence. The NKX2-3 gene has been localized to on human chromosome 10q24.2.

Gene location information for NKX2-3 is set forth in, e.g., GeneID: 159296. The mRNA (coding) sequence and the corresponding polypeptide sequence of human NKX2-3 are set forth in, e.g., NM_145285.2 and NP_660328.2 respectively. In addition, the complete sequence of human 10 chromosome (10q24.2) GRCh37.p5 primary reference assembly, which includes NKX2-3, is set forth in, e.g., GenBank Accession No. NC_000010.10. Furthermore, the sequence of NKX2-3 from other species can be found in the GenBank database.

Various SNPs near and within the NKX2-3 gene have been previously described. For instance, NKX2-3 SNP rs10883365 has been associated with UC and CD in the Japanese population (Arai et al., *Hum. Immunol.*, 72:587-91 (2011)) and with susceptibility of CD in the Western European population (Meggyesi et al., *World J. Gastroenterol.*, 16:5233-5240 (2010)). Non-limiting examples of NKX2-3 SNPs include rs10883365, rs6584283, rs11190140, rs888208, rs11596008, rs7911680, rs7908704, rs41290504, rs7893840, rs884144, rs10082511, rs60505509 and rs59754112. The presence of the NKX2-3 SNP rs10883365 and other variants can be detected, for example, by allelic discrimination assays or sequence analysis.

4. STAT3

Signal transducer and activator of transcription 3 (STAT3), a member of the STAT protein family, is a transcription factor that regulates the expression of a variety of genes involved in many cellular processes such as cell growth, apoptosis, cell motility, and cytokine production. In response to cytokines and growth factors, STAT3 is activated by JAK kinases and translocates to the nucleus to act as a transcriptional activator. Studies have demonstrated that STAT3 plays an important role in various immune disorders including the pathogenesis of inflammatory bowel disease (see, e.g., Sugimoto, *World J. Gastroenterol.*, 14:5110-5114, (2008)).

Gene location information for STAT3 is set forth in, e.g., GeneID:6774. The mRNA (coding) sequences and the corresponding polypeptide sequences of human STAT3 are set forth in, e.g., NM_139276.2, NM_003150.3 and NM_213662.1, and NP_644805.1, NP_003141.2, and NP_998827.1, respectively. In addition, the complete sequence of human chromosome 17q21.31 GRCh37.p5 primary assembly, which includes STAT3, is set forth in e.g., GenBank Accession No. NC_000017.10. Furthermore, the sequence of STAT3 from other species can be found in the Genbank database.

Various SNPs near and within the STAT3 gene have been described previously (see, Franke et al., *Nature Genetics*, 40:713-715 (2008); Sato et al., *J. Clin. Immunol.*, 29:815-25 (2009); Ferguson et al., *Mutat. Res.*, 690:108-15 (2010)); Boland et al., *Dig. Dis.*, 28:590-5 (2010)). Non-limiting examples of STAT3 SNPs include rs744166, rs11547455, rs957970, rs2291281, rs1064111, rs10775, rs9912773, rs2306580, rs1905340, rs12947808, rs12949918, rs34460718, rs1064110, rs1053004, rs3736164, rs7211777, rs1064118, rs12721576, rs35499754, rs4796644, rs3736163, rs3809758, rs3744483, rs17885291, rs6503698 and rs77479856. The presence of the STAT3 SNP rs744166 and other variants can be detected, for example, by allelic discrimination assays or sequence analysis.

5. NOD2/CARD15

The determination of the presence or absence of allelic variants such as SNPs in the NOD2/CARD15 gene can also be useful in the present invention. As used herein, the term "NOD2/CARD15 variant" or "NOD2 variant" includes a nucleotide sequence of a NOD2 gene containing one or more changes as compared to the wild-type NOD2 gene or an amino acid sequence of a NOD2 polypeptide containing one or more changes as compared to the wild-type NOD2 polypeptide sequence. NOD2, also known as CARD15, has been localized to the IBD1 locus on chromosome 16 and identified by positional-cloning (Hugot et al., *Nature*, 411: 599-603 (2001)) as well as a positional candidate gene strategy (Ogura et al., *Nature*, 411:603-606 (2001); Hampe et al., *Lancet*, 357:1925-1928 (2001)). The IBD1 locus has a high multipoint linkage score (MLS) for inflammatory bowel disease (MLS=5.7 at marker D16S411 in 16q12). See, e.g., Cho et al., *Inflamm. Bowel Dis.*, 3:186-190 (1997); Akolkar et al., *Am. J. Gastroenterol.*, 96:1127-1132 (2001); Ohmen et al., *Hum. Mol. Genet.*, 5:1679-1683 (1996); Parkes et al., *Lancet*, 348:1588 (1996); Cavanaugh et al., *Ann. Hum. Genet.*, 62:291-8 (1998); Brant et al., *Gastroenterology*, 115:1056-1061 (1998); Curran et al., *Gastroenterology*, 115:1066-1071 (1998); Hampe et al., *Am. J. Hum. Genet.*, 64:808-816 (1999); and Annese et al., *Eur. J. Hum. Genet.*, 7:567-573 (1999).

The mRNA (coding) and polypeptide sequences of human NOD2 are set forth in, e.g., Genbank Accession Nos. NM_022162 and NP_071445, respectively. In addition, the complete sequence of human chromosome 16 clone RP11-327F22, which includes NOD2, is set forth in, e.g., Genbank Accession No. AC007728. Furthermore, the sequence of NOD2 from other species can be found in the GenBank database.

The NOD2 protein contains amino-terminal caspase recruitment domains (CARDs), which can activate NF-kappa B (NF-kB), and several carboxy-terminal leucine-rich repeat domains (Ogura et al., *J. Biol. Chem.*, 276:4812-4818 (2001)). NOD2 has structural homology with the apoptosis regulator Apaf-1/CED-4 and a class of plant disease resistant gene products (Ogura et al., supra). Similar to plant disease resistant gene products, NOD2 has an amino-terminal effector domain, a nucleotide-binding domain and leucine rich repeats (LRRs). Wild-type NOD2 activates nuclear factor NF-kappa B, making it responsive to bacterial lipopolysaccharides (LPS; Ogura et al., supra; Inohara et al., *J. Biol. Chem.*, 276:2551-2554 (2001). NOD2 can function as an intercellular receptor for LPS, with the leucine rich repeats required for responsiveness.

Variations at three single nucleotide polymorphisms in the coding region of NOD2 have been previously described. These three SNPs, designated R702W ("SNP 8"), G908R ("SNP 12"), and 1007fs ("SNP 13"), are located in the carboxy-terminal region of the NOD2 gene (Hugot et al., supra). A further description of SNP 8, SNP 12, and SNP 13, as well as additional SNPs in the NOD2 gene suitable for use in the invention, can be found in, e.g., U.S. Pat. Nos. 6,835,815; 6,858,391; and 7,592,437; and U.S. Patent Publication Nos. 20030190639, 20050054021, and 20070072180.

In some embodiments, a NOD2 variant is located in a coding region of the NOD2 locus, for example, within a region encoding several leucine-rich repeats in the carboxy-terminal portion of the NOD2 polypeptide. Such NOD2 variants located in the leucine-rich repeat region of NOD2 include, without limitation, R702W ("SNP 8") and G908R ("SNP 12"). A NOD2 variant useful in the invention can also encode a NOD2 polypeptide with reduced ability to activate NF-kappa B as compared to NF-kappa B activation by a wild-type NOD2 polypeptide. As a non-limiting example, the NOD2 variant 1007fs ("SNP 13") results in a truncated NOD2 polypeptide which has reduced ability to induce NF-kappa B in response to LPS stimulation (Ogura et al., *Nature*, 411:603-606 (2001)).

A NOD2 variant useful in the invention can be, for example, R702W, G908R, or 1007fs. R702W, G908R, and 1007fs are located within the coding region of NOD2. In one embodiment, a method of the invention is practiced with the R702W NOD2 variant. As used herein, the term "R702W" includes a single nucleotide polymorphism within exon 4 of the NOD2 gene, which occurs within a triplet encoding amino acid 702 of the NOD2 protein. The wild-type NOD2 allele contains a cytosine (c) residue at position 138,991 of the AC007728 sequence, which occurs within a triplet encoding an arginine at amino acid 702. The R702W NOD2 variant contains a thymine (t) residue at position 138,991 of the AC007728 sequence, resulting in an arginine (R) to tryptophan (W) substitution at amino acid 702 of the NOD2 protein. Accordingly, this NOD2 variant is denoted "R702W" or "702W" and can also be denoted "R675W" based on the earlier numbering system of Hugot et al., supra. In addition, the R702W variant is also known as the "SNP 8" allele or a "2" allele at SNP 8. The NCBI SNP ID number for R702W or SNP 8 is rs2066844. The presence of the R702W NOD2 variant and other NOD2 variants can be conveniently detected, for example, by allelic discrimination assays or sequence analysis.

A method of the invention can also be practiced with the G908R NOD2 variant. As used herein, the term "G908R" includes a single nucleotide polymorphism within exon 8 of the NOD2 gene, which occurs within a triplet encoding amino acid 908 of the NOD2 protein. Amino acid 908 is located within the leucine rich repeat region of the NOD2 gene. The wild-type NOD2 allele contains a guanine (g) residue at position 128,377 of the AC007728 sequence, which occurs within a triplet encoding glycine at amino acid 908. The G908R NOD2 variant contains a cytosine (c) residue at position 128,377 of the AC007728 sequence, resulting in a glycine (G) to arginine (R) substitution at amino acid 908 of the NOD2 protein. Accordingly, this NOD2 variant is denoted "G908R" or "908R" and can also be denoted "G881R" based on the earlier numbering system of Hugot et al., supra. In addition, the G908R variant is also known as the "SNP 12" allele or a "2" allele at SNP 12. The NCBI SNP ID number for G908R SNP 12 is rs2066845.

A method of the invention can also be practiced with the 1007fs NOD2 variant. This variant is an insertion of a single nucleotide that results in a frame shift in the tenth leucine-rich repeat of the NOD2 protein and is followed by a premature stop codon. The resulting truncation of the NOD2 protein appears to prevent activation of NF-kappaB in response to bacterial lipopolysaccharides (Ogura et al., supra). As used herein, the term "1007fs" includes a single nucleotide polymorphism within exon 11 of the NOD2 gene, which occurs in a triplet encoding amino acid 1007 of the NOD2 protein. The 1007fs variant contains a cytosine which has been added at position 121,139 of the AC007728 sequence, resulting in a frame shift mutation at amino acid 1007. Accordingly, this NOD2 variant is denoted "1007fs" and can also be denoted "3020insC" or "980fs" based on the earlier numbering system of Hugot et al., supra. In addition, the 1007fs NOD2 variant is also known as the "SNP 13" allele or a "2" allele at SNP 13. The NCBI SNP ID number for 1007fs or SNP 13 is rs2066847.

One skilled in the art recognizes that a particular NOD2 variant allele or other polymorphic allele can be conveniently defined, for example, in comparison to a Centre d'Etude du Polymorphisme Humain (CEPH) reference individual such as the individual designated 1347-02 (Dib et al., Nature, 380:152-154 (1996)), using commercially available reference DNA obtained, for example, from PE Biosystems (Foster City, Calif.). In addition, specific information on SNPs can be obtained from the dbSNP of the National Center for Biotechnology Information (NCBI).

A NOD2 variant can also be located in a non-coding region of the NOD2 locus. Non-coding regions include, for example, intron sequences as well as 5' and 3' untranslated sequences. A non-limiting example of a NOD2 variant allele located in a non-coding region of the NOD2 gene is the JW1 variant, which is described in Sugimura et al., Am. J. Hum. Genet., 72:509-518 (2003) and U.S. Patent Publication No. 20070072180. Examples of NOD2 variant alleles located in the 3' untranslated region of the NOD2 gene include, without limitation, the JW15 and JW16 variant alleles, which are described in U.S. Patent Publication No. 20070072180. Examples of NOD2 variant alleles located in the 5' untranslated region (e.g., promoter region) of the NOD2 gene include, without limitation, the JW17 and JW18 variant alleles, which are described in U.S. Patent Publication No. 20070072180.

As used herein, the term "JW1 variant allele" includes a genetic variation at nucleotide 158 of intervening sequence 8 (intron 8) of the NOD2 gene. In relation to the AC007728 sequence, the JW1 variant allele is located at position 128, 143. The genetic variation at nucleotide 158 of intron 8 can be, but is not limited to, a single nucleotide substitution, multiple nucleotide substitutions, or a deletion or insertion of one or more nucleotides. The wild-type sequence of intron 8 has a cytosine at position 158. As non-limiting examples, a JW1 variant allele can have a cytosine (c) to adenine (a), cytosine (c) to guanine (g), or cytosine (c) to thymine (t) substitution at nucleotide 158 of intron 8. In one embodiment, the JW1 variant allele is a change from a cytosine (c) to a thymine (t) at nucleotide 158 of NOD2 intron 8.

The term "JW15 variant allele" includes a genetic variation in the 3' untranslated region of NOD2 at nucleotide position 118,790 of the AC007728 sequence. The genetic variation at nucleotide 118,790 can be, but is not limited to, a single nucleotide substitution, multiple nucleotide substitutions, or a deletion or insertion of one or more nucleotides. The wild-type sequence has an adenine (a) at position 118,790. As non-limiting examples, a JW15 variant allele can have an adenine (a) to cytosine (c), adenine (a) to guanine (g), or adenine (a) to thymine (t) substitution at nucleotide 118,790. In one embodiment, the JW15 variant allele is a change from an adenine (a) to a cytosine (c) at nucleotide 118,790.

As used herein, the term "JW16 variant allele" includes a genetic variation in the 3' untranslated region of NOD2 at nucleotide position 118,031 of the AC007728 sequence. The genetic variation at nucleotide 118,031 can be, but is not limited to, a single nucleotide substitution, multiple nucleotide substitutions, or a deletion or insertion of one or more nucleotides. The wild-type sequence has a guanine (g) at position 118,031. As non-limiting examples, a JW16 variant allele can have a guanine (g) to cytosine (c), guanine (g) to adenine (a), or guanine (g) to thymine (t) substitution at nucleotide 118,031. In one embodiment, the JW16 variant allele is a change from a guanine (g) to an adenine (a) at nucleotide 118,031.

The term "JW17 variant allele" includes a genetic variation in the 5' untranslated region of NOD2 at nucleotide position 154,688 of the AC007728 sequence. The genetic variation at nucleotide 154,688 can be, but is not limited to, a single nucleotide substitution, multiple nucleotide substitutions, or a deletion or insertion of one or more nucleotides. The wild-type sequence has a cytosine (c) at position 154,688. As non-limiting examples, a JW17 variant allele can have a cytosine (c) to guanine (g), cytosine (c) to adenine (a), or cytosine (c) to thymine (t) substitution at nucleotide 154,688. In one embodiment, the JW17 variant allele is a change from a cytosine (c) to a thymine (t) at nucleotide 154,688.

As used herein, the term "JW18 variant allele" includes a genetic variation in the 5' untranslated region of NOD2 at nucleotide position 154,471 of the AC007728 sequence. The genetic variation at nucleotide 154,471 can be, but is not limited to, a single nucleotide substitution, multiple nucleotide substitutions, or a deletion or insertion of one or more nucleotides. The wild-type sequence has a cytosine (c) at position 154,471. As non-limiting examples, a JW18 variant allele can have a cytosine (c) to guanine (g), cytosine (c) to adenine (a), or cytosine (c) to thymine (t) substitution at nucleotide 154,471. In one embodiment, the JW18 variant allele is a change from a cytosine (c) to a thymine (t) at nucleotide 154,471.

It is understood that the methods of the invention can be practiced with these or other NOD2 variant alleles located in a coding region or non-coding region (e.g., intron or promoter region) of the NOD2 locus. It is further understood that the methods of the invention can involve determining the presence of one, two, three, four, or more NOD2 variants, including, but not limited to, the SNP 8, SNP 12, and SNP 13 alleles, and other coding as well as non-coding region variants.

L. Other Diagnostic Markers

Additional diagnostic markers suitable for use in the present invention include, but are not limited to, lactoferrin, anti-lactoferrin antibodies, elastase, calprotectin, hemoglobin, and combinations thereof.

The determination of the presence or level of lactoferrin in a sample can be useful in the present invention. In certain instances, the presence or level of lactoferrin is detected at the level of mRNA expression with an assay such as, for example, a hybridization assay or an amplification-based assay. In certain other instances, the presence or level of lactoferrin is detected at the level of protein expression using, for example, an immunoassay (e.g., ELISA) or an immunohistochemical assay. An ELISA kit available from Calbiochem (San Diego, Calif.) can be used to detect human lactoferrin in a plasma, urine, bronchoalveolar lavage, or cerebrospinal fluid sample. Similarly, an ELISA kit available from U.S. Biological (Swampscott, Mass.) can be used to determine the level of lactoferrin in a plasma sample. Likewise, ELISA kits available from TECHLAB, Inc. (Blacksburg, Va.) can be used to determine the level of lactoferrin in a stool sample. Additionally, U.S. Patent Publication No. 20040137536 describes an ELISA assay for determining the presence of elevated lactoferrin levels in a stool sample, and U.S. Patent Publication No. 20040033537 describes an ELISA assay for determining the concentration of endogenous lactoferrin in a stool, mucus, or bile sample. In some embodiments, then presence or level of anti-lactoferrin antibodies can be detected in a sample using, e.g., lactoferrin protein or a fragment thereof.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar colorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045, 5,081,040, and 5,310,684.

Calprotectin is a calcium and zinc-binding protein found in all cells, tissues, and fluids in the body. Calprotectin is a major protein in neutrophilic granulocytes and macrophages and accounts for as much as 60% of the total protein in the cytosolic fraction of these cells. It is therefore a surrogate marker of neutrophil turnover. Its concentration in stool correlates with the intensity of neutrophil infiltration of the intestinal mucosa and with the severity of inflammation. Calprotectin can be measured with an ELISA using small (50-100 mg) fecal samples (see, e.g., Johne et al., *Scand J. Gastroenterol.*, 36:291-296 (2001)).

VI. Assays

Any of a variety of assays, techniques, and kits known in the art can be used to detect or determine the presence or level of one or more IBD markers in a sample to diagnose IBD and to classify the diagnosis of IBD (e.g., IC, CD or UC).

The present invention relies, in part, on determining the presence or level of at least one marker in a sample obtained from an individual. As used herein, the term "detecting the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "detecting the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for detecting the level of each marker of interest. One skilled in the art will appreciate that any assay useful for detecting the level of a marker is also useful for detecting the presence or absence of the marker.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Flow cytometry can be used to detect the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop and Davis, *J. Immunol. Methods*, 210:79-87 (1997); McHugh et al., *J. Immunol. Methods*, 116:213 (1989); Scillian et al., *Blood*, 73:2041 (1989)).

Phage display technology for expressing a recombinant antigen specific for a marker can also be used to detect the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.*, 267, San Diego: Academic Press, Inc. (1996)).

A variety of immunoassay techniques, including competitive and non-competitive immunoassays, can be used to detect the presence or level of one or more markers in a sample (see, e.g., Self and Cook, *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis*, 18:2184-2193

(1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

Antigen capture ELISA can be useful for detecting the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for detecting the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for detecting the presence or level of one or more markers in a sample. As a non-limiting example, a fixed neutrophil ELISA is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. An ELISA using I2 protein or a fragment thereof is useful for determining whether a sample is positive for anti-I2 antibodies, or for determining anti-I2 antibody levels in a sample. An ELISA using flagellin protein (e.g., Cbir-1 flagellin, Fla2 flagellin, FlaX flagellin) or a fragment thereof is useful for determining whether a sample is positive for anti-flagellin antibodies, or for determining anti-flagellin antibody levels in a sample. In addition, the immunoassays described above are particularly useful for detecting the presence or level of other markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays described herein can be automated or performed robotically, and the signal from multiple samples can be detected simultaneously.

Quantitative Western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to detect or determine the presence or level of one or more markers in a sample. The term "immunohistochemical assay" encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, SELDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for detecting the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful prognostic and predictive information to facilitate in the treatment of IBD.

A panel for measuring one or more of the markers described above may be constructed to provide relevant information related to the approach of the invention for diagnosing IBD, for predicting the probable course and outcome of IBD, and for predicting the likelihood of response to IBD therapy. Such a panel may be constructed to detect or determine the presence or level of 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment, diagnosis, and prognosis in a timely fashion.

In view of the above, one skilled in the art realizes that the methods of the invention for providing diagnostic information regarding IBD or clinical subtypes thereof, for providing prognostic and predictive information regarding the outcome and course of progression of IBD, and for providing information regarding the selection of a suitable therapeutic regimen for the treatment of IBD (e.g., by determining the presence or concentration level of one or more IBD markers as described herein) can be practiced using one or any combination of the well-known assays described above or other assays known in the art.

VII. Methods of Genotyping

A variety of means can be used to genotype an individual at a polymorphic site in a gene or any other genetic marker described herein to determine whether a sample (e.g., a nucleic acid sample) contains a specific variant allele or haplotype. For example, enzymatic amplification of nucleic acid from an individual can be conveniently used to obtain nucleic acid for subsequent analysis. The presence or absence of a specific variant allele or haplotype in one or more genetic markers of interest can also be determined directly from the individual's nucleic acid without enzymatic amplification. In some preferred embodiments, an individual is genotyped at the ATG16L1 locus. In other preferred embodiments, an individual is genotyped at the NKX2-3 locus. In yet other preferred embodiments, an individual is genotyped at the STAT3 locus. In further preferred embodiments, an individual is genotyped at the ECM1 locus.

Genotyping of nucleic acid from an individual, whether amplified or not, can be performed using any of various techniques. Useful techniques include, without limitation, polymerase chain reaction (PCR) based analysis, sequence analysis, and electrophoretic analysis, which can be used alone or in combination. As used herein, the term "nucleic acid" means a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

Material containing nucleic acid is routinely obtained from individuals. Such material is any biological matter from which nucleic acid can be prepared. As non-limiting examples, material can be whole blood, serum, plasma, saliva, cheek swab, sputum, or other bodily fluid or tissue that contains nucleic acid. In one embodiment, a method of the present invention is practiced with whole blood, which can be obtained readily by non-invasive means and used to prepare genomic DNA. In another embodiment, genotyping involves amplification of an individual's nucleic acid using the polymerase chain reaction (PCR). Use of PCR for the amplification of nucleic acids is well known in the art (see, e.g., Mullis et al. (Eds.), *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor groove binder.

Any of a variety of different primers can be used to amplify an individual's nucleic acid by PCR in order to determine the presence or absence of a variant allele in one or more genes or other genetic marker in a method of the invention. Non-limiting examples of genes include ATG16L1, STAT3, ECM1 and NKX2-3. For example, the PCR primers can be used to amplify specific regions of the ATG16L1 locus. As understood by one skilled in the art, additional primers for PCR analysis can be designed based on the sequence flanking the polymorphic site(s) of interest in the ATG16L1 gene or other genetic marker. As a non-limiting example, a sequence primer can contain from about 15 to about 30 nucleotides of a sequence upstream or downstream of the polymorphic site of interest in the ATG16L1 gene or other genetic marker. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a particular variant allele or haplotype in the one or more of the ATG16L1, ECM1, STAT3, NKX2-3 genes, or other genetic marker described herein. In a Taqman® allelic discrimination assay, a specific fluorescent dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the individual. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor groove binder (MGB) group to a DNA probe as described, e.g., in Kutyavin et al., *Nuc. Acids Research* 28:655-661 (2000). Minor groove binders include, but are not limited to, compounds such as dihydrocyclopyrroloindole tripeptide (DPI3). Exemplary Taqman® probes suitable for detecting the allelic variants in the ATG16L1, STAT3, NKX2-3 and ECM1 genes are commercially available from Applied Biosystems. Non-limiting examples include catalog numbers: C__9095577__20 and C__11530586__10 (ATG16L1); C__29560274__10, C__25803068__10, and C__8690827__20 (ECM1); C__3140282__10 (STAT3); C__3018644__10, C__31657361__10 and C__3018642__10 (NKX2-3).

In some embodiments, the probes for detecting ATG16L1 SNP rs2241880 comprise the following sequences: CCCAGTCCCCCAGGACAATGTGGATACT-CATCCTGGTTCTGGTAAAGAAGT; and CCCAGTC-CCCCAGGACAATGTGGATGCTCATCCTG-GTTCTGGTAAAGAAGT; both derived from CCCAGTCCCCCAGGACAATGTGGAT[A/G]CTCATC-CTGGTTCTGGTAAAGAAGT; wherein the notation [A/G] represents the location of the rs2241880 SNP. In further embodiments, the first probe is VIC™ dye labeled and contains the A allele and the second probe is FAM™ labeled and contains the G allele. For detecting the presence or the absence of the rs2241880 SNP, a FAM/FAM (G/G) signal or a VIC/VIC (A/A) signal would indicate a homozygous genotype; and a VIC/FAM signal would indicate a heterozygous mutant genotype.

In some embodiments, the probes for detecting the STAT3 SNP rs744166 comprise the following sequences: CTGTTTGTTCTATAAATTACTGT-CAAGCTCGATTCCCTCAAGACATTACAG; and CTGTTTGTTCTATAAATTACTGTCAG-GCTCGATTCCCTCAAGACATTACAG; both derived from CTGTTTGTTCTATAAATTACTGTCA[A/G]GCTCGAT-TCCCTCAAGACATTACAG, wherein the notation [A/G] represents the location of the rs744166 SNP. In further embodiments, the first probe is VIC™ dye labeled and contains the A allele and the second probe is FAM™ labeled and contains the G allele. For detecting the presence or the absence of the rs744166 SNP, a FAM/FAM (G/G) signal or a VIC/VIC (A/A) signal would indicate a homozygous genotype; and a VIC/FAM signal would indicate a heterozygous mutant genotype.

In some embodiments, the probes for detecting ECM1 SNP rs3737240 comprise the following sequences: CCCACT-GTTTTCCCCATTCCAGGAACGCCAGCTC- CATTTGGGGACCAGAGC; and CCACTGTTTTC-CCCATTCCAGGAATGCCAGCTCCATTTGGGGACCAGAGC; both derived from CCCACTGTTTTCCCCATTCCAGGAA [C/T]GCCAGCTCCATTTGGGGACCAGAGC; wherein the notation [C/T] represents the location of the rs3737240 SNP. In further embodiments, the first probe is VIC™ dye labeled and contains the C allele and the second probe is FAM™ labeled and contains the T allele. For detecting the presence or the absence of the rs3737240SNP, a FAM/FAM (T/T) signal or a VIC/VIC (C/C) signal would indicate a homozygous genotype; and a VIC/FAM signal would indicate a heterozygous mutant genotype.

In some embodiments, the probes for detecting ECM1 SNP rs13294 comprise the following sequences: CCGGGA-CATCTTGACCATTGACATCAGTCGAGT-CACCCCCAACCTCATGGG; and CCGGGACATCT-TGACCATTGACATCGGTCGAGTCACCCCCAACCTCATGGG; both derived from CCGGGACATCTTGACCATTGACATC [A/G]GTCGAGTCACCCCCAACCTCATGGG; wherein the notation [A/G] represents the location of the rs13294 SNP. In further embodiments, the first probe is VIC™ dye labeled and contains the A allele and the second probe is FAM™ labeled and contains the G allele. For detecting the presence or the absence of the rs13294 SNP, a FAM/FAM (G/G) signal or a VIC/VIC (A/A) signal would indicate a homozygous genotype; and a VIC/FAM signal would indicate a heterozygous mutant genotype.

In some embodiments, the probes for detecting NKX2-3 SNP rs10883365 comprise the following sequences: TTTCGTTCTCAGACGGTTTGAAGG-TATTTGTGCCAACGTGACCCCCGGGGA; and TTTCGTTCTCAGACGGTTTGAAGGT-GTTTGTGCCAACGTGACCCCCGGGGA; both derived from TTTCGTTCTCAGACGGTTTGAAGGT[A/G] TTTGTGCCAACGTGACCCCCGGGGA; wherein the notation [A/G] represents the location of the rs10883365 SNP. In further embodiments, the first probe is VIC™ dye labeled and contains the A allele and the second probe is FAM™ labeled and contains the G allele. For detecting the presence or the absence of the rs10883365 SNP, a FAM/FAM (G/G) signal or a VIC/VIC (A/A) signal would indicate a homozygous genotype; and a VIC/FAM signal would indicate a heterozygous mutant genotype.

In some embodiments, the probes for detecting NKX2-3 SNP rs6584283 comprise the following sequences: CTGCA-GAGCGTCTGTGGGCGTGTATCGGCGAT-CAGGCGCTGGAGGGGCGCT; and CTGCA-GAGCGTCTGTGGGCGTGTATTGGCGATCAGGCGCTGGAGGGGCGCT; both derived from CTGCAGAGCGTCTGTGGGCGTGTAT [C/T]GGCGATCAGGCGCTGGAGGGGCGCT; wherein the notation [C/T] represents the location of the rs6584283 SNP. In further embodiments, the first probe is VIC™ dye labeled and contains the C allele and the second probe is FAM™ labeled and contains the T allele. For detecting the presence or the absence of the rs6584283 SNP, a FAM/FAM (T/T) signal or a VIC/VIC (A/A) signal would indicate a homozygous genotype; and a VIC/FAM signal would indicate a heterozygous mutant genotype.

In some embodiments, the probes for detecting ECM1 SNP rs7511649 comprise the following sequences: TTTCT-GACTTCTCCCTGTAAATCTTCTTCTG-TATGATTTATTTTGGTAGAT; and TTTCTGACTTCTC-CCTGTAAATCTTTTTCTGTATGATTTATTTTGGTAGAT; both derived from TTTCTGACTTCTCCCTGTAAATCTT [C/T]TTCTGTATGATTTATTTTGGTAGAT; wherein the notation [C/T] represents the location of the rs7511649 SNP. In further embodiments, the first probe is VIC™ dye labeled and contains the C allele and the second probe is FAM™ labeled and contains the T allele. For detecting the presence or the absence of the rs7511649 SNP, a FAM/FAM (T/T) signal or a VIC/VIC (A/A) signal would indicate a homozygous genotype; and a VIC/FAM signal would indicate a heterozygous mutant genotype.

In other embodiments, the probes for detecting NKX2-3 SNP rs11190140 comprise the following sequences: CAT-TCAGGCTCCTGATTTCAATAGGCG-GAAAAGAAGGCTGCCAAGGCTGGG; and CATTCAG-GCTCCTGATTTCAATAGGTGGAAAAGAAGGCTGCCAAGGCTGGG; both derived from CATTCAGGCTCCTGATTTCAATAGG [C/T]GGAAAAGAAGGCTGCCAAGGCTGGG; wherein the notation [C/T] represents the location of the rs11190140 SNP. In further embodiments, the first probe is VIC™ dye labeled and contains the C allele and the second probe is FAM™ labeled and contains the T allele. For detecting the presence or the absence of the rs11190140 SNP, a FAM/FAM (T/T) signal or a VIC/VIC (C/C) signal would indicate a homozygous genotype; and a VIC/FAM signal would indicate a heterozygous mutant genotype.

Sequence analysis can also be useful for genotyping an individual according to the methods described herein to determine the presence or absence of a particular variant allele or haplotype in the NOD2 gene or other genetic marker. As is known by those skilled in the art, a variant allele of interest can be detected by sequence analysis using the appropriate primers, which are designed based on the sequence flanking the polymorphic site of interest in one or more of the ATG16L1, ECM1, STAT3, NKX2-3 genes, or another genetic marker. Additional or alternative sequence primers can contain from about 15 to about 30 nucleotides of a sequence that corresponds to a sequence about 40 to about 400 base pairs upstream or downstream of the polymorphic site of interest in one or more of the ATG16L1, ECM1, STAT3, NKX2-3 genes, or another genetic marker. Such primers are generally designed to have sufficient guanine and cytosine content to attain a high melting temperature which allows for a stable annealing step in the sequencing reaction.

The term "sequence analysis" includes any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (see, Sears et al., *Biotechniques* 13:626-633 (1992)); solid-phase sequencing (see, Zimmerman et al., *Methods Mol. Cell. Biol.* 3:39-42 (1992); and sequencing with mass spectrometry, such as matrix-assisted laser desorption/ionization time-of-flight mass spectrometry (see, MALDI-TOF MS; Fu et al., *Nature Biotech.* 16:381-384 (1998)). The term sequence analysis further includes, but is not limited to, sequencing by hybridization (SBH), which relies on an array of all possible short oligonucleotides to identify a segment of sequence (see, Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis also can be useful in genotyping an individual according to the methods of the present invention to determine the presence or absence of a particular variant allele or haplotype in one or more of the ATG16L1, ECM1, STAT3, NKX2-3 genes, or another genetic marker. "Electrophoretic analysis" as used herein in reference to one or more nucleic acids such as amplified fragments includes a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping an individual according to the methods of the present invention to determine the presence or absence of a particular variant allele or haplotype in the NOD2 gene or other genetic marker (see, Jarcho et al. in Dracopoli et al., *Current Protocols in Human Genetics* pages 2.7.1-2.7.5, John Wiley & Sons, New York; Innis et al., (Ed.), *PCR Protocols*, San Diego: Academic Press, Inc. (1990)). As used herein, "restriction fragment length polymorphism analysis" includes any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping an individual in the methods described herein to determine the presence or absence of a particular variant allele or haplotype in one or more of the ATG16L1, ECM1, STAT3, NKX2-3 genes, or another genetic marker r. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping in the methods of the present invention to determine the presence or absence of a particular variant allele or haplotype in one or more of the ATG16L1, ECM1, STAT3, NKX2-3 genes, or another genetic marker. HMA is useful for detecting the presence of a variant allele since a DNA duplex carrying a mismatch has reduced mobility in a polyacrylamide gel compared to the mobility of a perfectly base-paired duplex (see, Delwart et al., *Science,* 262:1257-1261 (1993); White et al., *Genomics,* 12:301-306 (1992)).

The technique of single strand conformational polymorphism (SSCP) can also be useful for genotyping in the methods described herein to determine the presence or absence of a particular variant allele or haplotype in one or more of the ATG16L1, ECM1, STAT3, NKX2-3 genes, or another genetic marker (see, Hayashi, *Methods Applic.,* 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can also be useful in the methods of the invention to determine the presence or absence of a particular variant allele or haplotype in one or more of the ATG16L1, ECM1, STAT3, NKX2-3 genes, or another genetic marker. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (see, Sheffield et al., "Identifying DNA Polymorphisms by Denaturing Gradient Gel Electrophoresis" in Innis et al., supra, 1990).

Other molecular methods useful for genotyping an individual are known in the art and useful in the methods of the present invention. Such well-known genotyping approaches include, without limitation, automated sequencing and RNase mismatch techniques (see, Winter et al., *Proc. Natl. Acad. Sci.,* 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the invention for providing diagnostic information regarding IBD or clinical subtypes thereof, for providing prognostic and predictive information regarding the outcome and course of progression of IBD, and for providing information regarding the selection of a suitable therapeutic regimen for the treatment of IBD (e.g., by determining the presence or absence of one or more variant alleles of genes such as, but not limited to, ATG16L1, STAT3, ECM1, and NKX2-3) can be practiced using one or any combination of the well-known genotyping assays described above or other assays known in the art.

VIII. Statistical Analysis

In some aspects, the present invention provides methods and systems for diagnosing IBD or non-IBD, for classifying the diagnosis of IBD (e.g., CD, UC, or inconclusive for CD or UC), for classifying the subtype of IBD as UC, CD, or IC, or for differentiating between UC and CD. In some embodiments, one or more learning statistical classifier systems are applied to the presence, level, and/or genotype of one or more IBD markers determined by any of the assays described herein to diagnose IBD or to determine the subtype thereof. In other embodiments, quantile analysis is applied to the presence, level, and/or genotype of one or more IBD markers determined by any of the assays described herein to diagnose IBD or to determine the subtype thereof. As described herein, the statistical analyses of the invention advantageously provide improved sensitivity, specificity, negative predictive value, positive predictive value, and/or overall accuracy for diagnosing IBD or for determining the subtype thereof.

The term "statistical analysis" or "statistical algorithm" or "statistical process" includes any of a variety of statistical methods and models used to determine relationships between variables. In the present invention, the variables are the presence, level, or genotype of at least one marker of interest. Any number of markers can be analyzed using a statistical analysis described herein. For example, the presence or level of 1, 2, 3, 4, 5, 6, 7, 8, 9, 10, 11, 12, 13, 14, 15, 16, 17, 18, 19, 20, 25, 30, 35, 40, 45, 50, 55, 60, or more markers can be included in a statistical analysis. In one embodiment, logistic regression is used. In another embodiment, linear regression is used. In certain embodiments, the statistical analyses of the present invention comprise a quantile measurement of one or more markers, e.g., within a given population, as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In certain embodiments, the present invention involves detecting or determining the presence, level (e.g., magnitude), and/or genotype of one or more markers of interest using quartile analysis. In this type of statistical analysis, the level of a marker of interest is defined as being in the first quartile (<25%), second quartile (25-50%), third quartile (51%-<75%), or fourth quartile (75-100%) in relation to a reference database of samples. These quartiles may be assigned a quartile score of 1, 2, 3, and 4, respectively. In certain instances, a marker that is not detected in a sample is assigned a quartile score of 0 or 1, while a marker that is detected (e.g., present) in a sample (e.g., sample is positive for the marker) is assigned a quartile score of 4. In some embodiments, quartile 1 represents samples with the lowest marker levels, while quartile 4 represent samples with the highest marker levels. In other embodiments, quartile 1 represents samples with a particular marker genotype (e.g., wild-type allele), while quartile 4 represent samples with another particular marker genotype (e.g., allelic variant). The reference database of samples can include a large spectrum of IBD (e.g., CD and/or UC) patients. From such a database, quartile cut-offs can be established. A non-limiting example of quartile analysis suitable for use in the present invention is described in, e.g., Mow et al., *Gastroenterology*, 126:414-24 (2004).

In preferred embodiments, the statistical analyses of the invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001), for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM-$^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological and/or genomic samples) from healthy individuals and IBD (e.g., CD and/or UC) patients. For example, samples from patients diagnosed by a physician, and preferably by a gastroenterologist, as having IBD or a clinical subtype thereof using a biopsy, colonoscopy, or an immunoassay as described in, e.g., U.S. Pat. No. 6,218,129, are suitable for use in training and testing the statistical methods and models of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the statistical methods and models of the present invention.

As used herein, the term "sensitivity" refers to the probability that a diagnostic or predictive method, system, or code of the present invention gives a positive result when the sample is positive, e.g., having the predicted diagnosis. Sensitivity is calculated as the number of true positive results divided by the sum of the true positives and false negatives. Sensitivity essentially is a measure of how well the present invention correctly identifies those who have the predicted diagnosis from those who do not have the predicted diagnosis. The statistical methods and models can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" refers to the probability that a diagnostic or predictive method, system, or code of the present invention gives a negative result when the sample is not positive, e.g., not having the predicted diagnosis. Specificity is calculated as the number of true negative results divided by the sum of the true negatives and false positives. Specificity essentially is a measure of how well the present invention excludes those who do not have the predicted diagnosis from those who do have the predicted diagnosis. The statistical methods and models can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

As used herein, the term "negative predictive value" or "NPV" refers to the probability that an individual identified as not having the predicted diagnosis actually does not have the predicted diagnosis. Negative predictive value can be calculated as the number of true negatives divided by the sum of the true negatives and false negatives. Negative predictive value is determined by the characteristics of the diagnostic or predictive method, system, or code as well as the prevalence of the disease in the population analyzed. The statistical methods and models can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" refers to the probability that an individual identified as having the predicted diagnosis actually has the predicted diagnosis. Positive predictive value can be calculated as the number of true positives divided by the sum of the true positives and false positives. Positive predictive value is determined by the characteristics of the diagnostic or predictive method, system, or code as well as the prevalence of the disease in the population analyzed. The statistical methods and models can be selected such that the positive predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the present invention, the statistical methods and models can be selected to produce a desired clinical parameter for a clinical population with a particular IBD prevalence. For example, statistical methods and models can be selected for an IBD prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a diagnostic or predictive method, system, or code of the invention diagnoses or predicts IBD. Overall accuracy is calculated as the sum of the true positives and true negatives divided by the total number of sample results and is affected by the prevalence of the disease in the population analyzed. For example, the statistical methods and models of the invention can be selected such that the overall accuracy in a patient population having a disease prevalence is at least about 40%, and can be, e.g., at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In particular embodiments, the statistical methods and models described herein for predictive modeling of diagnostic markers related to IBD utilize the random forest method of model construction. A random forest is generally a classifier made up of many decision trees with a random component to building each tree. Each decision tree addresses the same classification problem, but with a different collection of examples and a different subset of features randomly selected from the dataset of examples provided.

In some embodiments, a single tree might be built using a random ⅔ of the available samples (e.g., training set), with a random ⅔ of the features selected to make a decision split at each node of the tree. Once the forest is built during training, new examples are classified by taking a vote across all the decision trees. In the simplest case for a 2-class random forest classifier, the class with the most votes wins. In other instances, the cutoff for a winning number of votes, as established during training is preset to optimize performance measures. In some instances, if false positives are more costly than false negatives, the cutoff might be set higher.

The method is very robust for modeling this type of statistical data because it is highly accurate. Since each decision tree is built from a different subset of the data, it is less prone to over-fitting of the data than other machine learning approaches. The method is also inherently resistant to over-training due to its ensemble nature. Typically, a large number of trees are grown and trained to random subsets of training data and predictions are made by averaging the results of individual trees. Any over-fitting or underperforming by an individual tree tends to cancel out when the ensemble average is computed. The advantages of random forest modeling include minimal over-training due to cancellation, creation of arbitrary-shaped regions in the predictor space, creation of arbitrary non-linear mappings, variable importance, and out-lyingness. The method has the ability to rank importance of variables (markers) and has computational efficiency when re-sampling.

In some aspects, random forest modeling of the present invention comprises an ensemble method, wherein the forest comprises thousands of decision trees. A decision tree can be used to predict by generating a sequence of questions (e.g., splits). At a given node in the sequence, the question (e.g., split) that is asked depends upon the answers to the previous questions. A tree chooses the best split at each node based on how well it can separates classes. The trees are produced by using different random subsamples of training data. In other instances, trees are produced using different random subsets of markers at each node. During the prediction mode, the probability of each class is a fraction of the trees in the algorithm predicting it.

In some embodiments, the general steps of a random forest include: (1) constructing a conventional recursive partitioning tree from roughly ⅔ of the data available for training, wherein no subsequent pruning is employed; (2) considering only a small and different subset of available variables at each node, wherein the subset is no larger than the square root of the number of variables; (3) repeating steps 1 and 2 a plurality of times to create multiple trees (a forest); and (4) during the prediction mode, reporting a score which is the fraction of trees in the forest that predict a given class. A cut-off can then be employed to produce a class prediction (e.g., IBD, non-IBD, IC, UC or CD diagnosis or categorizing the sample as inconclusive for CD and UC).

In certain embodiments, the IBD diagnostic algorithm is established using a retrospective cohort of predicted diagnoses with known presence, absence and/or levels of sero-genetic-inflammation markers (e.g., examples). In some embodiments, the examples used (e.g., training and test sets) to build the random forest are from studies using the methods described herein.

In particular embodiments, text-based measurements of the presence, absence and/or levels of sero-genetic-inflammation markers and the known disease diagnosis are assigned a binary value based on determined rules. In some embodiments, pANCA measurements determined to be not detected or DNAse sensitive (cytoplasmic) are assigned a value of 0. In other embodiments, pANCA measurements determined to be DNase sensitive 1+P, 2+P, 3+P or 4+P are assigned a value of 1. In some embodiments, pANCA2 measurements determined to be not detected, DNAse sensitive (cytoplasmic) or DNase sensitive 1+P are assigned a value of 0. In other embodiments, pANCA2 measurements determined to be DNase sensitive 2+P, 3+P or 4+P are assigned a value of 1.

In certain embodiments, correlations and associations for all possible pairwise combinations of the variables (e.g., genetic markers, serology markers and known disease diagnoses) used in some part of the IBD diagnostic algorithm were calculated. For continuous variable pairs and for continuous-binary variable pairs, Pearson correlation coefficients and their p-values can be calculated. For binary-binary variable pairs, association can be evaluated with Chi-squared analysis. All calculations can also be performed using the software program Matlab.

In some embodiments, the IBD diagnostic algorithm comprises a random forest model for predicting IBD vs. non-IBD using all training data after sample removal, wherein samples meeting a determined criteria are removed from the training data, a random forest for predicting UC vs. CD uses training data from only known IBD patients that are not IC, and a decision tree or set of rules is based on the "indeterminate" rules. In certain embodiments, when the IBD diagnostic algorithm is in the prediction mode, it can predict IBD vs. non-IBD with the first model (e.g., random forest for IBD vs. non-IBD). If non-IBD is predicted, the algorithm is done. Otherwise, the algorithm applies the "indeterminate" rules at the decision tree or set of rules. Samples that are not categorized as inconclusive for CD and UC based on the "indeterminate" rules are processed by applying a second model (e.g., random forest for UC vs. CD). The IBD diagnostic algorithm can classify an individual as a non-IBD, CD or UC patient, or can categorize an individual with IBD as inconclusive for CD and UC.

In certain embodiments, the "indeterminate" rules or set of rules can be ANCA≥Q3, pANCA2 positive, and either anti-Cbir1 antibody or anti-Fla2 antibody or anti-FlaX antibody≥Q3. In other embodiments, the "indeterminate" rules or set of rules can be pANCA2 positive, and any two of the serological anti-flagellin antibody (e.g., anti-Cbir1 antibody or anti-Fla2 antibody or anti-FlaX antibody) markers≥Q3.

In some embodiments, the IBD diagnostic algorithm includes a method of internal validation, wherein both training and testing iterations (e.g., resampling) are repeated. In certain instances, resampling is repeated about 100 times to obtain statistics. Internal validation comprises dividing a training set into ⅔ to make a model-training set and ⅓ to make a test set; constructing an algorithm (e.g., a pair of random forest models) using the model-training set; and computing performance using the test set. In other embodiments, internal validation includes applying the same sample removal rules and "indeterminate" rules to a validation set as applied to a training set and computing the performance of the algorithm. In certain instances, failure to apply the same culling rules can result in a performance degradation of ≥2%.

In some embodiments, a sample is removed from random forest models for predicting either IBD vs. non-IBD or UC vs. CD: if a sample is from a patient who last experienced symptoms more than 6 months prior to a doctors visit; if a sample is from a patient whose last symptom was described as "not available" and who enrolled in the study prior to a certain date; if the patient did not meet inclusion/exclusion criteria of the study; and if information is lacking regarding the patient's duration of disease.

In some embodiments, a sample is removed: if a sample is from a patient who last experienced symptoms more than 6 months prior to a doctors visit; if a sample is from a patient whose last symptom was described as "not available" and who enrolled in the study prior to a certain date; if the patient did not meet inclusion/exclusion criteria of the study; and if information is lacking regarding the patient's duration of disease. In other embodiments, a sample is removed from the random forest model for UC vs. CD diagnosis. In some instances, a sample with the following characteristics is removed from the training dataset used to construct the UC vs. CD random forest model. The characteristics include: (1) UC diagnosis; (2) ANCA level at <quartile score (Q) 3, pANCA2 negative; and (3) two or more markers (e.g., ASCA-A, ASCA-G, anti-OmpC, anti-CBir1, anti-Fla2, anti-FlaX) with a Q≥3. Typically, 90% of these samples are from CD patients. In some instances, a sample meeting the following criteria is eliminated: (1) known CD diagnosis; (2) ANCA<16.8 EU/ml, pANCA2 negative; and (3) two or more of these conditions satisfied: ASCA-A≥10.675 EU/ml, ASCA-G≥14.175 EU/ml, anti-OmpC≥9.4 EU/ml, anti-CBir1≥29.475 EU/ml, anti-Fla2≥34.5 EU/ml, or anti-FlaX≥28.875 EU/ml. In other instances, a subject's sample is removed from the training dataset used to construct the UC vs. CD random forest model if (1) the subject has a UC diagnosis; (2) ANCA≥16.8 EU/ml; pANCA2 positive; and (3) all of the following conditions are satisfied: ASCA-A<20.675 EU/ml, ASCA-G<14.175 EU/ml, anti-OmpC<9.4 EU/ml, anti-CBir1<29.475 EU/ml, anti-Fla2<34.5 EU/ml and anti-FlaX<28.875 EU/ml. 90% of these subjects are typically from UC patients. In yet other instances, a sample is excluded from the training set (e.g., training and validation sets) if it meets one of the following criteria: (1) has pANCA2=1 and ANCA<11.9; (2) has pANCA2=0 and ANCA≥11.9; (3) is affected by a clear error; and (4) is normally retested.

In some embodiments, the disease classification algorithm of the present invention uses the entire training set to build one or a plurality of random forest models. It establishes a cut-off for classifying disease from the average cut-offs from the resampling phase. The algorithm internally validates by dividing a training set repeatedly into ⅓ for a validation set and ⅔ for both model training and test sets; creating one algorithm on the model-training set and the test set using average cut-off values; computing performance on the validation set and comparing it to the average performance on the test set; and comparing the average probabilities on test sets to final probabilities on the validation set. In addition, performance of the test set is computed from an algorithm based on a pair of random forest models created from a model-training set and a test set which was a subset of the model-training/test set that was a subset of the entire training set.

In certain embodiments, the IBD diagnostic algorithm of the present invention uses measurements from 17 sero-genetic-inflammatory biological markers (e.g., ANCA, ASCA-A, ASCA-G, pANCA, anti-FlaX, SAA, anti-Fla2, ICAM, anti-OmpC, anti-CBir1, VCAM, CRP, NKX2-3, ATG16L1, STAT3, ECM1, VEGF, and a combination thereof) to compute a model score based on the first random forest model for predicting IBD vs. non-IBD. The first random model determines if a patient has IBD. If the score is less than the IBD vs. non-IBD cut-off (e.g., <0.64), the sample is predicted to be from a patient having IBD. Otherwise, the sample is predicted to be from a patient having non-IBD. Samples predicted to have IBD proceed to the next step of the algorithm, which is a decision tree or set of rules designed to rule out inconclusives based on marker patterns. If a sample matches the pattern for either of the "indeterminate" rules, the algorithm predicts the sample as having IBD, but categorizes the sample as inconclusive for CD and UC. Otherwise, the sample proceeds to the next step of the algorithm, which is a second random forest model for predicting UC vs. CD. The diagnostic algorithm then uses measurements from 11 sero-genetic-inflammatory biological markers (e.g., ANCA, ASCA-A, ASCA-G, anti-FlaX, anti-Fla2, pANCA, anti-OmpC, anti-CBir1, ECM1, STAT3, VEGF, and combinations thereof) to compute a model score based on the second random forest model for predicting UC vs. CD. If the score is less than the UC vs. CD cut-off (e.g., 0.35), the algorithm predicts the sample as having CD. Otherwise, the algorithm predicts the sample as having UC.

In some embodiments, the sero-genetic-inflammation markers used in the IBD vs. non-IBD model are ranked by an importance measure. The markers listed in descending order of importance in the training set are: ANCA, ASCA-A, ASCA-G, pANCA, anti-FlaX, SAA, anti-Fla2, ICAM, anti-OmpC, anti-CBir1, VCAM, CRP, NKX2-3, ATG16L1, STAT3, ECM1, and VEGF. In other embodiments, the sero-genetic-inflammation markers used in the UC vs. CD model are ranked by an importance measure and are listed in descending order of importance in the training set: ANCA, ASCA-A, ASCA-G, anti-FlaX, anti-Fla2, pANCA, anti-OmpC, anti-CBir1, ECM1, STAT3, and VEGF. The importance measure of a marker is described herein, see Example 3.

In certain other embodiments, the IBD diagnostic algorithm of the present invention comprises an initial step of determining whether a sample is pANCA2 negative to direct a sample to either the first random forest model for predicting IBD vs. non-IBD or to a separate pANCA decision tree analysis (see, FIG. 2 and Example 9). In certain instances, pANCA2 samples with either a negative (0 or "not detected") or a weak (+1) pANCA determination are removed from the two-step random forest algorithm queue and subjected to a decision matrix or set of rules for making a clinical prediction of IBD. A non-limiting example of a decision matrix for predicting IBD following pANCA decision tree analysis is described in Example 9. As such, in certain aspects, the pANCA decision tree can be implemented as an alternate path for making predictive IBD diagnoses in samples with pANCA2 (−) assay results.

IX. Disease Classification System

Figure 3:
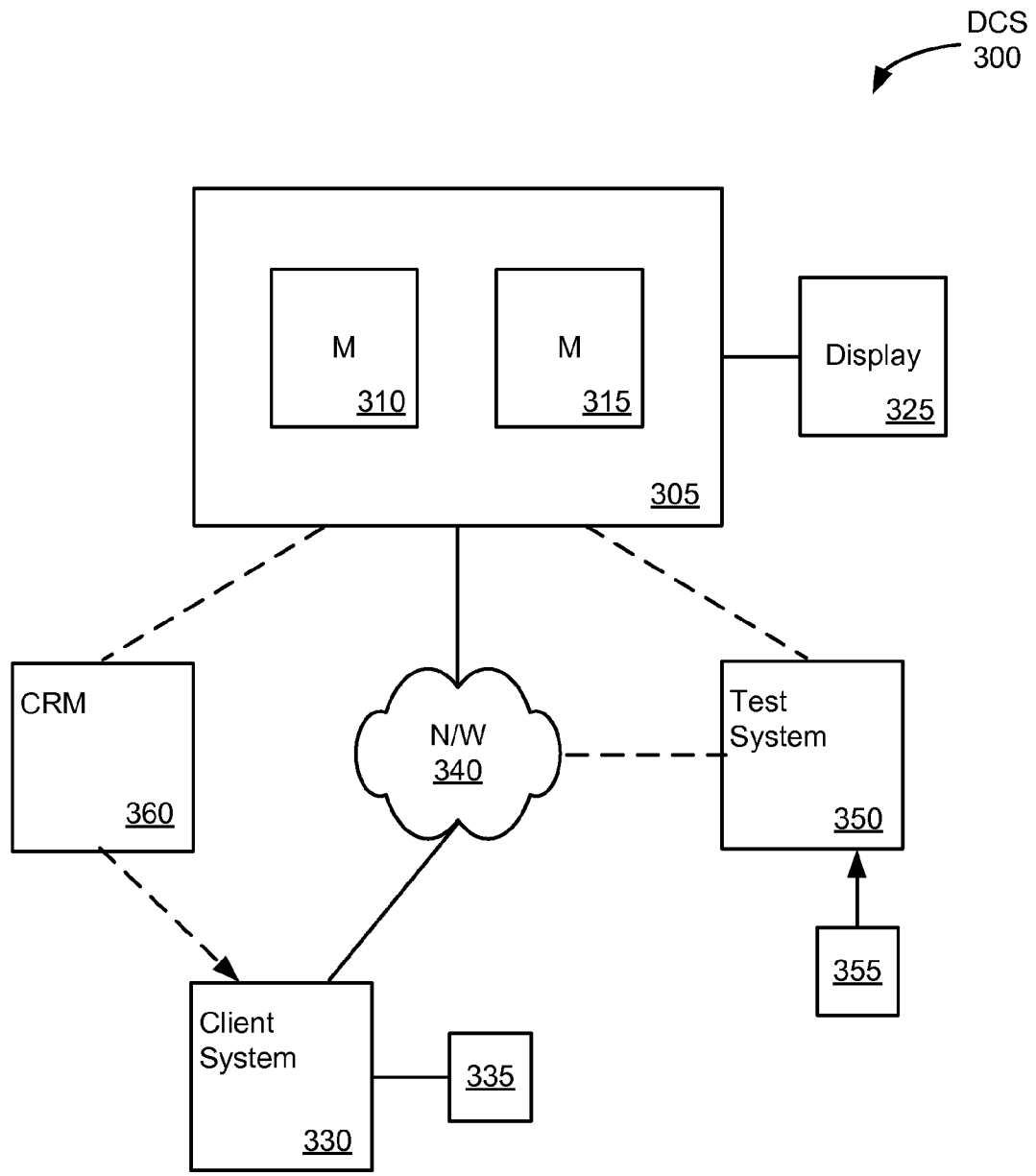
FIG. 3 illustrates an exemplary embodiment of a disease classification system (DCS) of the present invention.

FIG. 3 illustrates a disease classification system (DCS) (300) according to one embodiment of the present invention. As shown therein, a DCS includes a DCS intelligence module (305), such as a computer, having a processor (315) and memory module (310). The intelligence module also includes communication modules (not shown) for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module (325), such as a monitor or printer. In one aspect, the intelligence module receives data such as patient test results from a data acquisition module such as a test system (350), either through a direct connection or over a network (340). For example, the test system may be configured to run multianalyte tests on one or more patient samples (355) and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems (330) over the network as is well known. For example, a requesting physician or healthcare provider may obtain and view a report from the intelligence module, which may be resident in a laboratory or hospital, using a client system (330).

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system shown in FIG. 3 may include conventional, well-known elements that need not be explained in detail here. For example, the intelligence module could be implemented as a desktop personal computer, workstation, mainframe, laptop, etc. Each client system could include a desktop personal computer, workstation, laptop, PDA, cell phone, or any WAP-enabled device or any other computing device capable of interfacing directly or indirectly to the Internet or other network connection. A client system typically runs an HTTP client, e.g., a browsing program, such as Microsoft's Internet Explorer™ browser, Netscape's Navigator™ browser, Opera's browser, or a WAP-enabled browser in the case of a cell phone, PDA or other wireless device, or the like, allowing a user of the client system to access, process, and view information and pages available to it from the intelligence module over the network. Each client system also typically includes one or more user interface devices, such as a keyboard, a mouse, touch screen, pen or the like, for interacting with a graphical user interface (GUI) provided by the browser on a display (e.g., monitor screen, LCD display, etc.) (335) in conjunction with pages, forms, and other information provided by the intelligence module. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel® Pentium® processor or the like. Similarly, the intelligence module and all of its components might be operator configurable using application(s) including computer code run using a central processing unit (315) such as an Intel Pentium processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium (360) capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in R, C, C++, C#, HTML, Java, JavaScript, or any other scripting language, such as VBScript. The R programming language is preferred. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/I P, HTTP, HTTPS, Ethernet, etc.) as are well known.

According to one embodiment, the intelligence module implements a disease classification process for analyzing patient test results to determine a diagnosis of IBD or a clinical subtype thereof such as CD or UC. The data may be stored in one or more data tables or other logical data structures in memory (310) or in a separate storage or database system coupled with the intelligence module. One or more statistical analyses or processes are typically applied to a data set including test data for a particular patient. For example, the test data might include a diagnostic marker profile, which comprises data indicating the presence, level, and/or genotype of at least one or a panel of markers in a sample from the patient. In one embodiment, a statistical analysis such as a random forest is applied to test data for a particular patient, wherein the test data comprises the presence, level, and/or genotype of at least one or a panel of markers determined in a sample from the patient. The statistically derived decision(s) may be displayed on a display device associated with or coupled to the intelligence module, or the decision(s) may be provided to and displayed at a separate system, e.g., a client system (330). In particular embodiments, the statistically derived decision(s) may be displayed in the form of a report or print-out, which can optionally include a look-up table, chart, graph, or model to enable a physician to compare and interpret the displayed results to make a reasoned IBD diagnosis or prediction.

X. Therapy and Therapeutic Monitoring

Once a diagnosis of IBD has been classified or predicted according to the methods described herein, the present invention may further comprise recommending a course of therapy based upon the classification or prediction. In certain instances, the present invention may further comprise administering to the individual a therapeutically effective amount of an IBD therapeutic agent useful for treating one or more symptoms associated with IBD, CD, UC, IC, or inconclusive IBD. For therapeutic applications, the IBD therapeutic agent can be administered alone or co-administered in combination with one or more additional IBD therapeutic agents and/or one or more drugs that reduce the side-effects associated with the IBD therapeutic agent. Examples of IBD therapeutic agents include, but are not limited to, biologic agents, conventional drugs, and combinations thereof. As such, the present invention advantageously enables a clinician to practice "personalized medicine" by guiding treatment decisions and informing therapy selection for IBD such that the right drug is given to the right patient at the right time.

IBD therapeutic agents can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that an IBD therapeutic agent is administered at the same time, just prior to, or just after the administration of a second drug (e.g., another IBD therapeutic agent, a drug useful for reducing the side-effects of the IBD therapeutic agent, etc.).

A therapeutically effective amount of an IBD therapeutic agent may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, forms, or the like, preferably in unit dosage forms suitable for simple administration of precise dosages.

As used herein, the term "unit dosage form" includes physically discrete units suitable as unitary dosages for human subjects and other mammals, each unit containing a predetermined quantity of an IBD therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the IBD therapeutic agent.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an IBD therapeutic agent, any of the following: a diluent such as lactose, sucrose, dicalcium phosphate, and the like; a disintegrant such as starch or derivatives thereof a lubricant such as magnesium stearate and the like; and a binder such a starch, gum acacia, polyvinylpyrrolidone, gelatin, cellulose and derivatives thereof. An IBD therapeutic agent can also be formulated into a suppository disposed, for example, in a polyethylene glycol (PEG) carrier.

Liquid dosage forms can be prepared by dissolving or dispersing an IBD therapeutic agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBD therapeutic agent can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBD therapeutic agent can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of IBD or a clinical subtype thereof, an IBD therapeutic agent can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBD symptoms, and the IBD therapeutic agent being employed. For example, dosages can be empirically determined considering the type and severity of IBD symptoms in an individual classified as having a particular clinical subtype of IBD according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular IBD therapeutic agent in an individual. Determination of the proper dosage for a particular situation is within the skill of the practitioner. Generally, treatment is initiated with smaller dosages which are less than the optimum dose of the IBD therapeutic agent. Thereafter, the dosage is increased by small increments until the optimum effect under circumstances is reached. For convenience, the total daily dosage may be divided and administered in portions during the day, if desired.

As used herein, the term "IBD therapeutic agent" includes all pharmaceutically acceptable forms of a drug that is useful for treating one or more symptoms associated with IBD. For example, the IBD therapeutic agent can be in a racemic or isomeric mixture, a solid complex bound to an ion exchange resin, or the like. In addition, the IBD therapeutic agent can be in a solvated form. The term is also intended to include all pharmaceutically acceptable salts, derivatives, and analogs of the IBD therapeutic agent being described, as well as combinations thereof. For example, the pharmaceutically acceptable salts of an IBD therapeutic agent include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an IBD therapeutic agent is suitable for use in the methods of the present invention, e.g., a pharmaceutically acceptable salt of an IBD therapeutic agent, a free base of an IBD therapeutic agent, or a mixture thereof. Examples of suitable IBD therapeutic agents include, but are not limited to, biologic agents, conventional drugs, and combinations thereof.

Biologic agents include, e.g., anti-cytokine and chemokine antibodies such as anti-tumor necrosis factor alpha (TNFα) antibodies. Non-limiting examples of anti-TNFα antibodies include: chimeric monoclonal antibodies such as infliximab (Remicade®) (Centocor, Inc.; Horsham, Pa.), which is a chimeric IgG1 anti-TNFα monoclonal antibody; humanized monoclonal antibodies such as CDP571 and the PEGylated CDP870; fully human monoclonal antibodies such as adalimumab (Humira®) (Abbott Laboratories; Abbott Park, Ill.); p75 fusion proteins such as etanercept (Enbrel®) (Amgen; Thousand Oaks, Calif.; Wyeth Pharmaceuticals Inc.; Collegeville, Pa.), small molecules (e.g., MAP kinase inhibitors); and combinations thereof. See, Ghosh, *Novartis Found Symp.*, 263:193-205 (2004).

Other biologic agents include, e.g., anti-cell adhesion antibodies such as natalizumab (Tysabri®) (Elan Pharmaceuticals, Inc.; Dublin, Ireland; Biogen Idec; Cambridge, Mass.), which is a humanized monoclonal antibody against the cellular adhesion molecule α4-integrin, and MLN-02 (Millennium Pharmaceuticals; Cambridge, Mass.), which is a humanized IgG1 anti-α4β7-integrin monoclonal antibody; anti-T cell agents; anti-CD3 antibodies such as visilizumab (Nuvion®) (PDL BioPharma; Incline Village, Nev.), which is a humanized IgG2M3 anti-CD3 onoclonal antibody; anti-CD4 antibodies such as priliximab (cM-T412) (Centocor, Inc.; Horsham, Pa.), which is a chimeric anti-CD4 monoclonal antibody; anti-IL-2 receptor alpha (CD25) antibodies such as daclizumab Zenapax®) (PDL BioPharma; Incline Village, Nev.; Roche; Nutley, N.J.), which is a humanized IgG1 anti-CD25 monoclonal antibody, and basiliximab (Simulect®) (Novartis; Basel, Switzerland), which is a chimeric IgG1 anti-CD25 monoclonal antibody; and combinations thereof.

In addition to the foregoing biological agents, miRs or inhibitors of miRs are useful in the present invention. As such, in certain embodiments, the present invention provides treatment or prevention of IBD by introducing into or providing to a patient with IBD an effective amount of i) an miRNA inhibitor molecule or ii) a miRNA molecule.

One useful formulation for the delivery of miRs are liposomes. Liposomes and emulsions are well-known examples of delivery vehicles that may be used to deliver nucleic acids of the invention. A nucleic acid of the invention can be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877, 302, 6,008,336, 6,077,835, 5,972,901, 6,200,801, and 5,972, 900, which are incorporated by reference for those aspects. The nucleic acids may also be administered in combination with a cationic amine such as poly (L-lysine).

Examples of conventional drugs include, without limitation, aminosalicylates (e.g., mesalazine, sulfasalazine, and the like), corticosteroids (e.g., prednisone), thiopurines (e.g., azathioprine, 6-mercaptopurine, and the like), methotrexate, free bases thereof, pharmaceutically acceptable salts thereof, derivatives thereof, analogs thereof, and combinations thereof.

One skilled in the art will know of additional IBD therapeutic agents suitable for use in the present invention (see, e.g., Sands, *Surg. Clin. North Am.*, 86:1045-1064 (2006); Danese et al., *Mini Rev. Med. Chem.*, 6:771-784 (2006); Domenech, *Digestion*, 73 (Suppl. 1):67-76 (2006); Nakamura et al., *World J. Gastroenterol.*, 12:4628-4635 (2006); and Gionchetti et al., *World J. Gastroenterol.*, 12:3306-3313 (2006)).

An individual can also be monitored at periodic time intervals to assess the efficacy of a certain therapeutic regimen once diagnostic and/or predictive information has been obtained from the individual's sample. For example, the presence or level of certain markers may change based on the therapeutic effect of a treatment such as a drug. In certain embodiments, the patient can be monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

XI. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Random Forest Modeling of IBD Diagnostics Using Sero-Genetic-Inflammation (sgi) Markers This example illustrates a method of training and validating a learning statistical classifier system comprising one or a plurality of random forest models. In some embodiments, the method of creating a random forest model for diagnosing disease comprises a method of converted text-based measurements of sero-genetic-inflammation (sgi) markers into binary variables. In other embodiments, a method of creating a random forest model for diagnosing disease comprises a method of step-wise variable elimination with incomplete sample reclamation and performance error estimation through resampling. This example also illustrates a method of creating a random forest model for diagnosing disease comprising determining the importance of various sgi markers to the predictability of the model.

In some embodiments, the statistical methods and models described herein for predictive modeling of diagnostic markers related to IBD utilize the random forest method of model construction. A random forest is a classifier made up of many decision trees with a random component to building each tree. Each decision tree addresses the same classification problem, but with a different collection of examples and a different subset of features randomly selected from the dataset of examples provided. For instance, a single tree might be built using a random ⅔ of the available examples, with a random ⅔ of the features selected to make a decision split at each node of the tree. Once the forest is built during training, new examples are classified by taking a vote across all the decision trees. In the simplest case for a 2-class random forest classifier, the class with the most votes wins. In other instances, the cutoff for a winning number of votes, as established during training, is preset to optimize performance measures. In some instances, if false positives are more costly than false negatives, the cutoff might be set higher.

Random forest analysis is very robust for modeling this type of statistical data because it is highly accurate. Since each decision tree is built from a different subset of the data, random forests are less prone to over-fitting of data than other machine learning approaches. Any over-fitting or underperforming by an individual tree tends to cancel out when the ensemble average is computed.

In certain embodiments, an IBD diagnostic algorithm is established using a retrospective cohort of predicted diagnoses with known presence, absence and/or levels of sero-genetic-inflammation (sgi) markers. In some embodiments, the samples used (e.g., training and validation datasets) to build the random forest are from studies using the methods described herein. Briefly, a training dataset is used for training the algorithm and a validation dataset is used to determine the performance of the trained algorithm. The method of random forest modeling allows for comparisons of markers and thus, marker importance to predicting diagnosis can be determined.

A. Conversion of Text-Based Measurements of Sero-Genetic-Inflammation Markers into Binary Variables In some aspects, binary values are defined based on the dataset of samples (see, Table 1). In certain embodiments, the datasets comprise data of subjects predicted to have IBD, CD, UC or Irritable Bowel Syndrome (IBS), and healthy control subjects.

TABLE 1

Defined Binary Columns Added to Dataset.

| New Column Name | Binary value | Definition |
|---|---|---|
| DxIBD | 1 | If Diagnosis column is IBD CD or UC |
|  | 0 | If healthy, HC, or IBS |
| DxUC | 1 | If Diagnosis is UC |
|  | 0 | If CD |
| pANCA | 1 | If "ANCA IFA M3 (pANCA)" column is "Not Detected" or "DNAse Resistant" |
|  | 0 | If anything else (except blank) |
| GLI1 | 1 | If "GLI1 - G933D - rs2228224" is TT |
|  | 0 | If BOTH or FAM |
|  | (blank) | If UNDETERMINED |
| MDR1 | 1 | If "MDR1 Triallelic - rs2032582" is TT |
|  | 0 | If AA, GA, GG, GT, or TA |
|  | (blank) | If UNDETERMINED |
| ATG | 1 | If "ATG16LI - T300A - rs2241880" is FAM |
|  | 0 | If BOTH or VIC |
|  | (blank) | If UNDETERMINED |
| ECM1 | 1 | If "ECM1 - rs3737240" is FAM |
|  | 0 | If BOTH or VIC |
|  | (blank) | If UNDETERMINED |
| IRGM89 | 1 | If "IRGM - rs13361189" is VIC |
|  | 0 | If BOTH or FAM |
|  | (blank) | If UNDETERMINED |
| IRGM47 | 1 | If "IRGM - rs4958847" is VIC |
|  | 0 | If BOTH or FAM |
|  | (blank) | If UNDETERMINED |
| NKX2 | 1 | If "NKX2-3 - rs10883365" is FAM |
|  | 0 | If BOTH or VIC |
|  | (blank) | If UNDETERMINED |
| MAGI2 | 1 | If "MAGI2 rs2160322" is VIC |
|  | 0 | If BOTH or FAM |
|  | (blank) | If UNDETERMINED |
| STAT3 | 1 | If "STAT3 rs744166" is VIC |
|  | 0 | If BOTH or FAM |
|  | (blank) | If UNDETERMINED |

B. Step-Wise Variable Elimination with Incomplete Sample Reclamation and Performance Error Estimation Through Resampling In other embodiments, a method of creating a random forest model for diagnosing disease comprises a method of step-wise variable elimination with incomplete sample reclamation and performance error estimation through resampling. In certain embodiments, methods are used to determine whether markers could improve diagnostic predictions. In some instances when there is limited data with complete entries for all markers, all markers are used during training. And then, after eliminating less important markers, samples are reclaimed that were missing the less important marker and used in the training dataset.

In some aspects, the following steps of the "Variable Elimination Protocol" are used:
1) Temporarily eliminate incomplete rows of data
2) Split data at random into a training dataset (⅔ of rows) and a test dataset (⅓ of rows); Note: this will be repeated numerous times.
3) Create a random forest model from the training dataset
4) Determine performance using predictions on test data
   a. ROC score
   b. Sensitivity/specificity using a cutoff that maximizes an objective function, where W is an adjustable fractional weight set to 0.3:
      1. $W(1-\text{sensitivity})^2 + (1-W)(1-\text{specificity})^2$
5) Compute importance measure of each variable for the given forest a. Randomly permute values of one variable for the given forest
b. Determine resulting degradation in accuracy
c. Repeat for every variable
6) Compute standard error from the different random splits of data performed so far
7) If the standard error is small enough or we have exceeded a maximum allowable number of iterations, we eliminate one variable:
a. Find the variable whose average importance over the multiple data splittings is smallest
b. Go back to the data set before the last elimination of incomplete rows
c. Delete the "unimportant" variable
d. If any variables remain go back to the beginning of the protocol The protocol listed above is used for determining which sero-genetic-inflammation (sgi) markers can improve the prediction of IBD vs. non-IBD diagnosis. Table 2 illustrates the variable importance for IBD vs. non-IBD diagnosis using 23 sero-genetic-inflammation markers, such as ASCA-A, IRGM47, IRGM89, MDR1, ECM1, VEGF, CRP, NKX2-3, STAT3, ATG16L1, SAA, GLI1, MAGI2, anti-OmpA, ICAM, anti-Fla2, ASCA-G, ANCA, anti-FlaX, VCAM-1, anti-Cbir1, anti-OmpC, and pANCA. In this exemplary description of random forest modeling of IBD diagnostics, the following criteria were required: a minimum number of resamplings of 5, a maximum of 20, and a standard error goal of 0.01 in the ROC score on separate test data. The term "Least_IMP" refers to the variable having the smallest average importance. The term "OOB_ROC" refers to the ROC score computed on the out-of-bag predictions during training. The term "TEST_Roc" refers to the ROC score on the separate test set, not used to create the forest. The terms "SENS" and "SPEC" refer to sensitivity and specificity, respectively, on the test set. The term "NTRAIN0" refers to the number of training samples with DxIBD equal to 0 (i.e., non-IBD). The term "NTRAIN1" refers to the number of training samples with DxIBD equal to 1 (i.e., IBD). The terms "NTEST0" and "NTEST1" are the number of test samples. Notably, all numbers in the table below are averages over multiple re-splittings, and error bars are standard errors (i.e., estimates of the error in means). "NVAR" refers to the determined importance of a sero-genetic-inflammation marker to IBD diagnostics. Table 2 shows that pANCA has the most importance and ASCA-A has less importance in the algorithm.

TABLE 2

Marker Importance for IBD vs. non-IBD Using Sero-Genetic-Inflammation Markers.

|    | NVAR | OOB_ROC | TEST_ROC | SENS | SPEC | LEAST_IMP | NTRAIN0 | NTRAIN1 | NTEST0 | NTEST1 |
|----|------|---------|----------|------|------|-----------|---------|---------|--------|--------|
| 1  | 23 | 0.919 +− 0.007 | 0.937 +− 0.010 | 0.897 +− 0.018 | 0.913 +− 0.014 | ASCAA | 59.7 +− 1.4 | 53.3 +− 1.4 | 30.3 +− 1.4 | 26.7 +− 1.4 |
| 2  | 22 | 0.903 +− 0.006 | 0.943 +− 0.010 | 0.846 +− 0.018 | 0.951 +− 0.020 | IRGM47 | 59.8 +− 1.9 | 53.2 +− 1.9 | 30.2 +− 1.9 | 26.8 +− 1.9 |
| 3  | 21 | 0.918 +− 0.005 | 0.914 +− 0.011 | 0.855 +− 0.017 | 0.889 +− 0.012 | IRGM89 | 60.5 +− 0.7 | 54.5 +− 0.7 | 29.5 +− 0.7 | 28.5 +− 0.7 |
| 4  | 20 | 0.908 +− 0.004 | 0.955 +− 0.006 | 0.910 +− 0.007 | 0.934 +− 0.019 | MDR1 | 60.0 +− 1.4 | 57.0 +− 1.4 | 30.0 +− 1.4 | 29.0 +− 1.4 |
| 5  | 19 | 0.917 +− 0.006 | 0.941 +− 0.010 | 0.904 +− 0.015 | 0.942 +− 0.012 | ECM1 | 60.1 +− 0.6 | 56.9 +− 0.6 | 29.9 +− 0.6 | 29.1 +− 0.6 |
| 6  | 18 | 0.903 +− 0.004 | 0.908 +− 0.008 | 0.774 +− 0.018 | 0.914 +− 0.016 | VEGF | 87.2 +− 2.2 | 281.8 +− 2.2 | 41.8 +− 2.2 | 143.2 +− 2.2 |
| 7  | 17 | 0.893 +− 0.003 | 0.903 +− 0.009 | 0.770 +− 0.011 | 0.906 +− 0.009 | CRP | 132.2 +− 1.4 | 283.8 +− 1.4 | 61.8 +− 1.4 | 146.2 +− 1.4 |
| 8  | 16 | 0.899 +− 0.004 | 0.900 +− 0.006 | 0.807 +− 0.020 | 0.877 +− 0.011 | NKX2 | 130.4 +− 2.8 | 285.6 +− 2.8 | 63.6 +− 2.8 | 144.4 +− 2.8 |
| 9  | 15 | 0.890 +− 0.007 | 0.918 +− 0.010 | 0.807 +− 0.019 | 0.885 +− 0.012 | STAT3 | 133.4 +− 2.0 | 283.6 +− 2.0 | 60.6 +− 2.0 | 148.4 +− 2.0 |
| 10 | 14 | 0.897 +− 0.004 | 0.910 +− 0.006 | 0.760 +− 0.014 | 0.923 +− 0.013 | ATG16L1 | 132.4 +− 1.6 | 286.6 +− 1.6 | 61.6 +− 1.6 | 148.4 +− 1.6 |
| 11 | 13 | 0.904 +− 0.003 | 0.905 +− 0.005 | 0.778 +− 0.019 | 0.918 +− 0.012 | SAA | 132.0 +− 2.2 | 292.0 +− 2.2 | 63.0 +− 2.2 | 149.0 +− 2.2 |
| 12 | 12 | 0.899 +− 0.002 | 0.893 +− 0.005 | 0.779 +− 0.029 | 0.879 +− 0.021 | GLI1 | 125.6 +− 1.6 | 306.4 +− 1.6 | 69.4 +− 1.6 | 146.6 +− 1.6 |
| 13 | 11 | 0.902 +− 0.006 | 0.906 +− 0.006 | 0.778 +− 0.018 | 0.910 +− 0.012 | MAGI2 | 129.4 +− 2.4 | 307.6 +− 2.4 | 70.6 +− 2.4 | 148.4 +− 2.4 |
| 14 | 10 | 0.905 +− 0.004 | 0.907 +− 0.004 | 0.758 +− 0.014 | 0.899 +− 0.007 | OmpA | 139.6 +− 3.8 | 316.4 +− 3.8 | 70.4 +− 3.8 | 157.6 +− 3.8 |
| 15 | 9 | 0.890 +− 0.003 | 0.876 +− 0.007 | 0.740 +− 0.022 | 0.872 +− 0.017 | ICAM | 162.8 +− 1.6 | 323.2 +− 1.6 | 85.2 +− 1.6 | 158.8 +− 1.6 |
| 16 | 8 | 0.886 +− 0.004 | 0.890 +− 0.007 | 0.763 +− 0.024 | 0.894 +− 0.025 | Fla2 | 169.6 +− 2.1 | 325.4 +− 2.1 | 86.4 +− 2.1 | 161.6 +− 2.1 |
| 17 | 7 | 0.879 +− 0.005 | 0.880 +− 0.009 | 0.716 +− 0.028 | 0.907 +− 0.007 | ASCAG | 173.8 +− 1.5 | 324.2 +− 1.5 | 86.2 +− 1.5 | 163.8 +− 1.5 |
| 18 | 6 | 0.878 +− 0.005 | 0.887 +− 0.008 | 0.773 +− 0.019 | 0.878 +− 0.015 | ANCA | 173.4 +− 1.8 | 324.6 +− 1.8 | 86.6 +− 1.8 | 163.4 +− 1.8 |
| 19 | 5 | 0.868 +− 0.005 | 0.893 +− 0.007 | 0.739 +− 0.014 | 0.917 +− 0.008 | Flax | 170.2 +− 2.0 | 327.8 +− 2.0 | 89.8 +− 2.0 | 160.2 +− 2.0 |
| 20 | 4 | 0.868 +− 0.006 | 0.869 +− 0.007 | 0.741 +− 0.013 | 0.898 +− 0.013 | VCAM | 172.8 +− 4.0 | 331.2 +− 4.0 | 89.2 +− 4.0 | 162.8 +− 4.0 |
| 21 | 3 | 0.820 +− 0.006 | 0.809 +− 0.005 | 0.666 +− 0.023 | 0.865 +− 0.017 | CBir1 | 254.2 +− 1.0 | 442.8 +− 1.0 | 120.8 +− 1.0 | 228.2 +− 1.0 |
| 22 | 2 | 0.786 +− 0.004 | 0.773 +− 0.009 | 0.592 +− 0.016 | 0.861 +− 0.008 | OmpC | 251.9 +− 4.1 | 445.1 +− 4.1 | 123.1 +− 4.1 | 225.9 +− 4.1 |

TABLE 2-continued

Marker Importance for IBD vs. non-IBD Using Sero-Genetic-Inflammation Markers.

| | NVAR | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 23 | 1 | 0.507 +− 0.003 | 0.731 +− 0.006 | 0.5036 +− | 0.913 +− 0.014 | pANCA 0.004 | 242.4 +− 3.0 | 454.6 +− 3.0 | 132.6 +− 3.0 | 216.4 +− 3.0 |

In some instances, the size of the training and test datasets increased as less important variables were deleted and rows were restored. In other instances, a ROC score on the test dataset was as high as 0.95. In certain instances, two markers (i.e., VCAM and anti-FlaX) displaced two serological markers (i.e., ASCA-G and ASCA-A) as one of the most important markers. Table 3 shows that pANCA was the most important marker for predicting IBD vs. non-IBD when using only serology markers, and ASCA-G was less important in this cohort. In certain instances, the best test ROC score was 0.8, which indicates that the markers tested can considerably reduce error.

TABLE 3

Marker Importance for IBD vs. non-IBD Using Only Serology Markers.

| | NVAR | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 1 | 6 | 0.846 +− 0.007 | 0.850 +− 0.010 | 0.699 +− 0.019 | 0.893 +− 0.010 | ASCAG | 248.3 +− 3.1 | 448.7 +− 3.1 | 126.7 +− 3.1 | 222.3 +− 3.1 |
| 2 | 5 | 0.845 +− 0.005 | 0.843 +− 0.008 | 0.707 +− 0.013 | 0.853 +− 0.010 | ANCA | 254.4 +− 3.9 | 442.6 +− 3.9 | 120.6 +− 3.9 | 228.4 +− 3.9 |
| 3 | 4 | 0.843 +− 0.005 | 0.852 +− 0.010 | 0.714 +− 0.010 | 0.877 +− 0.013 | ASCAA | 246.2 +− 3.8 | 450.8 +− 3.8 | 128.8 +− 3.8 | 220.2 +− 3.8 |
| 4 | 3 | 0.817 +− 0.006 | 0.815 +− 0.008 | 0.669 +− 0.014 | 0.870 +− 0.007 | CBir1 | 248.8 +− 1.9 | 448.2 +− 1.9 | 126.2 +− 1.9 | 222.8 +− 1.9 |
| 5 | 2 | 0.776 +− 0.009 | 0.784 +− 0.010 | 0.618 +− 0.014 | 0.876 +− 0.014 | OmpC | 248.7 +− 2.0 | 448.3 +− 2.0 | 126.3 +− 2.0 | 222.7 +− 2.0 |
| 6 | 1 | 0.511 +− 0.002 | 0.742 +− 0.005 | 1.000 +− 0.000 | 0.976 +− 0.005 | pANCA | 248.0 +− 3.0 | 449.0 +− 3.0 | 127.0 +− 3.0 | 222.0 +− 3.0 |

The protocol described above can also be used for determining the sero-genetic-inflammation markers that can help improve the prediction of UC vs. CD. Table 2 illustrates the marker importance for UC vs. CD diagnosis using 23 sero-genetic-inflammation markers, such as ASCA-A, IRGM47, IRGM89, MDR1, ECM1, VEGF, CRP, NKX2-3, STAT3, ATG16L1, SAA, GLI1, MAGI2, anti-OmpA, ICAM, anti-Fla2, ASCA-G, ANCA, anti-FlaX, VCAM-1, anti-Cbir1, anti-OmpC, and pANCA. In some instances, the data was limited wherein the cohort contains no samples with all 23 markers and a diagnosis of UC. In certain instances, each marker can be compared to the number of diagnoses in the cohort and then it can be determined whether a variable (e.g., marker) can be eliminated (see, Table 4).

TABLE 4

Number of UC Diagnoses (NUC) and Number of CD Diagnoses (NCD) for Each Marker.

| | MARKER | NUC | NCD |
|---|---|---|---|
| 1 | ANCA | 435 | 236 |
| 2 | pANCA | 435 | 236 |
| 3 | ASCAA | 435 | 236 |
| 4 | ASCAG | 435 | 236 |
| 5 | OmpC | 435 | 236 |
| 6 | CBir1 | 435 | 236 |
| 7 | GLI1 | 433 | 243 |
| 8 | MDR1 | 432 | 242 |

TABLE 4-continued

Number of UC Diagnoses (NUC) and Number of CD Diagnoses (NCD) for Each Marker.

| | MARKER | NUC | NCD |
|---|---|---|---|
| 9 | ATG16L1 | 430 | 243 |
| 10 | ECM1 | 108 | 171 |
| 11 | IRGM89 | 427 | 231 |
| 12 | IRGM47 | 425 | 229 |
| 13 | NKX2 | 402 | 202 |
| 14 | MAGI2 | 401 | 200 |

TABLE 4-continued

Number of UC Diagnoses (NUC) and Number of CD Diagnoses (NCD) for Each Marker.

| | MARKER | NUC | NCD |
|---|---|---|---|
| 15 | STAT3 | 401 | 200 |
| 16 | Flax | 405 | 231 |
| 17 | Fla2 | 405 | 232 |
| 18 | OmpA | 397 | 231 |
| 19 | CRP | 327 | 176 |
| 20 | SAA | 315 | 174 |
| 21 | ICAM | 322 | 177 |
| 22 | VCAM | 326 | 168 |
| 23 | VEGF | 427 | 236 |

In this instance, the marker ECM1 was associated with the fewest number of UC diagnoses and thereby eliminated from the step-wise Variable Elimination Protocol. The methods of the present invention and a dataset of 22 sero-genetic-inflammation markers for predicting UC vs. CD can be used to build a random forest classifier (see, Table 5).

TABLE 5

Marker Importance for UC vs. CD Prediction for 22 Markers Except ECM1.

|  | NVAR | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 1 | 22 | 0.932 +− 0.005 | 0.944 +− 0.007 | 0.877 +− 0.013 | 0.913 +− 0.012 | STAT3 | 84.8 +− 2.7 | 191.2 +− 2.7 | 47.2 +− 2.7 | 91.8 +− 2.7 |
| 2 | 21 | 0.940 +− 0.004 | 0.919 +− 0.010 | 0.850 +− 0.015 | 0.869 +− 0.022 | MDR1 | 88.3 +− 0.8 | 189.7 +− 0.8 | 46.7 +− 0.8 | 93.3 +− 0.8 |
| 3 | 20 | 0.939 +− 0.004 | 0.928 +− 0.009 | 0.833 +− 0.012 | 0.901 +− 0.011 | GLI1 | 89.0 +− 1.1 | 189.0 +− 1.1 | 46.0 +− 1.1 | 94.0 +− 1.1 |
| 4 | 19 | 0.941 +− 0.003 | 0.930 +− 0.003 | 0.865 +− 0.010 | 0.895 +− 0.016 | MAGI2 | 89.6 +− 1.5 | 189.4 +− 1.5 | 45.4 +− 1.5 | 94.6 +− 1.5 |
| 5 | 18 | 0.938 +− 0.004 | 0.951 +− 0.005 | 0.876 +− 0.016 | 0.921 +− 0.011 | NKX2 | 90.2 +− 2.1 | 189.8 +− 2.1 | 46.8 +− 2.1 | 94.2 +− 2.1 |
| 6 | 17 | 0.940 +− 0.004 | 0.954 +− 0.004 | 0.868 +− 0.017 | 0.930 +− 0.006 | IRGM47 | 100.2 +− 2.3 | 187.8 +− 2.3 | 48.8 +− 2.3 | 96.2 +− 2.3 |
| 7 | 16 | 0.938 +− 0.003 | 0.937 +− 0.007 | 0.882 +− 0.013 | 0.903 +− 0.010 | VCAM | 105.0 +− 1.5 | 190.0 +− 1.5 | 52.0 +− 1.5 | 96.0 +− 1.5 |
| 8 | 15 | 0.947 +− 0.001 | 0.942 +− 0.008 | 0.871 +− 0.029 | 0.910 +− 0.024 | CRP | 114.6 +− 1.5 | 185.4 +− 1.5 | 50.4 +− 1.5 | 100.6 +− 1.5 |
| 9 | 14 | 0.946 +− 0.003 | 0.938 +− 0.010 | 0.834 +− 0.029 | 0.920 +− 0.010 | IRGM89 | 109.1 +− 1.8 | 190.9 +− 1.8 | 55.9 +− 1.8 | 95.1 +− 1.8 |
| 10 | 13 | 0.942 +− 0.003 | 0.944 +− 0.005 | 0.853 +− 0.010 | 0.927 +− 0.009 | ATG16L1 | 110.4 +− 1.6 | 195.6 +− 1.6 | 60.6 +− 1.6 | 93.4 +− 1.6 |
| 11 | 12 | 0.944 +− 0.003 | 0.944 +− 0.009 | 0.888 +− 0.009 | 0.894 +− 0.014 | VEGF | 107.8 +− 1.8 | 202.2 +− 1.8 | 63.2 +− 1.8 | 92.8 +− 1.8 |
| 12 | 11 | 0.944 +− 0.002 | 0.936 +− 0.004 | 0.838 +− 0.014 | 0.907 +− 0.013 | pANCA | 115.4 +− 3.1 | 198.6 +− 3.1 | 55.6 +− 3.1 | 101.4 +− 3.1 |
| 13 | 10 | 0.943 +− 0.005 | 0.947 +− 0.006 | 0.869 +− 0.027 | 0.916 +− 0.008 | CBir1 | 111.8 +− 0.8 | 202.2 +− 0.8 | 59.2 +− 0.8 | 97.8 +− 0.8 |
| 14 | 9 | 0.943 +− 0.002 | 0.939 +− 0.005 | 0.855 +− 0.020 | 0.923 +− 0.017 | Fla2 | 116.8 +− 1.6 | 197.2 +− 1.6 | 54.2 +− 1.6 | 102.8 +− 1.6 |
| 15 | 8 | 0.937 +− 0.004 | 0.944 +− 0.010 | 0.836 +− 0.018 | 0.929 +− 0.010 | OmpA | 115.6 +− 2.6 | 198.4 +− 2.6 | 55.4 +− 2.6 | 102.6 +− 2.6 |
| 16 | 7 | 0.938 +− 0.003 | 0.953 +− 0.004 | 0.849 +− 0.016 | 0.947 +− 0.016 | SAA | 114.2 +− 0.7 | 205.8 +− 0.7 | 56.8 +− 0.7 | 103.2 +− 0.7 |
| 17 | 6 | 0.942 +− 0.004 | 0.942 +− 0.008 | 0.838 +− 0.016 | 0.897 +− 0.008 | ANCA | 112.7 +− 2.5 | 215.3 +− 2.5 | 61.3 +− 2.5 | 103.7 +− 2.5 |
| 18 | 5 | 0.938 +− 0.004 | 0.946 +− 0.006 | 0.859 +− 0.008 | 0.900 +− 0.013 | Flax | 116.8 +− 1.9 | 211.2 +− 1.9 | 57.2 +− 1.9 | 107.8 +− 1.9 |
| 19 | 4 | 0.946 +− 0.004 | 0.934 +− 0.007 | 0.892 +− 0.023 | 0.889 +− 0.013 | ASCAA | 117.0 +− 2.7 | 215.0 +− 2.7 | 60.0 +− 2.7 | 107.0 +− 2.7 |
| 20 | 3 | 0.913 +− 0.005 | 0.917 +− 0.008 | 0.820 +− 0.020 | 0.899 +− 0.007 | ICAM | 113.4 +− 1.7 | 218.6 +− 1.7 | 63.6 +− 1.7 | 103.4 +− 1.7 |
| 21 | 2 | 0.801 +− 0.006 | 0.813 +− 0.008 | 0.632 +− 0.019 | 0.829 +− 0.019 | OmpC | 158.2 +− 2.6 | 288.8 +− 2.6 | 77.8 +− 2.6 | 146.2 +− 2.6 |
| 22 | 1 | 0.754 +− 0.007 | 0.748 +− 0.007 | 0.584 +− 0.014 | 0.773 +− 0.009 | ASCAG | 157.6 +− 1.7 | 289.4 +− 1.7 | 78.4 +− 1.7 | 145.6 +− 1.7 |

Table 5 shows that ASCA-G was the most important sero-genetic-inflammation marker for predicting UC vs. CD, and STAT3 was less important when using the random forest model for the cohort. In this instance, a ROC score on the test set was as high as 0.95 with the 7 markers determined to have the highest marker importance (e.g., ASCA-G, ICAM, ASCA-A, anti-FlaX, ANCA and SAA). Notably, two markers (i.e., VCAM and anti-FlaX) in the top 6 most important variables displaced two serological markers.

Since data is limited for all 22 markers together, samples were reclaimed during training as less important variables were deleted. The variable importance of using only serology markers (e.g., ASCA-G, pANCA, anti-OmpC, ANCA, ASCA-A and anti-CBir1) was determined using the methods described herein (see, Table 6). The best test ROC score was 0.89, which is significantly less than the 0.95 score seen for the top 7 markers.

TABLE 6

Marker Importance for UC vs. CD Prediction Using Only Serology Markers.

|  | NVAR | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 1 | 6 | 0.880 +− 0.005 | 0.879 +− 0.009 | 0.764 +− 0.016 | 0.850 +− 0.015 | CBir1 | 156.0 +− 1.9 | 291.0 +− 1.9 | 80.8 +− 1.9 | 144.0 +− 1.9 |
| 2 | 5 | 0.878 +− 0.006 | 0.890 +− 0.009 | 0.768 +− 0.028 | 0.860 +− 0.014 | ASCAA | 157.0 +− 2.0 | 290.0 +− 2.0 | 79.0 +− 2.0 | 145.0 +− 2.0 |
| 3 | 4 | 0.842 +− 0.006 | 0.870 +− 0.009 | 0.771 +− 0.014 | 0.821 +− 0.013 | ANCA | 158.2 +− 2.1 | 288.8 +− 2.1 | 77.8 +− 2.1 | 146.2 +− 2.1 |
| 4 | 3 | 0.852 +− 0.004 | 0.848 +− 0.004 | 0.748 +− 0.010 | 0.823 +− 0.003 | OmpC | 161.6 +− 2.8 | 285.4 +− 2.8 | 74.4 +− 2.8 | 149.6 +− 2.8 |
| 5 | 2 | 0.801 +− 0.006 | 0.805 +− 0.007 | 0.628 +− 0.024 | 0.822 +− 0.023 | pANCA | 159.0 +− 2.5 | 288.0 +− 2.5 | 77.0 +− 2.5 | 147.0 +− 2.5 |

TABLE 6-continued

Marker Importance for UC vs. CD Prediction Using Only Serology Markers.

| NVAR | | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 6 | 1 | 0.735 +− 0.007 | 0.742 +− 0.009 | 0.595 +− 0.022 | 0.755 +− 0.019 | ASCAG | 157.0 +− 2.8 | 290.0 +− 2.8 | 79.0 +− 2.8 | 145.0 +− 2.8 |

Correlations and associations for all possible pairwise combinations of the 17 markers used in some part of the sgi algorithm were calculated. For continuous variable pairs and for continuous-binary variable pairs, Pearson correlation coefficients and their p-values were calculated. For binary-binary variable pairs, association was evaluated with Chi-squared analysis. All calculations were done using the software program Matlab.

The results are presented in Tables 7 and 8. Table 7 lists pairwise correlations between continuous variables and between continuous and binary variables, along with their p-values. Note that associations between binary variables transformed from text-based data are not shown here. Table 8 lists statistically significant pairwise correlations. 42 significant correlations were found. None involved associations between genetic markers, pANCA, or pANCA2. All but one (ANCA and ASCA-G) showed positive correlations.

C. Pairwise Correlations Among Markers Used in the sgi Algorithm.

Correlations were calculated using all pairwise combinations of continuous variables, and of continuous and binary variables. Pearson correlation coefficients and the p-value for each correlation coefficient are shown. The p-value represents statistical significance relative to a correlation coefficient of 0; p-values of 0.0000 are less than $10^{-4}$.

TABLE 7

Correlations for All Unique Pairwise Combinations.

| Marker 1 | Marker 2 | Correlation Coefficient | P-value |
|---|---|---|---|
| ASCAA | ASCAG | 0.7472 | 0.0000 |
| ASCAA | ANCA | −0.0915 | 0.0004 |
| ASCAA | OmpC | 0.2191 | 0.0000 |
| ASCAA | CBir1 | 0.2878 | 0.0000 |
| ASCAA | Fla2 | 0.3742 | 0.0000 |
| ASCAA | FlaX | 0.4015 | 0.0000 |
| ASCAA | pANCA | −0.0204 | 0.4270 |
| ASCAA | VEGF | 0.1004 | 0.0001 |
| ASCAA | CRP | 0.1160 | 0.0000 |
| ASCAA | SAA | 0.1451 | 0.0000 |
| ASCAA | ICAM | 0.0721 | 0.0049 |
| ASCAA | VCAM | 0.0714 | 0.0054 |
| ASCAA | ATG16L1 | 0.0340 | 0.1847 |
| ASCAA | NKX23 | −0.0050 | 0.8443 |
| ASCAA | ECM1 | −0.0357 | 0.1641 |
| ASCAA | STAT3 | −0.0150 | 0.5601 |
| ASCAA | pANCA2 | −0.0798 | 0.0018 |
| ASCAG | ANCA | −0.0987 | 0.0001 |
| ASCAG | OmpC | 0.1837 | 0.0000 |
| ASCAG | CBir1 | 0.2932 | 0.0000 |
| ASCAG | Fla2 | 0.3646 | 0.0000 |
| ASCAG | FlaX | 0.3882 | 0.0000 |
| ASCAG | pANCA | −0.0448 | 0.0806 |
| ASCAG | VEGF | 0.0970 | 0.0002 |
| ASCAG | CRP | 0.1029 | 0.0001 |
| ASCAG | SAA | 0.1222 | 0.0000 |
| ASCAG | ICAM | 0.0543 | 0.0343 |
| ASCAG | VCAM | 0.0640 | 0.0125 |
| ASCAG | ATG16L1 | 0.0259 | 0.3133 |
| ASCAG | NKX23 | 0.0150 | 0.5595 |
| ASCAG | ECM1 | −0.0682 | 0.0078 |

TABLE 7-continued

Correlations for All Unique Pairwise Combinations.

| Marker 1 | Marker 2 | Correlation Coefficient | P-value |
|---|---|---|---|
| ASCAG | STAT3 | −0.0069 | 0.7868 |
| ASCAG | pANCA2 | −0.0858 | 0.0008 |
| ANCA | OmpC | 0.0177 | 0.4895 |
| ANCA | CBir1 | −0.0514 | 0.0451 |
| ANCA | Fla2 | −0.0555 | 0.0304 |
| ANCA | FlaX | −0.0600 | 0.0193 |
| ANCA | pANCA | 0.6071 | 0.0000 |
| ANCA | VEGF | 0.0511 | 0.0462 |
| ANCA | CRP | 0.0654 | 0.0108 |
| ANCA | SAA | 0.0670 | 0.0090 |
| ANCA | ICAM | 0.0980 | 0.0001 |
| ANCA | VCAM | 0.0760 | 0.0030 |
| ANCA | ATG16L1 | 0.0389 | 0.1291 |
| ANCA | NKX23 | 0.0408 | 0.1117 |
| ANCA | ECM1 | 0.0032 | 0.9022 |
| ANCA | STAT3 | −0.0383 | 0.1358 |
| ANCA | pANCA2 | 0.8180 | 0.0000 |
| OmpC | CBir1 | 0.0798 | 0.0019 |
| OmpC | Fla2 | 0.1332 | 0.0000 |
| OmpC | FlaX | 0.1451 | 0.0000 |
| OmpC | pANCA | 0.0398 | 0.1211 |
| OmpC | VEGF | 0.0763 | 0.0029 |
| OmpC | CRP | 0.0697 | 0.0066 |
| OmpC | SAA | 0.0827 | 0.0013 |
| OmpC | ICAM | 0.0784 | 0.0022 |
| OmpC | VCAM | 0.1000 | 0.0001 |
| OmpC | ATG16L1 | 0.0198 | 0.4408 |
| OmpC | NKX23 | 0.0133 | 0.6030 |
| OmpC | ECM1 | −0.0308 | 0.2308 |
| OmpC | STAT3 | −0.0189 | 0.4622 |
| OmpC | pANCA2 | 0.0077 | 0.7634 |
| CBir1 | Fla2 | 0.7023 | 0.0000 |
| CBir1 | FlaX | 0.7190 | 0.0000 |
| CBir1 | pANCA | −0.0419 | 0.1025 |
| CBir1 | VEGF | 0.0819 | 0.0014 |
| CBir1 | CRP | 0.0724 | 0.0048 |
| CBir1 | SAA | 0.0771 | 0.0026 |
| CBir1 | ICAM | 0.0556 | 0.0302 |
| CBir1 | VCAM | 0.0119 | 0.6417 |
| CBir1 | ATG16L1 | 0.0260 | 0.3120 |
| CBir1 | NKX23 | 0.0327 | 0.2026 |
| CBir1 | ECM1 | 0.0121 | 0.6374 |
| CBir1 | STAT3 | 0.0093 | 0.7186 |
| CBir1 | pANCA2 | −0.0598 | 0.0198 |
| Fla2 | FlaX | 0.9530 | 0.0000 |
| Fla2 | pANCA | −0.0136 | 0.5975 |
| Fla2 | VEGF | 0.1232 | 0.0000 |
| Fla2 | CRP | 0.1097 | 0.0000 |
| Fla2 | SAA | 0.1167 | 0.0000 |
| Fla2 | ICAM | 0.0365 | 0.1545 |
| Fla2 | VCAM | 0.0249 | 0.3328 |
| Fla2 | ATG16L1 | 0.0392 | 0.1269 |
| Fla2 | NKX23 | 0.0210 | 0.4139 |
| Fla2 | ECM1 | −0.0107 | 0.6779 |
| Fla2 | STAT3 | 0.0064 | 0.8023 |
| Fla2 | pANCA2 | −0.0482 | 0.0602 |
| FlaX | pANCA | −0.0147 | 0.5659 |
| FlaX | VEGF | 0.1380 | 0.0000 |
| FlaX | CRP | 0.1305 | 0.0000 |
| FlaX | SAA | 0.1321 | 0.0000 |
| FlaX | ICAM | 0.0342 | 0.1827 |
| FlaX | VCAM | 0.0186 | 0.4697 |
| FlaX | ATG16L1 | 0.0336 | 0.1898 |

TABLE 7-continued

Correlations for All Unique Pairwise Combinations.

| Marker 1 | Marker 2 | Correlation Coefficient | P-value |
|---|---|---|---|
| FlaX | NKX23 | 0.0236 | 0.3569 |
| FlaX | ECM1 | −0.0119 | 0.6433 |
| FlaX | STAT3 | 0.0084 | 0.7427 |
| FlaX | pANCA2 | −0.0562 | 0.0284 |
| pANCA | VEGF | 0.0259 | 0.3132 |
| pANCA | CRP | 0.0659 | 0.0101 |
| pANCA | SAA | 0.0584 | 0.0227 |
| pANCA | ICAM | 0.0729 | 0.0045 |
| pANCA | VCAM | 0.0573 | 0.0254 |
| VEGF | CRP | 0.3037 | 0.0000 |
| VEGF | SAA | 0.2628 | 0.0000 |
| VEGF | ICAM | 0.1413 | 0.0000 |
| VEGF | VCAM | 0.1017 | 0.0001 |
| VEGF | ATG16L1 | 0.0519 | 0.0429 |
| VEGF | NKX23 | 0.0442 | 0.0853 |
| VEGF | ECM1 | 0.0434 | 0.0904 |
| VEGF | STAT3 | −0.0102 | 0.6899 |
| VEGF | pANCA2 | 0.0484 | 0.0591 |
| CRP | SAA | 0.8056 | 0.0000 |
| CRP | ICAM | 0.2810 | 0.0000 |
| CRP | VCAM | 0.2625 | 0.0000 |
| CRP | ATG16L1 | 0.0023 | 0.9289 |
| CRP | NKX23 | 0.0311 | 0.2255 |
| CRP | ECM1 | 0.0253 | 0.3251 |
| CRP | STAT3 | 0.0410 | 0.1102 |
| CRP | pANCA2 | 0.0640 | 0.0126 |
| SAA | ICAM | 0.2487 | 0.0000 |
| SAA | VCAM | 0.2611 | 0.0000 |
| SAA | ATG16L1 | 0.0347 | 0.1763 |
| SAA | NKX23 | 0.0064 | 0.8046 |
| SAA | ECM1 | 0.0090 | 0.7259 |
| SAA | STAT3 | 0.0455 | 0.0765 |
| SAA | pANCA2 | 0.0681 | 0.0079 |
| ICAM | VCAM | 0.6830 | 0.0000 |
| ICAM | ATG16L1 | 0.0033 | 0.8979 |
| ICAM | NKX23 | 0.0052 | 0.8410 |
| ICAM | ECM1 | 0.0034 | 0.8945 |
| ICAM | STAT3 | 0.0149 | 0.5607 |
| ICAM | pANCA2 | 0.0741 | 0.0039 |
| VCAM | ATG16L1 | 0.0087 | 0.7337 |
| VCAM | NKX23 | −0.0053 | 0.8370 |
| VCAM | ECM1 | 0.0222 | 0.3873 |
| VCAM | STAT3 | −0.0003 | 0.9903 |
| VCAM | pANCA2 | 0.0613 | 0.0169 |

42 statistically significant correlations were identified among a subset of all possible unique pairwise combinations of the 18 variables used in some part of the sgi algorithm (see, Table 8). Correlation coefficients and their p-values are shown. The p-value represents statistical significance relative to a correlation coefficient of 0; p-values of 0.00E+00 are below the limit if the MATLAB software. A Bonferroni correction was applied to test for statistical significance at true $p<0.05$.

TABLE 8

Statistically Significant Correlations of All Unique Pairwise Combinations.

| Marker 1 | Marker 2 | Correlation Coefficient | P-value |
|---|---|---|---|
| Fla2 | FlaX | 0.9530 | 0.00E+00 |
| pANCA2 | ANCA | 0.8180 | 0.00E+00 |
| SAA | CRP | 0.8056 | 0.00E+00 |
| ASCAG | ASCAA | 0.7472 | 1.35E−271 |
| pANCA | pANCA2 | 0.7332 | 1.53E−256 |
| CBir1 | FlaX | 0.7190 | 3.55E−242 |
| Fla2 | CBir1 | 0.7023 | 2.39E−226 |
| VCAM | ICAM | 0.6830 | 2.42E−209 |

TABLE 8-continued

Statistically Significant Correlations of All Unique Pairwise Combinations.

| Marker 1 | Marker 2 | Correlation Coefficient | P-value |
|---|---|---|---|
| ANCA | pANCA | 0.6071 | 8.89E−154 |
| ASCAA | FlaX | 0.4015 | 5.59E−60 |
| ASCAG | FlaX | 0.3882 | 7.49E−56 |
| ASCAA | Fla2 | 0.3742 | 1.01E−51 |
| ASCAG | Fla2 | 0.3646 | 5.53E−49 |
| VEGF | CRP | 0.3037 | 8.51E−34 |
| ASCAG | CBir1 | 0.2932 | 1.62E−31 |
| ASCAA | CBir1 | 0.2878 | 2.25E−30 |
| CRP | ICAM | 0.2810 | 5.54E−29 |
| SAA | VEGF | 0.2628 | 1.98E−25 |
| CRP | VCAM | 0.2625 | 2.26E−25 |
| SAA | VCAM | 0.2611 | 4.14E−25 |
| SAA | ICAM | 0.2487 | 7.35E−23 |
| ASCAA | OmpC | 0.2191 | 5.60E−18 |
| ASCAG | OmpC | 0.1837 | 5.22E−13 |
| OmpC | FlaX | 0.1451 | 1.34E−08 |
| ASCAA | SAA | 0.1451 | 1.34E−08 |
| VEGF | ICAM | 0.1413 | 3.16E−08 |
| VEGF | FlaX | 0.1380 | 6.62E−08 |
| OmpC | Fla2 | 0.1332 | 1.87E−07 |
| FlaX | SAA | 0.1321 | 2.37E−07 |
| FlaX | CRP | 0.1305 | 3.33E−07 |
| VEGF | Fla2 | 0.1232 | 1.44E−06 |
| ASCAG | SAA | 0.1222 | 1.76E−06 |
| Fla2 | SAA | 0.1167 | 5.07E−06 |
| ASCAA | CRP | 0.1160 | 5.77E−06 |
| CRP | Fla2 | 0.1097 | 1.83E−05 |
| ASCAG | CRP | 0.1029 | 5.88E−05 |
| VEGF | VCAM | 0.1017 | 7.09E−05 |
| VEGF | ASCAA | 0.1004 | 8.78E−05 |
| OmpC | VCAM | 0.1000 | 9.46E−05 |
| ANCA | ICAM | 0.0980 | 1.30E−04 |
| VEGF | ASCAG | 0.0970 | 1.53E−04 |
| ANCA | ASCAG | −0.0987 | 1.16E−04 |

As such, this example demonstrates that random forest modeling in accordance with the present invention is particularly useful in diagnosing IBD vs. non-IBD and distinguishing between UC and CD.

Example 2

3-Class Random Forest Modeling for IBD Diagnostics

This example illustrates a method of random forest modeling of IBD diagnostics wherein the training set does not contain samples from healthy controls. This example illustrates training an algorithm with a dataset that excludes healthy control samples. This example also illustrates random forest modeling of 7 serological markers for predicting IBD vs. non-IBD, wherein the training cohort comprises IBD and irritable bowel syndrome (IBS) patients. This example further illustrates random forest modeling for predicting three disease classifications, such as non-IBD, CD and UC. This example also illustrates a random forest model for predicting IBS vs. healthy subjects.

A. Random Forest Modeling that Excludes Healthy Controls

In some embodiments, an IBD diagnostic algorithm of a plurality of random forest models is trained and validated using dataset from retrospective cohorts of predicted diagnoses with known presence, absence and/or levels of sero-genetic-inflammation markers. In certain instances, the datasets comprise data of subjects predicted to have IBD, CD, UC or Irritable Bowel Syndrome (IBS) (see, Table 9). In certain instances, data from healthy control patients are excluded from the random forest modeling. In some instances, datasets include 23 markers such as, but not limited to, ASCA-A, ASCA-G, IRGM47, IRGM89, MAGI2, MDR1, anti-OmpA, anti-OmpC, anti-CBir1, anti-Fla2, anti-FlaX, VEGF, CRP, SAA, ICAM, VCAM, ANCA, pANCA, pANCA2, ATG16L1, ECM1, STAT3, and NKX2-3. Table 9 illustrates the variable (e.g., marker) importance for IBD vs. non-IBD diagnosis for 23 sero-genetic-inflammation markers using only IBD and IBS patients (excluding healthy controls). In this exemplary description of random forest modeling of IBD diagnostics, the following criteria were required: a minimum number of resamplings of 5, a maximum of 20, and a standard error goal of 0.01 in the ROC score on separate test data. The term "Least_IMP" refers to the variable having the smallest average importance. The term "OOB_ROC" refers to the ROC score computed on the out-of-bag predictions during training. The term "TEST_Roc" refers to the ROC score on the separate test set, not used to create the forest. The terms "SENS" and "SPEC" refer to sensitivity and specificity, respectively, on the test set. The term "NTRAIN0" refers to the number of training samples with DxIBD equal to 0 (i.e., non-IBD). The term "NTRAIN1" refers to the number of training samples with DxIBD equal to 1 (i.e., IBD). The terms "NTEST0" and "NTEST1" are the number of test samples. Notably, all numbers in the following table are averages over multiple re-splittings, and error bars are standard errors (i.e., estimates of the error in means). Table 9 shows that the most important sero-genetic-inflammation marker for predicting IBD vs. non-IBD is pANCA and that a less important marker is ASCA-A, when the random forest model is built without samples from the cohort.

TABLE 9

Modeling for IBD vs. Non-IBD for 23 Sero-Genetic-Inflammation Markers Using Only IBD and IBS Patients.

| | NVAR | OOB_ROC | TEST_ROC | SENS | SPEC | LEAST_IMP |
|---|---|---|---|---|---|---|
| 1 | 23 | 0.919 +− 0.007 | 0.937 +− 0.010 | 0.897 +− 0.018 | 0.913 +− 0.014 | ASCAA |
| 2 | 22 | 0.903 +− 0.006 | 0.943 +− 0.010 | 0.846 +− 0.018 | 0.951 +− 0.020 | IRGM47 |
| 3 | 21 | 0.918 +− 0.005 | 0.914 +− 0.011 | 0.855 +− 0.017 | 0.889 +− 0.012 | IRGM89 |
| 4 | 20 | 0.908 +− 0.004 | 0.955 +− 0.006 | 0.910 +− 0.007 | 0.934 +− 0.019 | MDR1 |
| 5 | 19 | 0.917 +− 0.006 | 0.941 +− 0.010 | 0.904 +− 0.015 | 0.942 +− 0.012 | ECM1 |
| 6 | 18 | 0.903 +− 0.004 | 0.908 +− 0.008 | 0.774 +− 0.018 | 0.914 +− 0.016 | VEGF |
| 7 | 17 | 0.904 +− 0.005 | 0.902 +− 0.010 | 0.799 +− 0.025 | 0.887 +− 0.013 | NKX2 |
| 8 | 16 | 0.897 +− 0.004 | 0.909 +− 0.008 | 0.789 +− 0.007 | 0.914 +− 0.012 | CRP |
| 9 | 15 | 0.899 +− 0.004 | 0.917 +− 0.009 | 0.797 +− 0.030 | 0.892 +− 0.011 | STAT3 |
| 10 | 14 | 0.912 +− 0.003 | 0.896 +− 0.008 | 0.766 +− 0.007 | 0.892 +− 0.013 | SAA |
| 11 | 13 | 0.901 +− 0.005 | 0.920 +− 0.004 | 0.801 +− 0.025 | 0.902 +− 0.027 | GLI1 |
| 12 | 12 | 0.903 +− 0.004 | 0.909 +− 0.009 | 0.800 +− 0.022 | 0.896 +− 0.016 | ATG16L1 |
| 13 | 11 | 0.909 +− 0.003 | 0.903 +− 0.009 | 0.810 +− 0.011 | 0.876 +− 0.014 | MAGI2 |
| 14 | 10 | 0.906 +− 0.005 | 0.912 +− 0.008 | 0.816 +− 0.017 | 0.883 +− 0.012 | ICAM |
| 15 | 9 | 0.896 +− 0.005 | 0.914 +− 0.006 | 0.774 +− 0.022 | 0.921 +− 0.008 | Flax |
| 16 | 8 | 0.909 +− 0.003 | 0.899 +− 0.009 | 0.775 +− 0.018 | 0.902 +− 0.012 | VCAM |
| 17 | 7 | 0.904 +− 0.002 | 0.910 +− 0.006 | 0.792 +− 0.017 | 0.886 +− 0.012 | ANCA |
| 18 | 6 | 0.892 +− 0.005 | 0.905 +− 0.005 | 0.785 +− 0.022 | 0.902 +− 0.011 | ASCAG |
| 19 | 5 | 0.884 +− 0.006 | 0.899 +− 0.009 | 0.797 +− 0.017 | 0.888 +− 0.016 | OmpA |
| 20 | 4 | 0.853 +− 0.005 | 0.844 +− 0.004 | 0.678 +− 0.013 | 0.873 +− 0.012 | OmpC |
| 21 | 3 | 0.802 +− 0.009 | 0.827 +− 0.009 | 0.672 +− 0.025 | 0.855 +− 0.023 | Fla2 |
| 22 | 2 | 0.746 +− 0.007 | 0.754 +− 0.008 | 0.621 +− 0.039 | 0.846 +− 0.025 | CBir1 |
| 23 | 1 | 0.630 +− 0.004 | 0.735 +− 0.006 | 0.502 +− 0.018 | 0.874 +− 0.022 | pANCA |

| | NTRAIN0 | NTRAIN1 | NTEST0 | NTEST1 | NRESAMPLE | RANSEED |
|---|---|---|---|---|---|---|
| 1 | 59.7 +− 1.4 | 53.3 +− 1.4 | 30.3 +− 1.4 | 26.7 +− 1.4 | 7 | 1008 |
| 2 | 59.8 +− 1.9 | 53.2 +− 1.9 | 30.2 +− 1.9 | 26.8 +− 1.9 | 5 | 1013 |
| 3 | 60.5 +− 0.7 | 54.5 +− 0.7 | 29.5 +− 0.7 | 28.5 +− 0.7 | 20 | 1033 |
| 4 | 60.0 +− 1.4 | 57.0 +− 1.4 | 30.0 +− 1.4 | 29.0 +− 1.4 | 5 | 1038 |
| 5 | 60.1 +− 0.6 | 56.9 +− 0.6 | 29.9 +− 0.6 | 29.1 +− 0.6 | 8 | 1046 |
| 6 | 87.2 +− 2.2 | 281.8 +− 2.2 | 41.8 +− 2.2 | 143.2 +− 2.2 | 5 | 1051 |
| 7 | 89.0 +− 2.1 | 283.0 +− 2.1 | 40.0 +− 2.1 | 147.0 +− 2.1 | 6 | 1057 |
| 8 | 83.2 +− 1.5 | 290.8 +− 1.5 | 45.8 +− 1.5 | 141.2 +− 1.5 | 5 | 1062 |
| 9 | 86.6 +− 2.0 | 287.4 +− 2.0 | 42.4 +− 2.0 | 144.6 +− 2.0 | 5 | 1067 |
| 10 | 89.2 +− 1.9 | 286.8 +− 1.9 | 39.8 +− 1.9 | 148.2 +− 1.9 | 5 | 1072 |
| 11 | 85.4 +− 1.9 | 298.6 +− 1.9 | 43.6 +− 1.9 | 148.4 +− 1.9 | 5 | 1077 |
| 12 | 85.8 +− 1.7 | 300.2 +− 1.7 | 43.2 +− 1.7 | 149.8 +− 1.7 | 6 | 1083 |
| 13 | 85.3 +− 2.2 | 304.7 +− 2.2 | 44.7 +− 2.2 | 151.3 +− 2.2 | 10 | 1093 |
| 14 | 83.6 +− 1.4 | 318.4 +− 1.4 | 46.4 +− 1.4 | 155.6 +− 1.4 | 5 | 1098 |
| 15 | 88.0 +− 4.0 | 317.0 +− 4.0 | 42.0 +− 4.0 | 161.0 +− 4.0 | 5 | 1103 |
| 16 | 86.7 +− 1.2 | 319.3 +− 1.2 | 43.3 +− 1.2 | 160.7 +− 1.2 | 10 | 1113 |
| 17 | 88.2 +− 1.5 | 416.8 +− 1.5 | 43.8 +− 1.5 | 209.2 +− 1.5 | 5 | 1118 |
| 18 | 86.8 +− 1.2 | 418.2 +− 1.2 | 45.2 +− 1.2 | 207.8 +− 1.2 | 5 | 1123 |
| 19 | 86.7 +− 1.9 | 418.3 +− 1.9 | 45.3 +− 1.9 | 207.7 +− 1.9 | 6 | 1129 |
| 20 | 116.4 +− 0.4 | 424.6 +− 0.4 | 58.6 +− 0.4 | 212.4 +− 0.4 | 5 | 1134 |
| 21 | 114.2 +− 3.6 | 426.8 +− 3.6 | 60.8 +− 3.6 | 210.2 +− 3.6 | 5 | 1139 |
| 22 | 117.8 +− 2.0 | 448.2 +− 2.0 | 60.2 +− 2.0 | 222.8 +− 2.0 | 5 | 1144 |
| 23 | 120.0 +− 3.0 | 446.0 +− 3.0 | 58.0 +− 3.0 | 225.0 +− 3.0 | 5 | 1149 |

In other instances, a random forest model for IBD vs. non-IBD was determined for only serology markers using only samples from IBD and IBS patients. Table 10 illustrates the variable importance for IBD vs. non-IBD diagnosis for the serology markers. pANCA has the most importance and ASCA-A has less importance for predicting IBD vs. non-IBD.

A step-wise variable elimination was performed on the single 3-class model, wherein the "least important" variable is selected and eliminated for the entire diagnostic domain. A 3-class random forest model was built from 7 serology markers for predicting non-IBD, UC and CD for each sample (see, Table 11). In Table 11, the first row includes all 7 markers, the second row includes all but the least important marker, and so on. The term "IBD_TEST_ROC" refers to using the non-IBD test vs/IBD cut-off (e.g., first cut-off) and the entire test dataset. The term "UC_TEST_ROC" refers to using the UC vs. CD cut-off and only samples for the test dataset known to be IBD. In some instances, the remaining sensitivities and selectivities are determined on the entire test dataset. In a particular instance, the IBD performance in the last row of Table 11 is an artifact in the statistical program R for the Random Forest method on a single binary variable and should not be considered further.

TABLE 10

Modeling for IBD vs. Non-IBD Using Only Serology Markers and Only IBD and IBS Patients.

| | NVAR | OOB_ROC | TEST_ROC | SENS | SPEC | LEAST_IMP |
|---|---|---|---|---|---|---|
| 1 | 6 | 0.842 +− 0.006 | 0.864 +− 0.004 | 0.766 +− 0.011 | 0.872 +− 0.009 | ASCAA |
| 2 | 5 | 0.852 +− 0.005 | 0.827 +− 0.010 | 0.669 +− 0.034 | 0.870 +− 0.006 | ANCA |
| 3 | 4 | 0.828 +− 0.006 | 0.844 +− 0.007 | 0.701 +− 0.014 | 0.868 +− 0.017 | ASCAG |
| 4 | 3 | 0.818 +− 0.004 | 0.825 +− 0.008 | 0.686 +− 0.026 | 0.871 +− 0.018 | CBir1 |
| 5 | 2 | 0.767 +− 0.010 | 0.781 +− 0.009 | 0.633 +− 0.022 | 0.855 +− 0.006 | OmpC |
| 6 | 1 | 0.629 +− 0.006 | 0.731 +− 0.009 | 0.508 +− 0.021 | 0.871 +− 0.019 | pANCA |

| | NTRAIN0 | NTRAIN1 | NTEST0 | NTEST1 | NRESAMPLE | RANSEED |
|---|---|---|---|---|---|---|
| 1 | 119.0 +− 4.1 | 447.0 +− 4.1 | 59.0 +− 4.1 | 224.0 +− 4.1 | 5 | 1006 |
| 2 | 120.3 +− 2.5 | 445.7 +− 2.5 | 57.7 +− 2.5 | 225.3 +− 2.5 | 6 | 1012 |
| 3 | 114.6 +− 3.1 | 451.4 +− 3.1 | 63.4 +− 3.1 | 219.6 +− 3.1 | 5 | 1017 |
| 4 | 120.4 +− 3.4 | 445.6 +− 3.4 | 57.6 +− 3.4 | 225.4 +− 3.4 | 5 | 1022 |
| 5 | 116.7 +− 2.5 | 449.3 +− 2.5 | 61.3 +− 2.5 | 221.7 +− 2.5 | 6 | 1028 |
| 6 | 121.8 +− 2.8 | 444.2 +− 2.8 | 56.2 +− 2.8 | 226.8 +− 2.8 | 5 | 1033 |

B. Random Forest Modeling of Three Classifications of Disease

To test the performance of the algorithm, a single model with 3-class predictions (e.g., non-IBD, CD and UC) was developed. The method of variable elimination and resampling as described in the "Variable Elimination Protocol" was adjusted such that two cut-off values for prediction were established. One cut-off value was used for IBD vs. non-IBD, and the other was for UC vs. CD given that IBD was determined. In certain instances, the full test dataset can be used for the IBD vs. non-IBD model to find a non-IBD probability cut-off, above which is predicted as non-IBD and below which the algorithm continues to the second cut-off. The first cut-off value can be used to determine the ROC value for IBD vs. non-IBD. To determine the second cut-off, the test dataset of known IBD patients can be used to find a cut-off for p(UC)/(p(CD)+(UC)), where p(UC) and p(CD) are the model probabilities for UC and CD, respectively. The second cut-off value can be used to determine the ROC value for UC vs. CD. A single confusion matrix for the 3 classes (e.g., non-IBD, CD and UC) based on the two cut-offs were used to predict the diagnosis of each test sample.

TABLE 11

3-class Random Forest Model for Predicting non-IBD, UC or CD for 7 Sero-Genetic-Inflammation Markers.

| | NVAR | IBD_TEST_ROC | UC_TEST_ROC | IBD_SENS | IBD_SPEC | CD_SENS | CD_SPEC | UC_SENS |
|---|---|---|---|---|---|---|---|---|
| 1 | 6 | 0.850 +− 0.008 | 0.872 +− 0.010 | 0.754 +− 0.018 | 0.836 +− 0.009 | 0.601 +− 0.031 | 0.871 +− 0.007 | 0.616 +− 0.026 |
| 2 | 5 | 0.843 +− 0.007 | 0.883 +− 0.009 | 0.721 +− 0.012 | 0.859 +− 0.014 | 0.608 +− 0.020 | 0.909 +− 0.016 | 0.612 +− 0.015 |
| 3 | 4 | 0.833 +− 0.009 | 0.852 +− 0.007 | 0.726 +− 0.012 | 0.869 +− 0.007 | 0.606 +− 0.027 | 0.905 +− 0.008 | 0.608 +− 0.015 |
| 4 | 3 | 0.784 +− 0.005 | 0.864 +− 0.006 | 0.669 +− 0.014 | 0.848 +− 0.018 | 0.536 +− 0.017 | 0.893 +− 0.009 | 0.567 +− 0.020 |
| 5 | 2 | 0.763 +− 0.006 | 0.785 +− 0.010 | 0.613 +− 0.010 | 0.831 +− 0.012 | 0.434 +− 0.022 | 0.862 +− 0.008 | 0.495 +− 0.015 |
| 6 | 1 | 0.746 +− 0.006 | 0.691 +− 0.010 | 1.000 +− 0.000 | 0.000 +− 0.000 | 0.356 +− 0.135 | 0.685 +− 0.119 | 0.835 +− 0.063 |

| | UC_SPEC | LEAST_IMP | NTRAIN0 | NTRAIN1 | NTRAIN2 | NTEST0 | NTEST1 | NTEST2 |
|---|---|---|---|---|---|---|---|---|
| 1 | 0.912 +− 0.007 | ANCA | 249.4 +− 2.9 | 155.3 +− 2.6 | 292.3 +− 4.3 | 125.6 +− 2.9 | 80.7 +− 2.6 | 142.7 +− 4.3 |
| 2 | 0.911 +− 0.008 | ASCAA | 250.7 +− 3.6 | 156.1 +− 3.1 | 290.1 +− 3.8 | 124.3 +− 3.6 | 79.9 +− 3.1 | 144.9 +− 3.8 |
| 3 | 0.915 +− 0.008 | CBir1 | 248.2 +− 2.9 | 161.7 +− 2.2 | 287.2 +− 5.0 | 126.8 +− 2.9 | 74.3 +− 2.2 | 147.8 +− 5.0 |
| 4 | 0.925 +− 0.005 | OmpC | 249.6 +− 2.3 | 157.8 +− 1.9 | 289.6 +− 2.9 | 125.4 +− 2.3 | 78.2 +− 1.9 | 145.4 +− 2.9 |
| 5 | 0.928 +− 0.008 | ASCAG | 247.7 +− 2.2 | 159.7 +− 1.6 | 289.7 +− 2.7 | 127.3 +− 2.2 | 76.3 +− 1.6 | 145.3 +− 2.7 |
| 6 | 0.439 +− 0.166 | pANCA | 250.1 +− 2.5 | 158.1 +− 2.3 | 288.8 +− 2.6 | 124.9 +− 2.5 | 77.9 +− 2.3 | 146.2 +− 2.6 |

A 3-class random forest model was also built using 22 sero-genetic-inflammation markers for predicting non-IBD, UC and CD for each sample. Table 12 shows that in this model, the most important marker is pANCA and a less important marker is MDR1.

TABLE 12

3-class Random Forest Model Predicting non-IBD, UC or CD for 22 Sero-Genetic-Inflammation Markers.

| | NVAR | IBD_TEST_ROC | UC_TEST_ROC | IBD_SENS | IBD_SPEC | CD_SENS | CD_SPEC | UC_SENS |
|---|---|---|---|---|---|---|---|---|
| 1 | 22 | 0.922 +− 0.006 | 0.933 +− 0.006 | 0.830 +− 0.027 | 0.894 +− 0.017 | 0.814 +− 0.029 | 0.903 +− 0.021 | 0.691 +− 0.016 |
| 2 | 21 | 0.920 +− 0.009 | 0.928 +− 0.009 | 0.847 +− 0.018 | 0.877 +− 0.011 | 0.814 +− 0.010 | 0.930 +− 0.013 | 0.723 +− 0.022 |
| 3 | 20 | 0.909 +− 0.010 | 0.924 +− 0.009 | 0.823 +− 0.016 | 0.865 +− 0.016 | 0.792 +− 0.016 | 0.888 +− 0.009 | 0.666 +− 0.022 |
| 4 | 19 | 0.911 +− 0.006 | 0.936 +− 0.007 | 0.818 +− 0.014 | 0.866 +− 0.009 | 0.813 +− 0.029 | 0.904 +− 0.012 | 0.675 +− 0.025 |
| 5 | 18 | 0.915 +− 0.009 | 0.932 +− 0.007 | 0.810 +− 0.015 | 0.902 +− 0.013 | 0.804 +− 0.031 | 0.914 +− 0.005 | 0.665 +− 0.013 |
| 6 | 17 | 0.916 +− 0.007 | 0.937 +− 0.010 | 0.818 +− 0.026 | 0.894 +− 0.015 | 0.808 +− 0.017 | 0.907 +− 0.014 | 0.667 +− 0.018 |
| 7 | 16 | 0.933 +− 0.009 | 0.933 +− 0.009 | 0.855 +− 0.013 | 0.903 +− 0.024 | 0.819 +− 0.017 | 0.914 +− 0.011 | 0.715 +− 0.022 |
| 8 | 15 | 0.918 +− 0.008 | 0.920 +− 0.009 | 0.819 +− 0.018 | 0.895 +− 0.009 | 0.800 +− 0.031 | 0.915 +− 0.014 | 0.680 +− 0.015 |
| 9 | 14 | 0.909 +− 0.009 | 0.935 +− 0.009 | 0.819 +− 0.015 | 0.880 +− 0.018 | 0.794 +− 0.024 | 0.918 +− 0.009 | 0.685 +− 0.017 |
| 10 | 13 | 0.911 +− 0.010 | 0.933 +− 0.005 | 0.830 +− 0.015 | 0.890 +− 0.015 | 0.792 +− 0.018 | 0.920 +− 0.007 | 0.688 +− 0.016 |
| 11 | 12 | 0.907 +− 0.003 | 0.930 +− 0.005 | 0.794 +− 0.017 | 0.888 +− 0.013 | 0.748 +− 0.024 | 0.916 +− 0.010 | 0.675 +− 0.025 |
| 12 | 11 | 0.911 +− 0.008 | 0.929 +− 0.010 | 0.813 +− 0.019 | 0.895 +− 0.010 | 0.758 +− 0.020 | 0.918 +− 0.010 | 0.684 +− 0.028 |
| 13 | 10 | 0.910 +− 0.003 | 0.923 +− 0.009 | 0.825 +− 0.007 | 0.884 +− 0.006 | 0.779 +− 0.015 | 0.907 +− 0.009 | 0.691 +− 0.013 |
| 14 | 9 | 0.902 +− 0.005 | 0.933 +− 0.009 | 0.802 +− 0.010 | 0.862 +− 0.013 | 0.777 +− 0.020 | 0.916 +− 0.011 | 0.667 +− 0.029 |
| 15 | 8 | 0.903 +− 0.008 | 0.947 +− 0.009 | 0.798 +− 0.010 | 0.896 +− 0.007 | 0.788 +− 0.027 | 0.929 +− 0.006 | 0.677 +− 0.016 |
| 16 | 7 | 0.889 +− 0.006 | 0.933 +− 0.009 | 0.793 +− 0.017 | 0.872 +− 0.016 | 0.787 +− 0.019 | 0.933 +− 0.008 | 0.660 +− 0.023 |
| 17 | 6 | 0.877 +− 0.005 | 0.931 +− 0.007 | 0.747 +− 0.018 | 0.892 +− 0.008 | 0.732 +− 0.016 | 0.938 +− 0.003 | 0.642 +− 0.026 |
| 18 | 5 | 0.836 +− 0.005 | 0.866 +− 0.010 | 0.722 +− 0.006 | 0.846 +− 0.011 | 0.579 +− 0.028 | 0.894 +− 0.011 | 0.602 +− 0.022 |
| 19 | 4 | 0.825 +− 0.009 | 0.842 +− 0.007 | 0.715 +− 0.017 | 0.841 +− 0.008 | 0.592 +− 0.015 | 0.886 +− 0.008 | 0.576 +− 0.022 |
| 20 | 3 | 0.781 +− 0.006 | 0.835 +− 0.008 | 0.642 +− 0.012 | 0.846 +− 0.020 | 0.457 +− 0.016 | 0.890 +− 0.016 | 0.555 +− 0.012 |
| 21 | 2 | 0.753 +− 0.006 | 0.795 +− 0.010 | 0.613 +− 0.018 | 0.821 +− 0.021 | 0.456 +− 0.028 | 0.865 +− 0.015 | 0.495 +− 0.020 |
| 22 | 1 | 0.731 +− 0.006 | 0.693 +− 0.010 | 1.000 +− 0.000 | 0.000 +− 0.000 | 0.000 +− 0.000 | 1.000 +− 0.000 | 1.000 +− 0.000 |

| | UC_SPEC | LEAST_IMP | NTRAIN0 | NTRAIN1 | NTRAIN2 | NTEST0 | NTEST1 | NTEST2 |
|---|---|---|---|---|---|---|---|---|
| 1 | 0.936 +− 0.010 | MDR1 | 84.2 +− 1.9 | 90.6 +− 2.2 | 186.2 +− 2.0 | 42.8 +− 1.9 | 41.4 +− 2.2 | 96.8 +− 2.0 |
| 2 | 0.899 +− 0.003 | CRP | 83.4 +− 0.7 | 88.8 +− 1.8 | 188.8 +− 2.2 | 43.6 +− 0.7 | 43.2 +− 1.8 | 94.2 +− 2.2 |
| 3 | 0.922 +− 0.011 | STAT3 | 84.4 +− 1.5 | 87.9 +− 1.3 | 188.7 +− 1.5 | 42.6 +− 1.5 | 44.1 +− 1.3 | 94.3 +− 1.5 |
| 4 | 0.920 +− 0.012 | GLI1 | 88.4 +− 1.7 | 92.0 +− 1.7 | 182.6 +− 1.7 | 38.6 +− 1.7 | 43.0 +− 2.2 | 100.4 +− 1.7 |
| 5 | 0.926 +− 0.008 | NKX2 | 85.5 +− 2.4 | 86.8 +− 2.5 | 191.7 +− 3.9 | 41.5 +− 2.4 | 48.2 +− 2.5 | 92.3 +− 3.9 |
| 6 | 0.925 +− 0.007 | ATG16L1 | 85.6 +− 2.5 | 90.7 +− 2.1 | 187.7 +− 1.3 | 41.4 +− 2.5 | 44.3 +− 2.1 | 96.3 +− 1.3 |
| 7 | 0.913 +− 0.012 | IRGM47 | 86.2 +− 2.1 | 90.0 +− 2.2 | 189.8 +− 2.1 | 41.8 +− 2.1 | 45.0 +− 2.2 | 97.2 +− 2.1 |
| 8 | 0.917 +− 0.014 | MAGI2 | 86.7 +− 1.6 | 93.7 +− 2.4 | 190.7 +− 3.1 | 41.3 +− 1.6 | 45.3 +− 2.4 | 99.3 +− 3.1 |
| 9 | 0.916 +− 0.009 | IRGM89 | 84.6 +− 2.2 | 104.5 +− 1.7 | 193.9 +− 2.1 | 43.4 +− 2.2 | 52.5 +− 1.7 | 96.1 +− 2.1 |
| 10 | 0.903 +− 0.010 | VEGF | 87.9 +− 1.6 | 106.8 +− 1.5 | 196.3 +− 2.3 | 42.1 +− 1.6 | 55.2 +− 1.5 | 98.7 +− 2.3 |
| 11 | 0.937 +− 0.007 | SAA | 138.8 +− 2.7 | 106.8 +− 1.9 | 202.4 +− 1.5 | 71.2 +− 2.7 | 55.2 +− 1.9 | 97.6 +− 1.5 |
| 12 | 0.923 +− 0.009 | Fla2 | 138.7 +− 2.6 | 111.0 +− 2.0 | 206.3 +− 2.7 | 71.3 +− 2.6 | 54.0 +− 2.0 | 102.7 +− 2.7 |
| 13 | 0.933 +− 0.010 | OmpA | 141.7 +− 3.3 | 110.3 +− 2.6 | 206.0 +− 2.9 | 71.3 +− 3.3 | 54.7 +− 2.6 | 104.0 +− 2.9 |
| 14 | 0.918 +− 0.005 | ANCA | 166.8 +− 1.2 | 111.2 +− 0.7 | 212.0 +− 1.8 | 85.2 +− 1.2 | 53.8 +− 0.7 | 106.0 +− 1.8 |
| 15 | 0.936 +− 0.005 | VCAM | 167.8 +− 2.2 | 110.8 +− 1.9 | 211.4 +− 2.9 | 84.2 +− 2.2 | 54.2 +− 1.9 | 106.6 +− 2.9 |
| 16 | 0.911 +− 0.010 | Flax | 171.1 +− 1.3 | 114.9 +− 1.8 | 213.0 +− 1.9 | 84.9 +− 1.3 | 59.1 +− 1.8 | 106.0 +− 1.9 |
| 17 | 0.932 +− 0.010 | ICAM | 173.8 +− 1.2 | 117.6 +− 4.4 | 213.6 +− 4.4 | 85.2 +− 1.2 | 59.4 +− 4.6 | 108.4 +− 4.4 |
| 18 | 0.906 +− 0.004 | ASCAA | 247.6 +− 5.3 | 155.0 +− 4.3 | 294.4 +− 4.0 | 127.4 +− 5.3 | 81.0 +− 4.3 | 140.6 +− 4.0 |
| 19 | 0.907 +− 0.009 | CBir1 | 248.6 +− 2.9 | 158.1 +− 1.8 | 290.3 +− 2.4 | 126.4 +− 2.9 | 77.9 +− 1.8 | 144.7 +− 2.4 |
| 20 | 0.917 +− 0.006 | OmpC | 252.4 +− 1.3 | 157.4 +− 2.1 | 287.2 +− 2.5 | 122.6 +− 1.3 | 78.6 +− 2.1 | 147.8 +− 2.5 |
| 21 | 0.924 +− 0.009 | ASCAG | 252.5 +− 3.6 | 158.5 +− 2.5 | 286.0 +− 3.5 | 122.5 +− 3.6 | 77.5 +− 2.5 | 149.0 +− 3.5 |
| 22 | 0.000 +− 0.000 | pANCA | 242.4 +− 3.0 | 158.6 +− 3.3 | 296.0 +− 4.3 | 132.6 +− 3.0 | 77.4 +− 3.3 | 139.0 +− 4.3 |

C. Random Forest Modeling for Diagnosing IBS vs. Healthy Individuals

To distinguish between healthy subjects and patients predicted to have IBS, another random forest model was created. The 7 serology markers described above were used in the model (see, Table 13).

TABLE 13

Random Forest Model for IBS vs. Healthy Controls.

| | NVAR | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 1 | 6 | 0.776 +− 0.005 | 0.775 +− 0.010 | 0.639 +− 0.020 | 0.794 +− 0.007 | pANCA | 130.9 +− 1.1 | 119.1 +− 1.1 | 66.1 +− 1.1 | 58.9 +− 1.1 |
| 2 | 5 | 0.785 +− 0.006 | 0.760 +− 0.010 | 0.630 +− 0.026 | 0.782 +− 0.023 | CBir1 | 133.6 +− 1.6 | 116.4 +− 1.6 | 63.4 +− 1.6 | 61.6 +− 1.6 |
| 3 | 4 | 0.782 +− 0.007 | 0.791 +− 0.010 | 0.704 +− 0.016 | 0.777 +− 0.011 | ANCA | 130.4 +− 1.0 | 119.6 +− 1.0 | 66.6 +− 1.0 | 58.4 +− 1.0 |
| 4 | 3 | 0.758 +− 0.006 | 0.766 +− 0.010 | 0.643 +− 0.017 | 0.820 +− 0.018 | ASCAA | 131.1 +− 1.0 | 118.9 +− 1.0 | 65.9 +− 1.0 | 59.1 +− 1.0 |
| 5 | 2 | 0.736 +− 0.009 | 0.711 +− 0.009 | 0.595 +− 0.016 | 0.761 +− 0.012 | ASCAG | 130.9 +− 1.2 | 119.1 +− 1.2 | 66.1 +− 1.2 | 58.9 +− 1.2 |
| 6 | 1 | 0.597 +− 0.009 | 0.624 +− 0.011 | 0.488 +− 0.022 | 0.745 +− 0.014 | OmpC | 130.6 +− 0.7 | 119.5 +− 0.7 | 66.5 +− 0.7 | 58.5 +− 0.7 |

Table 14 shows yet another random forest model by modifying the random forest model for IBS vs. healthy controls. In this embodiment, a marker was incorporated in turn into the model, starting with the most important marker. The model was determined to be complete when there is no longer complete data for one of the classes. Table 14 shows the predictions of the random forest model for predicting IBS vs. healthy subjects using 17 sero-genetic-inflammation markers.

rithms described herein. This example further illustrates methods for creating diagnostic algorithms.

The IBD sgi diagnostic algorithm utilizes measurements of 17 markers (18 values as pANCA is measured twice). Table 15 describes the markers and exemplary assay methods for measuring the markers.

TABLE 14

Random Forest Model for IBS vs. Healthy Controls Using 17 Sero-Genetic-Inflammation Markers.

| | NVAR | OOB_ROC | TEST_ROC | SENS | SPEC | LEAST_IMP | NTRAIN0 | NTRAIN1 | NTEST0 | NTEST1 |
|---|---|---|---|---|---|---|---|---|---|---|
| 1 | 17 | 0.883 +− 0.006 | 0.877 +− 0.010 | 0.775 +− 0.024 | 0.882 +− 0.020 | CRP | 43.5 +− 0.8 | 86.5 +− 0.8 | 22.5 +− 0.8 | 43.5 +− 0.8 |
| 2 | 16 | 0.874 +− 0.008 | 0.900 +− 0.010 | 0.827 +− 0.019 | 0.878 +− 0.011 | STAT3 | 43.4 +− 0.9 | 87.6 +− 0.9 | 22.6 +− 0.9 | 43.4 +− 0.9 |
| 3 | 15 | 0.884 +− 0.005 | 0.900 +− 0.011 | 0.818 +− 0.014 | 0.879 +− 0.014 | GLI1 | 45.0 +− 0.7 | 86.0 +− 0.7 | 21.0 +− 0.7 | 45.0 +− 0.7 |
| 4 | 14 | 0.896 +− 0.004 | 0.901 +− 0.010 | 0.805 +− 0.022 | 0.883 +− 0.010 | MAGI2 | 45.6 +− 0.8 | 87.4 +− 0.8 | 23.4 +− 0.8 | 43.6 +− 0.8 |
| 5 | 13 | 0.885 +− 0.005 | 0.901 +− 0.010 | 0.804 +− 0.020 | 0.886 +− 0.015 | NKX2 | 46.9 +− 0.7 | 87.1 +− 0.7 | 23.1 +− 0.7 | 43.9 +− 0.7 |
| 6 | 12 | 0.889 +− 0.005 | 0.922 +− 0.010 | 0.845 +− 0.015 | 0.889 +− 0.012 | ATG16L1 | 45.7 +− 1.2 | 88.3 +− 1.2 | 24.3 +− 1.2 | 42.7 +− 1.2 |
| 7 | 11 | 0.888 +− 0.008 | 0.901 +− 0.010 | 0.836 +− 0.021 | 0.867 +− 0.012 | pANCA | 55.3 +− 1.2 | 86.7 +− 1.2 | 25.7 +− 1.2 | 45.3 +− 1.2 |
| 8 | 10 | 0.887 +− 0.004 | 0.897 +− 0.010 | 0.807 +− 0.020 | 0.878 +− 0.019 | ASCAA | 52.0 +− 0.8 | 90.0 +− 0.8 | 29.0 +− 0.8 | 42.0 +− 0.8 |
| 9 | 9 | 0.888 +− 0.009 | 0.900 +− 0.010 | 0.780 +− 0.020 | 0.910 +− 0.014 | CBir1 | 54.0 +− 1.5 | 88.0 +− 1.5 | 27.0 +− 1.5 | 44.0 +− 1.5 |
| 10 | 8 | 0.879 +− 0.009 | 0.913 +− 0.010 | 0.802 +− 0.019 | 0.905 +− 0.008 | SAA | 54.2 +− 1.5 | 87.8 +− 1.5 | 26.8 +− 1.5 | 44.2 +− 1.5 |
| 11 | 7 | 0.880 +− 0.006 | 0.888 +− 0.009 | 0.802 +− 0.022 | 0.860 +− 0.012 | ANCA | 54.6 +− 1.0 | 87.4 +− 1.0 | 26.4 +− 1.0 | 44.6 +− 1.0 |
| 12 | 6 | 0.879 +− 0.005 | 0.878 +− 0.010 | 0.768 +− 0.021 | 0.864 +− 0.010 | Fla2 | 53.4 +− 0.7 | 88.6 +− 0.7 | 27.6 +− 0.7 | 43.4 +− 0.7 |
| 13 | 5 | 0.869 +− 0.005 | 0.900 +− 0.009 | 0.826 +− 0.035 | 0.866 +− 0.012 | ASCAG | 55.4 +− 1.9 | 88.6 +− 1.9 | 28.6 +− 1.9 | 43.4 +− 1.9 |
| 14 | 4 | 0.867 +− 0.003 | 0.853 +− 0.006 | 0.772 +− 0.033 | 0.822 +− 0.024 | Flax | 56.8 +− 2.0 | 87.2 +− 2.0 | 27.2 +− 2.0 | 44.8 +− 2.0 |
| 15 | 3 | 0.839 +− 0.008 | 0.845 +− 0.010 | 0.730 +− 0.015 | 0.830 +− 0.016 | OmpA | 55.4 +− 0.8 | 88.6 +− 0.8 | 28.6 +− 0.8 | 43.4 +− 0.8 |
| 16 | 2 | 0.767 +− 0.008 | 0.784 +− 0.010 | 0.577 +− 0.029 | 0.861 +− 0.019 | OmpC | 57.4 +− 1.2 | 114.6 +− 1.2 | 27.6 +− 1.2 | 59.4 +− 1.2 |
| 17 | 1 | 0.688 +− 0.010 | 0.718 +− 0.015 | 0.619 +− 0.025 | 0.732 +− 0.011 | ICAM | 56.8 +− 0.8 | 115.2 +− 0.8 | 28.2 +− 0.8 | 58.8 +− 0.8 |

Of the 17 markers used, the algorithm shows that the most important markers for predicting IBS vs. healthy patients are ICAM, anti-OmpC, anti-OmpA, and anti-FlaX. In certain aspects, random forest modeling in accordance with the present invention can be useful in diagnosing IBS by predicting patients as having IBS versus healthy control patients.

Example 3

IBD Sero-Genetic-Inflammation (sgi) Diagnostic Algorithm

This example illustrates the development and validation of the IBD sero-genetic-inflammation (sgi) diagnostic algorithm. In certain aspects, the diagnostic algorithm is a component of an IBD sgi diagnostic test which can be used to diagnose inflammatory bowel disease (IBD) versus non-inflammatory bowel disease (non-IBD) and/or subtypes thereof including ulcerative colitis (UC), Crohn's disease (CD), indeterminate colitis (IC), and IBD inconclusive for CD and UC. This example also illustrates methods for predicting IBD, non-IBD, UC, CD, IC, and/or IBD inconclusive using algo-

TABLE 15

Sero-genetic-inflammatory (sgi) markers of the IBP diagnostic algorithm.

| | Marker | Assay format |
|---|---|---|
| 1 | ASCA-IgA | ELISA |
| 2 | ASCA-IgG | ELISA |
| 3 | Anti-OmpC | ELISA |
| 4 | Anti-CBir1 | ELISA |
| 5 | pANCA | Indirect Immunofluorescence |
| 6 | pANCA2 | Indirect Immunofluorescence |
| 7 | ANCA | ELISA |
| 8 | Anti-Fla2 | ELISA |
| 9 | Anti-FlaX | ELISA |
| 10 | CRP | ELISA |
| 11 | SAA | ELISA |
| 12 | ICAM | ELISA |
| 13 | VCAM | ELISA |
| 14 | VEGF | ELISA |
| 15 | ATG16L1 | Genotyping PCR |
| 16 | ECM1 | Genotyping PCR |
| 17 | NKX2-3 | Genotyping PCR |
| 18 | STAT3 | Genotyping PCR |

In certain embodiments, the IBD sgi diagnostic test also comprises a data analysis computational algorithm. In certain embodiments, the final test result is a probability score reflecting a prediction of the patient's IBD status.

The IBD sgi diagnostic test of the present invention advantageously uses serologic, genetic and inflammatory data to diagnose or help physicians diagnose whether a patient has IBD and/or a subtype such as UC, CD, IC, and/or IBD that is inconclusive for CD and UC. In certain embodiments, the diagnostic test uses 13 serological and inflammatory biomarkers and 4 genetic markers to assess a patient's risk profile. In certain other embodiments, the test takes the measurements of the biological markers and uses a computational algorithm to predict a patient's IBD status. In particular, the test can predict whether a patient has IBD or non-IBD. The test can also examine the marker measurements from the patient predicted to have IBD and excluded from having indeterminate colitis (IC) and/or IBD inconclusive for CD and UC, and can predict whether the patient has UC or CD. The diagnostic test provides comprehensive results that help physicians, optionally in combination with additional clinical findings, make the most informed decisions for management of their patients.

A. Measuring Sero-Genetic-Inflammation (sgi) Markers

The IBD sgi diagnostic test takes the measurement of a plurality of sero-genetic-inflammation (sgi) markers and uses a computational algorithm to predict a patient's IBD status. Methods of measuring sero-genetic-inflammation (sgi) markers are described, for example, in U.S. Pat. Nos. 5,750, 479; 5,830,675; and 7,873,479, U.S. Patent Publication No. 2011/0045476, and PCT Application No. PCT/US2011/039174, which are incorporated herein by reference in their entirety for all purposes.

B. IBD sgi Diagnostic Algorithm

The IBD sgi diagnostic algorithm takes advantage of a computational algorithm (termed sero-genetic-inflammation (sgi) algorithm) to predict a patient's IBD status. The steps of one embodiment of the algorithm are illustrated in FIG. 1. Firstly, the algorithm uses a random forest model based on measurement data of 17 biological markers (serologic, genetic, and inflammation markers) and predicts whether a patient has IBD or does not have IBD (non-IBD). Next, a decision tree or a set of rules is used to determine whether a patient predicted to have IBD has a biomarker pattern consistent with an inconclusive diagnosis (e.g., a diagnosis that is inconclusive for CD versus UC). Then, another random forest-based algorithm that uses 11 biomarker measurements predicts whether the patient predicted to have IBD has either UC or CD. As such, the IBD sgi diagnostic algorithm of the invention classifies a patient as having non-IBD, UC, CD, or IBD that is inconclusive for CD and UC.

C. Modeling Strategy and Training Set

Components of the sgi algorithm utilize a type of computational classifier known as a random forest model, which is made up of many decision trees with a random component to building each tree. For the sgi algorithm, forests with 10,000 trees were built for each of the IBD vs. non-IBD and UC vs. CD classifications. Each decision tree in the forest addresses the same classification problem, but with a different collection of examples and a different subset of features randomly selected from the dataset of examples provided. For instance, a single tree might be built using a random two-thirds of the available examples, with a random two-thirds of the features selected to make a decision split at each node of the tree. Once the forest is built, new examples are classified by taking a new vote across all the decision trees. In the simplest case, a 2-class classifier, the class with the most votes wins. In some cases, the cutoff for a winning number of votes is preset to optimize performance measures. For example, in instances when false positives are more costly than false negatives, the cutoff is set at a higher value.

The random forest classifiers of the sgi algorithm were built from training data which is a collection of samples (dataset of samples from cohorts of patient having known diagnoses) based on biological data from known non-IBD, CD and UC patients. The samples were provided in a structured format that includes data about features (e.g., biological markers) suspected to be linked to the classification, along with the true classification for each example. This computational classifier approach is referred to as "supervised machine learning", in that (1) the true classes of the examples are known beforehand (supervised); (2) the computer does the processing (machine); and (3) the algorithm discovers and recognizes feature patterns that distinguish the different classes (learning). After feature patterns are learned, the classifier can predict the classifications of new examples.

A 2-class random forest classifier to predict IBD vs. non-IBD diagnosis was built from a collection of data of sero-genetic-inflammatory biological markers from known non-IBD, CD and UC patients. 2420 samples with measurements for 26 markers were originally considered. The sero-genetic-inflammatory biological markers include, but are not limited to, anti-*Saccharomyces cerevisiae* antibodies (e.g., ASCA-IgA, ASCA-IgG), anti-neutrophil antibodies (e.g., ANCA, pANCA such as IFA perinuclear pattern and DNase sensitivity), anti-microbial and -flagellin antibodies (e.g., antibodies to OmpA, OmpC, CBir1, A4-Fla2, FlaX), growth factors (e.g., VEGF), acute phase proteins (e.g., CRP), apolipoproteins (e.g., SAA), cellular adhesion molecules (e.g., ICAM-1, VCAM-1), and SNPs (e.g., ATG16L1 1155 (A>G), GUI 2876 (G>A), IL10 (A>G), IRGM (A>G), IRGM (C>T), MAGI2 (C>G), TL1A (C>T) XBP1 (A>G), MDR1 2677 (G>T/A), ECM1 588 (C>T), NKX2-3 (A>G) and STAT3 (A>G)).

The modeling strategy uses available data from samples (patients) of a known diagnosis to create, test and validate an algorithm. Initially the available data was divided into a training dataset and a validation dataset. In order to give a fair account of the ability of the resultant algorithm to predict new samples, all experimentation with basic modeling technique, variable selection, and model architecture was restricted to only using the training dataset. During evaluations of effectiveness of different approaches, the training dataset was further divided at random into two-thirds model training used to create an algorithm, and one-third test dataset used to measure performance. All experiments during modeling of the algorithm were repeated from about 50-100 times by re-dividing the training and test datasets at random (a process termed "resampling"), comparing mean values, and ensuring that the standard error in the means were smaller than the difference in performance.

The available samples included data of 26 biological markers. In order to determine if subsets of markers have a higher predictive value, a variable elimination protocol was followed. Briefly, the protocol includes determining mean and standard error importance for each marker through re-sampling, deleting the least important marker, and repeating until all markers have a positive importance greater than its standard error. The final set of markers (e.g., 17 markers) used to build the IBD vs. non-IBD model was selected by considering variable importance, assay stability, and availability. Not all of these markers proved to be significant for the UC vs. CD model and thus, only a subset of the markers (e.g., 11 markers) was used for this model.

After settling on all the training criteria and markers, a IBD vs. non-IBD model was created using all the training data. Then, a UC vs. CD model was created on an appropriate subset of this data.

The known CD and UC samples (e.g., samples from patients previous diagnosed as having CD or UC) in the training dataset were stratified as follows: diagnosis as CD or UC, ethnicity/race as Jewish or all others, sample source as community or academic, time from diagnosis as <5 years or ≥5 years. The disease control samples were stratified by diagnosis of Hepatitis, GERD or all others, ethnicity/race; and sample source. In addition, two other constraints were applied. In certain instances, no African-American or pediatric samples were used in either the training or validation sets. And, 174 CD samples from a particular cohort were not used in the validation set as they were used as part of another protocol.

D. Transformation of Text into Discrete Numeric Marker Measure

Since the sgi algorithm requires numeric values, text-based data for any biological marker is transformed into binary variables by correlating a value of 0 or 1 to a set of rules (see, Table 16).

TABLE 16

Rules for transforming text-based data into discrete numeric data (e.g., binary variables) for 6 sero-genetic-inflammatory biological markers.

| Biomarker | Data assigned to a value of 0 | Data for assigned to a value of 1 |
| --- | --- | --- |
| pANCA | Not detected<br>DNase sensitive (cytoplasmic) | DNase sensitive 1 + P<br>DNase sensitive 2 + P<br>DNase sensitive 3 + P<br>DNase sensitive 4 + P |
| pANCA2 | Not detected<br>DNase sensitive (cytoplasmic)<br>DNase sensitive 1 + P | DNase sensitive 2 + P<br>DNase sensitive 3 + P<br>DNase sensitive 4 + P |
| ATG1L1 | VIC<br>Both | FAM |
| ECM1 | VIC<br>Both | FAM |
| NKX2-3 | VIC<br>Both | FAM |
| STAT3 | Both<br>FAM | VIC |

The pANCA and pANCA2 data refers to the amount and location of the fluorescence label for ANCA detected in the patient sample. The term "not detected" indicates that no label was detected, and thus the sample was considered negative and assigned a value of 0. Samples referred to as "DNAse resistant" indicate that the label fails to disappear after DNase treatment and were considered "not detected". It should be noted that this label pattern was not observed in the data sample set used to establish the sgi algorithm used in this example. However, "DNAse resistant" samples usually occur in 2% of the sample set. The term "DNase sensitive (cytoplasmic)" indicates that after DNase treatment, the label was distributed with the cytoplasm of cells, and the sample was considered negative. It was also assigned a value of 0. The terms "DNase sensitive 1+P", "DNase sensitive 2+P", "DNase sensitive 3+P", "DNase sensitive 4+P" indicated that label was observed by visual assessment to be surrounding the nuclei of cells (perinuclear pattern) with increasing intensity and amount of label seen from 1+P through 4+P, wherein 4+P correlates to the largest amount of label. For pANCA, these labels are considered detected and positive, and thus assigned a value of 1. For pANCA2, only labels from 2+P through 4+P are considered positive and given a value of 1.

Figure 4:
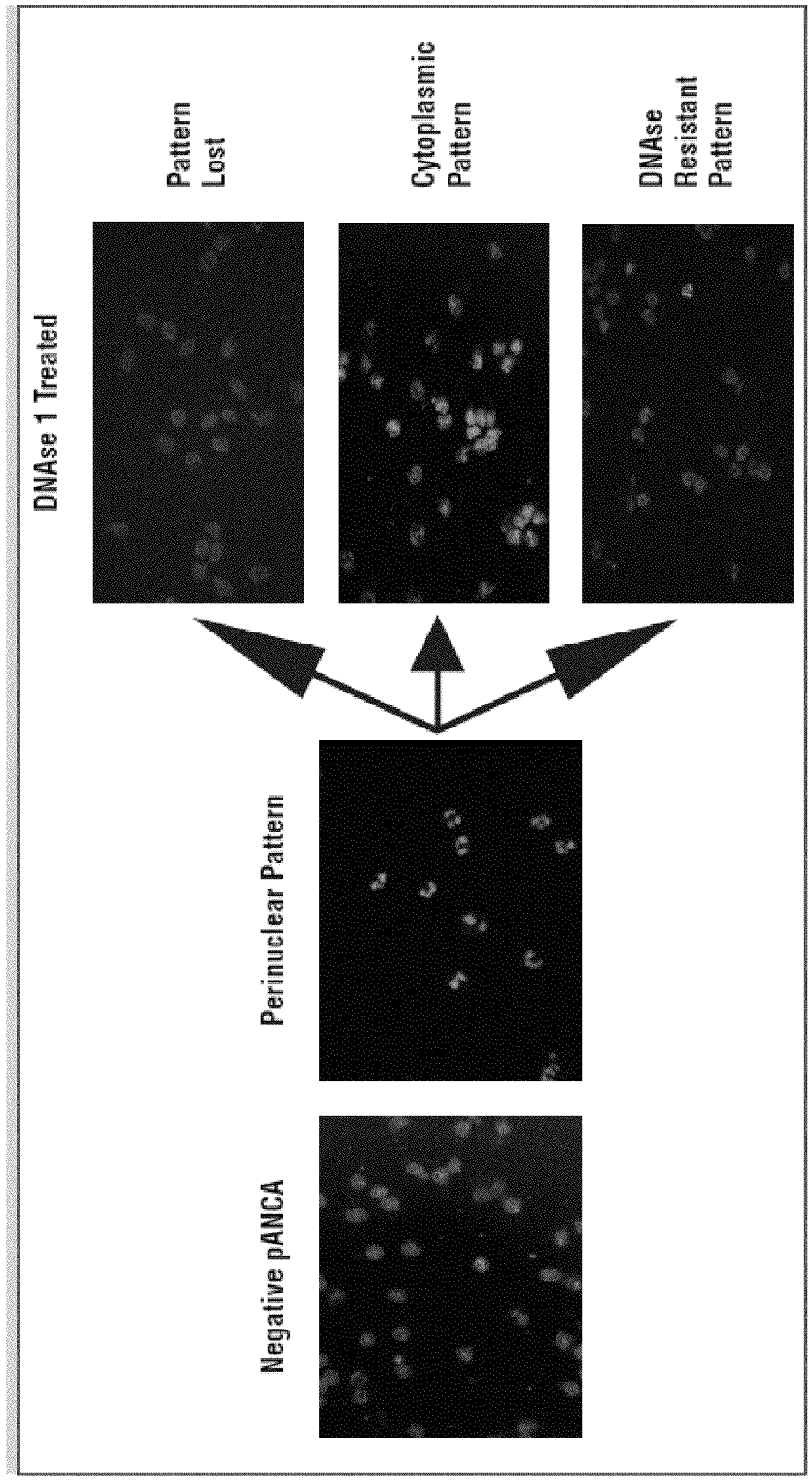
FIG. 4 illustrates the pANCA staining pattern by immunofluorescence followed by DNAse treatment on fixed neutrophils.

Notably, pANCA and pANCA2 are two independently determined measurements of a single marker. FIG. 4 shows examples of different pANCA staining patterns, including a perinuclear pattern, a DNase sensitive cytoplasmic pattern, and a DNAse resistant pattern.

For genetic markers such as ATG16L1, ECM1, NKX2-3 and STAT3, VIC and FAM refer to fluorescent reporter dyes used to label different alleles of each gene. Either the VIC or the FAM dye is used to label the disease allele for each gene. The text data "VIC" "FAM", or "Both" indicates whether the normal allele, the disease allele, or both alleles are seen in the sample. In some embodiments, if only the dye for the normal allele ("VIC" or "FAM", depending on the gene) is detected, the patient is homozygous for the normal allele and the marker data is assigned a value of 0. In certain instances, if on the dye for the disease allele, ("VIC" or "FAM", depending on the gene) is detected, this indicates that the patient is homozygous for the disease allele, and assigned a value of 1. In other instances, if both dyes are detected and described as "Both", this indicates that the patient is heterozygous for the disease allele and assigned a value of 0.

E. Sample Elimination

To build the sgi algorithm, the available data for the samples were reviewed and samples were eliminated from the data set if they were in accordance with a defined criteria. Examples of a defined criteria include: if a sample is from a patient who last experienced symptoms more than 6 months prior to a doctor's visit, or if a sample is from a patient whose last symptom was described as "not available" and who enrolled in the study prior. Other examples of patients that were excluded are those that failed to meet the inclusion and exclusion criteria for the study and those in which information regarding the length of disease was lacking. Patient samples having pANCA2 positive and an ANCA<11.9 EU/ml were eliminated from the data. Likewise, those with pANCA2 negative and ANCA>11.9 EU/ml were also excluded. This left 1,083 samples for the training set and 437 samples for the validation set.

F. First Random Forest Modeling to Predict IBD Vs. Non-IBD Diagnosis

All the remaining samples were used to build the 2-class random forest classifier predicting IBD vs. non-IBD diagnosis using a supervised machine learning approach, such as the RandomForest package from R. 17 sero-genetic-inflammation (sgi) markers were used including anti-*Saccharomyces cerevisiae* antibodies (e.g., ASCA-IgA and ASCA-IgG), anti-neutrophil antibodies (e.g., pANCA and ANCA), anti-microbial and -flagellin antibodies (e.g., anti-OmpC, anti-CBir1, anti-Fla2 and anti-FlaX), growth factors (e.g., VEGF), acute phase proteins (CRP), apolipoproteins (e.g., SAA), cellular adhesion molecules (e.g., ICAM and VCAM), and SNPs (e.g., ATG16L1, ECM1, NKX2-3 and STAT3). The score cutoff was set to 0.64 in order to achieve the desired tradeoff between sensitivity and specificity.

The sgi algorithm uses scores from 17 sero-genetic-inflammation biological markers to compute a first model score for a new sample in the diagnostic test. If the score is <0.64, the sample is predicted to be from a patient having IBD. Otherwise, the sample is predicted to be from a patient having non-IBD. Samples predicted to have IBD proceed to the next step of the algorithm, wherein a decision tree or a set of rules is utilized to predict an inconclusive sample.

G. Decision Tree or Set of Rules to Determine if the Sample is Inconclusive

In certain embodiments, a decision tree or set of rules is used to determine if a sample, classified in the first random forest model as having IBD, also has ambiguous marker patterns, such that the sample can be classified as inconclusive. If ANCA is ≥16.8 EU/ml, the pANCA2 score is positive, and one or more of the following conditions are true: CBir1≥29.475 EU/ml, Fla2≥34.5 EU/ml or FlaX≥28.875 EU/ml, then the sample is determined to be "indeterminate" and the patient is "inconclusive" for CD and UC. Similarly, if the pANCA2 score is positive and any 2 or more of these conditions are true: CBir1≥29.475 EU/ml, Fla2≥34.5 EU/ml or FlaX≥28.875 EU/ml, then the sample also is "indeterminate" and the patient is "inconclusive" for CD and UC. Reference values in the classifications and rules described herein are from the third quartiles of the training set.

H. Second Random Forest Modeling to Predict UC vs. CD Diagnosis

A second random forest model for predicting UC vs. CD was created from a subset of the original training dataset. Samples determined to be known non-IBD samples, indeterminate samples, and samples meeting the Rule 1 (also referred to as Group 1) or Rule 2 (also referred to as Group 2) violation criteria were excluded from the training dataset. A detailed description of Rule 1 and Rule 2 violations is described in Table 17.

TABLE 17

Violation criteria used to exclude samples used in building the second random forest classifier to predict UC vs. CD.

| Rule 1 violation | Rule 2 violation |
|---|---|
| Prior diagnosis is UC | Prior diagnosis is CD |
| ANCA <16.8 | ANCA ≥16.8 EU/ml |
| pANCA2 negative | All of these conditions are satisfied: |
|  | ASCAA <10.675 EU/ml |
|  | ASCAG <14.175 EU/ml |
|  | OmpC <9.4 EU/ml |
|  | CBir1 <29.475 EU/ml |
|  | Fla2 <34.5 EU/ml |
|  | FlaX <28.875 EU/ml |
| 2 or more of these conditions are satisfied: |  |
| ASCAA ≥10.675 EU/ml |  |
| ASCAG ≥14.175 EU/ml |  |
| OmpC ≥9.4 EU/ml |  |
| CBir1 ≥29.475 EU/ml |  |
| Fla2 ≥34.5 EU/ml |  |
| FlaX ≥28.875 EU/ml |  |

Due to these sample exclusion criteria, 540 samples were used to determine a 2-class random forest classifier for predicting UC vs. CD diagnosis. The same methods of marker selection used in the IBD vs. non-IBD random forest model were used. The sero-genetic-inflammation markers selected were ASCA-IgA, ASCA-IgG, pANCA, ANCA, OmpC, CBir1, Fla2 and FlaX, VEGF, ECM1 and STAT3. The score cutoff for the second random forest classifier was set to 0.35.

In certain embodiments, the sgi diagnostic algorithm applies scores from 11 sero-genetic-inflammatory biological markers to compute a second model score for a new sample. If the score is <0.35, the sample is predicted to be from a patient having CD. Otherwise, the sample is predicted to be from a patient having UC.

I. Exemplary Algorithm for Predicting Diagnosis in New Samples

In certain embodiments, the IBD sgi diagnostic algorithm of the present invention uses measurements from 17 sero-genetic-inflammatory (sgi) biological markers (e.g., ANCA, ASCA-A, ASCA-G, anti-FlaX, anti-A4-Fla2, pANCA, anti-OmpC, anti-CBir1, ATG16L1, CRP, SAA, ICAM, VCAM, ECM1, STAT3, VEGF, NKX2-3, and combinations thereof) and computes a score based on the first random forest model for predicting IBD vs. non-IBD (see, FIG. 1, 110). The first random forest model determines if a patient has IBD. If the score is less than the IBD vs. non-IBD cut-off (e.g., <0.64), the sample is predicted to be from a patient having IBD (125). Otherwise, the sample is predicted to be from a patient having non-IBD (120). Samples predicted to have IBD proceed to the next step of the algorithm, which is a decision tree or set of rules designed to rule out categorizing the sample as inconclusive (130). If a sample matches the pattern for either of the "indeterminate" rules, the algorithm predicts that the sample as having IBD, but is inconclusive for UC and CD (135). Otherwise, the sample proceeds to the next step of the algorithm (140), which is a second random forest model for predicting UC vs. CD (150). The diagnostic algorithm of the present invention uses measurements from 11 sero-genetic-inflammatory biological markers (e.g., ANCA, ASCA-A, ASCA-G, anti-FlaX, anti-A4-Fla2, pANCA, anti-OmpC, anti-CBir1, ECM1, STAT3, VEGF, and combinations thereof) to compute a model score based on the second random forest model for predicting UC vs. CD. If the score is less than the UC vs. CD cut-off (e.g., 0.35), the algorithm predicts the sample as having CD (153). Or else, the algorithm predicts the sample as having UC (155).

J. Performance Evaluation

Figure 5:
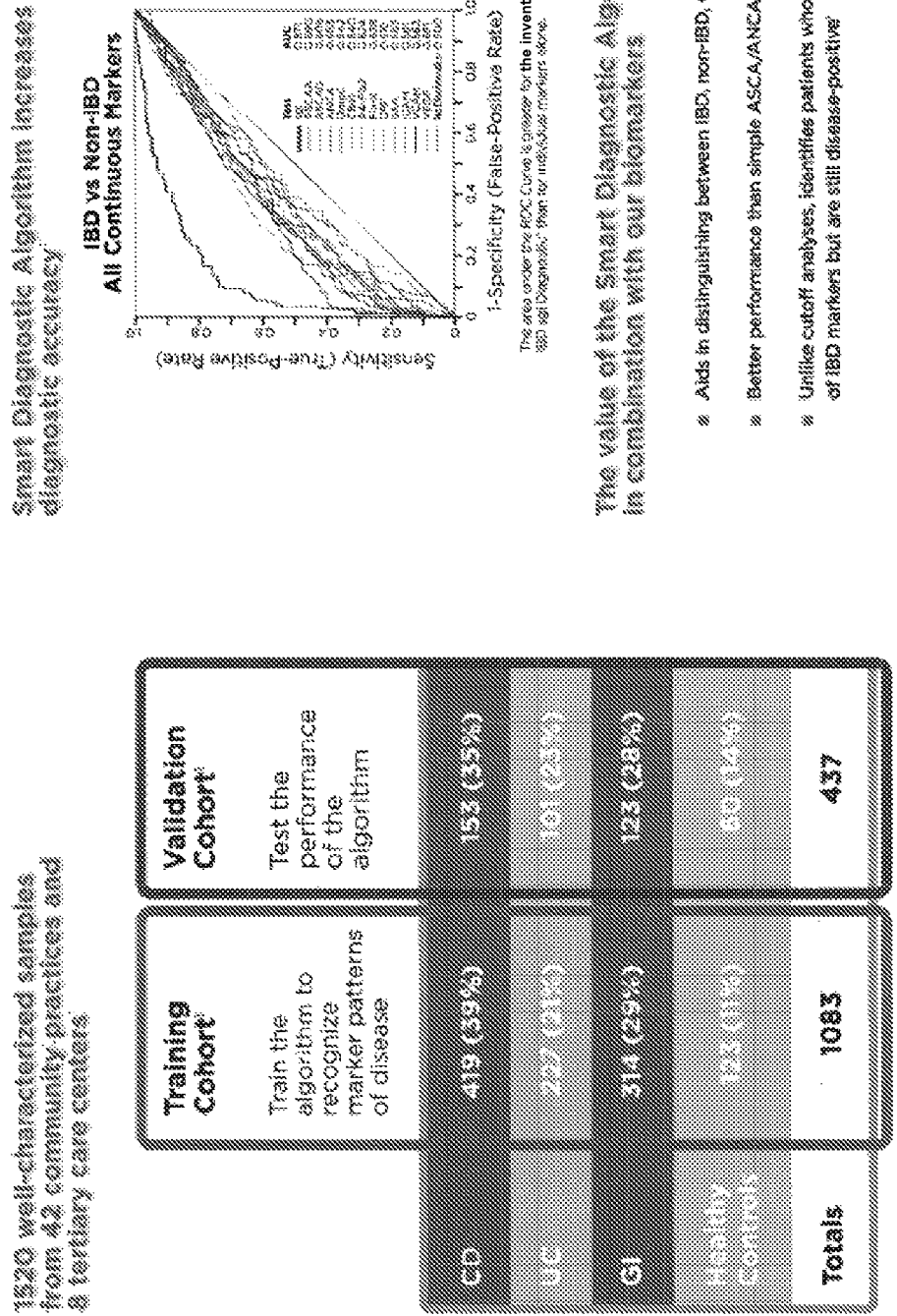
FIG. 5 illustrates training and validation cohort characteristics and the area under the ROC curve for the sgi algorithm and for individual markers.

The performance for the sgi algorithm was measured against a separate validation set that satisfied the same exclusion criteria as used during training. After applying the same set of exclusions used for the training of the first random forest model, the validation set consisted of 437 samples. The same rules for exclusion that were applied during training of the second random forest model (e.g., indeterminate patients and also "Rule 1/Rule 2" violations) were used prior to determining the performance of UC vs. CD calls. This left 199 samples as known UC or known CD. The results are presented in Table 18. The data show that the sgi algorithm predicts IBD, CD and UC with high sensitivity and specificity. FIG. 5 provides training and validation cohort characteristics and illustrates that the area under the ROC curve is greater for the sgi algorithm than for individual markers alone. As such, the sgi algorithm of the invention advantageously (i) aids in distinguishing between IBD, non-IBD, CD, and UC, (ii) has better performance than ASCA/ANCA cutoff testing, and (iii) identifies patients who have low levels of IBD markers but are still disease-positive.

TABLE 18

Performance results for sgi algorithm on a separate validation set.

| Performance | sgi |
|---|---|
| IBD/Non-IBD ROC | 0.871 |
| UC/CD ROC | 0.929 |
| IBD sensitivity | 0.736 |
| IBD specificity | 0.896 |
| CD sensitivity | 0.889 |
| CD specificity | 0.810 |
| UC sensitivity | 0.977 |
| UC specificity | 0.835 |

K. Marker Importance

Random forest modeling provides a method for determining the importance of variables (e.g., markers). This is done by scrambling the measurements for one marker among all samples and then determining the average drop in accuracy in trees in the forest. In this way any significant correlation between the marker and the predicted outcome is likely to be broken, while at the same time preserving all the features of the statistical distribution of the marker. Only samples not used in the training of a particular tree ("out-of-bag") are used for the accuracy determination. The procedure is then repeated for each of the other markers. The reported score is the average decrease in accuracy divided by its variance. Since two random forest models are in the sgi algorithm, two sets of importance are needed. These are shown in Tables 19 and 20. Note that all of the markers kept for each model have at least some importance. Together with practical concerns such as assay stability and cost, the measured importance was used to decide which markers were retained in the assays.

TABLE 19

Importance measure of markers used in the IBD vs. non-IBD model, in descending order of importance in the training set.

| Marker | Importance |
|---|---|
| ANCA | 4.57 |
| ASCAA | 4.32 |
| ASCAG | 3.84 |
| pANCA | 3.75 |
| FlaX | 3.67 |
| SAA | 2.96 |
| Fla2 | 2.88 |
| ICAM | 2.23 |
| OmpC | 2.02 |
| CBir1 | 1.84 |
| VCAM | 1.84 |
| CRP | 1.35 |
| NKX2 | 0.65 |
| ATG16L1 | 0.41 |
| STAT3 | 0.23 |
| ECM1 | 0.20 |
| VEGF | 0.19 |

TABLE 20

Importance measure of markers used in the UC vs. CD model, in descending order of importance in the training set.

| Marker | Importance |
|---|---|
| ANCA | 6.37 |
| ASCAA | 5.62 |
| ASCAG | 4.75 |
| FlaX | 4.73 |
| Fla2 | 4.45 |
| pANCA | 3.62 |
| OmpC | 3.59 |
| CBir1 | 3.40 |
| ECM1 | 0.92 |
| STAT3 | 0.38 |
| VEGF | 0.17 |

One skilled in the art would know that according to the importance value, ANCA has the most importance and VEGF has less importance in the IBD vs. non-IBD model. Similarly, ANCA has the highest importance value and VEGF has the lowest importance value in the UC vs. CD model. One of skill would also know that an algorithm used to determine or predict a diagnosis of IBD vs. non-IBD can include one or a plurality of the markers listed in Table 19. Likewise, one of skill would know that an algorithm used to determine or predict a diagnosis of UC vs. CD can include one or a plurality of the markers listed in Table 20.

Example 4

Logistic Regression Modeling of IBD Diagnostics Using Sero-Genetic-Inflammation Markers This example illustrates a method of creating an algorithm for IBD diagnostics based on logistic regression modeling.

This example further illustrates a method of building an algorithm comprising two logistic regression models, wherein one model can predict an IBD vs. non-IBD diagnosis, and another model can predict a CD vs. UC diagnosis.

A logistic regression model (also referred to as a logistic model or a logit model) is used for prediction of the probability of occurrence of an event by fitting data to a logit function logistic curve. In some instances, it is a generalized linear model used for binomial regression.

In some embodiments, the logistic regression models use the same sero-genetic-inflammation markers and the cohort composition as those used to build the random forest models described in Example 3. 17 sero-genetic-inflammation markers include, but are not limited to, anti-*Saccharomyces cerevisiae* antibodies (e.g., ASCA-IgA and ASCA-IgG), anti-neutrophil antibodies (e.g., pANCA and ANCA), anti-microbial and anti-flagellin antibodies (e.g., antibodies to OmpC, CBir1, Fla2 and FlaX), growth factors (e.g., VEGF), acute phase proteins (CRP), apolipoproteins (e.g., SAA), cellular adhesion molecules (e.g., ICAM and VCAM), and SNPs (e.g., ATG16L1, ECM1, NKX2-3 and STAT3).

Samples were selected for exclusion from training and validation sets following similar rules as described in Example 3. The logistic regression models were built from 1083 samples in the training set. The models were then tested for prediction performance using a validation set of 437 samples of known diagnoses.

Figure 6:
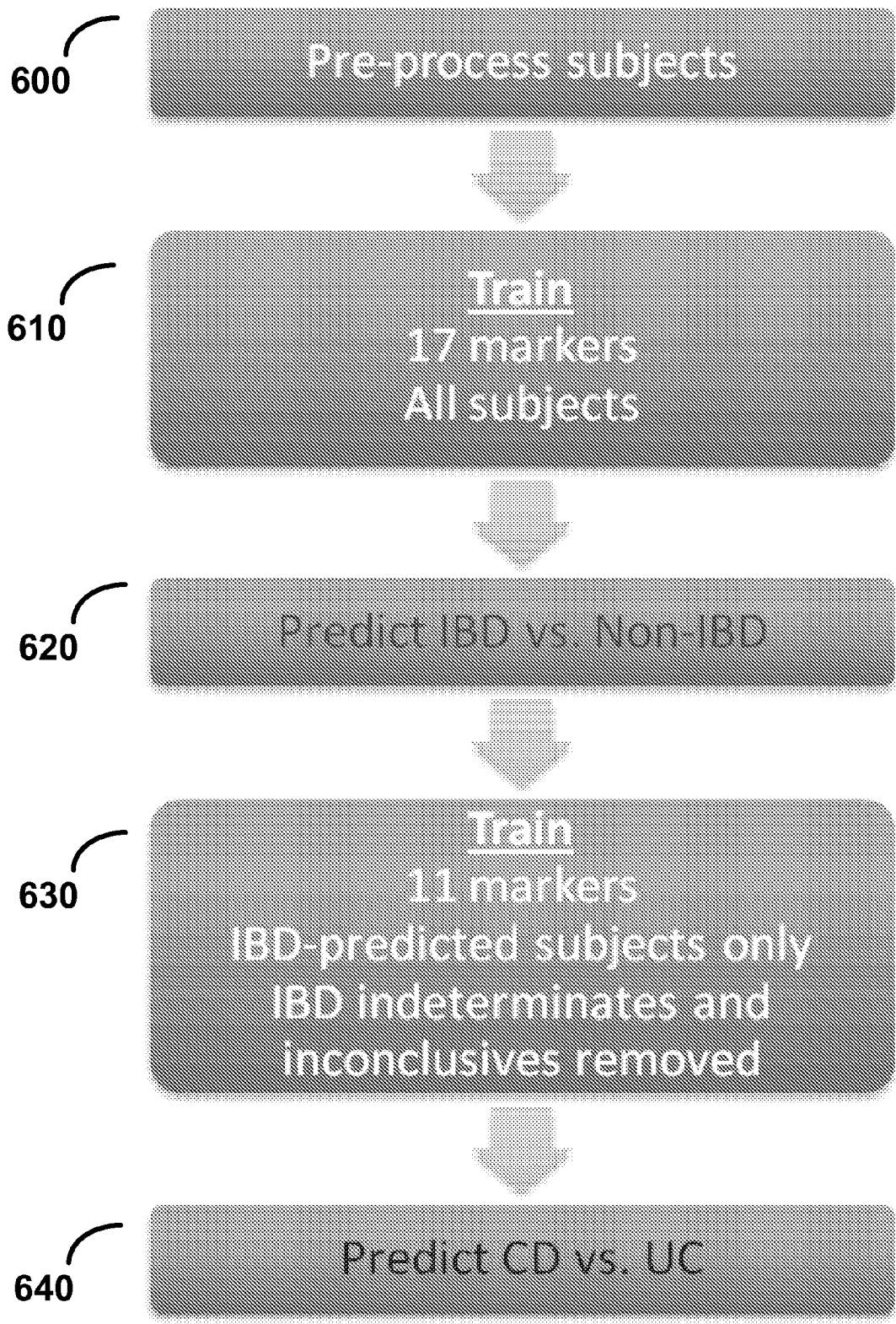
FIG. 6 illustrates an exemplary embodiment of a logistic regression model for predicting IBD diagnostics.

The logit models were created using the same sero-genetic-inflammation markers and the cohort composition as those used to build the random forest models described in Example 3. The method of developing the algorithm is illustrated in FIG. 6. To train the logistic regression model for predicting IBD vs. non-IBD diagnosis (610), 17 sero-genetic-inflammation markers consisting of anti-*Saccharomyces cerevisiae* antibodies (e.g., ASCA-IgA and ASCA-IgG), anti-neutrophil antibodies (e.g., pANCA and ANCA), anti-microbial and anti-flagellin antibodies (e.g., antibodies to OmpC, CBir1, Fla2 and FlaX), growth factors (e.g., VEGF), acute phase proteins (CRP), apolipoproteins (e.g., SAA), cellular adhesion molecules (e.g., ICAM and VCAM), and SNPs (e.g., ATG16L1, ECM1, NKX2-3 and STAT3) were used. Thus, the computational statistical algorithm is created that can predict whether a sample is from a patient predicted to have IBD or non-IBD (620).

Samples predicted to have IBD are used to create the second logit model after the samples determined to be IBD indeterminate samples are removed (630). Similar to the decision tree analysis described in Example 3, indeterminate samples are defined as those meeting one of the following two criteria: 1) an ANCA score$\geq$16.8 EU/ml, pANCA2 score positive, and one or more of the following conditions as being true: CBir1$\geq$29.475 EU/ml, Fla2$\geq$34.5 EU/ml or FlaX$\geq$28.875 EU/ml; or pANCA2 positive and any 2 or more of these conditions as being true: CBir1$\geq$29.475 EU/ml, Fla2$\geq$34.5 EU/ml or FlaX$\geq$28.875 EU/ml. If a sample was predicted to have IBD according to the logistic regression model for IBD vs. non-IBD, and was determined to be an indeterminate sample or inconclusive, the sample is predicted to have indeterminate colitis (IC) or is inconclusive. 11 sero-genetic-inflammation markers (e.g., ANCA, ASCA-A, ASCA-G, anti-FlaX, anti-Fla2, pANCA, anti-OmpC, anti-CBir1, ECM1, STAT3, VEGF, and combinations thereof) were used to train the second logit model (630). The trained and validated algorithm can predict whether a patient has CD vs. UC (640).

The performance of the logit model algorithm can be analyzed by testing the algorithm on a validation set of sample of known diagnoses. A comparison of the performance of the random forest algorithm described in Example 3 and the logistic regression algorithm described above shows that the random forest demonstrates more IBD specificity, CD sensitivity and specificity, and UC specificity (Table 21).

TABLE 21

Comparison of Algorithm Performances.

|  | Random Forest | logistic Regression |
| --- | --- | --- |
| IBD ROC AUC | 0.871 | 0.862 |
| UC ROC AUC | 0.929 | 0.948 |
| IBD Sensitivity | 0.736 | 0.744 |
| IBD Specificity | 0.896 | 0.858 |
| CD Sensitivity | 0.889 | 0.878 |
| CD Specificity | 0.810 | 0.803 |
| UC Sensitivity | 0.977 | 0.978 |
| UC Specificity | 0.835 | 0.800 |

Table 22 shows the performance of the algorithm for predicting IBD, CD and UC. Sensitivity is calculated using the following equation: true positives/(true positives+false negatives). Specificity is calculated using the equation: true negative/(true negative+false positive). Accuracy is calculated with the formula: (true positive+true negative)/(true positive+true negative+false positive+false negative). Precision is calculated from the equation: true positive/(true positive+false positive). The algorithm has high sensitivity and accuracy for predicting UC.

TABLE 22

Performance of Logistic Regression Algorithm.

|  | IBD | CD | UC |
| --- | --- | --- | --- |
| True Positives | 189 | 79 | 45 |
| True Negatives | 157 | 57 | 92 |
| False Positives | 26 | 14 | 23 |
| False Negatives | 65 | 11 | 1 |
| Sensitivity | 0.744 | 0.878 | 0.978 |
| Specificity | 0.858 | 0.803 | 0.800 |
| Accuracy | 0.792 | 0.845 | 0.851 |
| Precision | 0.879 | 0.849 | 0.662 |

Figure 7:
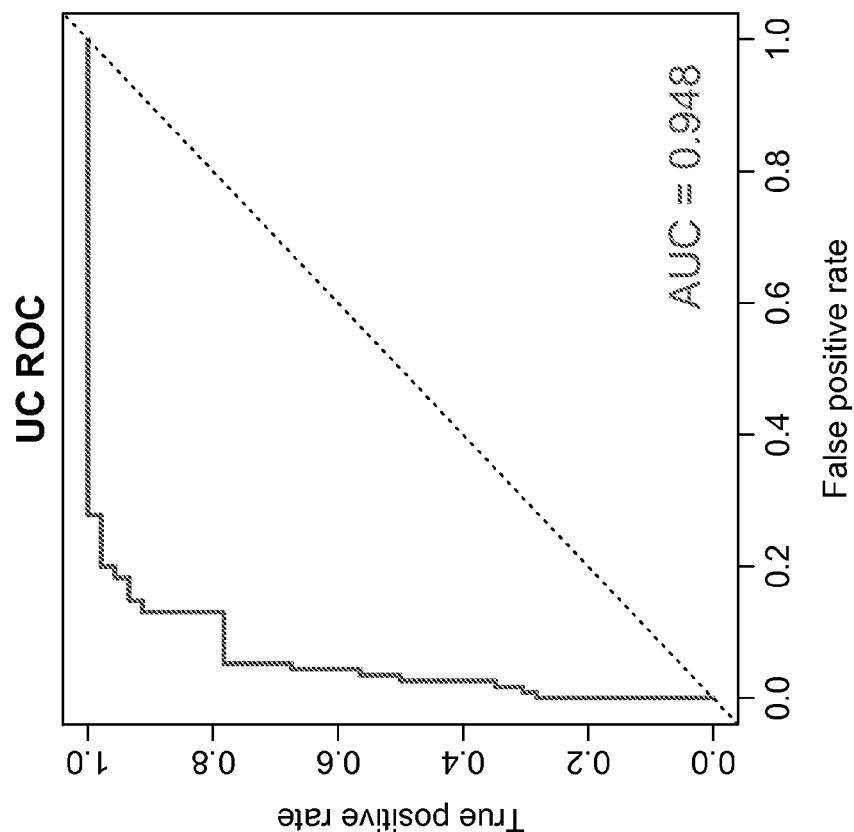
FIG. 7A illustrates that the IBD model is a good classifier system for predicting IBD.
FIG. 7B illustrates that the UC model is a good classifier system for predicting UC.
Figure 7:
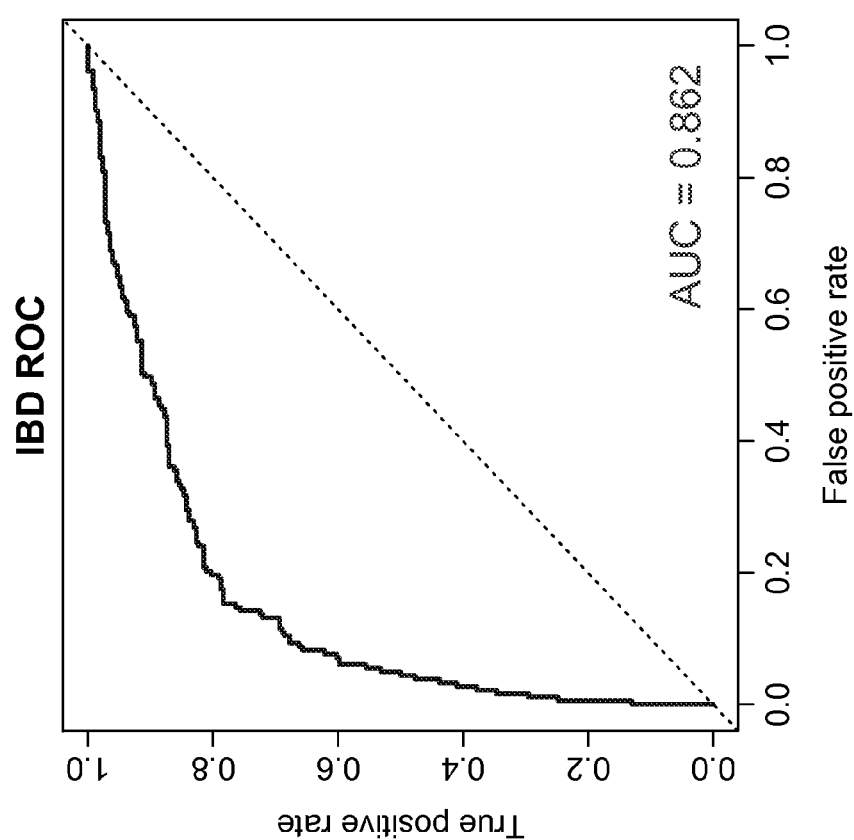

Sensitivity of the algorithm can be analyzed and plotted as two receiver operating characteristic (ROC) curves, one representing the IBD logit model and the other representing the UC logic model. FIG. 7A illustrates that the IBD model is a good classifier system for predicting IBD. FIG. 7B illustrates that the UC model is a good classifier system for predicting UC.

Figure 8:
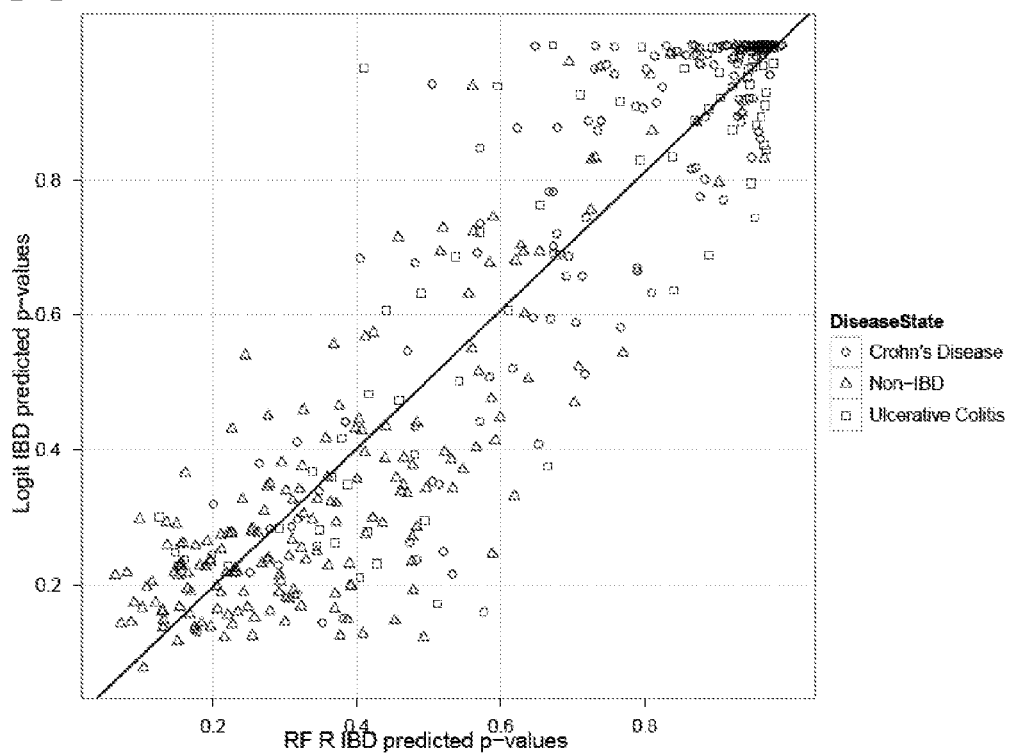
FIG. 8A illustrates a scatter plot of predicted p-values for an IBD logit model versus an IBD random forest model created in R.
FIG. 8B illustrates a scatter plot of an IBD random forest model created in Matlab versus an IBD logic model.
Figure 8:
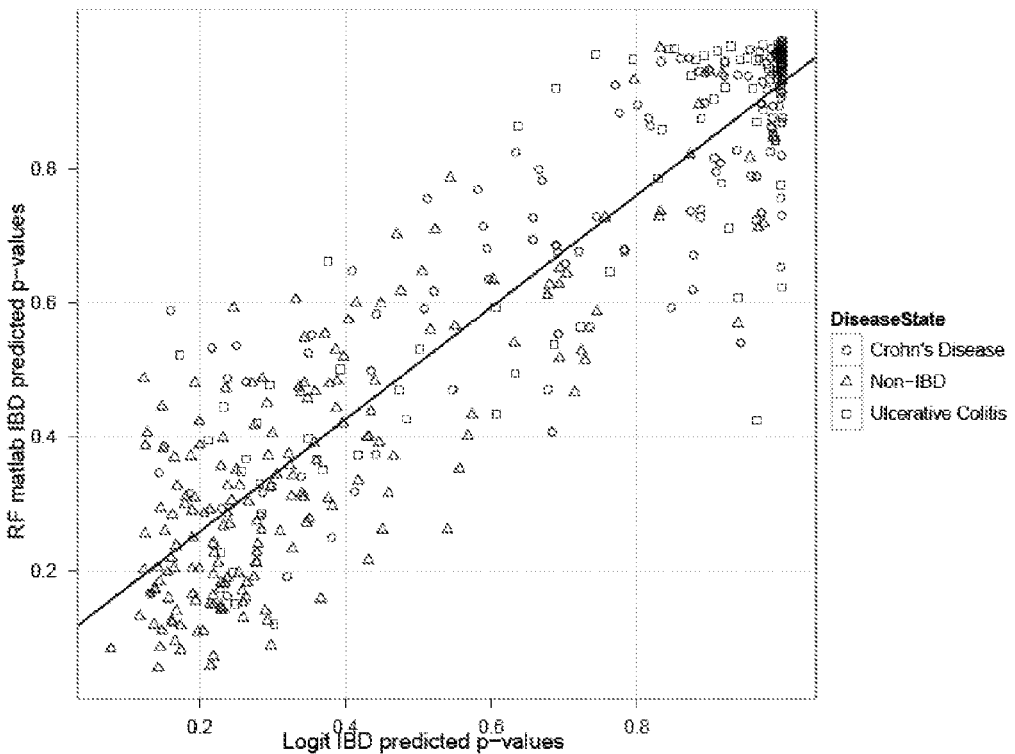
Figure 9:
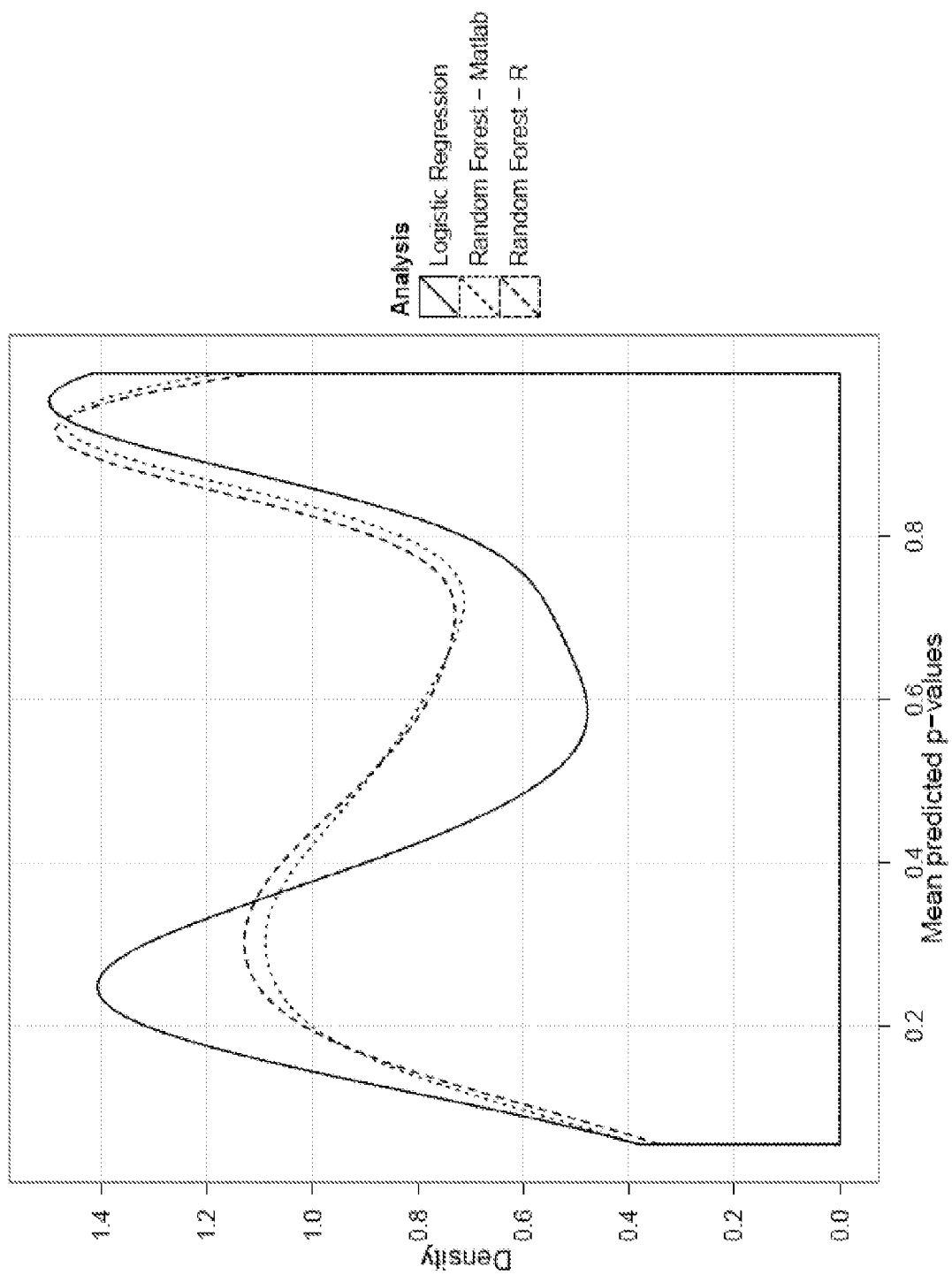
FIG. 9 illustrates a density graph of predicted p-values for an IBD logit model and two IBD random forest models. The graph compares the similarities of the models at predicting non-IBD, CD and UC.

The similarity of the algorithms based on either the IBD logit model or the IBD random forest model can be compared in a scatter plot of predicted p-values (FIG. 8) or a density plot of mean predicted p-values (FIG. 9). FIG. 9 illustrates that there are some differences between the logistic regression model and either of the random forest models.

Figure 10:
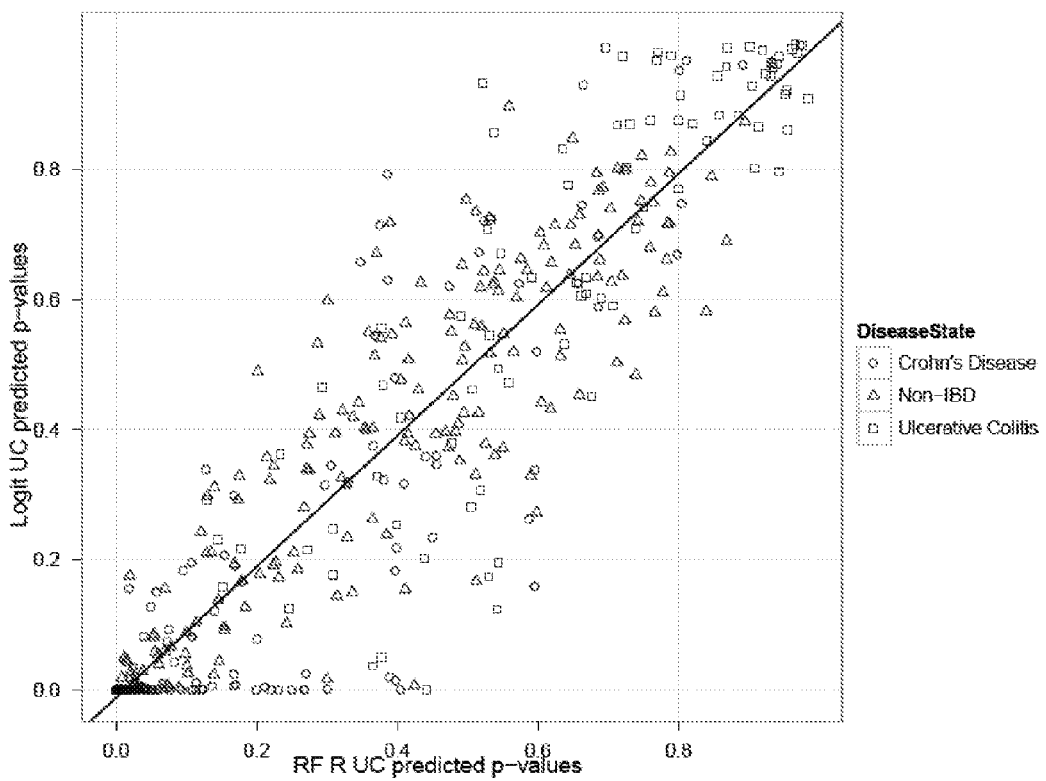
FIG. 10A illustrates a scatter plot of predicted p-values for a UC logit model and a UC random forest model created in R.
FIG. 10B illustrates a scatter plot of predicted p-values for a UC logit model and a UC random forest model created in Matlab.
Figure 10:
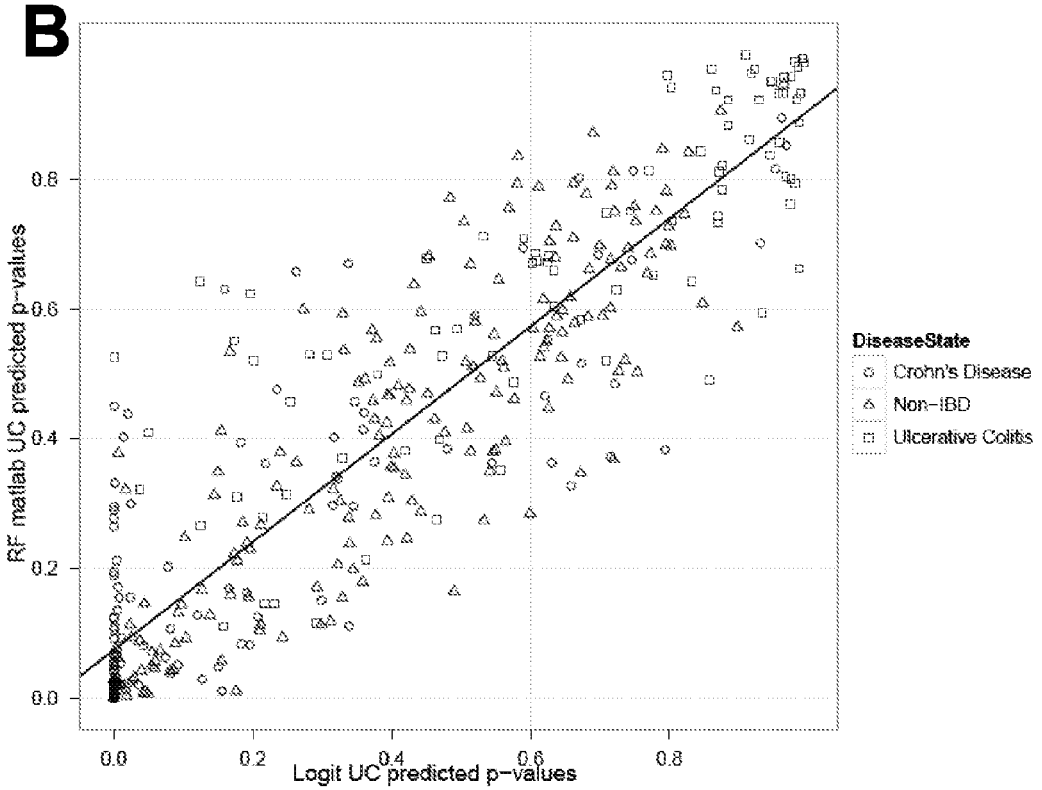
Figure 11:
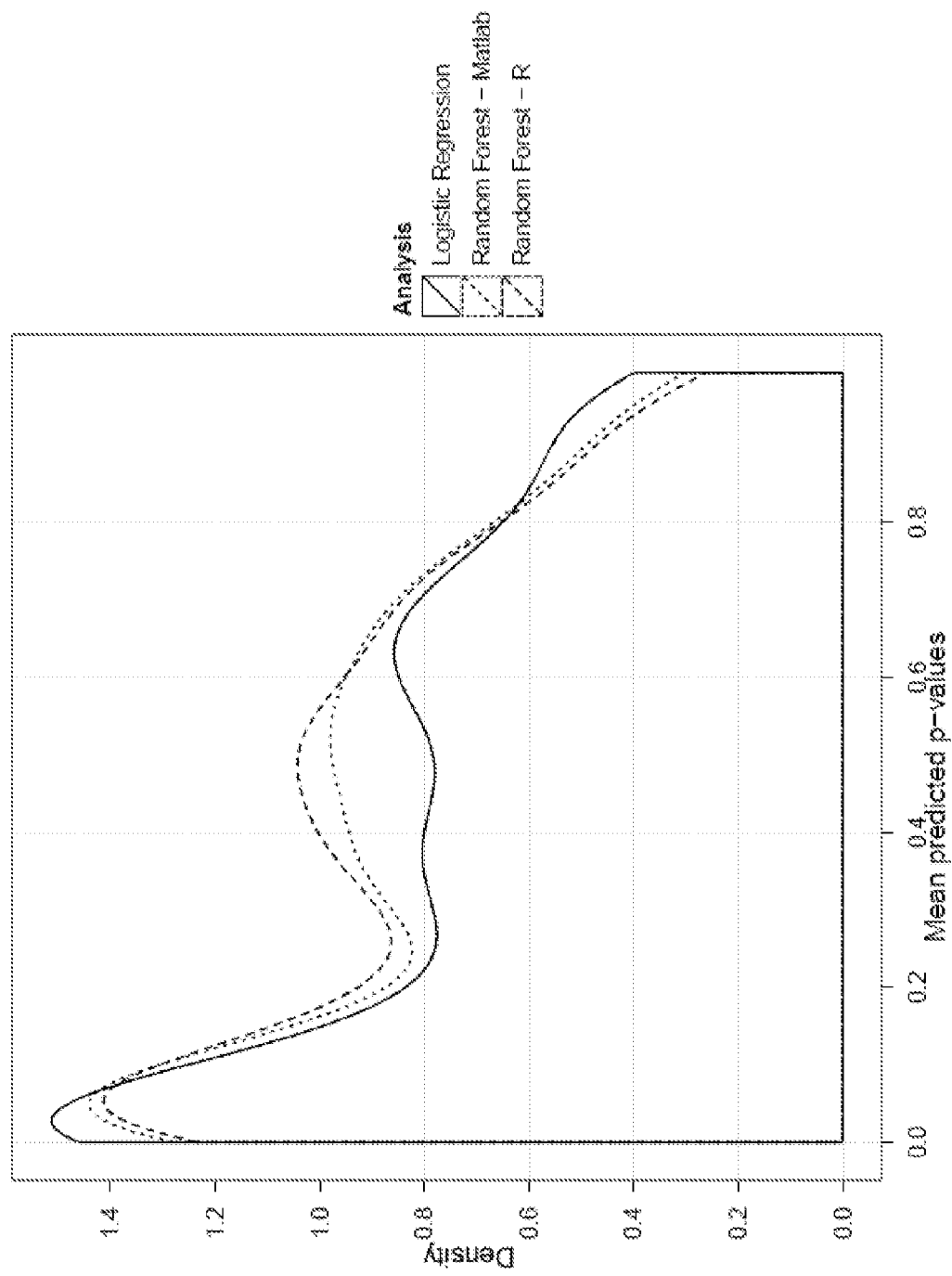
FIG. 11 illustrates a density graph of predicted p-values for a UC logit model and two UC random forest models. The graph compares the similarities of the models at predicting non-IBD, CD and UC.

In addition, the similarities of the algorithms based on either the UC logit model or the UC vs. CD random forest model can be compared in a scatter plot of predicted p-values (FIG. 10) or a density plot of mean predicted p-values (FIG. 11). FIG. 11 shows that there are some differences between the logistic regression model and either of the random forest models.

Example 5

Improved IBD Diagnostics Using sgi Algorithm Based on Two Random Forest Models

This example illustrates methods for improving IBD diagnosis using an algorithm based on sero-genetic-inflammation (sgi) markers to predict a patient's IBD status (e.g, non-IBD, UC, CD, IC, or IBD but inconclusive for UC and CD). In some embodiments, the sgi algorithm comprises one or a plurality of random forest models that uses known sero-genetic-inflammation marker measurements from samples from patients classified with non-IBD, IC, UC or CD to build a computer-based classifier. In some embodiments, the sgi algorithm can have a random forest model that predicts IBD vs. non-IBD. In another embodiment, the sgi algorithm can have a random forest model that predicts UC vs. CD.

The steps of one embodiment of the IBD sgi algorithm of the present invention are illustrated in FIG. 1. Firstly, the sgi algorithm uses a random forest classifier based on measurement data of 17 biological markers (18 values as pANCA is measured twice) and predicts whether a patient is non-IBD or has IBD (110). Next, a decision tree or set of rules is used to determine whether a patient predicted to have IBD has a biomarker pattern that is consistent with an inconclusive diagnosis (e.g., a diagnosis that is inconclusive for CD versus UC) (130). Then, another random forest-based algorithm that uses 11 marker measurements predicts whether the patient predicted to have IBD has either UC or CD (150). Thus, the sgi algorithm test classifies a sample as from a non-IBD (120), inconclusive (135), CD (153) or UC (155) patient.

The sgi algorithm is constructed through a series of training, testing and resampling steps that utilize a training dataset (e.g., training set) which contains the known marker measurement from samples from non-IBD, IC, UC and/or CD patients. The training set is divided such that two-thirds comprise the model-training set and one-third comprises the test set.

In certain instances, a sample of the training dataset is removed from further analysis if it meets any of the following criteria: (1) subject's last experience of symptoms was more than 6 months prior to a doctor's visit; (2) subject's last symptom was described as "N/A" and subject enrolled in study; (3) subject did not meet the inclusion/exclusion criteria of the study; and (4) subject history lacking information regarding length of disease affliction.

In some instances, a sample is removed from the training data set for the UC vs. CD random forest model. In some instances, a sample meeting the following criteria is eliminated: 1) known CD diagnosis; 2) ANCA<16.8 EU/ml; pANCA2 negative; and 3) two or more of these conditions satisfied: ASCA-A≥10.675 EU/ml, ASCA-G≥14.175 EU/ml, OmpC≥9.4 EU/ml, CBir1≥29.475 EU/ml, Fla2≥34.5 EU/ml, or FlaX≥28.875 EU/ml. In other instances, a subject's sample is removed from the training dataset used to construct the UC vs. CD random forest model if: 1) the subject has a UC diagnosis; 2) ANCA≥16.8 EU/ml; pANCA2 positive; and 3) all of the following conditions are satisfied: ASCA-A<20.675 EU/ml, ASCA-G<14.175 EU/ml, OmpC<9.4 EU/ml, CBir1<29.475 EU/ml, Fla2<34.5 EU/ml and FlaX<28.875 EU/ml. In yet other instances, a sample is excluded from the training set if it is a known non-IBD sample, e.g., previously diagnosed to have non-IBD. In some instances, a sample determined to be indeterminate, wherein it meets either of the following conditions is also excluded from the training set. One condition includes: ANCA>16.8 EU/ml, pANCA2 positive, and one or more of these criteria, wherein CBir1≥29.475

EU/ml, Fla2≥34.5 EU/ml or FlaX≥28.875 EU/ml. Another condition includes: pANCA2 positive, and any two or more of these criteria, wherein CBir1≥29.475 EU/ml, Fla2≥34.5 EU/ml or FlaX≥28.875 EU/ml. In yet other instances, samples are excluded if it meets one of the following criteria: (1) pANCA2=1 and ANCA<11.9 EU/ml; (2) pANCA2=0 and ANCA≥11.9 EU/ml; (3) is clearly affected by an error; or 4) is normally retested during the production mode.

This example illustrates a method for building an IBD sgi algorithm using a training set to model. This example also illustrates a method of validating an IBD sgi algorithm. In some embodiments, initial cut-offs are set as the average cut-offs from the resampling phase of the algorithm. Probabilities and predictions on artificial marker data can be made such that a final model can be compared to average resampled models. In some instances, artificial marker data is a dataset that efficiently spans the clinical relevant space of markers with similar distributions. In certain embodiments, an algorithm creates a statistical value (e.g., octile or a quantile with 8 regions) of the continuous markers and generates a random marker value by picking an octile at random or by picking a uniformly distributed random number within that octile. In the case of binary value markers, an octile can be picked at random, except if pANCA2=1, then pANCA is set to equal 1, or if all other markers are generated independently.

In some instances, a sample is classified as from a patient with indeterminate colitis (IC). In particular instances, a sample that is determined to have IBD, an ANCA level≥Q3, pANCA2 positive, and anti-CBir1 or anti-Fla2 or anti-FlaX≥Q3, is predicted to be from a patient with IC. In other instances, an IC patient can be a patient determined to have IBD who is also pANCA2 positive and expresses two out of three markers (e.g., anti-CBir1, anti-Fla2 and anti-FlaX)≥Q3. Table 23 shows the performance of the sgi algorithm compared to the "Serology 7" assay (Prometheus Laboratories Inc., San Diego, Calif.). Notably, Table 23 shows that the performance of the sgi algorithm is improved over the "Serology 7" assay.

TABLE 23

Performance of sgi Algorithm.

| Performance | sgi | "Serology 7" |
| --- | --- | --- |
| IBD/Non ROC | 0.871 | 0.831 |
| UC/CD ROC | 0.929 | 0.902 |
| IBD sensitivity | 0.736 | 0.717 |
| IBD specificity | 0.896 | 0.825 |
| CD sensitivity | 0.889 | 0.871 |
| CD specificity | 0.810 | 0.686 |
| UC sensitivity | 0.977 | 0.815 |
| UC specificity | 0.835 | 0.778 |

Table 24 shows the performance of the SGI algorithm with a validation set (e.g., test set) compared to the performance with two cohorts not used for training or testing the algorithm. It should be noted that the pediatrics cohort is relatively small with 61 samples after sample exclusion rules are followed. The performance of the SGI algorithm on a validation set is better than on sample sets from cohorts not used in the training.

TABLE 24

Performance of sgi Algorithm with Validation Set.

| Performance | sgi Validation | African-American | Pediatrics |
| --- | --- | --- | --- |
| IBD/Non ROC | 0.871 | 0.797 | 0.925 |
| UC/CD ROC | 0.929 | 0.908 | 0.905 |
| IBD sensitivity | 0.736 | 0.691 | 0.487 |
| IBD specificity | 0.896 | 0.791 | 1.0 |
| CD sensitivity | 0.889 | 0.893 | 1.0 |
| CD specificity | 0.810 | 0.542 | 1.0 |
| UC sensitivity | 0.977 | 1.0 | 1.0 |
| UC specificity | 0.835 | 0.857 | 1.0 |

Figure 12:
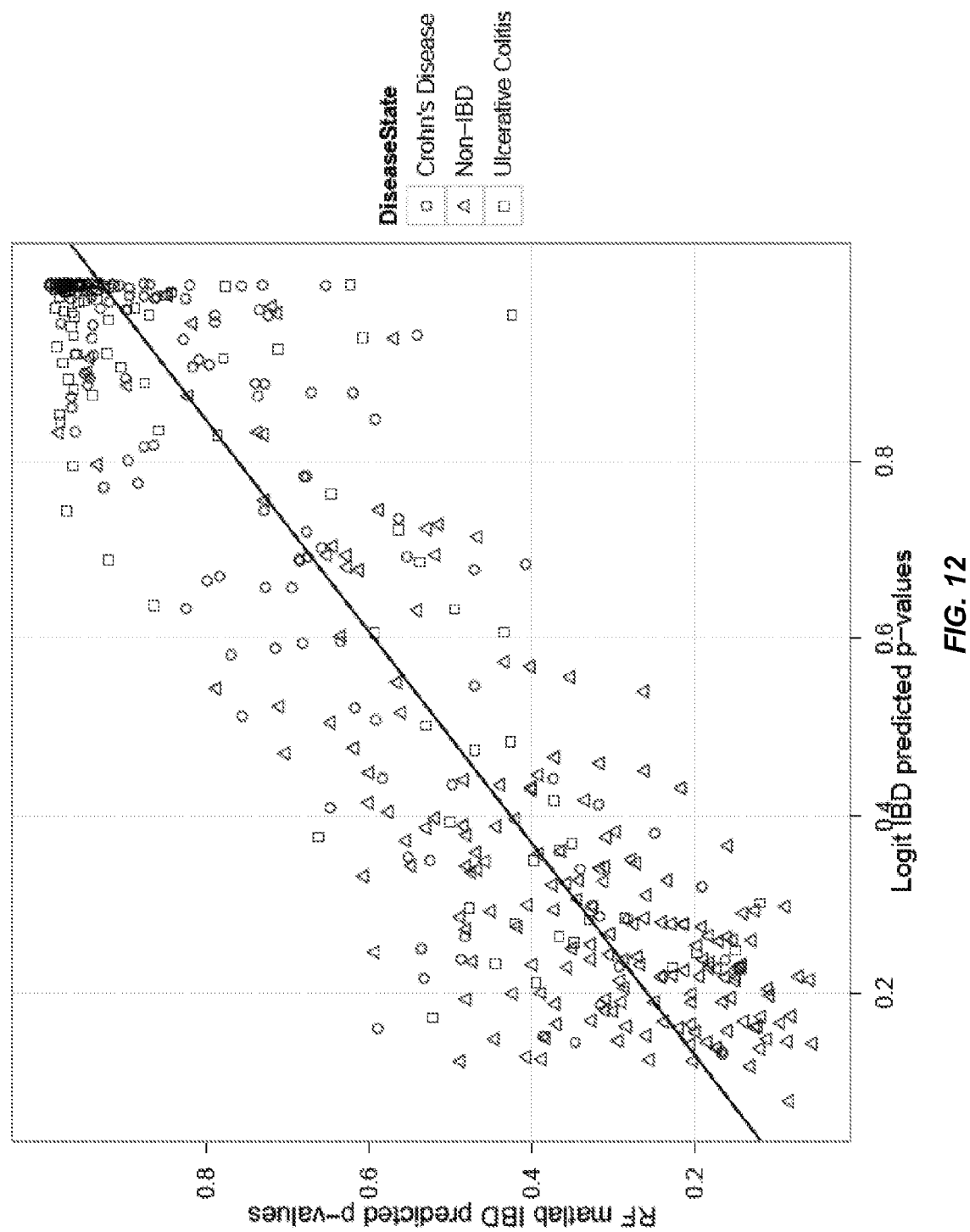
FIG. 12 illustrates a scatter plot of logit modeling vs. random forest modeling for predicting IBD vs. non-IBD.
Figure 13:
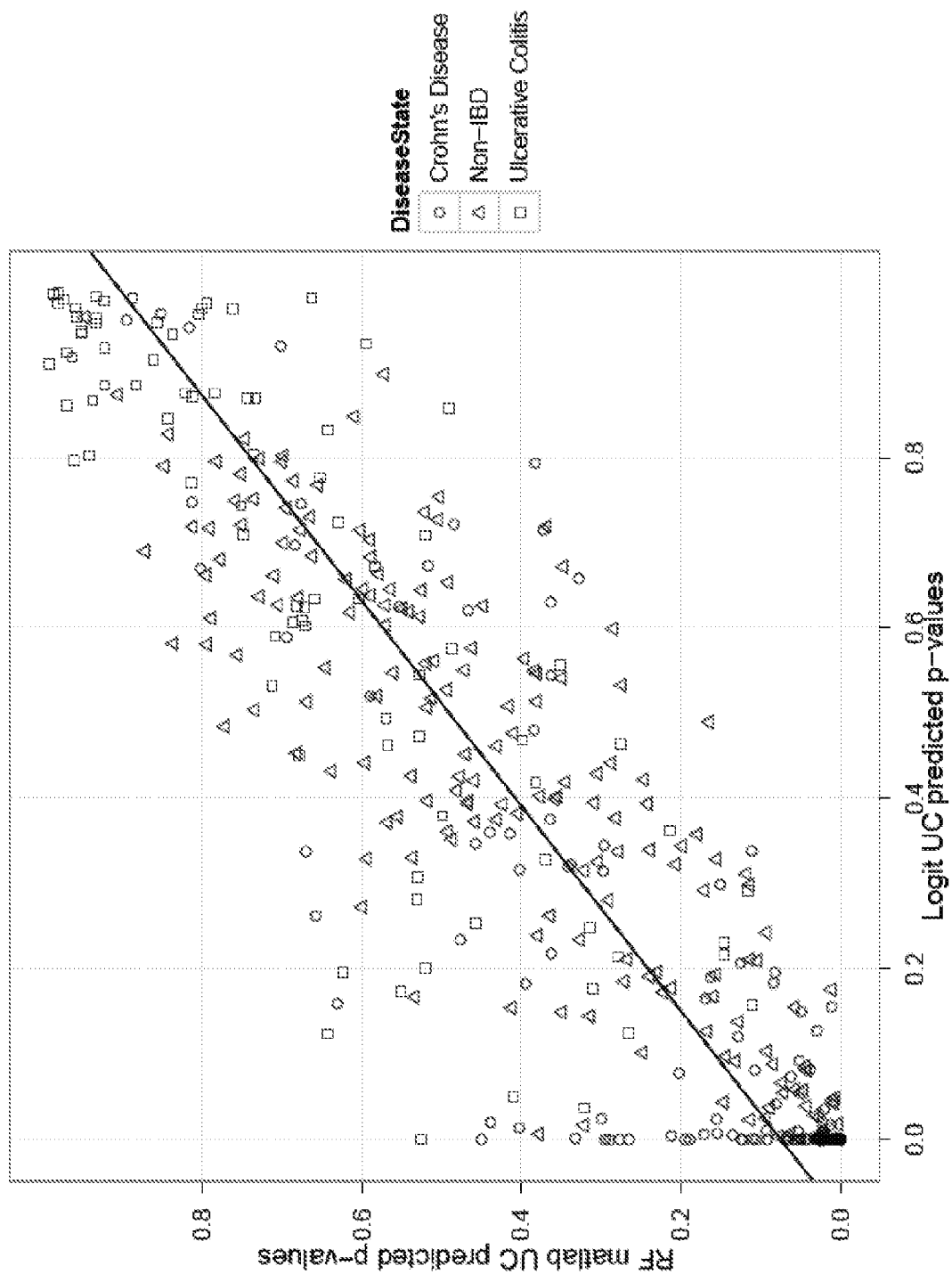
FIG. 13 illustrates a scatter plot of logit modeling vs. random forest modeling for predicting UC vs. CD.
Figure 14:
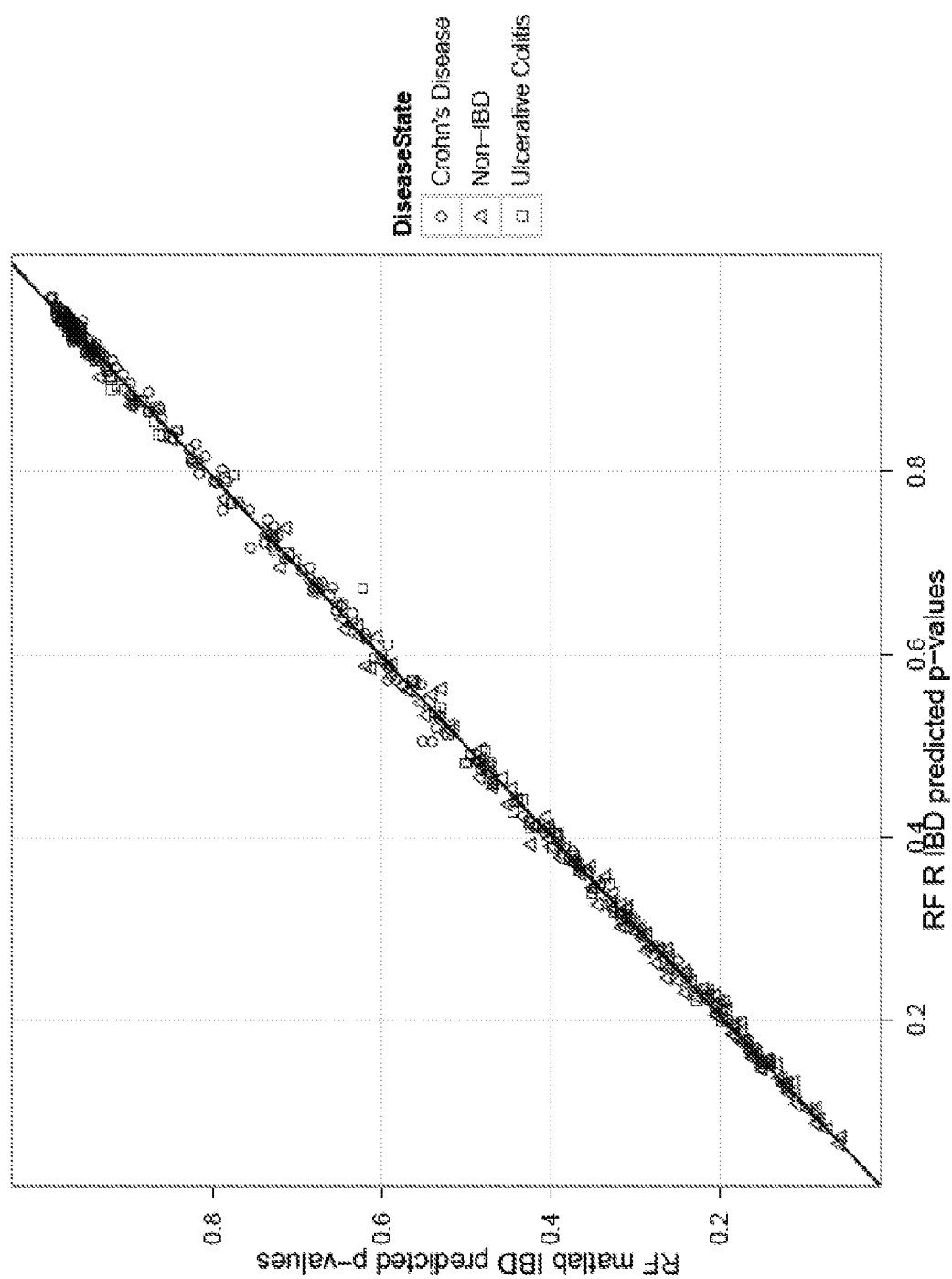
FIG. 14 illustrates a scatter plot for two random forest IBD vs. non-IBD models created in either R or Matlab.
Figure 15:
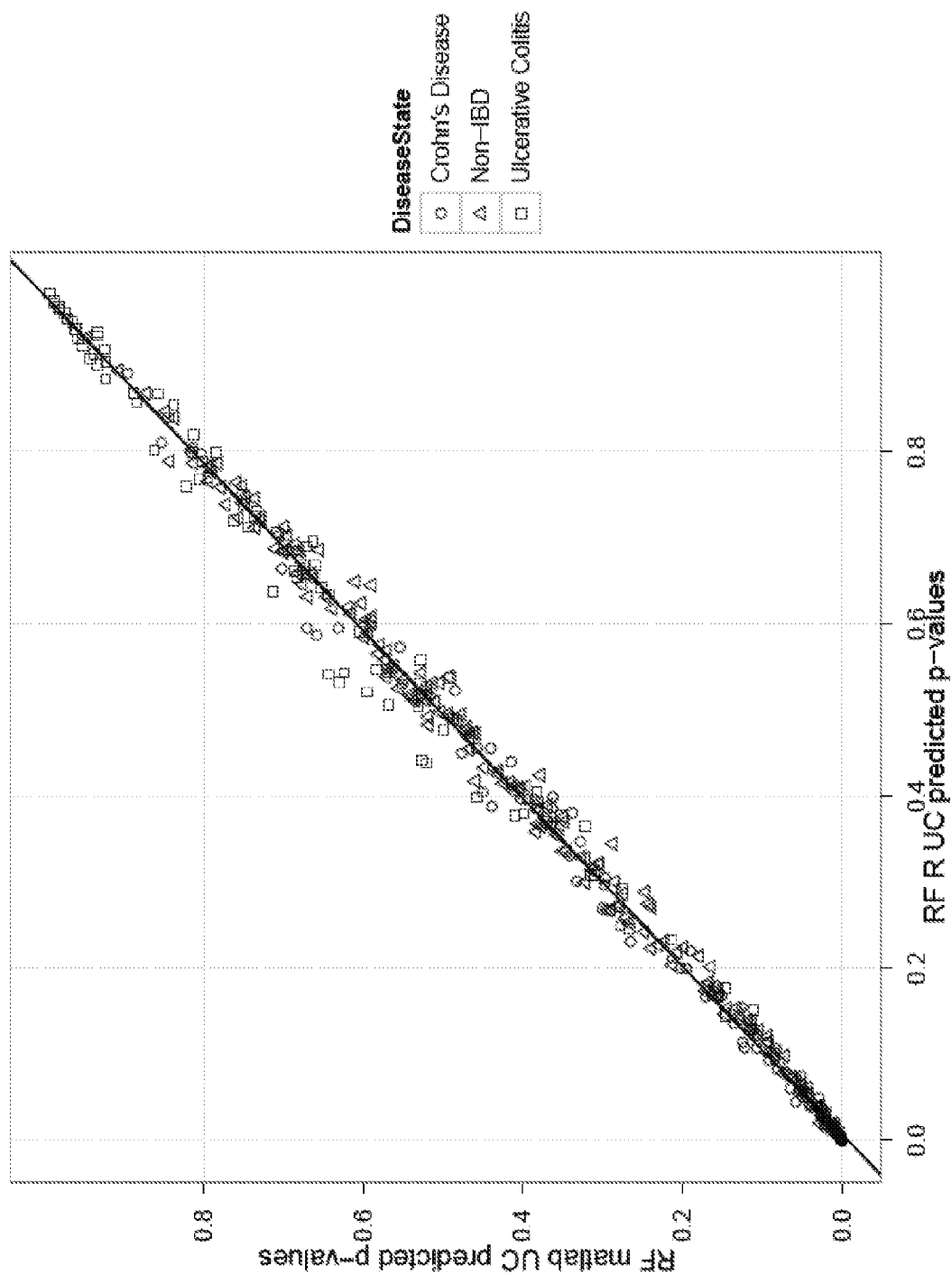
FIG. 15 illustrates a scatter plot for two random forest UC vs. CD models created in either R or Matlab.

The data show a comparison of the random forest models of the sgi algorithm to a logistic regression model. FIG. 12 illustrates a scatter plot of the p-values of an IBD logistic regression model (see; Example 4) along the y-axis and the p-values of an IBD random forest model created in R along the x-axis. FIG. 13 illustrates a scatter plot of the p-values of a UC vs. CD logistic regression model (see, Example 4) along the y-axis and the p-values of a UC vs. CD random forest model along the x-axis. FIGS. 14 and 15 illustrate the performance differences between the two algorithms.

The data show a comparison of the sgi algorithm using two different statistical analysis programs (e.g., R and Matlab). FIG. 14 shows a comparison of the IBD vs. non-IBD model. FIG. 15 shows a comparison between the UC vs. CD model. The data indicate that the software programs generated similar results.

Example 6

IBD sgi Diagnostic Algorithm and Datasets to Predict IBD Diagnostics

A random forest modeling algorithm is created through a process of training the computational model using a training set of data of samples from a cohort. The trained algorithm is validated using a validation set of data of samples from a cohort. This example illustrates the use of a training set and a validation set in random forest modeling.

This example illustrates a method of using samples with measurements for biological makers to train and validate a diagnostic algorithm of random forest machine learning modeling. This example shows that the methods described herein (see, e.g., Examples 1-5) can be used to predict or diagnose non-IBD, IBD, IC, CD, UC, and/or IBD inconclusive for UC and CD. The example also illustrates that rules for the exclusion of samples can be applied in the algorithm.

In some embodiments, the training and validation sets comprise measurements of sero-genetic-inflammation (sgi) markers (e.g., ASCA-A, ASCA-G, pANCA, ANCA, anti-OmpC, anti-Fla2, anti-FlaX, VEGF, CRP, SAA, ICAM, VCAM, ATG16L1, ECM1, NKX2-3, and STAT3) from samples with known diagnoses, such as non-IBD, CD and UC. The known diagnosis of samples in the training set are listed in column "Dx3" of Table 29, wherein "0" refers to non-IBD diagnosis, "1" refers to CD diagnosis, and "2" refers to UC diagnosis. The term "known diagnosis" refers to the diagnosis of a patient using a method not comprising random forest modeling. In some instances, the known diagnosis is determined. The detection of sero-genetic-inflammatory biological markers in samples from different cohorts was performed as described herein. Table 25 shows measurements of samples #1-14 of the training set (DataSet 1). DataSet 1 having 14 samples is merely a representative subset of a much larger data set having an n value of about 1490 samples. Text-based biological marker data were transformed into discrete numeric variables (see, e.g. Example 3 and Table 16. Table 26 below shows the transformed measurements of markers such as pANCA, ATG16L1, ECM1, NKX2-3 and STAT3.

Again, the validation set shown here (samples 15-28) is merely a representative subset of a much larger data set having an n value of about 679 samples.

TABLE 25

Biological Markers in Training Set.

| Sample #. | Identifier | Data Set | ASCAA | ASCAG | ANCA | OmpC | CBir1 | Fla2 | Flax | VEGF | CRP | SAA | ICAM | VCAM |
|---|---|---|---|---|---|---|---|---|---|---|---|---|---|---|
| 1 | 10-IBD-07.059-081 | 1 | 3 | 9.1 | 3 | 3 | 18.1 | 14.7 | 11.6 | 45 | 13706 | 3935 | 507 | 544 |
| 2 | 10-IBD-07.079-002 | 1 | 6.2 | 3 | 8.2 | 3 | 8.1 | 29.9 | 6.5 | 184 | 751 | 2088 | 240 | 487 |
| 3 | 10-IBD-01.009-024 | 1 | 23 | 27.1 | 28.7 | 7.9 | 26.3 | 34.1 | 35.7 | 171 | 5470 | 4341 | 513 | 971 |
| 4 | 10-IBD-01.009-026 | 1 | 78.3 | 46 | 23 | 11.4 | 100 | 100 | 100 | 543 | 29610 | 85380 | 441 | 677 |
| 5 | 10-IBD-07.040-004 | 1 | 3 | 3 | 5.3 | 3 | 7.3 | 5.3 | 3.3 | 116 | 1369 | 2727 | 511 | 452 |
| 6 | 10-IBD-07.040-006 | 1 | 3 | 3 | 4.5 | 6.6 | 11 | 17.2 | 15 | 30 | 15826 | 7843 | 409 | 511 |
| 7 | 10-IBD-01.005-031 | 1 | 100.1 | 49.8 | 84.4 | 6.2 | 83.5 | 95.5 | 70 | 71 | 3430 | 11039 | 488 | 545 |
| 8 | 10-IBD-01.013-028 | 1 | 60 | 100.1 | 12 | 7.4 | 82.5 | 100 | 100 | 106 | 149199 | 204889 | 950 | 1273 |
| 9 | 10-IBD-07.059-085 | 1 | 3 | 9.6 | 3 | 5.1 | 30.6 | 47.9 | 24.6 | 56 | 386 | 1684 | 340 | 554 |
| 10 | 10-IBD-07.036-021 | 1 | 3 | 16.2 | 3 | 3 | 31.6 | 18.3 | 16.3 | 30 | 4831 | 139982 | 536 | 736 |
| 11 | 10-IBD-01.002-008 | 1 | 3 | 3 | 19.7 | 3 | 8.3 | 15.7 | 11.7 | 76 | 2618 | 5638 | 329 | 458 |
| 12 | 10-IBD-01.011-007 | 1 | 4 | 3 | 28 | 8.5 | 17.4 | 22.2 | 16 | 218 | 1385 | 2918 | 690 | 878 |
| 13 | 10-IBD-01.001-026 | 1 | 42.8 | 8.8 | 85.5 | 53.7 | 10.9 | 7.8 | 8.8 | 298 | 18723 | 46041 | 672 | 1118 |
| 14 | 10-IBD-01.001-028 | 1 | 10.6 | 15.2 | 65.5 | 18 | 19.2 | 21.2 | 23.1 | 479 | 7782 | 3768 | 417 | 794 |

TABLE 26

Binary Variables of Text-Based Biological Markers in Training Set.

| Sample # | Subject Identifier | Data Set | pANCA | ATG16L1 | ECM1 | NKX2-3 | STAT3 |
|---|---|---|---|---|---|---|---|
| 1 | 10-IBD-07.059-081 | 1 | 0 | 0 | 0 | 0 | 0 |
| 2 | 10-IBD-07.079-002 | 1 | 0 | 1 | 0 | 1 | 0 |
| 3 | 10-IBD-01.009-024 | 1 | 1 | 1 | 0 | 1 | 0 |
| 4 | 10-IBD-01.009-026 | 1 | 0 | 0 | 0 | 0 | 1 |
| 5 | 10-IBD-07.040-004 | 1 | 1 | 0 | 0 | 0 | 0 |
| 6 | 10-IBD-07.040-006 | 1 | 0 | 0 | 0 | 0 | 0 |
| 7 | 10-IBD-01.005-031 | 1 | 1 | 1 | 0 | 0 | 0 |
| 8 | 10-IBD-01.013-028 | 1 | 1 | 1 | 0 | 1 | 1 |
| 9 | 10-IBD-07.059-085 | 1 | 1 | 0 | 0 | 0 | 1 |
| 10 | 10-IBD-07.036-021 | 1 | 0 | 0 | 0 | 0 | 0 |
| 11 | 10-IBD-01.002-008 | 1 | 1 | 0 | 0 | 0 | 1 |
| 12 | 10-IBD-01.011-007 | 1 | 1 | 0 | 0 | 0 | 0 |
| 13 | 10-IBD-01.001-026 | 1 | 1 | 0 | 0 | 0 | 0 |
| 14 | 10-IBD-01.001-028 | 1 | 1 | 1 | 0 | 1 | 1 |

The trained random forest model was validated using the validation set of samples listed in Table 27 and Table 28.

TABLE 27

Biological Markers in Validation Set.

| Sample # | Subject Identifier | Data Set | ASCA-A | ASCA-G | ANCA | OmpC | CBir1 | Fla2 | Flax | VEGF | CRP | SAA | ICAM | VCAM |
|---|---|---|---|---|---|---|---|---|---|---|---|---|---|---|
| 15 | 10-IBD-07.118-074 | 2 | 11.4 | 45.2 | 11.7 | 3 | 26.7 | 48.4 | 53.2 | 318 | 270 | 3852 | 286 | 554 |
| 16 | 10-IBD-07.118-098 | 2 | 3 | 3 | 100 | 3.2 | 4 | 35.8 | 29.3 | 77 | 432 | 2118 | 264 | 289 |
| 17 | 10-IBD-07.319-164 | 2 | 3 | 3.2 | 15.3 | 6.3 | 11.4 | 12.1 | 8.8 | 63 | 978 | 3343 | 325 | 474 |
| 18 | 10-IBD-07.319-169 | 2 | 7.7 | 12.9 | 27.2 | 3.9 | 7.6 | 7.1 | 5.7 | 57 | 1417 | 1753 | 280 | 439 |
| 19 | 10-IBD-07.319-156 | 2 | 3 | 18.3 | 9.8 | 3 | 67 | 31.1 | 36.2 | 66 | 2685 | 1162 | 281 | 354 |
| 20 | 10-IBD-07.319-161 | 2 | 3 | 3.7 | 11 | 3 | 14.7 | 6.7 | 6.4 | 103 | 5831 | 7248 | 343 | 568 |
| 21 | 10-IBD-07.324-004 | 2 | 8.8 | 12.4 | 45.7 | 3 | 100 | 17 | 11.3 | 346 | 894 | 2118 | 376 | 706 |
| 22 | 10-IBD-07.320-011 | 2 | 57.3 | 44.5 | 47.4 | 3 | 100 | 100 | 100 | 251 | 16935 | 48907 | 412 | 596 |
| 23 | 10-IBD-07.136-070 | 2 | 3 | 7.8 | 7.1 | 3.2 | 16.8 | 41 | 40.8 | 78 | 1879 | 6519 | 367 | 371 |
| 24 | 10-IBD-07.136-083 | 2 | 6 | 8.7 | 6 | 3 | 30 | 56.7 | 57.6 | 53 | 4301 | 5288 | 368 | 502 |
| 25 | 10-IBD-07.118-102 | 2 | 3 | 5.8 | 20.6 | 3 | 3.2 | 28.2 | 17.6 | 244 | 838 | 1557 | 318 | 526 |
| 26 | 10-IBD-07.118-104 | 2 | 3 | 4 | 35.4 | 3 | 12.2 | 23.2 | 18.2 | 49 | 1346 | 1903 | 272 | 393 |
| 27 | 10-IBD-07.321-003 | 2 | 4 | 12.6 | 3 | 6.4 | 21.6 | 11 | 10.2 | 125 | 9459 | 12652 | 630 | 608 |

TABLE 27-continued

Biological Markers in Validation Set.

| Sample # | Subject Identifier | Data Set | ASCA-A | ASCA-G | ANCA | OmpC | CBir1 | Fla2 | Flax | VEGF | CRP | SAA | ICAM | VCAM |
|---|---|---|---|---|---|---|---|---|---|---|---|---|---|---|
| 28 | 10-IBD-07.323-011 | 2 | 100.1 | 44.1 | 8.3 | 41.9 | 66.9 | 100 | 100 | 162 | 14971 | 73366 | 831 | 927 |

TABLE 28

Binary Variables of Text-Based Biological Markers in Validation Set.

| Sample # | Subject Identifier | Data Set | pANCA | ATG16L1 | ECM1 | NKX2 | STAT3 |
|---|---|---|---|---|---|---|---|
| 15 | 10-IBD-07.118-074 | 2 | 1 | 0 | 0 | 0 | 1 |
| 16 | 10-IBD-07.118-098 | 2 | 1 | 1 | 0 | 0 | 0 |
| 17 | 10-IBD-07.319-164 | 2 | 0 | 0 | 1 | 1 | 1 |
| 18 | 10-IBD-07.319-169 | 2 | 0 | 1 | 1 | 1 | 1 |
| 19 | 10-IBD-07.319-156 | 2 | 0 | 0 | 0 | 0 | 1 |
| 20 | 10-IBD-07.319-161 | 2 | 0 | 1 | 0 | 1 | 1 |
| 21 | 10-IBD-07.324-004 | 2 | 1 | 0 | 1 | 1 | 0 |
| 22 | 10-IBD-07.320-011 | 2 | 1 | 0 | 0 | 0 | 0 |
| 23 | 10-IBD-07.136-070 | 2 | 1 | 0 | 0 | 1 | 0 |
| 24 | 10-IBD-07.136-083 | 2 | 0 | 1 | 1 | 0 | 0 |
| 25 | 10-IBD-07.118-102 | 2 | 1 | 0 | 0 | 1 | 0 |
| 26 | 10-IBD-07.118-104 | 2 | 1 | 0 | 1 | 0 | 0 |
| 27 | 10-IBD-07.321-003 | 2 | 0 | 1 | 0 | 0 | 1 |
| 28 | 10-IBD-07.323-011 | 2 | 1 | 0 | 0 | 0 | 1 |

Table 29 illustrates that the diagnostic algorithm can predict diagnoses of the samples in the training set and validation set. In particular, the values in column "RF Dx4" describe the predicted diagnosis as such: "0" refers to non-IBD; "1" refers to CD; "2" refers to UC; and "3" refers to IC. Table 29 also shows that samples were excluded or not excluded (e.g., included) in the datasets of the algorithm based on sample elimination criteria, indeterminate sample determination, Group 1 violations and Group 2 violations (see, e.g., Examples 1-4). Table 29 also shows the known diagnoses of the samples as determined prior to training and validating the diagnostic algorithm of the present invention (see, column "Dx3" in Table 29).

TABLE 29

Predicted Diagnoses of Samples in Training Set and Validation Set.

| Sample # | Subject Identifier | DataSet | Dx3 | IBD Exclusion Reason | UC Exclusion Reason | RF Dx4 |
|---|---|---|---|---|---|---|
| 1 | 10-IBD-07.059-081 | 1 | 1 | Greater than 6 Months | Greater than 6 Months | 0 |
| 2 | 10-IBD-07.079-002 | 1 | 2 | Greater than 6 Months | Greater than 6 Months | 0 |
| 3 | 10-IBD-01.009-024 | 1 | 1 | Inconsistent ANCA/pANCA2 | Inconsistent ANCA/pANCA2 | 1 |
| 4 | 10-IBD-01.009-026 | 1 | 1 | Inconsistent ANCA/pANCA2 | Inconsistent ANCA/pANCA2 | 1 |
| 5 | 10-IBD-07.040-004 | 1 | 0 | Included | Non-IBD | 0 |
| 6 | 10-IBD-07.040-006 | 1 | 0 | Included | Non-IBD | 0 |
| 7 | 10-IBD-01.005-031 | 1 | 1 | Included | Indeterminate | 3 |
| 8 | 10-IBD-01.013-028 | 1 | 1 | Included | Indeterminate | 3 |
| 9 | 10-IBD-07.059-085 | 1 | 2 | Included | Group 1 Violation | 1 |
| 10 | 10-IBD-07.036-021 | 1 | 2 | Included | Group 1 Violation | 1 |
| 11 | 10-IBD-01.002-008 | 1 | 1 | Included | Group 2 Violation | 2 |
| 12 | 10-IBD-01.011-007 | 1 | 1 | Included | Group 2 Violation | 2 |
| 13 | 10-IBD-01.001-026 | 1 | 1 | Included | Included | 1 |
| 14 | 10-IBD-01.001-028 | 1 | 1 | Included | Included | 1 |
| 15 | 10-IBD-07.118-074 | 2 | 1 | Clinical Exclusion Criteria | Clinical Exclusion Criteria | 1 |
| 16 | 10-IBD-07.118-098 | 2 | 2 | Clinical Exclusion Criteria | Clinical Exclusion Criteria | 3 |
| 17 | 10-IBD-07.319-164 | 2 | 0 | Inconsistent ANCA/pANCA2 | Inconsistent ANCA/pANCA2 | 0 |
| 18 | 10-IBD-07.319-169 | 2 | 0 | Inconsistent ANCA/pANCA2 | Inconsistent ANCA/pANCA2 | 0 |
| 19 | 10-IBD-07.319-156 | 2 | 0 | Included | Non-IBD | 0 |
| 20 | 10-IBD-07.319-161 | 2 | 0 | Included | Non-IBD | 0 |
| 21 | 10-IBD-07.324-004 | 2 | 2 | Included | Indeterminate | 3 |
| 22 | 10-IBD-07.320-011 | 2 | 1 | Included | Indeterminate | 3 |
| 23 | 10-IBD-07.136-070 | 2 | 2 | Included | Group 1 Violation | 1 |
| 24 | 10-IBD-07.136-083 | 2 | 2 | Included | Group 1 Violation | 1 |
| 25 | 10-IBD-07.118-102 | 2 | 1 | Included | Group 2 Violation | 2 |
| 26 | 10-IBD-07.118-104 | 2 | 1 | Included | Group 2 Violation | 2 |
| 27 | 10-IBD-07.321-003 | 2 | 1 | Included | Included | 0 |
| 28 | 10-IBD-07.323-011 | 2 | 1 | Included | Included | 1 |

Samples #1 and 2 were excluded from the training set used to construct both the random forest models of the sgi algorithm because these samples met an exclusion rule. Samples #7 and 8 were used to construct the IBD vs. non-IBD model and were determined to be indeterminate samples because they met the appropriate conditions. Samples #9, 10, 11 and 12 were excluded from the training set for constructing the UC vs. CD model because they satisfied the conditions for a Group 1 violation (#9 and 10) or Group 2 violation (#11 and 12). Samples #5 and 6 were in the training set and predicted to have non-IBD. Samples #13 and 14 were predicted to have IBD in the first random forest model and CD in the second model. Samples #15-28 are of the validation set. Samples #15-18 were excluded because they met exclusion conditions. Sample #19 and 20 were predicted to have non-IBD by the sgi algorithm, which corresponds to the known or prior diagnosis. Samples #21 and 22 were predicted to have IC, while their known diagnoses were UC and CD, respectively. Samples #27 and 28 have a known diagnosis of CD, yet the sgi algorithm predicted that #27 has non-IBD and #28 has CD.

This example demonstrates that the sgi algorithm is a valid model to predict a non-IBD, IC, UC, or CD diagnosis. This example also demonstrates that combinatorial use of serological, genetic, and inflammatory markers provides an improved diagnostic test to distinguish between IBD subtypes such as IC, UC and CD and to identify IBD inconclusive for UC and CD.

Example 7

IBD sgi Diagnostic Algorithm Training and Validation Sets

This example illustrates the use of a training set and a validation set in random forest modeling. A random forest modeling algorithm is created through a process of training the computational model using a training set of data of samples from a cohort. The trained algorithm is validated using a validation set of data of samples from a cohort.

Figure 16:
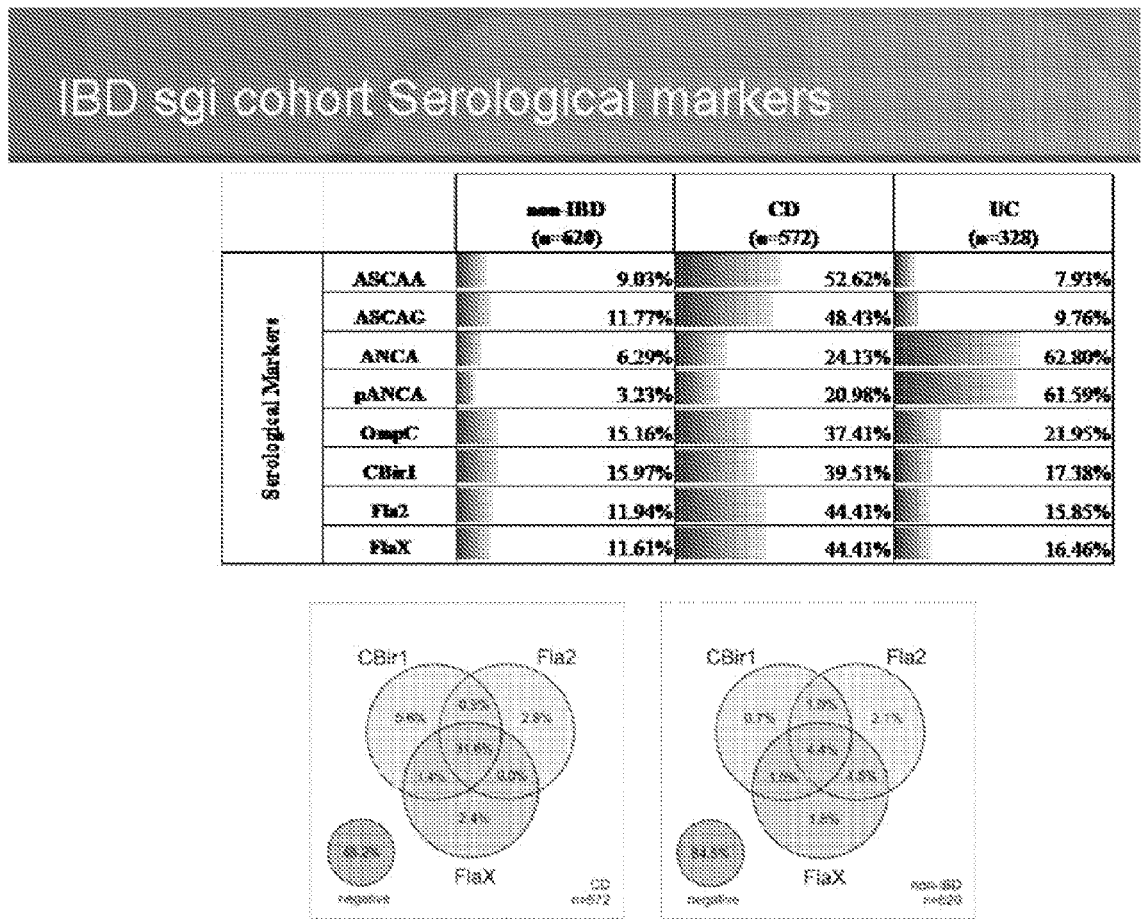
FIG. 16 illustrates IBD sgi cohort serological markers.

FIG. 16 shows the percent of each of the serological markers present in the training and/or validation cohorts. The Venn diagram on the left shows the overlap of CBir1, Fla2 and FlaX antibodies in CD. The Venn diagram on the right shows the overlap of CBir1, Fla2 and FlaX antibodies in non-IBD.

Figure 17:
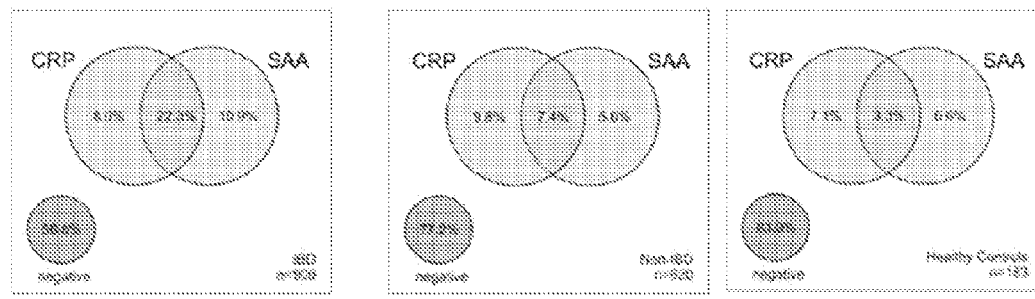
FIG. 17 illustrates IBD sgi cohort inflammatory markers.

FIG. 17 shows the percent of each of the inflammatory markers present in the training and/or validation cohorts. The left Venn diagram shows the overlap of CRP and SAA in IBD. The middle Venn diagram shows the overlap of CRP and SAA in Non-IBD. The right Venn diagram shows the overlap of CRP and SAA in healthy controls.

Figure 18:
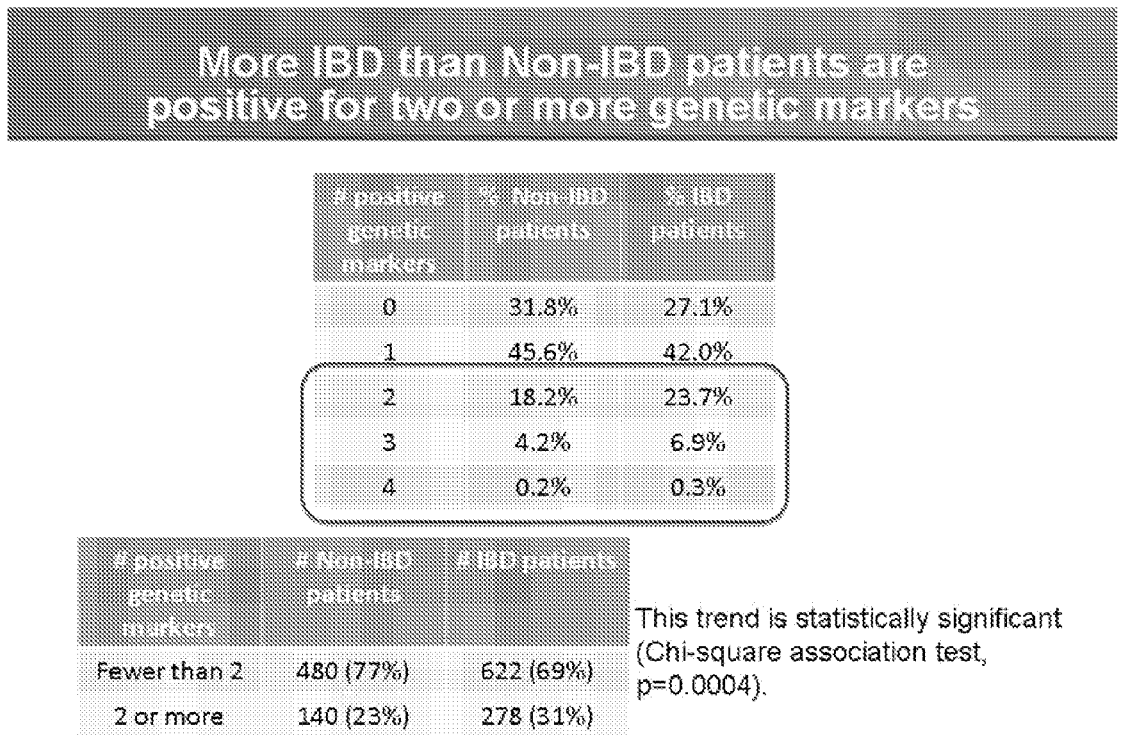
FIG. 18 illustrates an embodiment where more IBD than non-IBD patients are positive for two or more genetic markers.

FIG. 18 shows the number of patients positive for two or more genetic markers in the training and/or validation cohorts. The results show that the percent of IBD patients with two or more genetic markers is higher than in non-IBD patients. The trend is statistically significant.

Moreover, the results presented herein show that the pathogenesis of IBD reflects a dysregulated immunologic response to diverse antigens (e.g., yeast, bacteria, flagellins, auto-antibodies) in a genetically susceptible person resulting in inflammation and tissue injury.

A random forest model that analyzes the complex interactions between the three classes of markers (serology, genetics, inflammation) is more accurate at detecting patterns that differentiate IBD vs. non-IBD patients and CD vs. UC patients than using a single class of markers (e.g., serology).

Example 8

Combined Serologic, Genetic, and Inflammatory (sgi) Markers Accurately Differentiates Non-IBD, Crohn's Disease, and Ulcerative Colitis Patients This example illustrates the use of the methods of the present invention to accurately differentiate between non-IBD, Crohn's disease and ulcerative colitis. This example also describes a study that identified a combination of established and new biomarkers that can improve the identification and stratification of IBD.

A diagnosis of IBD is complex, based on a combination of clinical exam, imaging, endoscopy with histopathology, and laboratory testing. Serologic markers can provide important adjunct information. The use of serology to assist in IBD diagnosis has been extensively described in the literature. In addition to the auto- and anti-microbial antibodies typically associated with IBD, genetic variants and angiogenesis and inflammation molecules may help better identify IBD. An ideal tool for IBD diagnosis would (1) distinguish IBD patients from patients with other gastrointestinal (GI) disorders, and (2) differentiate UC from CD. In the study described herein, the diagnostic accuracy of a panel of serologic biomarkers (e.g., ASCA-A, ASCA-G, ANCA, pANCA, anti-OmpC, and anti-CBir1) was compared to a panel of 17 serologic, genetic, and inflammatory (sgi) biomarkers, including 4 gene variants (e.g., ATG16L1 rs2241880, NKX2-3 rs10883365, ECM1 rs3737240, and STAT3 rs744166), inflammatory markers (e.g., CRP, SAA, ICAM, VCAM, and VEGF), and serologic markers (e.g., ASCA-A, ASCA-G, ANCA, pANCA, anti-OmpC, anti-CBir1, anti-A4-Fla2, and anti-FlaX).

Well-characterized patient samples were collected from 8 academic and 42 community medical practices in North America. Samples from 1,520 patients were included: 572 CD, 328 UC, 183 healthy volunteer controls, and 437 non-IBD disease controls including irritable bowel syndrome, hepatitis, chronic constipation, GERD, celiac disease, diverticulitis, etc. Diagnostic algorithms were built using data from a 1,083 patient training set selected from the full cohort. The performance of the final algorithm was measured using a separate validation set of 437 patients. A receiver operating characteristic (ROC) area under the curve (AUC) was calculated using the random forest score (e.g., the proportion of decision trees for each classification) as the continuous variable. Cutoff scores selected during training were applied to calculate sensitivity and specificity.

Figure 19:
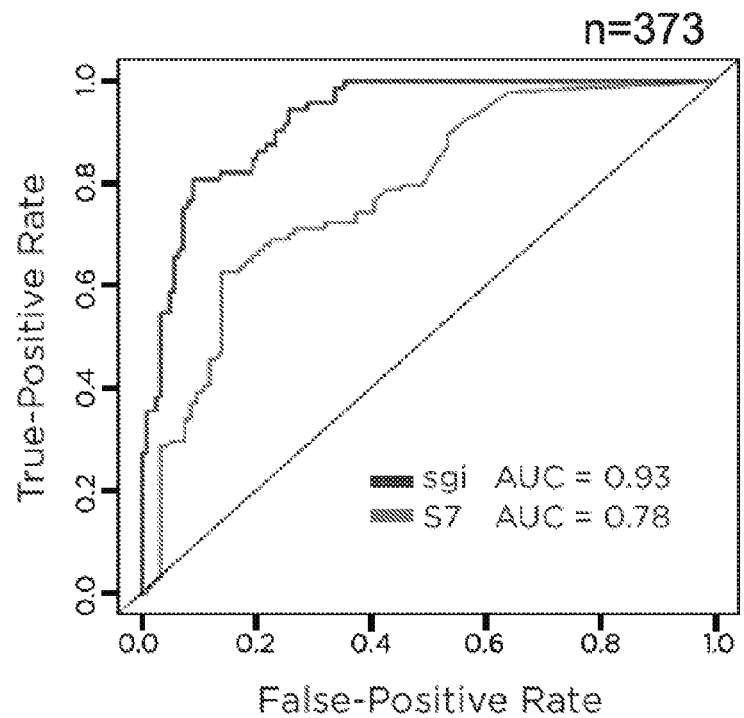
FIG. 19 illustrates one embodiment of a comparison between IBD sgi and IBD Serology 7 for differentiating CD from UC.
Figure 19:
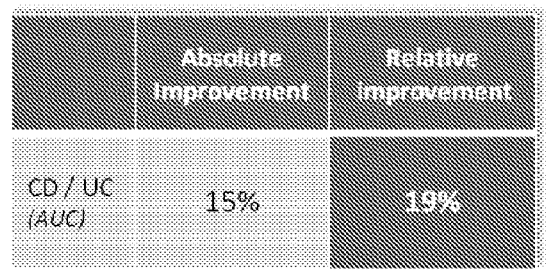

ROC analysis was used to compare the diagnostic accuracy of the panel of serologic biomakers alone to the 17 marker panel that also included four gene variants (e.g., ATG16L1 rs2241880, NKX2-3 rs10883365, ECM1 rs3737240, STAT3 rs744166), five inflammatory markers (e.g., CRP, SAA, ICAM, VCAM, VEGF), and two other anti-microbial serologic markers (e.g., antibodies to A4-Fla2 and FlaX). The additional markers increased the IBD vs. non-IBD discrimination, AUC from 0.80 (95% CI=0.7682-0.8507) to 0.87 (95% CI=0.8442-0.9070) (p<0.001). The UC vs. CD discrimination increased from 0.78 (95% CI=0.7144-0.8403) to 0.93 (95% CI=0.8585-0.9354) (p<0.001). See, FIGS. 19 and 20. Both increases in the discrimination of IBD vs. non-IBD and UC vs. CD were determined to be statistically significant (p<0.001). There were reductions in error rates of 18% for IBD, 18% for CD, and 29% for UC. The sensitivity in the performance of identifying possible disease was 74% for IBD, 89% for CD, and 98% for UC. The specificity in the performance of confirming disease was 90% for IBD, 81% for CD, and 84% for UC.

These results show that combining serology, genetics, and inflammation markers can be used to better classify IBD, CD, and UC patients with greater accuracy than serology markers alone.

Example 9 pANCA Decision Tree

This example illustrates a decision tree that was developed to improve diagnostic predictions in a population of patient specimens negative for pANCA2, e.g., to minimize the false positive IBD prediction rate. In certain embodiments, the pANCA2 definition includes all specimens with a negative (0 or "not detected") or weak (+1) pANCA determination. The methodology for developing that decision tree and its performance characteristics on a large group of clinically-characterized, biopsy-confirmed patient specimens are described herein.

Development Methodology

The laboratory data from the original pANCA2(−) training and validation specimens that met inclusion/exclusion criteria was parsed into a new file for the purpose of developing, testing and validating the new decision tree. Laboratory data from the original pANCA2(−), ANCA ELISA>11.9 EU/mL training only sub-group was used to develop the new decision tree, while the remainder were reserved for validation and calculation of performance metrics. Common confusion matrices comparing disease predictions against biopsy (reference) results were used to assess the effect of potential rules within the Decision Tree. It is important to note that a CD prediction on a known UC specimen (and vice versa) was scored as a false positive, while an Inconclusive IBD (IC) prediction on either a known CD or UC specimen was scored as a true positive for the purposes of evaluation. The rules were developed with an intent to limit IC predictions to <5% of all specimens.

The primary feature defining this group of specimens is low or undetectable serological evidence for neutrophil antinuclear antibodies (ANCA). ANCA reactivities in the IFA or ELISA assays are the primary determinates for a prediction of ulcerative colitis (UC), thus the approach to developing a new Decision Tree was to first rule out a UC prediction on any particular specimen by identifying patterns of non-IBD and/or Crohn's disease (CD) in that specimen prior to applying defined rules for making a UC prediction.

Direct Crohn's Disease Prediction

First, data from the selected specimens were reviewed and potential values for each of the individual CD markers (e.g., ASCA-A, ASCA-G, OmpC, Cbir1, Fla2 and FlaX) were assessed individually for their ability to drive accurate predictions. Through an iterative assessment, it was determined that certain assay values for either of the ASCAs or OmpC, if exceeded, could be used to make a CD prediction. If either ASCA-IgA≥69 EU/mL, ASCA-IgG≥40 EU/mL or OmpC≥60 EU/mL, then the specimen was predicted to be CD, and that specimen was removed from further consideration.

CD Inference by Use of a "Count"

Next, combinations of multiple CD markers were assessed for their ability to drive CD predictions. The concept of a CD "count" was utilized to effectively manage the multiple potential combinations of CD markers that could independently result in a CD prediction. Again, a highly iterative process was used, resulting in a fairly simple scheme of scoring that was based on stated reference ranges for each assay. The final CD count procedure weights the ASCA-A, ASCA-G and OmpC markers equally, while requiring at least two flagellin markers to exceed their respective reference range to have a positive impact on the CD count. Thus, any CD marker (or pair of flagellins) that equals or exceeds its respective upper reference limit results in an increase of +1 in the CD counter. In addition, if any flagellin is found to have an assay value≥100 EU/mL, then an additional +1 is added to the CD counter. Regardless of the number of flagellins that meet this ≥100 EU/mL rule, the total count only increases by +1. Any specimen with a final CD count≥2 is designated as CD.

pANCA Negative Specimens

Any remaining training specimens, for which a CD prediction was not made by use of the procedures above, were split into pANCA (−) (not detected) and pANCA+1 (weakly detected) subgroups for further analysis. It was found that, in the pANCA (−) group, use of the ANCA ELISA reference range was useful in designating nonIBD specimens. The limit for this designation was set slightly above the stated upper reference interval to balance performance in this prediction. It was also determined that an ANCA ELISA value limit could be set for making UC predictions, although this value left a gap between the direct nonIBD and UC predictions. The ANCA ELISA value gap, within which a clean nonIBD vs. UC prediction could not be made, was found to include a complicated mix of known nonIBD, CD and UC specimens. Thus, the Inconclusive IBD designation was applied to any specimen with a CD count=1, while all others in this gap were designated as nonIBD.

pANCA+1 Specimens

Finally, data from the remaining pANCA+1 specimens were reviewed. It was determined that an ANCA ELISA value lower than the stated upper reference interval could be used to effectively differentiate nonIBD from UC predictions in this group.

Decision Tree

The rule set is as follows—Any patient specimen submitted for IBD sgi (serology, genetics, and inflammation) processing found to be pANCA2 negative (i.e., pANCA=0 or +1) was removed from the sgi algorithm queue and subjected to the following decision matrix for making a clinical prediction:

1) Direct Crohn's Disease (CD) Prediction.
  a. If ASCA-IgA≥69 EU/mL, then designate result as "Pattern Consistent with IBD: Crohn's Disease"; or
  b. If ASCA-IgG≥40 EU/mL, then designate result as "Pattern Consistent with IBD: Crohn's Disease"; or
  c. If OmpC-IgA≥60 EU/mL, then designate result as "Pattern Consistent with IBD: Crohn's Disease"; else
2) CD Inference by use of a "count."
  a. Determine total "count"
    i. If ASCA-IgA≥8.5 EU/mL (above reference range), then add +1 to the CD count;
    ii. If ASCA-IgG≥17.8 EU/mL (above reference range), then add +1 to the CD count;
    iii. If OmpC-IgA≥10.9 EU/mL (above reference range), then add +1 to the CD count;
    iv. If ≥2 flagellin markers above their respective reference ranges (Cbir1-IgG≥78.4 EU/mL, A4-Fla2-IgG≥44.8 EU/mL, FlaX-IgG≥33.4 EU/mL), then add +1 to the CD count;
    v. If any flagellin≥100EU/mL, then add +1 to the CD count.
  b. If total CD count≥2, then designate result as "Pattern Consistent with IBD: Crohn's Disease"; else 3) pANCA Negative Specimens.
   a. If pANCA=0 (not detected) and ANCA ELISA<20 EU/mL, then designate result as "Pattern Not Consistent with IBD"; else
   b. If pANCA=0 (not detected) and ANCA ELISA>27.4 EU/mL, then designate result as "Pattern Consistent with IBD: Ulcerative Colitis"; else
   c. If pANCA=0 (not detected) and 20≤ANCA ELISA≤27.4 EU/mL and CD count from 2b above=0, then designate result as "Pattern Not Consistent with IBD"; else
   d. If pANCA=0 (not detected) and 20≤ANCA ELISA≤27.4 EU/mL and CD count from 2b above=1, then designate result as "Pattern Consistent with IBD: Inconclusive for Crohn's Disease vs. Ulcerative Colitis"; else
4) pANCA+1 Specimens.
   a. If pANCA=+1 and ANCA ELISA<13.7 EU/mL, then designate result as "Pattern Not Consistent with IBD"; else
   b. If pANCA=+1 and ANCA ELISA≥13.7 EU/mL, then designate result as "Pattern Consistent with IBD: Ulcerative Colitis"

Effect of the Rule

The cumulative effect of application of the rules described above on the intact data sets from pANCA2 (−) specimens are depicted in Tables 30 and 32. Table 30 demonstrates the effect of these rules on validation specimens with ANCA ELISA values≥11.9 EU/mL, while Table 32 contains data from those validation specimens with ANCA ELISA values<11.9 EU/mL. The reason for this distinction is that predictions from the specimens with ANCA ELISA values<11.9 EU/mL were included in calculating performance metrics for the IBD sgi algorithm because the algorithm performance was deemed adequate on those specimens, while it was agreed to remove the specimens with ANCA ELISA values≥11.9 EU/mL from the performance calculations and develop alternate methods for making predictions in that group. This change should not be construed to imply that the IBD sgi algorithm could not make predictions on pANCA2 (−) specimens with ANCA ELISA values≥11.9 EU/mL for several reasons. Because the Random Forest methodology is essentially a pattern-matching tool that does not rely on any single marker, an algorithm derived from this methodology can still be used to make predictions on specimens with an inaccurate (or missing) value for a single component marker. In addition, the IBD sgi algorithm was trained with 17 markers and predictive cut-offs were set high on the AUC curves to ameliorate the effect, if any, of missing or inaccurate individual markers. Thus, although the performance characteristics derived from the validation specimens does not include a subset of the pANCA2 (−) validation specimens, the actual overall accuracy of the sgi algorithm in the two pANCA (−) groups, as defined by their ANCA ELISA values, are very similar (see, performance for the Random Forest Algorithm in Tables 31 and 33). In fact, the calculated IBD sgi sensitivities and false positive rates between these two groups are virtually identical. Since the pANCA2 (−), ANCA ELISA, 11.9 EU/mL group was included in both the training and performance validation of the Random Forest Algorithm, the fact that the Random Forest performance was essential identical on the other group not included in the performance validation implies that the clinical predictions made for the latter group are as reliable as those made for the former group.

The tables below contain confusion matrices that demonstrate the effect of the Decision Tree prediction (Table 30) vs. the prediction made by the Random Forest algorithm (Table 31) on pANCA2 (−) specimens with ANCA ELISA assay values≥11.9 EU/mL.

TABLE 30

Decision Tree Performance.

| | | Clinical Diagnosis (Biopsy) | |
|---|---|---|---|
| | | Positive | Negative |
| Decision Tree | Positive | 138 | 49 |
| | Negative | 37 | 65 |

Sensitivity = (True Positive/(True Positive + False Negative)) * 100 = 78.9%
Specificity = (True Negative/(True Negative + False Positive)) * 100 = 57%
Accuracy = ((True Positive + True Negative)/total) * 100 = 70.2%
False Positive Rate = (False Positive/False Positive + True Negative) * 100 = 43%

TABLE 31

Random Forest Performance.

| | | Clinical Diagnosis (Biopsy) | |
|---|---|---|---|
| | | Positive | Negative |
| Decision Tree | Positive | 130 | 86 |
| | Negative | 27 | 46 |

Sensitivity = (True Positive/(True Positive + False Negative)) * 100 = 82.8%
Specificity = (True Negative/(True Negative + False Positive)) * 100 = 34.9%
Accuracy = ((True Positive + True Negative)/total) * 100 = 60.9%
False Positive Rate = (False Positive/False Positive + True Negative) * 100 = 65.2%

It is noted that, although the sensitivity of the Decision Tree is slightly lower than the Random Forest Algorithm, the overall accuracy of the Decision Tree is substantially higher, 70.2% vs. 60.9%, respectively and the false positive rate is also substantially reduced in the Decision Tree method compared to the Random Forest Algorithm, 43% vs. 65.2%, respectively.

Table 32 contains confusion matrices that demonstrate the effect of the Decision Tree prediction vs. the prediction made by the Random Forest Algorithm (Table 33) on pANCA2(−) specimens with ANCA ELISA assay values<11.9 EU/mL.

TABLE 32

Decision Tree Performance.

| | | Clinical Diagnosis (Biopsy) | |
|---|---|---|---|
| | | Positive | Negative |
| Decision Tree | Positive | 271 | 54 |
| | Negative | 289 | 589 |

Sensitivity = (True Positive/(True Positive + False Negative)) * 100 = 48.4%
Specificity = (True Negative/(True Negative + False Positive)) * 100 = 91.6%
Accuracy = ((True Positive + True Negative)/total) * 100 = 71.5%
False Positive Rate = (False Positive/False Positive + True Negative) * 100 = 8.4%

TABLE 33

Random Forest Performance.

|  |  | Clinical Diagnosis (Biopsy) | |
|---|---|---|---|
|  |  | Positive | Negative |
| Decision Tree | Positive | 213 | 311 |
|  | Negative | 287 | 392 |

Sensitivity = (True Positive/(True Positive + False Negative)) * 100 = 42.6%
Specificity = (True Negative/(True Negative + False Positive)) * 100 = 55.8%
Accuracy = ((True Positive + True Negative)/total) * 100 = 50.3%
False Positive Rate = (False Positive/False Positive + True Negative) * 100 = 44.2%

In this group of specimens, the sensitivity of the Decision Tree is slightly higher than the Random Forest Algorithm, while the specificity and overall accuracy of the Decision Tree Method is substantially higher compared to the Random Forest Algorithm. The Decision Tree Method effectively balances the true negative predictions against false positives, dramatically improving specificity while minimizing the false positive rate.

CONCLUSIONS

It is concluded from the foregoing data that the proposed rules comprising the Decision Tree Method produce IBD sgi predictions more accurate than the Random Forest Algorithm in the specific subgroup situation of pANCA2(−). The false positive rates are significantly reduced and the importance of this observation should not be ignored because the specimens of interest here likely represent very early disease with minimal serum reactivity to known IBD markers. It is important to minimize the rate at which false IBD predictions are made to avoid unnecessary risk (e.g., from further diagnostic procedures or unnecessary interventions) to the patient who does not have IBD.

In certain aspects, the Decision Tree Method described herein can be implemented as an alternate path for making predictive diagnoses in clinical specimens with pANCA2 (−) assay results. In particular embodiments, the modified algorithm would comprise an initial node as a first step to direct individual specimens to either the Decision Tree Method or the Random Forest Algorithm, depending on their pANCA2 value.

Example 10

Assay Descriptions for Genetic, Serology, and Inflammatory Markers

This example describes exemplary assays for detecting or measuring the sero-genetic-inflammation (sgi) markers used in the IBD diagnostic algorithms of the present invention.

A. Overview of the TaqMan Technology for SNP Genotyping

In some embodiments, the SNP genotyping assays in the IBD sgi Diagnostic panel are based on TaqMan SNP genotyping. The qualitative genotyping assays can use human blood genomic DNA (gDNA) or lysate samples to aid in the diagnosis and/or differential diagnosis of IBD; specifically CD and UC. These allelic discrimination PCR assays use two specific oligonucleotide sequences with two different fluorescent dyes in the 5' of the sequence (e.g., fluorogenic probe with FAM dye or VIC dye), each of them having a non-fluorescent quencher in the 3' of the sequence linked with minor groove binder (melting temperature enhancer).

During the PCR amplification, each probe anneals specifically to its complementary sequence between a forward and reverse primer on the target DNA. Because the DNA polymerase has an intrinsic 5' nuclease activity, a selective cleavage of the probes that hybridized to the genomic sequence occurs. This results in an increased fluorescence due to the separation of the reporter dye from the quencher. Therefore, the selective increase of one dye versus another (FAM vs. VIC) indicates the alleles that are present in the genomic DNA studied.

B. Allelic Discrimination

A sample genotype can be determined by the examination of the relative fluorescent intensity of each probe's dye. Using ABI's SDS software, a graphic plot of the two dyes intensities can be created. The homozygous wild type genotype is determined by a relatively high intensity of FAM (y-axis) and very low intensity of VIC (x-axis). The homozygous mutant genotype exhibits a similar but opposite pattern with high VIC (x-axis), low FAM (y-axis). Once the data has been analyzed, the allele "Call" is made with the ABI software to determine the genotype for each SNP.

In certain embodiments, the SNP genotyping assays employ a workflow which combines the use of ABI 7500 Fast for pre- and post-read data collection with offline PCR amplification step on Applied Biosystems Veriti 96-Well Fast Thermal Cycler (ABI Veriti). This combination enables one lab operator to simultaneously perform multiple genotyping runs (up to 96 samples per plate) on multiple ABI Veriti machines followed by a quick post-read of the each reaction plate on one ABI 7500 Fast instrument. For the SNP assays, once a PCR reaction mix is prepared in a 96-well plate either by a Tecan Freedom EVO 100 automation workstation automatically or manually, and a pre-read is performed on an ABI 7500 Fast real-time PCR system, the reaction plate is then transferred to the ABI Veriti for offline amplification steps. When the amplification is complete, the reaction plate is transferred back to the ABI 7500 Fast instrument for post-read and data analysis. This workflow enables multiple plates to be amplified simultaneously using a single ABI 7500 Fast instrument for pre- and post-amplification measurements.

C. Assay Data Report

The IBD sgi diagnostic test includes four SNP genotyping assays (see, Table 34) to evaluate the genetic susceptibility which influences immune responses.

TABLE 34

SNP Assay Data Output.

| Assay Name | SNP ID | ABI Readout (csv file) | Genotype (Call) |
|---|---|---|---|
| ATG16L1 SNP | rs2241880 | VIC_1 | Homozygous AA |
|  |  | Both | Homozygous AG |
|  |  | FAM_1 | Homozygous GG |
| ECM1 SNP | rs3737240 | VIC_2 | Homozygous CC |
|  |  | Both | Homozygous CT |
|  |  | FAM_2 | Homozygous TT |
| NKX2-3 SNP | rs10883365 | VIC_10 | Homozygous AA |
|  |  | Both | Homozygous AG |
|  |  | FAM_10 | Homozygous GG |
| STAT3 SNP | rs744166 | VIC_11 | Homozygous AA |
|  |  | Both | Homozygous AG |
|  |  | FAM_11 | Homozygous GG |

D. ATG16L1 SNP rs2241880 Genotyping Assay

The ATG16L1 gene is located on chromosome 2 and encodes a protein known to be involved in the formation of autophagosomes during autophagy. The ATG16L1 1155 (A>G) SNP (SNP ID: rs2241880) is located within the coding region position 1155 A>G for cDNA sequence which is T300A for AA position. The ATG16L1 SNP rs2241880 genotyping assay is a laboratory developed test (LDT) for detecting the ATG16L1 1155 (A>G) SNP in IBD patients using genomic DNA (gDNA) or lysate samples prepared from whole blood samples. This qualitative genotyping assay aids in the diagnosis of IBD.

For each genotype, previously genotyped blood lysates or gDNA samples are used as controls for each test run. The genotypes of these controls are confirmed by sequencing on both strands. Non-Template Control (NTC) is also included in each test run.

gDNA Controls are prepared from DNA isolated from whole blood samples, or blood lysates are prepared from the same whole blood samples. Three controls are run in each assay:
ATG16L1 1155 (A>G) SNP Genotyping Assay Control GG
ATG16L1 1155 (A>G) SNP Genotyping Assay Control AG
ATG16L1 1155 (A>G) SNP Genotyping Assay Control AA E. ECM1 SNP Genotyping Assay The ECM1 gene is located on chromosome 1 and encodes extra cellular matrix protein 1 which is implicated in maintaining the barrier function of the gut wall and actives the NF-κB inflammatory pathway. The ECM1 558 (C>T) SNP (SNP ID: rs3737240) is located within coding region position 588 C>T for cDNA sequence, which is T130M for AA position.

The ECM1 SNP rs3737240 genotyping assay is a laboratory developed test (LDT) for detecting the ECM1 558 (C>T) SNP genotype in IBD patients using gDNA or lysate samples prepared from whole blood samples. This qualitative genotyping assay aids in the diagnosis of IBD.

For each genotype, previously genotyped blood lysates or gDNA samples are used as controls for each test run. The genotypes of these controls are confirmed by sequencing on both strands). Non-Template Control (NTC) is also included in each test run. gDNA controls are prepared from whole blood samples or blood lysates are prepared from the same whole blood samples:
ECM1 558 (C>T) SNP Genotyping Control TT
ECM1 558 (C>T) SNP Genotyping Control CT
ECM1 558 (C>T) SNP Genotyping Control CC F. NKX2-3 SNP Genotyping Assay The NKX2-3 gene is located on chromosome 10. NKX2-3 (A>G) SNP (SNP ID: rs10883365) is located in the intron (position 101287764). The NKX2-3 rs10883365 genotyping assay is a laboratory developed test (LDT) for detecting the NKX2-3 (A>G) SNP genotype in IBD patients using genomic DNA (gDNA) or lysate samples prepared from whole blood samples. This qualitative genotyping assay aids in the diagnosis of IBD.

For each genotype, previously genotyped blood lysates or gDNA samples are used as controls for each test run. The genotypes of these controls are confirmed by sequencing on both strands. Non-Template Control (NTC) is also included in each test run. DNA controls are prepared from whole blood samples or blood lysates are prepared from the same whole blood samples:
NKX2-3 (A>G) SNP Genotyping Assay Control GG
NKX2-3 (A>G) SNP Genotyping Assay Control AG
NKX2-3 (A>G) SNP Genotyping Assay Control AA G. STAT3 SNP Genotyping Assay The STAT3 gene is located on chromosome 17, and it plays an important role in various autoimmune disorders including inflammatory bowel diseases (IBDs). The STAT3 (A>G) SNP (SNP ID: rs744166) is located 5' flanking region of the 3'UTR (position 40514201). The STAT3 rs744166 genotyping assay is a laboratory developed test (LDT) for detecting the STAT3 (A>G) SNP genotype in IBD patients using gDNA or lysate samples prepared from whole blood samples. This qualitative genotyping assay aids in the diagnosis of IBD.

For each genotype, previously genotyped blood lysates or gDNA samples are used as controls for each test run. The genotypes of these controls are confirmed by sequencing on both
STAT3 (A>G) SNP Genotyping Assay Control GG
STAT3 (A>G) SNP Genotyping Assay Control AG
STAT3 (A>G) SNP Genotyping Assay Control AA H. FlaX Assay In some embodiments, the FlaX assay employs recombinant FlaX bacterial antigen to measure anti-FlaX IgG antibodies in human serum. The assay aids in the diagnosis and differential diagnosis of IBD, especially CD and UC.

In some embodiments, the assay is an automated indirect ELISA run on a standard 96-well plate format. First, the recombinant FlaX antigen is coated on the well surface of the plate, followed by blocking. Diluted patient serum (1/100) is added to the well and incubated. After washing away the unbound molecules, the detection antibody labeled with Alkaline Phosphatase is incubated in the well. After a second wash, the substrate is added for development of a colorimetric signal. Upon adding the stop solution, the plate is read for optical density (OD). The anti-FlaX antibody concentration is calculated from a standard curve and reported in ELISA unit per milliliter serum (EU/mL).

I. Fla2 Assay

In some embodiments, the Fla2 assay employs recombinant Fla2 bacterial antigen to measure anti-Fla2 IgG antibodies in human serum. The Fla2 assay aids in the diagnosis and differential diagnosis of IBD, especially CD and UC.

In some embodiments, the assay is an automated indirect ELISA run on a standard 96-well plate format. First, the recombinant Fla2 antigen is coated on the well surface of the plate, followed by blocking. Diluted patient serum (1/100) is added to the well and incubated. After washing away the unbound molecules, the detection antibody labeled with Alkaline Phosphatase is incubated in the well. After a second wash, the substrate is added for development of a colorimetric signal. Upon adding the stop solution, the plate is read for optical density (OD). The anti-Fla2 antibody concentration is calculated from a standard curve and reported in ELISA unit per milliliter serum EU/mL).

J. VEGF Assay

In some embodiments, the Human VEGF kit is sandwich antigen detection ELISA assay for measuring human VEGF in serum (Thermo Scientific Inc.). The assay aids in the diagnosis and differential diagnosis of IBD, especially CD and UC.

In some embodiments, the assay runs on a standard 96-well plate format. The plate is coated with anti-VEGF antibody (capture antibody) by the manufacturer. When testing, the diluted patient serum (1/2) is added to the well for VEGF capture binding incubation. After washing away the unbound molecules, the biotinylated detecting antibody is added and binds to a second site of the VEGF. After the second wash, streptavidin-horseradish peroxidase is added that reacts with 3,3',5,5'-tetramethylbenzidine (TMB) to produce colorimetric signal measured by optical density (OD) reader. The value of the OD is calculated against the standard curve to generate value for the VEGF concentration reported in pictogram per milliliter serum (pg/mL).

Based on the manufacturer's recommended protocol, this assay was automated by employing the Tecan Freedom EVO150 system.

K. CRP, SAA, ICAM1 and VCAM1 Assays

In some embodiments, the Human Vascular Injury II assay is a multiplexed sandwich antigen detection assay based on MULTI-ARRAY technology. The assay is used for measuring CRP, SAA, ICAM1, and VCAM1 in human serum (Meso Scale Discovery Inc.). The assay aids in the diagnosis and differential diagnosis of IBD, especially CD and UC.

In some embodiments, the assay employs unique electrochemiluminescence detection and patterned array on a 96-well plate format. The plate is coated with four capture antibodies against each analyte of CRP, SAA, ICAM1, and VCAM1 on the surface electrode well. When testing, the diluted patient serum (1/1000) is added to the well for antigen capture incubation. After washing away the unbound molecules, the chemiluminescence (SULFO-TAG) labeled detecting antibody is added and binds to a second site of the analytes. After the second wash, the plate is read by applying electroexcitation which converts energy to luminescence emission light signal measured by Relative Luminescence Units (RLU). The RLU value is calculated against the standard curve to generate value for the concentration reported in milligram per liter serum (mg/L) for CRP and SAA, or microgram per milliliter (µg/mL) for VCAM1 and ICAM1.

Based on the manufacturer's recommended protocol, these assays were automated by employing the Tecan Freedom EVO150 system and PerkinElmer Janus system.

Example 11

Reference Range and Reference Call for the IBD sgi Test

This example illustrates reference ranges and reference calls for each of the sero-genetic-inflammation (sgi) markers detected or measured in the IBD diagnostic algorithms of the present invention. In certain embodiments, a reference range or call corresponds to a cut-off value, a cut point, the presence or absence of a mutation, or the presence or absence of an IFA pattern for a particular sgi marker.

The reference range and reference call for the IBD sgi test were determined based on each individual assays (see, Table 35).

TABLE 35

The reference range and reference call for IBD sgi assays.

| Assay Name | Reference value/call |
|---|---|
| ASCA IgA ELISA | <8.5 EU/mL |
| ASCA IgG ELISA | <17.8 EU/mL |
| Anti-OmpC ELISA | <10.9 EU/mL |
| Anti-CBir1 IgG ELISA | <78.4 EU/mL |
| Anti-A4-Fla2 IgG ELISA | <44.8 EU/mL |
| Anti-Flax IgG ELISA | <33.4 EU/mL |
| ANCA ELISA | <19.8 EU/mL |
| IBD-specific pANCA IFA Perinuclear Pattern | Not detected |
| IBD-specific pANCA DNase Sensitivity | Not detected |
| ATG16L1 SNP (rs2241880) | A/A, A/G |
| ECM1 SNP (rs3737240) | C/C, C/T |
| NKX2-3 SNP (rs10883365) | A/A, A/G |
| STAT3 SNP (rs744166) | G/G, A/G |
| ICAM1 | <0.54 µg/mL |
| VCAM1 | <0.68 µg/mL |
| CRP | <13.2 mg/L |
| SAA | <10.9 mg/L |
| VEGF | <345 pg/mL |

For serology and inflammatory marker assays, the reference ranges are the 95% lower confidence intervals (LCI) across 10,000 estimates of the upper reference range limits, where an upper reference range limit is the upper boundary of the central 95% of marker measurements. The LCI for each range limit was determined using simulations that randomly selected 120 subjects repeatedly from the Healthy Control database.

Genetic assays (ATG16L1 SNP rs2241880, ECM1 SNP rs3737240, NKX2-3 SNP rs10883365 and STAT3 SNP rs744166) are qualitative genotyping assays. For ATG16L1 SNP rs2241880, a reference value/call of A/A or A/G is equivalent to no mutation detected. For ECM1 SNP rs3737240, a reference value/call of C/C or C/T is equivalent to no mutation detected. For NKX2-3 SNP rs10883365, a reference value/call of A/A or A/G is equivalent to no mutation detected. For STAT3 SNP rs744166, a reference value/call of G/G or A/G is equivalent to mutation detected.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A method for diagnosing inflammatory bowel disease (IBD) and/or a clinical subtype thereof in an individual, said method comprising:

(a) analyzing a sample obtained from said individual to determine the presence or level or genotype of at least each of the following markers to obtain a marker profile: (i) the presence or level of each of the serological markers ASCA-A, ASCA-G, ANCA, pANCA, anti-OmpC antibody, anti-CBir1 antibody, anti-FlaX antibody, and anti-A4-Fla2 antibody; (ii) the presence or level of each of the inflammation markers VEGF, ICAM, VCAM, SAA, and CRP; and (iii) the genotype of each of the genetic markers ATG16L1, ECM1, NKX2-3, and STAT3;

(b) applying a first random forest statistical analysis to said marker profile to compute a first model score and comparing said first model score to a first cut-off value to obtain a decision whether said sample is an IBD sample or a non-IBD sample;

(c) if said sample is an IBD sample, then applying a decision tree to said IBD sample to determine if said IBD sample is or is not an inconclusive sample, wherein said IBD sample is an inconclusive sample when said IBD sample has an ANCA level greater than a quartile score of 3 (>Q3), is pANCA2 positive, and has a level of anti-CBir1 antibody or anti-A4-Fla2 antibody or anti-FlaX antibody >Q3, or wherein said IBD sample is an inconclusive sample when said IBD sample is pANCA2 positive and expresses two out of three markers selected from anti-CBir1 antibody, anti-A4-Fla2 antibody, and anti-FlaX antibody >Q3, and wherein the presence or level of pANCA is used to determine the value of pANCA2; and (d) if said IBD sample is not an inconclusive sample, then applying a second random forest statistical analysis to said IBD sample to compute a second model score and comparing said second model score to a second cut-off value to determine a clinical subtype of IBD.

2. The method of claim 1, wherein the presence or level of each of said serological markers or inflammation markers is independently detected with a hybridization assay, amplification-based assay, immunoassay, or immunohistochemical assay.

3. The method of claim 1, wherein the genotype of each of said genetic markers is independently detected by genotyping for the presence or absence of a single nucleotide polymorphism (SNP) in each of said genetic markers.

4. The method of claim 3, wherein said SNP is rs2241880 for ATG16L1, rs3737240 for ECM1, rs10883365 for NKX2-3, and/or rs744166 for STAT3.

5. The method of claim 1, wherein the clinical subtype of IBD is Crohn's disease (CD) or ulcerative colitis (UC).

6. The method of claim 1, wherein said second random forest statistical analysis is based upon (i) the presence or level of ASCA-A, ASCA-G, ANCA, pANCA, anti-OmpC antibody, anti-CBir1 antibody, anti-FlaX antibody, anti-A4-Fla2 antibody, and VEGF in said sample and (ii) the genotype of ECM1 and STAT3 in said sample.

7. The method of claim 1, wherein said sample is selected from the group consisting of serum, plasma, whole blood, and stool.

8. The method of claim 1, wherein when pANCA values are 0 or +1, the pANCA2 value is negative.

9. The method of claim 1, wherein when pANCA values are +2, +3 or +4, the pANCA2 value is positive.

10. The method of claim 8, wherein in said pANCA2 negative sample, further comprising:
(a) determining whether the pANCA2 negative sample is directly predictive of Crohn's disease by measuring a serum marker panel, wherein the serum marker panel is a member of the group consisting of ASCA-IgA, ASCA-IgG, and OmpC-IgA and comparing each of the serum markers of the serum marker panel to a cutoff value to determine if the sample is consistent with Crohn's disease; or
(b) determining whether the pANCA2 negative sample is consistent with Crohn's disease by measuring a CD count panel, wherein the CD count panel is a member of the group consisting of ASCA-IgA, ASCA-IgG, OmpC-IgA, CBir1-IgG, A4-Fla2-IgG and FlaX-IgG to form a CD count value, wherein when the CD count value is greater than or equal to 2, the sample is consistent with Crohn's disease; or
(c) determining whether the pANCA2 negative sample having a pANCA value of zero is consistent or inconsistent with IBD by measuring ANCA ELISA and comparing the ANCA ELISA value to a reference value and considering the CD count value to determine whether the sample is consistent or inconsistent with IBD; or
(d) determining whether the pANCA2 negative sample having a pANCA value of zero is consistent with IBD or is inconclusive of IBD by measuring ANCA ELISA and comparing the ANCA ELISA value and considering the CD count value to determine whether the sample is consistent or inconsistent with IBD or is consistent with IBD and inconclusive for Crohn's disease or ulcerative colitis; or
(e) determining whether the pANCA2 negative sample having a pANCA value of one is consistent or inconsistent with IBD by measuring ANCA ELISA and comparing the ANCA ELISA value to a cut-off value to determine whether the sample is consistent with IBD or is inconsistent with IBD.

11. The method of claim 10, wherein in part (a) above, if the value for ASCA-IgA is greater than or equal to 69 EU/mL, then designating the sample as being consistent with Crohn's disease.

12. The method of claim 10, wherein in part (a) above, if the value of ASCA-IgG is greater than or equal to 40 EU/mL, then designating the sample as being consistent with Crohn's disease.

13. The method of claim 10, wherein in part (a) above, if the value for OmpC-IgA is greater than or equal to 60 EU/mL, then designating the sample as being consistent with Crohn's disease.

14. The method of claim 10, wherein in part (b) above, further comprising assigning the CD count value by determining if:
i. ASCA-IgA is greater than or equal to 8.5 EU/mL, then adding +1 to the CD count value;
ii. ASCA-IgG is greater than or equal to 17.8 EU/mL, then adding +1 to the CD count value;
iii. OmpC-IgA is greater than or equal to 10.9 EU/mL, then adding +1 to the CD count value;
iv. 2 or more flagellin markers are above their respective reference ranges, then adding +1 to the CD count value;
v. any flagellin is greater than or equal to 100 EU/mL, then adding +1 to the CD count value;
and if the total CD count value is greater than or equal to 2, then designating that the sample is consistent with Crohn's disease.

15. The method of claim 14, wherein the reference value for CBir1-IgG is greater than or equal to 78.4 EU/mL.

16. The method of claim 14, wherein the reference value for A4-Fla2-IgG is greater than or equal to 44.8 EU/mL.

17. The method of claim 14, wherein the reference value for FlaX-IgG is greater than or equal to 33.4 EU/mL.

18. The method of claim 10, wherein in part (c) above, if pANCA is zero (not detected), further comprising:
i. designating the sample as being inconsistent with IBD if ANCA ELISA is less than 20 EU/mL; or
ii. designating the sample as being consistent with ulcerative colitis if ANCA ELISA is greater than 27.4 EU/mL; or
iii. designating the sample as being inconsistent with IBD if ANCA ELISA is greater than or equal to 20 and less than or equal to 27.4 EU/mL and the CD count value is zero; or
iv. designating the sample as being consistent with IBD but inconclusive for Crohn's disease or ulcerative colitis if ANCA ELISA is greater than or equal to 20 and less than or equal to 27.4 EU/mL and the CD count value is one.

19. The method of claim 10, wherein when pANCA is one, further comprising:
i. designating the sample as being inconsistent with IBD if ANCA ELISA is less than 13.7 EU/mL; or
ii. designating that the sample as being consistent with ulcerative colitis if ANCA ELISA is greater than or equal to 13.7 EU/mL.

20. A method for diagnosing inflammatory bowel disease (IBD) and/or a clinical subtype thereof in an individual, said method comprising:
(a) analyzing a sample obtained from said individual to determine the presence or level or genotype of at least each of the following markers to obtain a marker profile:
(i) the presence or level of each of the serological markers ASCA-A, ASCA-G, ANCA, pANCA, anti-OmpC antibody, anti-CBir1 antibody, anti-FlaX antibody, and anti-A4-Fla2 antibody; (ii) the presence or level of each of the inflammation markers VEGF, ICAM, VCAM, SAA, and CRP; and (iii) the genotype of each of the genetic markers ATG16L1, ECM1, NKX2-3, and STAT3;

(b) applying a first random forest statistical analysis to said marker profile to determine whether said sample is an IBD sample or a non-IBD sample with a sensitivity of at least 70%;

(c) if said sample is an IBD sample, then applying a decision tree to said IBD sample to determine if said IBD sample is or is not an inconclusive sample, wherein said IBD sample is an inconclusive sample when said IBD sample has an ANCA level greater than a quartile score of 3 (>Q3), is pANCA2 positive, and has a level of anti-CBir1 antibody or anti-A4-Fla2 antibody or anti-FlaX antibody >Q3, or wherein said IBD sample is an inconclusive sample when said IBD sample is pANCA2 positive and expresses two out of three markers selected from anti-CBir1 antibody, anti-A4-Fla2 antibody, and anti-FlaX antibody >Q3, and wherein the presence or level of pANCA is used to determine the value of pANCA2; and (d) if said IBD sample is not an inconclusive sample, then applying a second random forest statistical analysis to said IBD sample to determine a clinical subtype of IBD with a sensitivity of at least 85% for Crohn's disease (CD) and a sensitivity of at least 95% for ulcerative colitis (UC).

21. The method of claim 20, wherein the presence or level of each of said serological markers or inflammation markers is independently detected with a hybridization assay, amplification-based assay, immunoassay, or immunohistochemical assay.

22. The method of claim 20, wherein the genotype of each of said genetic markers is independently detected by genotyping for the presence or absence of a single nucleotide polymorphism (SNP) in each of said genetic markers.

23. The method of claim 22, wherein said SNP is rs2241880 for ATG16L1, rs3737240 for ECM1, rs10883365 for NKX2-3, and/or rs744166 for STAT3.

24. The method of claim 20, wherein said second random forest statistical analysis is based upon (i) the presence or level of ASCA-A, ASCA-G, ANCA, pANCA, anti-OmpC antibody, anti-CBir1 antibody, anti-FlaX antibody, anti-A4-Fla2 antibody, and VEGF in said sample and (ii) the genotype of ECM1 and STAT3 in said sample.

25. The method of claim 20, wherein said sample is selected from the group consisting of serum, plasma, whole blood, and stool.

26. The method of claim 20, wherein when pANCA values are 0 or +1, the pANCA2 value is negative.

27. The method of claim 20, wherein when pANCA values are +2, +3 or +4, the pANCA2 value is positive.

28. The method of claim 26, wherein in said pANCA2 negative sample, further comprising:

(a) determining whether the pANCA2 negative sample is directly predictive of Crohn's disease by measuring a serum marker panel, wherein the serum marker panel is a member of the group consisting of ASCA-IgA, ASCA-IgG, and OmpC-IgA and comparing each of the serum markers of the serum marker panel to a cutoff value to determine if the sample is consistent with Crohn's disease; or (b) determining whether the pANCA2 negative sample is consistent with Crohn's disease by measuring a CD count panel, wherein the CD count panel is a member of the group consisting of ASCA-IgA, ASCA-IgG, OmpC-IgA, CBir1-IgG, A4-Fla2-IgG and FlaX-IgG to form a CD count value, wherein when the CD count value is greater than or equal to 2, the sample is consistent with Crohn's disease; or (c) determining whether the pANCA2 negative sample having a pANCA value of zero is consistent or inconsistent with IBD by measuring ANCA ELISA and comparing the ANCA ELISA value to a reference value and considering the CD count value to determine whether the sample is consistent or inconsistent with IBD; or (d) determining whether the pANCA2 negative sample having a pANCA value of zero is consistent with IBD or is inconclusive of IBD by measuring ANCA ELISA and comparing the ANCA ELISA value and considering the CD count value to determine whether the sample is consistent or inconsistent with IBD or is consistent with IBD and inconclusive for Crohn's disease or ulcerative colitis; or (e) determining whether the pANCA2 negative sample having a pANCA value of one is consistent or inconsistent with IBD by measuring ANCA ELISA and comparing the ANCA ELISA value to a cut-off value to determine whether the sample is consistent with IBD or is inconsistent with IBD.

29. The method of claim 20, wherein in part (b) said IBD sample or non-IBD sample is determined with a specificity of at least 90%.

30. The method of claim 20, wherein in part (d) said clinical subtype of IBD is determined with a specificity of at least 80% for CD or UC.

* * * * *

SEQUENCE LISTING

<160> NUMBER OF SEQ ID NOS: 24

<210> SEQ ID NO 1
<211> LENGTH: 51
<212> TYPE: DNA
<213> ORGANISM: Artificial Sequence
<220> FEATURE:
<223> OTHER INFORMATION: synthetic probe for detecting ATG16L1 SNP rs2241880

<400> SEQUENCE: 1
cccagtcccc caggacaatg tggatactca tcctggttct ggtaaagaag t    51

```
<210> SEQ ID NO 2
<211> LENGTH: 51
<212> TYPE: DNA
<213> ORGANISM: Artificial Sequence
<220> FEATURE:
<223> OTHER INFORMATION: synthetic probe for detecting ATG16L1 SNP
      rs2241880

<400> SEQUENCE: 2
cccagtcccc caggacaatg tggatgctca tcctggttct ggtaaagaag t           51

<210> SEQ ID NO 3
<211> LENGTH: 51
<212> TYPE: DNA
<213> ORGANISM: Artificial Sequence
<220> FEATURE:
<223> OTHER INFORMATION: synthetic sequence from which to derive probes
      for detecting ATG16L1 SNP rs2241880

<400> SEQUENCE: 3
cccagtcccc caggacaatg tggatrctca tcctggttct ggtaaagaag t           51

<210> SEQ ID NO 4
<211> LENGTH: 51
<212> TYPE: DNA
<213> ORGANISM: Artificial Sequence
<220> FEATURE:
<223> OTHER INFORMATION: synthetic probe for detecting STAT3 SNP
      rs744166

<400> SEQUENCE: 4
ctgtttgttc tataaattac tgtcaagctc gattccctca agacattaca g           51

<210> SEQ ID NO 5
<211> LENGTH: 51
<212> TYPE: DNA
<213> ORGANISM: Artificial Sequence
<220> FEATURE:
<223> OTHER INFORMATION: synthetic probe for detecting STAT3 SNP
      rs744166

<400> SEQUENCE: 5
ctgtttgttc tataaattac tgtcaggctc gattccctca agacattaca g           51

<210> SEQ ID NO 6
<211> LENGTH: 51
<212> TYPE: DNA
<213> ORGANISM: Artificial Sequence
<220> FEATURE:
<223> OTHER INFORMATION: synthetic sequence from which to derive probes
      for detecting STAT3 SNP rs744166

<400> SEQUENCE: 6
ctgtttgttc tataaattac tgtcargctc gattccctca agacattaca g           51

<210> SEQ ID NO 7
<211> LENGTH: 51
<212> TYPE: DNA
<213> ORGANISM: Artificial Sequence
<220> FEATURE:
<223> OTHER INFORMATION: synthetic probe for detecting ECM1 SNP
      rs3737240

<400> SEQUENCE: 7
cccactgttt tccccattcc aggaacgcca gctccatttg gggaccagag c           51

<210> SEQ ID NO 8
<211> LENGTH: 50
```

```
<212> TYPE: DNA
<213> ORGANISM: Artificial Sequence
<220> FEATURE:
<223> OTHER INFORMATION: synthetic probe for detecting ECM1 SNP
      rs3737240

<400> SEQUENCE: 8
ccactgtttt ccccattcca ggaatgccag ctccatttgg ggaccagagc            50

<210> SEQ ID NO 9
<211> LENGTH: 51
<212> TYPE: DNA
<213> ORGANISM: Artificial Sequence
<220> FEATURE:
<223> OTHER INFORMATION: synthetic sequence from which to derive probes
      for detecting ECM1 SNP rs3737240

<400> SEQUENCE: 9
cccactgttt tccccattcc aggaaygcca gctccatttg gggaccagag c           51

<210> SEQ ID NO 10
<211> LENGTH: 51
<212> TYPE: DNA
<213> ORGANISM: Artificial Sequence
<220> FEATURE:
<223> OTHER INFORMATION: synthetic probe for detecting ECM1 SNP rs13294

<400> SEQUENCE: 10
ccgggacatc ttgaccattg acatcagtcg agtcaccccc aacctcatgg g          51

<210> SEQ ID NO 11
<211> LENGTH: 51
<212> TYPE: DNA
<213> ORGANISM: Artificial Sequence
<220> FEATURE:
<223> OTHER INFORMATION: synthetic probe for detecting ECM1 SNP rs13294

<400> SEQUENCE: 11
ccgggacatc ttgaccattg acatcggtcg agtcaccccc aacctcatgg g          51

<210> SEQ ID NO 12
<211> LENGTH: 51
<212> TYPE: DNA
<213> ORGANISM: Artificial Sequence
<220> FEATURE:
<223> OTHER INFORMATION: synthetic sequence from which to derive probes
      for detecting ECM1 SNP rs13294

<400> SEQUENCE: 12
ccgggacatc ttgaccattg acatcrgtcg agtcaccccc aacctcatgg g          51

<210> SEQ ID NO 13
<211> LENGTH: 51
<212> TYPE: DNA
<213> ORGANISM: Artificial Sequence
<220> FEATURE:
<223> OTHER INFORMATION: synthetic probe for detecting NKX2-3 SNP
      rs10883365

<400> SEQUENCE: 13
tttcgttctc agacggtttg aaggtatttg tgccaacgtg accccgggg a           51

<210> SEQ ID NO 14
<211> LENGTH: 51
<212> TYPE: DNA
<213> ORGANISM: Artificial Sequence
<220> FEATURE:
<223> OTHER INFORMATION: synthetic probe for detecting NKX2-3 SNP
``` rs10883365

<400> SEQUENCE: 14
tttcgttctc agacggtttg aaggtgtttg tgccaacgtg accccoggg a         51

<210> SEQ ID NO 15
<211> LENGTH: 51
<212> TYPE: DNA
<213> ORGANISM: Artificial Sequence
<220> FEATURE:
<223> OTHER INFORMATION: synthetic sequence from which to derive probes
      for detecting NKX2-3 SNP rs10883365

<400> SEQUENCE: 15
tttcgttctc agacggtttg aaggtrtttg tgccaacgtg acccccgggg a         51

<210> SEQ ID NO 16
<211> LENGTH: 51
<212> TYPE: DNA
<213> ORGANISM: Artificial Sequence
<220> FEATURE:
<223> OTHER INFORMATION: synthetic probe for detecting NKX2-3 SNP
      rs6584283

<400> SEQUENCE: 16
ctgcagagcg tctgtgggcg tgtatcggcg atcaggcgct ggaggggcgc t         51

<210> SEQ ID NO 17
<211> LENGTH: 51
<212> TYPE: DNA
<213> ORGANISM: Artificial Sequence
<220> FEATURE:
<223> OTHER INFORMATION: synthetic probe for detecting NKX2-3 SNP
      rs6584283

<400> SEQUENCE: 17
ctgcagagcg tctgtgggcg tgtattggcg atcaggcgct ggaggggcgc t         51

<210> SEQ ID NO 18
<211> LENGTH: 51
<212> TYPE: DNA
<213> ORGANISM: Artificial Sequence
<220> FEATURE:
<223> OTHER INFORMATION: synthetic sequence from which to derive probes
      for detecting NKX2-3 SNP rs6584283

<400> SEQUENCE: 18
ctgcagagcg tctgtgggcg tgtatyggcg atcaggcgct ggaggggcgc t         51

<210> SEQ ID NO 19
<211> LENGTH: 51
<212> TYPE: DNA
<213> ORGANISM: Artificial Sequence
<220> FEATURE:
<223> OTHER INFORMATION: synthetic probe for detecting ECM1 SNP
      rs7511649

<400> SEQUENCE: 19
tttctgactt ctccctgtaa atcttcttct gtatgattta ttttggtaga t         51

<210> SEQ ID NO 20
<211> LENGTH: 51
<212> TYPE: DNA
<213> ORGANISM: Artificial Sequence
<220> FEATURE:
<223> OTHER INFORMATION: synthetic probe for detecting ECM1 SNP
      rs7511649

```
<400> SEQUENCE: 20
tttctgactt ctccctgtaa atcttttct gtatgattta ttttggtaga t            51

<210> SEQ ID NO 21
<211> LENGTH: 51
<212> TYPE: DNA
<213> ORGANISM: Artificial Sequence
<220> FEATURE:
<223> OTHER INFORMATION: synthetic sequence from which to derive probes
      for detecting ECM1 SNP rs7511649

<400> SEQUENCE: 21
tttctgactt ctccctgtaa atcttyttct gtatgattta ttttggtaga t            51

<210> SEQ ID NO 22
<211> LENGTH: 51
<212> TYPE: DNA
<213> ORGANISM: Artificial Sequence
<220> FEATURE:
<223> OTHER INFORMATION: synthetic probe for detecting NKX2-3 SNP
      rs11190140

<400> SEQUENCE: 22
cattcaggct cctgatttca ataggcggaa aagaaggctg ccaaggctgg g            51

<210> SEQ ID NO 23
<211> LENGTH: 51
<212> TYPE: DNA
<213> ORGANISM: Artificial Sequence
<220> FEATURE:
<223> OTHER INFORMATION: synthetic probe for detecting NKX2-3 SNP
      rs11190140

<400> SEQUENCE: 23
cattcaggct cctgatttca ataggtggaa aagaaggctg ccaaggctgg g            51

<210> SEQ ID NO 24
<211> LENGTH: 51
<212> TYPE: DNA
<213> ORGANISM: Artificial Sequence
<220> FEATURE:
<223> OTHER INFORMATION: synthetic sequence from which to derive probes
      for detecting NKX2-3 SNP rs11190140

<400> SEQUENCE: 24
cattcaggct cctgatttca ataggyggaa aagaaggctg ccaaggctgg g            51
```